United States Patent
Iwasaki et al.

(10) Patent No.: US 12,331,072 B2
(45) Date of Patent: Jun. 17, 2025

(54) DEPROTECTION METHOD AND RESIN REMOVAL METHOD IN SOLID-PHASE REACTION FOR PEPTIDE COMPOUND OR AMIDE COMPOUND, AND METHOD FOR PRODUCING PEPTIDE COMPOUND

(71) Applicant: Chugai Seiyaku Kabushiki Kaisha, Tokyo (JP)

(72) Inventors: Kotaro Iwasaki, Tokyo (JP); Shio Komiya, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 31 days.

(21) Appl. No.: 18/203,371

(22) Filed: May 30, 2023

(65) Prior Publication Data

US 2023/0303619 A1    Sep. 28, 2023

Related U.S. Application Data

(63) Continuation of application No. 17/297,231, filed as application No. PCT/JP2019/046805 on Nov. 29, 2019, now Pat. No. 11,732,002.

(30) Foreign Application Priority Data

Nov. 30, 2018 (JP) ................. 2018-225518
May 31, 2019 (JP) ................. 2019-101971
Aug. 30, 2019 (JP) ................. 2019-158173

(51) Int. Cl.
C07K 1/06 (2006.01)
C07C 231/00 (2006.01)

(52) U.S. Cl.
CPC .............. *C07K 1/06* (2013.01); *C07C 231/00* (2013.01)

(58) Field of Classification Search
CPC ....... C07B 41/02; C07B 41/08; C07C 231/00; C07C 231/12; C07K 1/06
See application file for complete search history.

(56) References Cited

U.S. PATENT DOCUMENTS

| | | |
|---|---|---|
| 4,859,736 A | 8/1989 | Rink |
| 5,057,415 A | 10/1991 | Schuetz et al. |
| 5,059,679 A | 10/1991 | Yajima et al. |
| 7,288,372 B2 | 10/2007 | Olejnik et al. |
| 7,439,222 B2 | 10/2008 | Guinn et al. |
| 8,518,666 B2 | 8/2013 | Wang et al. |
| 8,809,280 B2 | 8/2014 | Strom et al. |
| 9,133,245 B2 | 9/2015 | Gao et al. |
| 9,409,952 B2 | 8/2016 | Kariyuki et al. |
| 9,701,993 B2 | 7/2017 | Suga et al. |
| 10,815,489 B2 | 10/2020 | Ohta et al. |
| 11,492,369 B2 | 11/2022 | Nomura et al. |
| 11,542,299 B2 | 1/2023 | Nomura et al. |
| 11,732,002 B2 * | 8/2023 | Iwasaki ............... C07K 1/04 530/333 |
| 11,787,836 B2 | 10/2023 | Nomura et al. |
| 2003/0219780 A1 | 11/2003 | Olejnik et al. |
| 2005/0165217 A1 | 7/2005 | Guinn et al. |
| 2008/0044854 A1 | 2/2008 | Wang et al. |
| 2008/0221303 A1 | 9/2008 | Katzhendler et al. |
| 2009/0247503 A1 * | 10/2009 | Yang ............... C07D 339/08 514/254.1 |
| 2010/0137561 A1 | 6/2010 | Chen |
| 2010/0292435 A1 | 11/2010 | Chen et al. |
| 2013/0035296 A1 | 2/2013 | Strom et al. |
| 2013/0217599 A1 | 8/2013 | Suga et al. |
| 2014/0194369 A1 | 7/2014 | Gao et al. |
| 2015/0080549 A1 | 3/2015 | Kariyuki et al. |
| 2016/0272964 A1 | 9/2016 | Murakami et al. |
| 2016/0311858 A1 | 10/2016 | Kariyuki et al. |
| 2018/0127761 A1 | 5/2018 | Ohta et al. |
| 2019/0338050 A1 | 11/2019 | Nakano et al. |
| 2020/0040372 A1 | 2/2020 | Tanaka et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |
| 2021/0061860 A1 | 3/2021 | Kariyuki et al. |
| 2021/0087572 A1 | 3/2021 | Ohta et al. |
| 2022/0024972 A1 | 1/2022 | Iwasaki et al. |

FOREIGN PATENT DOCUMENTS

| | | |
|---|---|---|
| CN | 1317011 A | 10/2001 |
| CN | 103764666 A | 4/2014 |
| CN | 106749545 A | 5/2017 |
| EP | 1277755 A1 | 1/2003 |
| EP | 1424395 A1 | 6/2004 |
| EP | 1964916 A1 | 9/2008 |
| EP | 2088202 A1 | 8/2009 |

(Continued)

OTHER PUBLICATIONS

Afonso, A., et al., "Solid-Phase Synthesis of Biaryl Cyclic Peptides Containing a 3-Aryltyrosine," European Journal of Organic Chemistry, 2012(31):6204-6211 (2012).

Alakhov, Y.B., et al., "Butylation of the Tryptophan Indole Ring: A Side Reaction During the Removal of t-butyloxycarbonyl and t-butyl Protecting Groups in Peptide Synthesis," Journal of the Chemical Society D: Chemical Communications, 7:406b-407 (1970).

Albericio, F., et al., "Fmoc Methodology: Cleavage from the Resin and Final Deprotection," Amino Acids, Peptides and Proteins in Organic Chemistry, 3:349-369 (2011).

Alex, A., et al., "Intramolecular Hydrogen Bonding to Improve Membrane Permeability and Absorption in Beyond Rule of Five Chemical Space," Medicinal Chemistry Communication, 2(7):669-674 (2011).

Alvaro, et al., "A Novel Activity of Immobilized Penicillin G Acylase: Removal of Benzyloxycarbonyl Amino Protecting Group," Biocatalysis and Biotransformation, 18(3):253-258 (2000).

(Continued)

*Primary Examiner* — Jeffrey E. Russel
(74) *Attorney, Agent, or Firm* — Nixon & Vanderhye P.C.

(57) ABSTRACT

The present inventors found that peptide compounds/amide compounds in which the protecting groups of interest are removed and/or which are removed from resins for solid-phase synthesis can be produced without main chain damage by contacting starting peptide compounds/amide compounds with silylating agents.

36 Claims, No Drawings

(56) References Cited

FOREIGN PATENT DOCUMENTS

| | | |
|---|---|---|
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 3031915 B1 | 3/2019 |
| EP | 2813512 B1 | 3/2021 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H0681759 B2 | 10/1994 |
| JP | 2513775 B2 | 7/1996 |
| JP | 2001048866 A | 2/2001 |
| JP | 2003508408 A | 3/2003 |
| JP | 2003531199 A | 10/2003 |
| JP | 2005095013 A | 4/2005 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 5808882 B2 | 11/2015 |
| JP | 2018509172 A | 4/2018 |
| WO | WO-9831700 A1 | 7/1998 |
| WO | WO00002898 A1 | 1/2000 |
| WO | WO-0181325 A2 | 11/2001 |
| WO | WO-02085923 A2 | 10/2002 |
| WO | WO-03014354 A1 | 2/2003 |
| WO | WO-03068990 A1 | 8/2003 |
| WO | WO-03089454 A2 | 10/2003 |
| WO | WO-2005063791 A2 | 7/2005 |
| WO | WO-2007066627 A1 | 6/2007 |
| WO | WO-2007103307 A2 | 9/2007 |
| WO | WO-2007120614 A2 | 10/2007 |
| WO | WO-2008117833 A1 | 10/2008 |
| WO | WO-2010053050 A1 | 5/2010 |
| WO | WO-2010062590 A2 | 6/2010 |
| WO | WO-2010063604 A1 | 6/2010 |
| WO | WO-2010125079 A2 | 11/2010 |
| WO | WO-2011049157 A1 | 4/2011 |
| WO | WO-2011051692 A1 | 5/2011 |
| WO | WO-2011058122 A1 | 5/2011 |
| WO | WO-2012026566 A1 | 3/2012 |
| WO | WO-2012033154 A1 | 3/2012 |
| WO | WO-2012074130 A1 | 6/2012 |
| WO | WO-2012122059 A1 | 9/2012 |
| WO | WO2012171982 A1 | 12/2012 |
| WO | WO-2013100132 A1 | 7/2013 |
| WO | WO-2014033466 A1 | 3/2014 |
| WO | WO-2014181888 A1 | 11/2014 |
| WO | WO-2015019192 A2 | 2/2015 |
| WO | WO-2015019999 A1 | 2/2015 |
| WO | WO-2015155676 A1 | 10/2015 |
| WO | WO-2015179434 A1 | 11/2015 |
| WO | WO-2015185162 A1 | 12/2015 |
| WO | WO-2016115168 A1 | 7/2016 |
| WO | WO-2016148044 A1 | 9/2016 |
| WO | WO-2016154675 A1 | 10/2016 |
| WO | WO-2017150732 A1 | 9/2017 |
| WO | WO-2017181061 A1 | 10/2017 |
| WO | WO-2018100561 A1 | 6/2018 |
| WO | WO-2018143145 A1 | 8/2018 |
| WO | WO-2018225851 A1 | 12/2018 |
| WO | WO-2018225864 A1 | 12/2018 |
| WO | WO-2019117274 A1 | 6/2019 |
| WO | WO-2020095983 A1 | 5/2020 |
| WO | WO-2020122182 A1 | 6/2020 |
| WO | WO-2020138336 A1 | 7/2020 |
| WO | WO-2020189540 A1 | 9/2020 |

OTHER PUBLICATIONS

Bastiaans, et al., "Flexible and Convergent Total Synthesis of Cyclotheonamide B," The Journal of Organic Chemistry, 62(12):3880-3889 (1997).

Beck, J.G., et al., "Intestinal Permeability of Cyclic Peptides: Common Key Backbone Motifs Identified," Journal of the American Chemical Society 134(29):12125-12133 (2012).

Behrendt, R., et al., "Advances in Fmoc Solid-Phase Peptide Synthesis," Journal of Peptide Science 22(1):4-27 (2016).

Bock, J.E., et al., "Getting in Shape: Controlling Peptide Bioactivity and Bioavailability Using Conformational Constraints," ACS Chemical Biology 8(3):488-499 (2013).

Bockus, A.T., et al., "Form and Function in Cyclic Peptide Natural Products: A Pharmacokinetic Perspective," Current Topics in Medicinal Chemistry, 13(7):821-836 (2013).

Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).

Brunner, J., "Biosynthetic Incorporation of Non-natural Amino Acids into Proteins," Chemical Society Reviews, 22(3):183-189 (1993).

Burkholder, T. P., et al., "Acid-catalyzed O-allylation of β-Hydroxy-α-Amino Acids: An Entry into Conformationally Constrained Dipeptide Surrogates," Bioorganic & Medicinal Chemistry Letters, 2(6):579-582 (1992).

Carpino, L.A., et al., "Dramatically Enhanced N→O Acyl Migration During the Trifluoroacetic Acid-based Deprotection Step in Solid Phase Peptide Synthesis," Tetrahedron Letters, 46(8):1361-1364 (2005).

Chatterjee, J., et al., "N-Methylation of Peptides: A New Perspective in Medicinal Chemistry," Accounts of Chemical Research 41(10):1331-1342 (2008).

Chen, C.C., et al., "A Mild Removal of Fmoc Group Using Sodium Azide," Amino Acids, 46(2):367-374 (2014).

Chen, J.F., et al., "Effect of Alanine-293 Replacement on the Activity, ATP Binding, and Editing of Escherichia Coli Leucyl-tRNA Synthetase," Biochemistry, 40(5):1144-1149 (2001).

Chen, S., et al., "Structurally Diverse Cyclisation Linkers Impose Different Backbone Conformations in Bicyclic Peptides," Chembiochem, 13(7):1032-1038 (2012).

Cornella, J., et al., "Practical Ni-Catalyzed Aryl-Alkyl Cross-Coupling of Secondary Redox- Active Esters," Journal of the American Chemical Society, 138(7):2174-2177 (2016).

Cox, A.D., et al., "Drugging the undruggable RAS: Mission possible?," Nature Reviews. Drug Discovery, 13(11):828-851 (2014).

Creighton, C.J., et al., "Mechanistic Studies of an Unusual Amide Bond Scission," Journal of the American Chemical Society, 121(29):6786-6791 (1999).

Cudic, M. and Fields, G.B., "Solid-Phase Peptide Synthesis," Molecular Biomethods Handbook, 515-546 (2008).

Cusack, S., et al., "The 2 A Crystal Structure of Leucyl-tRNA Synthetase and its Complex with a Leucyl-Adenylate Analogue," The EMBO Journal, 19(10):2351-2361 (2000).

Dailler, et al., "Divergent Synthesis of Aeruginosas Based on a C(sp(3))-H Activation Strategy," Chemistry, 21(26):9370-9379 (2015).

(56) References Cited

OTHER PUBLICATIONS

Dawson, P.E., et al., "Synthesis of Proteins by Native Chemical Ligation," Science, 266(5186):776-779 (1994).
Doi, Y., et al., "Elongation Factor Tu Mutants Expand Amino Acid Tolerance of Protein Biosynthesis System," Journal of the American Chemical Society 129(46):14458-14462 (2007).
Doublie, S., et al., "Tryptophanyl-tRNA Synthetase Crystal Structure Reveals an Unexpected Homology to Tyrosyl-tRNA Synthetase," Structure, 3(1):17-31 (1995).
Eberhard, H. and Seitz, O., "N--O-Acyl Shift in Fmoc-Based Synthesis of Phosphopeptides," Organic & Biomolecular Chemistry 6(8):1349-1355 (2008).
Fang, W.-J., et al., "Deletion of Ac-NMePhe(1) from [NMePhe(1)]arodyn Under Acidic Conditions, Part 1: Effects of Cleavage Conditions and N-terminal Functionality," Biopolymers 96(1):97-102 (2011).
Frankel, A., et al., "Encodamers: Unnatural Peptide Oligomers Encoded in RNA," Chemistry & Biology, 10(11):1043-1050 (2003).
Fujii, N., et al., "Trimethylsilyl Trifluoromethanesulphonate as a Useful Deprotecting Reagent in Both Solution and Solid Phase Peptide Syntheses," Journal of the Chemical Society, Chemical Communications, 4:274-275 (1987).
Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).
Fujino, T., et al., "Reevaluation of the D-Amino Acid Compatibility With the Elongation Event in Translation," Journal of the American Chemical Society 135(5):1830-1837 (2013).
Fujino, T., et al., "Ribosomal Synthesis of Peptides with Multiple beta-Amino Acids," Journal of the American Chemical Society 138(6):1962-1969 (2016).
Fukai, S., et al., "Mechanism of Molecular Interactions for tRNA(Val) Recognition by Valyl-tRNA Synthetase," RNA 9(1):100-111 (2003).
Fukai, S., et al., "Structural Basis for Double-Sieve Discrimination of L-Valine From L-Isoleucine and L-Threonine by the Complex of tRNA(Val) and Valyl-tRNA Synthetase," Cell 103(5):793-803 (2000).
Fukunaga, R. and Yokoyama, S., "Structural Basis for Non-Cognate Amino Acid Discrimination by the Valyl-tRNA Synthetase Editing Domain," The Journal of Biological Chemistry 280(33):29937-29945 (2005).
Ganesan, A., "The Impact of Natural Products Upon Modern Drug Discovery," Current Opinion in Chemical Biology, 12(3):306-317 (2008).
Genbank, "Valine-tRNA ligase [*Thermus thermophilus*]," Accession No. P96142, accessed on Jan. 27, 2021.
Gilon, C., et al., "Backbone Cyclization: A New Method for Conferring Conformational Constraint on Peptides," Biopolymers, 31(6):745-750 (1991).
Goto, et al., "Ribosomal Synthesis of Combinatorial Polypeptides Containing Unusual Amino Acid Blocks," Kagaku Kogyo, 58(4):255-262 (2007).
Goto, Y. and Suga, H., "Translation Initiation With Initiator tRNA Charged With Exotic Peptides," Journal of the American Chemical Society, 131(14):5040-5041 (2009).
Goto, Y., et al., "Flexizymes for Genetic Code Reprogramming," Nature Protocols, 6(6):779-790 (2011).
Gracia, S.R., et al., "Synthesis of Chemically Modified Bioactive Peptides: Recent Advances, Challenges and Developments for Medicinal Chemistry," Future Medicinal Chemistry 1(7):1289-1310 (2009).
Gravestock, et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Bjork, G.R., "Enzymatic Conversion of Cytidine to Lysidine in Anticodon of Bacterial Isoleucyl-tRNA—an Alternative Way of RNA Editing," Trends in Biochemical Sciences, 29(4):165-168 (2004).

Hartman, M.C., et al., "An Expanded Set of Amino Acid Analogs for the Ribosomal Translation of Unnatural Peptides," PLoS One 2(10):e972 (2007).
Hartman, M.C.T., et al., "Enzymatic Aminoacylation of tRNA With Unnatural Amino Acids," Proceedings of the National Academy of Sciences of the United States of America, 103(12):4356-4361 (2006).
Hayashi, G., et al., "Ribosomal Synthesis of Nonstandard Cyclic Peptides and its Application to Drug Discovery," The Journal of Japanese Biochemical Society, 82(6):505-514 (2010).
Hecht, S.M., et al., ""Chemical Aminoacylation" of tRNA's," The Journal of Biological Chemistry 253(13):4517-4520 (1978).
Heinis, C., et al., "Phage-Encoded Combinatorial Chemical Libraries Based on Bicyclic Peptides," Nature Chemical Biology, 5(7):502-507 (2009).
Higuchi, T. and Suga, H., "Programmed Synthesis of Natural Product-Like Non-Standard Peptides Using the Translation System and its Application," Journal of Synthetic Organic Chemistry, 68(3):217-227 (2010).
Hoogenboom, H.R., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry 267(15):4789-4798 (2000).
Hruby, V.J., et al., "Emerging Approaches in the Molecular Design of Receptor-Selective Peptide Ligands: Conformational, Topographical and Dynamic Considerations," The Biochemical Journal, 268(2):249-262 (1990).
Huihui, K.M.M., et al., "Decarboxylative Cross-Electrophile Coupling of N-Hydroxyphthalimide Esters With Aryl Iodides," Journal of the American Chemical Society, 138(15):5016-5019 (2016).
Ikeuchi, Y., et al., "Agmatine-conjugated Cytidine in a tRNA Anticodon Is Essential for AUA Decoding in Archaea," Nature Chemical Biology, 6(4):277-282 (2010).
Ikeuchi, Y., et al., "Molecular Mechanism of Lysidine Synthesis That Determines tRNA Identity and Codon Recognition," Molecular Cell, 19(2):235-246 (2005).
Isidro-Llobet, A., et al., "Amino Acid-Protecting Groups," Chemical Reviews, 109(6):2455-2504 (2009).
Itoh, Y., et al., "Crystallographic and Mutational Studies of Seryl-tRNA Synthetase From the Archaeon Pyrococcus Horikoshii," RNA Biology, 5(3):169-177 (2008).
Iwane, Y., et al., "Expanding the Amino Acid Repertoire of Ribosomal Polypeptide Synthesis via the Artificial Division of Codon Boxes," Nature Chemistry, 8(4):317-325 (2016).
Jaradat, D.M.M., "Thirteen Decades of Peptide Synthesis: Key Developments in Solid Phase Peptide Synthesis and Amide Bond Formation Utilized in Peptide Ligation," Amino Acids, 50(1):39-68 (2018).
Jones, A.B., et al., "A Formal Synthesis of FK-506. Exploration of Some Alternatives to Macrolactamization," The Journal of Organic Chemistry, 55(9):2786-2797 (1990).
Josephson, K., et al., "mRNA Display: From Basic Principles to Macrocycle Drug Discovery," Drug Discovery Today 19(4):388-399 (2014).
Josephson, K., et al., "Ribosomal Synthesis of Unnatural Peptides," Journal of the American Chemical Society, 127(33):11727-11735 (2005).
Kato, et al., Yakubutsutaishagaku. 2nd edition, pp. 9-13 (2000).
Kato, et al., Yakubutsutaishagaku. 3rd edition, pp. 43-46 (2010).
Katoh, T., et al., "Ribosomal Synthesis of Backbone Macrocyclic Peptides," Chemical Communications, 47(36):9946-9958 (2011).
Kawakami, T., et al., "Incorporation of Electrically Charged N-alkyl Amino Acids into Ribosomally Synthesized Peptides via Post-translational Conversion," Chemical Science, 5(3):887-893 (2014).
Kawakami, T., et al., "Messenger RNA-Programmed Incorporation of Multiple N-Methyl-Amino Acids into Linear and Cyclic Peptides," Chemistry & Biology 15(1):32-42 (2008).

(56) References Cited

OTHER PUBLICATIONS

Kawakami, T., et al., "Ribosomal Synthesis of Polypeptoids and Peptoid-Peptide Hybrids," Journal of the American Chemical Society 130(50):16861-16863 (2008).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).
Kawakami, T., et al., "Diverse Backbone-Cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).
Kiho, T., et al., "Total Synthesis of Pleofugin A, a Potent Inositol Phosphorylceramide Synthase Inhibitor," Organic Letters, 20(15):4637-4640 (2018).
Kleineweischede, R. and Hackenberger, C.P., "Chemoselective Peptide Cyclization by Traceless Staudinger Ligation," Angewandte Chemie (International ed. in English), 47(32):5984-5988 (2008).
Kobayashi, T., et al., "Recognition of Non-Alpha-Amino Substrates by pyrrolysyl-tRNA Synthetase," Journal of Molecular Biology, 385(5):1352-1360 (2009).
Kopina, B.J. and Lauhon, C.T., "Efficient Preparation of 2,4-diaminopyrimidine Nucleosides: Total Synthesis of Lysidine and Agmatidine," Organic Letters, 14(16):4118-4121 (2012).
Kuhn, B., et al., "Intramolecular Hydrogen Bonding in Medicinal Chemistry," Journal of Medicinal Chemistry, 53(6):2601-2611 (2010).
Lajoie, M.J., et al., "Overcoming Challenges in Engineering the Genetic Code," Journal of Molecular Biology, 428(5 Pt B):1004-1021 (2016).
Lassak, J., et al., "Stall No More at Polyproline Stretches With the Translation Elongation Factors EF-P and IF-5A," Molecular Microbiology 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W. and Briggs, J.M., "Molecular Modeling Study of the Editing Active Site of Escherichia coli leucyl-tRNA Synthetase: Two Amino Acid Binding Sites in the Editing Domain," Proteins, 54(4):693-704 (2004).
Lejeune, V., et al., "Towards a Selective Boc Deprotection on Acid Cleavable Wang Resin," Tetrahedron Letters, 44(25):4757-4759 (2003).
Lenzi, A., et al., "Synthesis of N-Boc-a-Amino Acids with Nucleobase Residues as Building Blocks for the Preparation of Chiral PNA (Peptidic Nucleic Acids)," Tetrahedron Letters, 36(10):1713-1716 (1995).
Li, H., et al., "Ni-Catalyzed Electrochemical Decarboxylative C-C Couplings in Batch and Continuous Flow," Organic letters, 20(5):1338-1341 (2018).
Li, S., et al., "In Vitro Selection of mRNA Display Libraries Containing an Unnatural Amino Acid," Journal of the American Chemical Society, 124(34):9972-9973 (2002).
Li, X., et al., "Salicylaldehyde Ester-Induced Chemoselective Peptide Ligations: Enabling Generation of Natural Peptidic Linkages at the Serine/Threonine Sites," Organic Letters, 12(8):1724-1727 (2010).
Liniger, M., et al., "Total Synthesis and Characterization of 7-Hypoquinuclidonium Tetrafluoroborate and 7-Hypoquinuclidone BF3 Complex," Journal of the American Chemical Society, 138(3):969-974 (2016).
Liu, Z., et al., "N-Boc Deprotection and Isolation Method for Water-soluble Zwitterionic Compounds," The Journal of Organic Chemistry, 79(23):11792-11796 (2014).
Liu, D.R., et al., "Engineering a tRNA and aminoacyl-tRNA Synthetase for the Site-Specific Incorporation of Unnatural Amino Acids into Proteins in Vivo," Proceedings of the National Academy of Sciences of the United States of America, 94(19):10092-10097 (1997).
Lodder, M., et al., "The N-Pentenoyl Protecting Group for Aminoacyl-tRNAs," Methods 36(3):245-251 (2005).

Loos, P., et al., "Unified Azoline and Azole Syntheses by Optimized Aza-Wittig Chemistry," European Journal of Organic Chemistry, 2013(16):3290-3315 (2013).
Lundquist, J.T. and Pelletier, J.C., "Improved Solid-Phase Peptide Synthesis Method Utilizing Alpha-Azide-Protected Amino Acids," Organic Letters, 3(5):781-783 (2001).
Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry, 81(2):532-544 (2016).
Maini, R., et al., "Protein Synthesis With Ribosomes Selected for the Incorporation of beta-Amino Acids," Biochemistry 54(23):3694-3706 (2015).
Maini, R., et al., "Ribosome-Mediated Synthesis of Natural Product-Like Peptides via Cell-Free Translation," Current Opinion in Chemical Biology 34:44-52 (2016).
Malhotra, R., et al., "Efficient Asymmetric Synthesis of N-Protected-B-Aryloxyamino Acids via Regioselective Ring Opening of Serine Sulfamidate Carboxylic Acid," Organic & Biomolecular Chemistry, 12(33):6507-6515 (2014).
Manfredini, S., et al., "Design and Synthesis of Phosphonoacetic Acid (PPA) Ester and Amide Bioisosters of Ribofuranosylnucleoside Diphosphates as Potential Ribonucleotide Reductase Inhibitors and Evaluation of Their Enzyme Inhibitory, Cytostatic and Antiviral Activity," Antiviral Chemistry and Chemotherapy, 14(4):183-194 (2003).
Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).
Marcucci, E., et al., "Solid-Phase Synthesis of NMe-IB-01212, a Highly N-Methylated Cyclic Peptide," Organic letters 14(2):612-615 (2012).
Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).
Meinnel, T., et al., "Methionine as Translation Start Signal: A Review of the Enzymes of the Pathway in Escherichia coli," Biochimie, 75(12):1061-1075 (1993).
Mermershtain, I., et al., "Idiosyncrasy and Identity in the Prokaryotic Phe-system: Crystal Structure of E. coli phenylalanyl-tRNA Synthetase Complexed With Phenylalanine and AMP," Protein Science, 20(1):160-167 (2011).
Merryman, C. and Green, R., "Transformation of Aminoacyl tRNAs for the in Vitro Selection of "Drug-Like" Molecules," Chemistry & Biology, 11(4):575-582 (2004).
Millward, S.W., et al., "Design of Cyclic Peptides That Bind Protein Surfaces With Antibody-Like Affinity," ACS Chemical Biology, 2(9):625-634 (2007).
Millward, S.W., et al., "A General Route for Post-Translational Cyclization of mRNA Display Libraries," Journal of the American Chemical Society 127(41):14142-14143 (2005).
Miyake, A., et al., "Design and Synthesis of N-[N-[(S)-1-ethoxycarbonyl-3-phenylpropyl]-I-alanyl]-N-(Indan-2-yl)glycine (CV-3317), a New, Potent Angiotensin Converting Enzyme Inhibitor," Chemical and Pharmaceutical Bulletin, 34(7):2852-2858 (1986).
Montalbetti, C.A.G.N. and Falque, V., "Amide Bond Formation and Peptide Coupling," Tetrahedron, 61(46):10827-10852 (2005).
Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).
Muramatsu, T., et al., "A Novel Lysine-Substituted Nucleoside in The First Position of the Anticodon of Minor Isoleucine tRNA from Escherichia coli," The Journal of Biological Chemistry, 263(19):9261-9267 (1988).
Murashige, R., et al., "Asymmetric and efficient synthesis of homophenylalanine derivatives via Friedel-Crafts reaction with trifluoromethanesulfonic acid," Tetrahedron Letters, 49(46):6566-6568. (2008).

(56) References Cited

OTHER PUBLICATIONS

Navo, C.D., et al., "Oxygen by Carbon Replacement at the Glycosidic Linkage Modulates the Sugar Conformation in Tn Antigen Mimics," ACS Omega, 3(12):18142-18152 (2018).
Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters, 27(12):2757-2761 (2017).
Ohta, A., et al., "Synthesis of Polyester by Means of Genetic Code Reprogramming," Chemistry & Biology, 14(12):1315-1322 (2007).
Ohtsuki, T., et al., "Phototriggered Protein Syntheses by Using (7-diethylaminocoumarin-4-yl) Methoxycarbonyl-Caged Aminoacyl tRNAs," Nature Communications 7:12501 (2016).
Ohwada, T., et al., "On the Planarity of Amide Nitrogen. Intrinsic Pyramidal Nitrogen of N-acyl-7-azabicyclo[2.2.1]heptanes," Tetrahedron Letters, 39(8):865-868 (1998).
Orain, D., et al., "Protecting Groups in Solid-Phase Organic Synthesis," Journal of Combinatorial Chemistry, 4(1):1-16 (2002).
Osawa, T., et al., "Structural Basis of tRNA Agmatinylation Essential for AUA Codon Decoding," Nature Structural & Molecular Biology, 18(11):1275-1280 (2011).
Ostrem, J.M.L., et al., "Direct Small-Molecule Inhibitors of KRAS: From Structural Insights to Mechanism-Based Design," Nature reviews. Drug discovery, 15(11):771-785 (2016).
Ovadia, O., et al., "Improvement of Drug-Like Properties of Peptides: The Somatostatin Paradigm," Expert Opinion on Drug Discovery, 5(7):655-671 (2010).
Parthasarathy, R., et al., "Sortase A as a Novel Molecular "Stapler" for Sequence-Specific Protein Conjugation," Bioconjugate Chemistry, 18(2):469-476 (2007).
Peacock, J.R., et al., "Amino Acid-Dependent Stability of the Acyl Linkage in aminoacyl-tRNA," RNA, 20(6):758-764 (2014).
Perona, J.J. and Hadd, A., "Structural Diversity and Protein Engineering of the aminoacyl-tRNA Synthetases," Biochemistry, 51(44):8705-8729 (2012).
Peschke, B., et al., "New Highly Potent Dipeptidic Growth Hormone Secretagogues with Low Molecular Weight," European Journal of Medicinal Chemistry, 35(6):599-618 (2000).
Piszkiewicz, D., et al., "Anomalous Cleavage of Aspartyl-Proline Peptide Bonds During Amino Acid Sequence Determinations," Biochemical and Biophysical Research Communications, 40(5):1173-1178 (1970).
Rader, A.F.B., et al., "Orally Active Peptides: Is There a Magic Bullet?," Angewandte Chemie, 57(44):14414-14438 (2018).
Rafi, S.B., et al., "Predicting and Improving The Membrane Permeability of Peptidic Small Molecules," Journal of Medicinal Chemistry, 55(7):3163-3169 (2012).
Reddy, P.R., et al., "Synthesis of Small Cyclic Peptides via Intramolecular Heck Reactions," Tetrahedron Letters, 44(2):353-356 (2003).
Rezai, T., et al., "Testing the Conformational Hypothesis of Passive Membrane Permeability Using Synthetic Cyclic Peptide Diastereomers," Journal of the American Chemical Society, 128(8):2510-2511 (2006).
Rodriguez, H., et al., "A Convenient Microwave-Enhanced Solid-phase Synthesis of Short Chain N-Methyl-Rich Peptides," Journal of Peptide Science 16(3):136-140 (2010).
Roodbeen, R., et al., "Microwave Heating in the Solid-Phase Synthesis of N-Methylated Peptides: When is Room Temperature Better?," European Journal of Organic Chemistry 2012(36):7106-7111 (2012).
Sakamoto, K., et al., "K-Ras(G12D)-Selective Inhibitory Peptides Generated by Random Peptide T7 Phage Display Technology," Biochemical and Biophysical Research Communications, 484(3):605-611 (2017).
Salowe, S.P., et al., "The Catalytic Flexibility of Trnaile-Lysidine Synthetase can Generate Alternative tRNA Substrates for Isoleucyl-tRNA Synthetase," The Journal of Biological Chemistry, 284(15):9656-9662 (2009).

Samatar, A.A., et al., "Targeting RAS-ERK Signalling in Cancer: Promises and Challenges," Nature reviews. Drug Discovery, 13(12):928-942 (2014).
Sang-Aroon, W., et al., "Theoretical Study on Isomerization and Peptide Bond Cleavage at Aspartic Residue," Journal of Molecular Modeling, 19(9):3627-3636 (2013).
Sankaranarayanan, R., et al., "The Structure of threonyl-tRNA synthetase-tRNA(THR) Complex Enlightens its Repressor Activity and Reveals an Essential Zinc Ion in the Active Site," Cell, 97(3):371-381 (1999).
Satyanarayanajois, S.D. and Hill, R.A., "Medicinal Chemistry for 2020," Future Medicinal Chemistry, 3(14):1765-1786 (2011).
Schlippe, Y.V.G., et al., "In Vitro Selection of Highly Modified Cyclic Peptides That Act as Tight Binding Inhibitors," Journal of the American Chemical Society, 134(25):10469-10477 (2012).
Sever, S., et al., "*Escherichia coli* tryptophanyl-tRNA Synthetase Mutants Selected for Tryptophan Auxotrophy Implicate the Dimer Interface in Optimizing Amino Acid Binding," Biochemistry, 35(1):32-40 (1996).
Shimizu, Y., et al., "Cell-Free Translation Reconstituted With Purified Components," Nature Biotechnology 19(8):751-755 (2001).
Shukla, G.S. and Krag, D.N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).
Sogabe, S., et al., "Crystal Structure of a Human K-Ras G12D Mutant in Complex with GDP and the Cyclic Inhibitory Peptide KRpep-2d," ACS Medicinal Chemistry Letters, 8(7):732-736 (2017).
Starosta, A.L., et al., "A Conserved Proline Triplet in Val-tRNA Synthetase and the Origin of Elongation Factor P," Cell Reports 9(2):476-483 (2014).
Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).
Struck, A., et al., "An Enzyme Cascade for Selective Modification of Tyrosine Residues in Structurally Diverse Peptides and Proteins," Journal of the American Chemical Society, 138(9):3038-3045 (2016).
Subtelny, A.O., et al., "Optimal Codon Choice Can Improve the Efficiency and Fidelity of N-methyl Amino Acid Incorporation into Peptides by in-Vitro Translation," Angewandte Chemie (International ed. in English) 50(14):3164-3167 (2011).
Subtelny, A.O., et al., "Ribosomal Synthesis of N-Methyl Peptides," Journal of the American Chemical Society 130(19):6131-6136 (2008).
Suenaga, K., et al., "Aurilide, A Cytotoxic Depsipeptide From the Sea Hare Dolabella Auricularia: Isolation, Structure Determination, Synthesis, and Biological Activity," Tetrahedron, 60(38):8509-8527 (2004).
Suenaga, K., et al., "Synthesis and Cytotoxicity of Aurilide Analogs," Bioorganic & Medicinal Chemistry Letters, 18(14):3902-3905 (2008).
Suzuki, T., et al., "Discovery and Characterization of tRNAIle Lysidine Synthetase (TilS)," FEBS Letters, 584(2):272-277 (2010).
Suzuki, T., "How to Decipher AUA Codon in Archaea," Kagaku to Seibutsu, 50(1):36-43 (2012).
Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).
Tan, Z., et al., "Amino Acid Backbone Specificity of the *Escherichia coli* Translation Machinery," Journal of the American Chemical Society, 126(40):12752-12753 (2004).
Teixido, M., et al., "Solid-Phase Synthesis and Characterization of N-Methyl-Rich Peptides," The Journal of Peptide Research 65(2):153-166 (2005).
Terasaka, et al., "Construction of Nonstandard Peptide Library by Genetic Code Reprogramming and Bioactive Peptide Discovery," Experimental Medicine, 29(7):1063-1070 (2011).
Terasaka, N., et al., "Recent Developments of Engineered Translational Machineries for the Incorporation of Non-Canonical Amino Acids into Polypeptides," International Journal of Molecular Sciences, 16(3):6513-6531 (2015).

(56) References Cited

OTHER PUBLICATIONS

Toriyama, F., et al., "Redox-Active Esters in Fe-catalyzed C-C Coupling," Journal of the American Chemical Society, 138(35):11132-11135 (2016).
Tsuda, et al., Amino Acids, Peptides and Proteins in Organic Chemistry, 3:201-406, 495-517, 549-569 (2011).
Tsukiji, S. and Nagamune, T., "Sortase-mediated Ligation: A Gift From Gram-positive Bacteria to Protein Engineering," Chembiochem, 10(5):787-798 (2009).
Urban, J., et al., "Lability of N-alkylated Peptides Towards TFA Cleavage," International Journal of Peptide and Protein Research 47(3):182-189 (1996).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry, 33(6):505-524 (1998).
Van Der Auwera, C.V.D., et al., "Easy Cleavage of C'-Terminal Iminoacids from Peptide Acids through Acidic Hydrolysis," International Journal of Peptide and Protein Research, 31(2):186-191 (1988).
Wang, S., et al., "Iridium/f-Amphox-Catalyzed Asymmetric Hydrogenation of Styrylglyoxylamides," Synlett, 29:2203-2207 (2018).
Wang, J., et al., "Kinetics of Ribosome-Catalyzed Polymerization Using Artificial Aminoacyl-tRNA Substrates Clarifies Inefficiencies and Improvements," ACS Chemical Biology 10(10):2187-2192 (2015).
Wang, T., et al., "Revisiting Oxytocin through the Medium of Isonitriles," Journal of the American Chemical Society, 134(32):13244-13247 (2012).
Watanabe, E., et al., "A Practical Method for Continuous Production of Sp3-Rich Compounds From (Hetero)Aryl Halides and Redox-Active Esters," Chemistry, 26(1):186-191 (2020).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wells, J.A. and McClendon, C.L., "Reaching for High-Hanging Fruit in Drug Discovery at Protein-Protein Interfaces," Nature, 450(7172):1001-1009 (2007).
Wenschuh, H., et al., "Stepwise Automated Solid Phase Synthesis of Naturally Occurring Peptaibols Using FMOC Amino Acid Fluorides," The Journal of Organic Chemistry 60(2):405-410 (1995).
Wermuth, C. G., editor, "The Practice of Medicinal Chemistry," 2nd Edition, Academic Press, pp. 52-53 (2003), English translation of Wermuth, C. G., editor, "The Practice of Medicinal Chemistry," 2nd Edition, vol. 1, P87 (2003).
White, T.R., et al., "On-Resin N-methylation of Cyclic Peptides for Discovery of Orally Bioavailable Scaffolds," Nature Chemical Biology 7(11):810-817 (2011).
White, C.J. and Yudin, A.K., "Contemporary Strategies for Peptide Macrocyclization," Nature Chemistry, 3(7):509-524 (2011).
Wu, N., et al., "A Genetically Encoded Photocaged Amino Acid," Journal of the American Chemical Society, 126(44):14306-14307 (2004).
Wu, J., et al., "Intrinsic Basicity of Oligomeric Peptides that Contain Glycine, Alanine, and Valine-the Effects of the Alkyl Side Chain on Proton Transfer Reactions," Journal of the American Society for Mass Spectrometry, 6(2):91-101 (1995).
Yajima, et al., "New Strategy for the Chemical Synthesis of Proteins," Tetrahedron, 44(3):805-819 (1988).
Yamagishi, Y., et al., "Natural Product-Like Macrocyclic N-Methyl-Peptide Inhibitors Against a Ubiquitin Ligase Uncovered From a Ribosome-Expressed De Novo Library," Chemistry & Biology 18(12):1562-1570 (2011).
Yamanoi, K., et al., "Synthesis of Trans and cis-a-(carboxycyclopropyl) Glycines Novel Neuroinhibitory Amino Acids as L-Glutamate Analogue," Tetrahedron Letters, 29(10):1181-1184 (1988).
Yanagisawa, T., et al., "Multistep Engineering of Pyrrolysyl-tRNA Synthetase to Genetically Encode N(epsilon)-(o-azidobenzyloxycarbonyl) Lysine for Site-Specific Protein Modification," Chemistry & Biology, 15(11):1187-1197 (2008).

Yang, Y., "Side Reactions in Peptide Synthesis," pp. 1-31 (2015).
Yao, G., et al., "Efficient Synthesis and Stereochemical Revision of Coibamide A," Journal of American Chemical Society, 137(42):13488-13491 (2015).
Yang, Y., Side Reactions in Peptide Synthesis, pp. 246 (2016).
Zhai, Y. and Martinis, S.A., "Two Conserved Threonines Collaborate in the Escherichia Coli Leucyl-tRNA Synthetase Amino Acid Editing Mechanism," Biochemistry, 44(47):15437-15443 (2005).
Zhang, B., et al., "Specificity of Translation for N-Alkyl Amino Acids," Journal of the American Chemical Society, 129(37):11316-11317 (2007).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
Zhang, A.J., et al., "A Method for Removal of N-BOC Protecting Groups from Substrates on TFA-Sensitive Resins," Tetrahedron Letters, 39(41):7439-7442 (1998).
Bodanszky, M., "Coupling in the absence of tertiary amines," Int J Peptide Protein Res., 26:550-556 (1985).
Chatterjee, J., et al., "N-Methylated Cyclic Petaalanine Peptides as Template Structures," J Am Chem Soc., 128:15164-15172 (2008).
U.S. Appl. No. 07/171,049, filed Mar. 21, 1988, Rink et al.
U.S. Appl. No. 07/251,176, filed Sep. 30, 1988, Hans-Jurgen et al.
U.S. Appl. No. 07/331,292, filed Mar. 30, 1989, Yajima et al.
U.S. Appl. No. 10/345,664, filed Jan. 16, 2003, Olejnik et al.
U.S. Appl. No. 11/682,272, filed Mar. 5, 2007, Wang et al.
U.S. Appl. No. 13/505,625, filed Oct. 22, 2012, Strom et al.
U.S. Appl. No. 13/816,911, filed Feb. 13, 2013, Suga et al.
U.S. Appl. No. 14/125,906, filed Mar. 10, 2014, Gao et al.
U.S. Appl. No. 14/368,564, filed Jun. 25, 2014, Kariyuki et al.
U.S. Appl. No. 14/889,868, filed Mar. 7, 2016, Murakami et al.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/479,736, filed Jul. 22, 2019, Tanaka et al., related application.
U.S. Appl. No. 16/619,014, filed Dec. 3, 2019, Muraoka et al.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/291,099, filed Jun. 3, 2021, Ishizawa, related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto, related application.
U.S. Appl. No. 17/738,283, filed May 6, 2022, Hou et al., related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/787,809, filed Jun. 21, 2022, Kagotani et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.
U.S. Appl. No. 17/976,942, filed Oct. 31, 2022, Nomura et al., related application.
U.S. Appl. No. 18/010,608, filed Dec. 15, 2022, Nishimura et al., related application.

(56) References Cited

OTHER PUBLICATIONS

Zhou, L., et al., "Reaction Mechanism for the Alkoxylation of a Silyl Ligand in the Silyl-(silylene)ruthenium Complex: A Density Functional Theory Study," Chin J Org Chem., 35:698-704 (2015), with English abstract.

U.S. Appl. No. 18/034,424, filed Apr. 28, 2023, Nomura et al., related application.

U.S. Appl. No. 18/289,592, filed Nov. 22, 2023, Kawada et al., related application.

U.S. Appl. No. 18/829,566, filed Sep. 10, 2024, Kawada et al., related application.

U.S. Appl. No. 18/854,568, filed Oct. 7, 2024, Shinohara et al., related application.

* cited by examiner

DEPROTECTION METHOD AND RESIN REMOVAL METHOD IN SOLID-PHASE REACTION FOR PEPTIDE COMPOUND OR AMIDE COMPOUND, AND METHOD FOR PRODUCING PEPTIDE COMPOUND

CROSS-REFERENCE TO RELATED APPLICATIONS

This application is a continuation of U.S. patent application Ser. No. 17/297,231, § 371 date May 26, 2021, which is a U.S. National Phase of PCT Application No. PCT/JP2019/046805, filed Nov. 29, 2019, which claims the benefit of Japanese Patent Application No. 2018-225518, filed Nov. 30, 2018, Japanese Patent Application No. 2019-101971, filed May 31, 2019, and Japanese Patent Application No. 2019-158173, filed Aug. 30, 2019. The entire contents of PCT Application No. PCT/JP2019/046805 are herein incorporated by reference.

TECHNICAL FIELD

The present invention relates to methods of deprotection of peptide compounds or amide compounds and methods of removing such compounds from resins in solid-phase reactions, and methods of producing peptide compounds.

BACKGROUND ART

Peptides are molecules in which many amino acids are linked together. Extensive research has been conducted not only on the synthesis of peptides produced by organisms, but also on peptides with artificially designed structures and desired functions (NPL 1).

Peptides can be produced by linking multiple amino acids by repeating the steps of (i) activating the carboxyl group of an N-terminally protected, C-terminally unprotected amino acid with a condensing agent or the like to provide an active ester, (ii) reacting the active ester with an N-terminally unprotected peptide to provide a peptide elongated with the amino acid, and (iii) removing the N-terminal protecting group from the elongated peptide (NPL 2).

Peptide production methods are roughly classified into solid-phase methods and liquid-phase methods. Solid-phase methods are performed by allowing the C-terminus of an amino acid or a derivative thereof (a protected amino acid) or a peptide or a derivative thereof to bind to a resin for solid-phase synthesis that contains a chlorotrityl group, a benzyl group, or the like, such as CTC resin, Wang resin, or SASRIN resin, and performing coupling reaction between the amino group of the resulting amino acid or peptide, which serves as a nucleophile, and the carbonyl group of an N-terminally protected peptide or amino acid, which serves as an electrophile. Liquid-phase methods are performed by coupling reaction between the carbonyl group of an N-terminally protected amino acid or peptide as an electrophile and the amino group of an amino acid or peptide as a nucleophile. When such coupling reactions may lead to undesired transformation of functional groups in the amino acid or peptide side chains, protecting groups must be previously introduced into these side chains. Protecting groups that can be removed under acidic conditions such as Boc, t-Bu, or trityl groups are generally used to protect the C-terminus of amino acids or peptides, the N-terminus of amino acids or peptides, and the side chains of amino acids or peptides. In resin removal reactions to cleave peptides from resin for solid-phase synthesis to which they are bound, resins for solid-phase synthesis that are removable under acidic conditions such as CTC resin, Wang resin, and SASRIN resin are generally used (NPL 4).

Protecting groups that can be removed under acidic conditions also include 3,5-dimethoxyphenylisopropoxycarbonyl (Ddz), benzyloxycarbonyl (Cbz), benzyl (Bn), and cyclohexyl (cHx) groups (NPL 4 and NPL 5). Under the conditions of their deprotection reactions or the resin removal reactions, side reactions may occur such as cleavage of amide bonds in peptides and unintended transformation of functional groups in amino acid side chains, resulting in by-product peptides having unintended sequences. Accordingly, there is a need to provide target peptides without reactions damaging the peptide main chain, such as amide bond cleavage reactions and rearrangement reactions of the peptide main chain.

The above-described protecting groups that can be removed under acidic conditions are often removed by treatment with hydrochloric acid, sulfuric acid, methanesulfonic acid, or TFA (NPL 2, NPL 3, and NPL 4). TFA is usually used in resin removal reaction in solid-phase synthesis (NPL 6). However, it has been described that amide bonds may be cleaved even under acidic conditions using TFA, the mildest acid among them (NPL 7).

It has also been described that an attempt to solve the problem of amide bond cleavage was made by conducting the reactions under diluted TFA conditions and the Boc deprotection reactions under mild conditions; however, the problem was not solved under both conditions (NPL 8, PTL 1). Methods of removing protecting groups from protected amino acids using less acidic TFE have also been reported (NPL 5, PTL 1). In these documents, the reaction conversion rate is low, and it is therefore necessary to add more acid or conduct the reactions under severer reaction conditions such as elevated reaction temperatures in order to advance the reactions. However, when reaction conditions including addition of acid or elevation of reaction temperatures are applied to a peptide, there is a concern that the main chain of the peptide may be damaged. Actually, when Boc-Leu-MeLeu-Thr(OBn)-MeGly-OAllyl was reacted with hydrogen chloride in TFE to perform Boc-deprotection reaction, main chain cleavage was observed before the Boc deprotection reaction was completed.

It has also been reported that amide bond cleavage was successfully suppressed by conducting the reaction under low-temperature conditions and stopping the reaction before side reactions occurred (NPL 9). However, this technique requires strict control of the reaction time, and it is easily presumed that such control is challenging in mass production, where it is difficult to stop reactions in a short time.

As a deprotection method under acidic conditions, an attempt to inhibit side reactions between side chains and t-Bu cation generated concomitantly in the removal of Boc or t-Bu group has been made by adding a cation scavenger (NPL 10).

In this case, the deprotection under acidic conditions was performed with sulfur-containing additives such as dimethyl sulfide and thioanisole to scavenge t-Bu cations derived from t-Bu groups, but it reportedly caused amide bond cleavage as a side reaction, resulting in reduced yield and purity (NPL 7).

A method of allowing thioanisole and TfOH to act in a TFA solution or allowing thioanisole and trimethylsilyl bromide or trimethylsilyl triflate to act in a TFA solution has also been reported (NPL 12).

However, many sulfur-containing additives, represented by dimethyl sulfide and thioanisole, have offensive odor and thus their effects on manufacturing workers are a concern. In addition, it is problematic that removal of such additives requires removal steps by column chromatography, which is unsuitable for mass production.

It has also been reported that even when using water as a cation scavenger, peptide chain cleavage was increased (NPL 11).

Deprotection methods using silicon-containing additives instead of sulfur-containing additives as cation scavengers have been reported, where N-Boc protected compounds containing amide bonds are treated with cation scavengers such as triisopropylsilane (iPr3SiH), for example, at a ratio of TFA:iPr3SiH:H2O=95:2.5:2.5 (NPL 13) or at a ratio of TFA:iPr3SiH:H2O:PhOH=1000:50:67:50 (NPL 14). However, as for these methods, only conditions difficult to achieve in mass production are described, such as performing the treatment for a short period of time of several minutes to suppress amide bond cleavage. In fact, when Boc-MeIle-Ala-MePhe-MeVal-Asp(pip)-MePhe-MeAla-Leu-MeLeu-Thr(OBn)-MeGly-OAllyl was subjected to Boc deprotection reaction by applying the conditions of NPL 13 and NPL 14, cleavage of the amide bond between MePhe and MeAla was observed before removal of the Boc group was completed. The cleavage rate was also increased over time.

As described above, when deprotection reactions and resin removal reactions in solid-phase synthesis are carried out under acidic conditions, they may involve not only desired deprotection or resin removal reactions but also damage to the peptide main chain such as the cleavage of amide bonds that constitute the peptide main chain and the rearrangement of functional groups of amino acid side chains to the main chain. Production of by-products due to such main chain damage is known to reduce the yield and purity of target products and is a problem for efficient synthesis of peptides.

In the meantime, it has also been reported that the structural features of peptides are associated with the stability or damageability of amide bonds.

For example, distortion of amide bonds is known to cause increased acid instability of the amide bonds (NPL 15 and NPL 16).

Furthermore, in addition to the bond distortion, in the case of peptide amide bonds, the types of the amino acid side chains, the modes of substitution of the nitrogen atoms, the number of amino acid residues in the peptide, and the amino acid sequence affect the modes of intramolecular hydrogen bonds and the stable conformation of the peptide. Depending on such conformational changes, carbonyl oxygens may become more basic and susceptible to protonation (NPL 18 and NPL 19). It is known that in some cases amide bonds are damaged by formation of oxazolone (NPL 17).

It has also been reported that peptides containing N-Me amino acids, which are amino acids with the nitrogen atom methylated, may undergo progressive amide bond cleavage under acidic conditions (NPL 11, NPL 17, and NPL 20). Moreover, it is known that when a peptide having an N-Me amino acid at the C-terminus is subjected to TFA acidic conditions, the amide bond between the first and second residues of the peptide may be cleaved, resulting in a by-product peptide lacking the C-terminal residue (NPL 21). Thus, it is known that amide bonds containing N-Me groups in N-Me amino acids are readily cleaved.

Additionally, it is known that peptides having a sequence with two or more consecutive N-Me amino acid residues are often labile to acid and undergo amide bond cleavage during resin removal reactions in solid-phase synthesis (NPL 11).

Thus, it is known that amide bonds containing N-Me groups in N-Me amino acids and/or amide bonds containing carbonyl groups in N-Me amino acids are readily cleaved.

Peptides containing Asp or Gln are also labile to acid in a sequence-dependent manner (NPL 22 and NPL 23). For example, it is known that when a peptide sequence having Asp is treated with acid such as hydrogen fluoride and methanesulfonic acid, the carbonyl group of its side chain is nucleophilically attacked by the nitrogen atom of a main chain amide, yielding aspartimide as a by-product (NPL 23). Thus, it is known that amide bonds are readily cleaved in sites containing an amino acid having a specific side chain, even if the amino acid is N-unsubstituted.

When this aspartimide intermediate is hydrolyzed, rearrangement by-products with altered amide structures and main chain-cleaved by-products are generated, thereby reducing the yield and purity of the target product. Formation of aspartimides is notable when peptides containing a sequence such as Asp(OBn)-Gly, Asp(OBn)-Ser, Asp(OBn)-Thr, Asp(OBn)-Asn, or Asp(OBn)-Gln are deprotected under acidic conditions. For example, it is known that when Boc-Phe-Asp(OBn)-Asn-Ala-OBn is deprotected by methanesulfonic acid, it is mostly converted to aspartimides and does not have a desired amino acid sequence, i.e., main chain-damaging reaction occurs (NPL 24).

It is also known that when peptide derivatives containing Asp-Pro in their sequences are subjected to acidic conditions such as trifluoroacetic acid, hydrofluoric acid, formic acid, and acetic acid, the side chain of Asp is reacted with the nitrogen atom of Pro as in the above-described side reaction and the amide bond is thus cleaved (NPL 25 and NPL 26).

There are some reports of methods for avoiding side reactions in deprotection reaction that are caused by the amino acid sequence-dependent instability of amide bonds against acid.

For example, a method of suppressing the formation of aspartimides in deprotection and resin removal reactions of aspartamide derivatives is known, where the carboxyl group of the side chain of aspartic acid is protected with a cyclohexyl group so that the nitrogen atoms of main-chain amides do not proceed with nucleophilic attacks under the deprotection conditions for the protecting group of interest. This method has been reported to significantly suppress the formation of aspartimides as compared with the case of using a benzyl protecting group as a side-chain protecting groups (NPL 27). However, subsequent removal of the cyclohexyl group requires highly corrosive, highly acidic conditions such as hydrofluoric acid, and it is readily presumed that both the reaction and the post-treatment cannot be conducted conveniently.

A method of treatment with 1 M trimethylsilyl bromide/TFA in the presence of thioanisole is also known (NPL 28). However, this condition is disadvantageous in that it requires the use of a solvent amount of TFA and the use of thioanisole, which is unsuitable for mass production as described above. Furthermore, it has been described that by-product aspartimides are significantly increased when trimethylsilyl triflate is used instead of trimethylsilyl bromide, suggesting that trimethylsilyl bromide is superior to trimethylsilyl triflate.

There is a known method in which Boc removal reaction of peptides and t-Bu removal reaction of esters are performed in the presence of a tertiary amine and in the presence of trimethylsilyl triflate or TBDMSOTf. A known example is to use 2,6-lutidine as a tertiary amine and perform N-Boc removal under TMSOTf/2,6-lutidine conditions in the presence of other functional groups, thereby removing Boc groups selectively (NPL 29, NPL 30, and NPL 31). In another known example, reactions for Boc removal and removal from resin for solid-phase synthesis, which may occur at the same time under acidic conditions using TFA, are performed under trimethylsilyl triflate/2,6-lutidine conditions to achieve Boc removal reaction selectively (NPL 32 and 33). These methods have also been applied to compounds having amide bonds, but not intended to avoid damaging amide bonds.

Selective deprotection of t-Bu esters in the presence of TBS and TIPS groups and thioacetal has been performed under trimethylsilyl triflate/2,6-lutidine conditions (NPL 34). Removal of t-Bu from peptide t-Bu esters using this technique has also been reported. For example, it is known that deprotection reaction of t-Bu esters was performed under TMSOTf/2,6-lutidine conditions (NPL 35 and NPL 36). This case, however, is also not intended to avoid amide bond cleavage.

It is known that when trimethylsilyl triflate/2,6-lutidine is used for N-Boc removal reactions in the total synthesis of a natural peptide compound that provides complex mixtures upon treatment with protonic acid, the reactions preferentially yield the target product while suppressing production of by-products (NPL 37). However, side reactions referred to therein are not described in detail, and these reaction conditions were not examined at all for the general versatility and the possibility of avoiding amide bond damage. Moreover, reagents are needed in large excess (20 equivalents or more), leaving problems from the viewpoint of the generality of applicable substrates and manufacturing cost. In this case, trimethylsilyl triflate/2,6-lutidine was merely applied to compounds having amide bonds, and it is not mentioned whether or not the side reactions were caused by amide bond cleavage.

As described above, treatment under acidic conditions using Bronsted acids represented by trifluoroacetic acid is generally used in reactions of cleaving peptides from peptide-loaded resins (resin removal reactions) to provide elongated peptides in the solid-phase methods, and in reactions of removing protecting groups removable under acidic conditions among N-terminal, C-terminal, and amino acid side-chain protecting groups in both the solid-phase methods and the liquid-phase methods. There are also known examples in which deprotection reactions are conducted in the presence of Lewis acids. However, despite the known fact that treatment of peptides containing unnatural amino acids represented by N-Me amino acids with conventional methods to perform resin removal reaction or deprotection reaction results in the intended reaction accompanied with progression of main-chain cleavage or rearrangement (main-chain damage) of the peptides and requires large quantities of reagents, no solution for these problems is known (NPL 20, NPL 22, and NPL 37).

In particular, since studies of unnatural artificial peptides often encounter unexpected side reactions when conventional synthesis methods are used, it is extremely important to develop industrially efficient techniques to synthesize unnatural artificial peptides and their derivatives. However, in producing such unnatural amino acid-containing peptides, only methods of preparing conventional peptides composed of natural amino acids have been used. There is no known efficient synthesis method that focuses on and solves the problems with the production of peptides containing unnatural amino acids, in particular the specific problem of main chain-damage caused in deprotection or resin removal reaction.

CITATION LIST

Patent Literature

[PTL 1] WO 2014/033466

Non-Patent Literature

[NPL 1] Future Med. Chem., 2009, 1, 1289-1310.
[NPL 2] Amino Acids, Peptides and Proteins in Organic Chemistry: Building Blocks, Catalysis and Coupling Chemistry, Volume 3, 2011
[NPL 3] Amino Acids, 2018, 50, 39-68.
[NPL 4] Chem. Rev., 2009, 109, 2455-2504.
[NPL 5] Russ. J. Bioorg. Chem. 2016, 42, 143-152.
[NPL 6] J. Comb. Chem. 2002, 4, 1-16.
[NPL 7] J. Am. Chem. Soc. 1999, 121, 6786-6791.
[NPL 8] Org. Lett. 2012, 14, 612-615.
[NPL 9] Eur. J. Med. Chem. 2000, 35, 599-618.
[NPL 10] J. Chem. Soc. D, 1970, 0, 406b-407.
[NPL 11] J. Peptide Res. 2005, 65, 153-166.
[NPL 12] J. Chem. Soc. Chem. Commun. 1987, 274-275.
[NPL 13] J. Am. Chem. Soc. 2015, 137, 13488-134918.
[NPL 14] J. Am. Chem. Soc. 2012, 134, 13244-13247.
[NPL 15] J. Am. Chem. Soc., 2016, 138, 969-974.
[NPL 16] Tetrahedron Lett., 1998, 39, 865-868.
[NPL 17] J. Mass. Spectrom., 1998, 33, 505-524.
[NPL 18] J. Am. Chem. Soc., 1994, 116, 11512-11521.
[NPL 19] J. Am. Soc. Mass Spectrom, 1995, 6, 91-101.
[NPL 20] Int. J. Peptide Protein Res. 1996, 47, 182-189.
[NPL 21] Int. J. Peptide Protein Res. 1988, 31, 186-191.
[NPL 22] Molecular Biomethods Handbook, p. 515-547.
[NPL 23] J. Mol. Model, 2013, 19, 3627-3636.
[NPL 24] Chem. Pharm. Bull., 1981, 29, 2825-2831.
[NPL 25] Side reactions in Peptide Synthesis, 2015, 1-31, Academic Press.
[NPL 26] Biochem. Biophys. Res. Commun. 1970, 40, 1173-1178.
[NPL 27] Tetrahedron Lett., 1979, 20, 4033-4036.
[NPL 28] Tetrahedron, 1988, 44, 805-819.
[NPL 29] Tetrahedron Lett., 1988, 29, 1181-1184.
[NPL 30] J. Org. Chem. 1997, 62, 3880-3889.
[NPL 31] Org. Lett. 2018, 20, 4637-4640.
[NPL 32] Eur. J. Org. Chem., 2012, 6204-6211
[NPL 33] Tetrahedron Lett., 1998, 39, 7439-7442.
[NPL 34] J. Org. Chem. 1990, 55, 2786-2797.
[NPL 35] Bioorg. Med. Chem. Lett. 2008, 18, 3902-3905.
[NPL 36] Tetrahedron 2004, 60, 8509-8527.
[NPL 37] J. Org. Chem., 2016, 81, 532-544.

SUMMARY OF INVENTION

Technical Problem

The present inventors subjected peptide compounds containing unnatural amino acids to the same conditions as in the treatment with acids represented by TFA that is generally used for removing protecting groups from amino acids or peptides or for cleaving peptides from resins in solid-phase reactions, as generally used in conventional peptide synthesis. As a result, the inventors found that the peptide compounds had significant damage in the main chain, such as amide bond cleavage or rearrangement, and were not obtained efficiently with intended sequences, leading to difficulty in manufacturing these peptide compounds. Specifically, the inventors found that under acidic conditions the main chain is susceptible to damage at the amide bonds of moieties containing N-substituted (e.g. N-alkylated) amino acid for peptide compounds containing such amino acids, or at the amide bonds of moieties containing aspartic acid. In addition to these problems, the present inventors further found many amino acid sequences that cause main-chain damage under conventional acidic conditions. An objective of the present invention is to provide techniques for reactions of removing protecting groups removable under acidic conditions and reactions of removing resins in solid-phase reactions while suppressing side reactions such as cleavage or rearrangement of amide bonds contained in peptide compounds, and to provide methods of obtaining deprotected and/or resin-removed peptide compounds in high yield and purity in a simple operation.

Solution to Problem

The present inventors conducted intensive studies mainly on reactions of removing protecting groups removable under acidic conditions or removing resins in solid-phase reactions while suppressing side reactions such as cleavage or rearrangement of amide bonds in peptide compounds containing N-substituted (e.g., N-alkylated) amino acids. The inventors investigated techniques of reacting with a silyl compound in the presence of an electrophilic species scavenger, and found that the treatment of peptide compounds containing acid-labile amide bonds with a silyl compound or acid in combination with an electrophilic species scavenger was able to remove protecting groups and/or resins without involving main-chain damage of concern, thereby giving deprotected and/or resin-removed target products in high yield and purity. For reagents for such deprotection and/or resin removal, the present inventors also found that compounds such as imidates (formula 2), amides (formula 3), ketene acetals (formula 4), ketene alkoxy hemiaminals (formula 4), enol ethers (formula 4), enol esters (formula 4), imines (formula 5), amines (formula 6), diamines (formula 7), dialkylcarbodiimides (formula 8), ureas (formula 9), or urethanes (formula 10) can be used as electrophilic species scavengers in combination with appropriate silyl compounds or acids. The present invention can provide target peptide compounds in higher yield and purity without involving amide bond cleavage, more efficiently than conventional techniques.

In a non-limiting specific embodiment, the present invention includes the following items.

[1] A method of producing a peptide compound in which a protecting group removable by a silylating agent is removed, the method comprising the step of contacting a starting peptide compound comprising natural amino acid residues and/or amino acid analog residues with the silylating agent in a solvent and thereby removing the protecting group from the starting peptide compound,
wherein the silylating agent is prepared by mixing a silyl compound or acid with an electrophilic species scavenger,
wherein the starting peptide compound comprises at least one protecting group removable by the silylating agent, and
wherein the starting peptide compound comprises at least one N-substituted amino acid residue.

[2] A method of producing a peptide compound in which a resin for solid-phase synthesis that is removable by a silylating agent is removed, the method comprising the step of contacting a starting peptide compound comprising natural amino acid residues and/or amino acid analog residues with the silylating agent in a solvent and thereby removing the resin for solid-phase synthesis from the starting peptide compound,
wherein the silylating agent is prepared by mixing a silyl compound or acid with an electrophilic species scavenger,
wherein the starting peptide compound is linked to the removable resin for solid-phase synthesis, and
wherein the starting peptide compound comprises at least one N-substituted amino acid residue.

[3] The method of [1] or [2], wherein the starting peptide compound comprises at least one structure in which at least two amino acid residues are linked to each other, wherein the structure is represented by general formula (I) below:

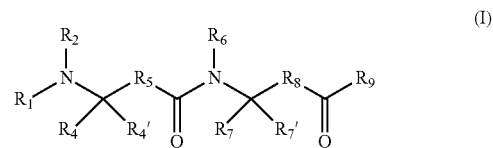

wherein
$R_1$ is hydrogen, $PG_1$, a natural amino acid residue, or an amino acid analog residue;
$R_2$ is selected from the group consisting of hydrogen and $C_1$-$C_6$ alkyl, or $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy, wherein $R_{4'}$ is hydrogen when $R_2$ and $R_4$ together form the heterocyclic ring, and $R_4$ is hydrogen when $R_2$ and $R_{4'}$ together form the heterocyclic ring;
except when $R_2$ and $R_4$, or $R_2$ and $R_{4'}$ together form the heterocyclic ring,
  (a) $R_{4'}$ is hydrogen, and $R_4$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_2$, N-$PG_3$-indol-3-ylmethyl, 4-($PG_2$O)benzyl, $PG_2$-O-methyl, 1-($PG_2$O)ethyl, 2-($PG_2$O)ethyl, $PG_2$-OCO($CH_2$)—, $PG_2$-OCO($CH_2$)$_2$—, $PG_3$N-n-butyl, —CON($R_{14A}$)($R_{14B}$), —$CH_2$—CON($R_{14A}$)($R_{14B}$), and —($CH_2$)$_2$CON($R_{14A}$)($R_{14B}$),
  (b) $R_4$ and $R_{4'}$ are independently optionally substituted $C_1$-$C_6$ alkyl, or
  (c) $R_4$ and $R_{4'}$, together with the carbon atom to which they are attached, form a 3- to 7-membered alicyclic ring;
$R_5$ is a single bond or —C($R_{5A}$)($R_{5B}$)—;
$R_{5A}$ and $R_{5B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
$R_6$ is selected from the group consisting of hydrogen and $C_1$-$C_6$ alkyl, or $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy, wherein $R_{7'}$ is hydrogen when R₆ and R₇ together form the heterocyclic ring, and R₇ is hydrogen when R₆ and R₇' together form the heterocyclic ring;

except when R₆ and R₇ or R₆ and R₇' together form the heterocyclic ring, (a) R₇' is hydrogen, and R₇ is selected from the group consisting of hydrogen, optionally substituted C₁-C₆ alkyl, C₃-C₆ cycloalkyl, C₃-C₆ cycloalkyl-C₁-C₄ alkyl, optionally substituted phenyl, optionally substituted phenylmethyl, optionally substituted phenylethyl, 2-(methylthio)ethyl, —CH₂SPG₄, N-PG₅-indol-3-ylmethyl, 4-(PG₄O)benzyl, PG₄-O-methyl, 1-(PG₄O)ethyl, 2-(PG₄O)ethyl, PG₄-OCO(CH₂)—, PG₄-OCO(CH₂)₂—, PG₅N-n-butyl, —CON(R₁₅ₐ)(R₁₅ᵦ), —CH₂—CON(R₁₅ₐ)(R₁₅ᵦ), and —(CH₂)₂CON(R₁₅ₐ)(R₁₅ᵦ), or (b) R₇ and R₇' are independently optionally substituted C₁-C₆ alkyl, or (c) R₇ and R₇', together with the carbon atom to which they are attached, form a 3- to 7-membered alicyclic ring;

R₈ is a single bond or —C(R₅ₐ)(R₅ᵦ)—;

R₈ₐ and R₈ᵦ are independently selected from the group consisting of hydrogen, C₁-C₆ alkyl, optionally substituted aryl, optionally substituted heteroaryl, optionally substituted aryl-C₁-C₄ alkyl, and optionally substituted heteroaryl-C₁-C₄ alkyl;

R₉ is hydroxy, —O-PG₆, a natural amino acid residue, an amino acid analog residue, —O-RES, or —NH-RES;

RES is a resin for solid-phase synthesis;

R₁₄ₐ and R₁₄ᵦ are independently hydrogen or C₁-C₄ alkyl, or R₁₄ₐ and R₁₄ᵦ, together with the nitrogen atom to which they are attached, form a 4- to 8-membered ring optionally comprising one or more additional heteroatoms;

R₁₅ₐ and R₁₅ᵦ are independently hydrogen or C₁-C₄ alkyl, or R₁₅ₐ and R₁₅ᵦ, together with the nitrogen atom to which they are attached, form a 4- to 8-membered ring optionally comprising one or more additional heteroatoms;

PG₁ is selected from the group consisting of Fmoc, Boc, Alloc, Cbz, Teoc, and trifluoroacetyl;

PG₂ and PG₄ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-C₁-C₄ alkyl, optionally substituted heteroaryl-C₁-C₄ alkyl, and 2-(trimethylsilyl)ethyl;

PG₃ and PG₈ are independently selected from the group consisting of hydrogen, Fmoc, Boc, Alloc, Cbz, Teoc, methoxycarbonyl, t-Bu, trityl, cumyl, and benzyl; and PG₆ is selected from the group consisting of t-Bu, trityl, cumyl, benzyl, methyl, ethyl, allyl, and 2-(trimethylsilyl)ethyl.

[4] The method of any one of [1] to [3], wherein the starting peptide compound comprises at the C-terminus a structure in which at least two amino acid residues are linked to each other, wherein the structure is represented by general formula (II) below:

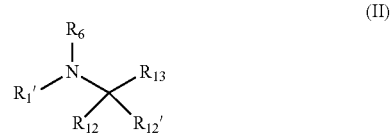

wherein

R₁' is a group represented by the formula (III):

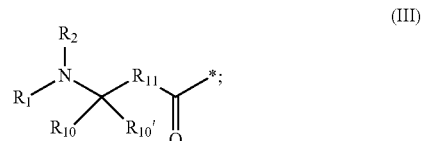

* represents the point of attachment;

R₁ is hydrogen, PG₁, a natural amino acid residue, or an amino acid analog residue;

R₂ is selected from the group consisting of hydrogen and C₁-C₆ alkyl, or R₂ and R₁₀, or R₂ and R₁₀', together with the nitrogen atom and carbon atom to which they are attached, form a 3- to 7-membered heterocyclic ring optionally substituted with hydroxy or C₁-C₄ alkoxy, wherein R₁₀' is hydrogen when R₂ and R₁₀ together form the heterocyclic ring, and R₁₀ is hydrogen when R₂ and R₁₀' together form the heterocyclic ring;

except when R₂ and R₁₀ or R₂ and R₁₀' together form the heterocyclic ring, (a) R₁₀' is hydrogen, and R₁₀ is selected from the group consisting of hydrogen, optionally substituted C₁-C₆ alkyl, C₃-C₆ cycloalkyl, C₃-C₆ cycloalkyl-C₁-C₄ alkyl, optionally substituted phenyl, optionally substituted phenylmethyl, optionally substituted phenylethyl, 2-(methylthio)ethyl, —CH₂SPG₈, N-PG₉-indol-3-ylmethyl, 4-(PG₈O)benzyl, PG₈-O-methyl, 1-(PG₈O)ethyl, 2-(PG₈O)ethyl, PG₈-OCO(CH₂)—, PG₈-OCO(CH₂)₂—, PG₉N-n-butyl, —CON(R₁₆ₐ)(R₁₆ᵦ), —CH₂—CON(R₁₆ₐ)(R₁₆ᵦ), and —(CH₂)₂CON(R₁₆ₐ)(R₁₆ᵦ), or (b) R₁₀ and R₁₀' are independently optionally substituted C₁-C₆ alkyl, C₃-C₆ cycloalkyl, or C₃-C₆ cycloalkyl-C₁-C₄ alkyl, or (c) R₁₀ and R₁₀', together with the carbon atom to which they are attached, form a 3 to 7-membered alicyclic ring;

R₁₁ is a single bond or —C(R₁₁ₐ)(R₁₁ᵦ)—;

R₁₁ₐ and R₁₁ᵦ are independently selected from the group consisting of hydrogen, C₁-C₆ alkyl, optionally substituted aryl, optionally substituted heteroaryl, optionally substituted aryl-C₁-C₄ alkyl, and optionally substituted heteroaryl-C₁-C₄ alkyl;

R₁₂ and R₁₂' are independently selected from the group consisting of hydrogen, PG₁₀-O-methyl, —(CH₂)ₙCOO-PG₁₀, —(CH₂)ₙCOO-RES, and —(CH₂)ₙCONH-RES;

RES is a resin for solid-phase synthesis;

n is 0, 1, or 2;

R₆ is selected from the group consisting of hydrogen and C₁-C₆ alkyl;

R₁₃ is C₁-C₄ alkyl or —(CH₂)ₘCON(R₁₇ₐ)(R₁₇ᵦ);

m is 0, 1, or 2;

$R_{16A}$ and $R_{16B}$ are independently hydrogen or $C_1$-$C_4$ alkyl, or $R_{16A}$ and $R_{16B}$, together with the nitrogen atom to which they are attached, form a 4- to 8-membered ring optionally comprising one or more additional heteroatoms;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_1$ is independently selected from the group consisting of Fmoc, Boc, Alloc, Cbz, Teoc, and trifluoroacetyl;

$PG_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;

$PG_9$ is selected from the group consisting of hydrogen, Fmoc, Boc, Alloc, Cbz, Teoc, methoxycarbonyl, t-Bu, trityl, cumyl, and benzyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl.

[5] A method of producing an amide compound in which a protecting group removable by a silylating agent is removed, the method comprising the step of contacting a starting amide compound with the silylating agent in a solvent and thereby removing the protecting group from the starting amide compound, wherein the silylating agent is prepared by mixing a silyl compound or acid with an electrophilic species scavenger, wherein the starting amide compound is represented by general formula (II) below:

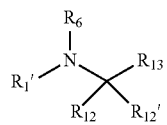

(II)

wherein $R_{1'}$ is a hydrogen atom or $PG_7$;

$R_{12}$ and $R_{12'}$ are independently selected from the group consisting of hydrogen, $PG_{10}$-O-methyl, —$(CH_2)_n$COO-$PG_{10}$, —$(CH_2)_n$COO-RES, and —$(CH_2)_n$CONH-RES;

RES is a resin for solid-phase synthesis;

n is 0, 1, or 2;

$R_6$ is selected from the group consisting of hydrogen and $C_1$-$C_6$ alkyl;

$R_{13}$ is $C_1$-$C_4$ alkyl or —$(CH_2)_m$CON($R_{17A}$)($R_{17B}$);

m is 0, 1, or 2;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_7$ is selected from the group consisting of Fmoc, Boc, Alloc, Cbz, Teoc, and trifluoroacetyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl, and wherein the starting amide compound comprises at least one protecting group removable by the silylating agent.

[6] A method of producing an amide compound in which a resin for solid-phase synthesis is removed, the method comprising the step of contacting a starting amide compound with a silylating agent in a solvent and thereby removing the starting amide compound from the resin for solid-phase synthesis, wherein the silylating agent is prepared by mixing a silyl compound or acid with an electrophilic species scavenger, and wherein the starting amide compound is represented by general formula (II) below:

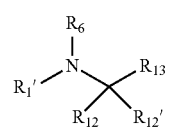

(II)

wherein $R_{1'}$ is a hydrogen atom or PGP;

$R_{12}$ and $R_{12'}$ are independently selected from the group consisting of hydrogen, $PG_{10}$-O-methyl, —$(CH_2)_n$COO-$PG_{10}$, —$(CH_2)_n$COO-RES, and —$(CH_2)_n$CONH-RES;

RES is a resin for solid-phase synthesis, wherein at least one of $R_{12}$ and $R_{12'}$ is —$(CH_2)_n$COO-RES or —$(CH_2)_n$CONH-RES;

RES is a resin for solid-phase synthesis;

n is 0, 1, or 2;

$R_6$ is selected from the group consisting of hydrogen and $C_1$-$C_6$ alkyl;

$R_{13}$ is $C_1$-$C_4$ alkyl or —$(CH_2)_m$CON($R_{17A}$)($R_{17B}$);

m is 0, 1, or 2;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_7$ is selected from the group consisting of Fmoc, Boc, Alloc, Cbz, Teoc, and trifluoroacetyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl.

[7] The method of any one of [1] and [3] to [5], wherein the removable protecting group is selected from the group consisting of t-Bu, triphenylmethyl, 2-(trimethylsilyl)-ethyl, Boc, Teoc, Cbz, methoxycarbonyl, tetrahydropyranyl, 1-ethoxyethyl, methoxytrityl, and cumyl.

[8] The method of any one of [1] to [7], wherein the silyl compound is represented by formula 1 below:

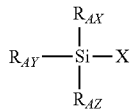
(1)

wherein $R_{AX}$, $R_{AY}$, and $R_{AZ}$ are independently $C_1$-$C_4$ alkyl or phenyl, and X is selected from the group consisting of —OTf, —OClO$_3$, Cl, Br, and I.

[9] The method of [8], wherein the silyl compound is selected from the group consisting of TMSOTf, TESOTf, TBSOTf, TIPSOTf, TBDPSOTf, TTMSOTf, TMSCl, TMSBr, TMSOClO$_3$, and TMSI.

[10] The method of any one of [1] to [7], wherein the acid is represented by HX, wherein X is selected from the group consisting of —OTf, —OClO$_3$, Cl, Br, and I.

[11] The method of any one of [1] to [10], wherein the electrophilic species scavenger is selected from the group consisting of formulas (2) to (10) below:

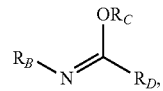
(2)

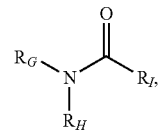
(3)

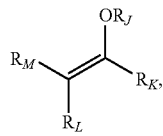
(4)

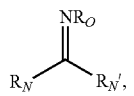
(5)

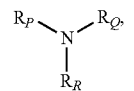
(6)

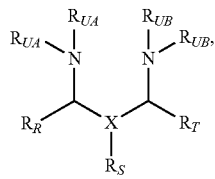
(7)

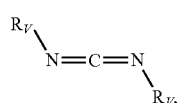
(8)

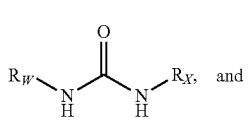
(9)

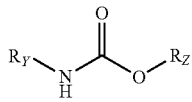
(10)

wherein in formula 2,
$R_B$ is a substituted silyl group and $R_C$ is a substituted silyl group, or
$R_B$ and $R_C$, together with the nitrogen atom and carbon atom to which they are attached, form a 5- to 7-membered ring; and
$R_D$ is $C_1$-$C_4$ alkyl optionally substituted with one or more fluorine atoms or is optionally substituted methylene, wherein when $R_D$ is optionally substituted methylene, formula 2 is dimerized to form a compound represented by the formula below:

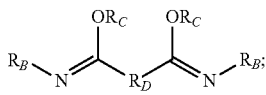

wherein in formula 3,
$R_G$ is a silyl group substituted with one or more $C_1$-$C_4$ alkyl;
$R_H$ is hydrogen or $C_1$-$C_4$ alkyl; and
$R_I$ is hydrogen, or $C_1$-$C_4$ alkyl optionally substituted with one or more fluorine atoms;
wherein in formula 4,
(a-1) RJ is a substituted silyl group, RK is C1-C4 alkoxy, and RM and RL are independently hydrogen or C1-C4 alkyl;
(a-2) RJ is a substituted silyl group, RM is hydrogen or C1-C4 alkyl, and RK and RL, together with the carbon atoms to which they are attached, form a 5- to 8-membered ring comprising an oxygen atom;
(b-1) RJ is a substituted silyl group, RK is C1-C4 alkyl, and RM and RL are independently hydrogen or C1-C4 alkyl;
(b-2) RJ is a substituted silyl group, RM is hydrogen or C1-C4 alkyl, and RK and RL are taken together with the carbon atoms to which they are attached, form a 5- to 8-membered ring; or
(c-1) RJ and RM, together with the carbon atoms to which they are attached, form a 5- to 7-membered ring comprising an oxygen atom, RK is hydrogen or C1-C4 alkyl, and RL is C1-C4 alkyl;
(c-2) RJ and RM, together with the carbon atoms to which they are attached, form a 5- to 7-membered ring comprising an oxygen atom, and RK and RL, together with the carbon atom to which they are attached, form a 5- to 8-membered ring;
(d-1) RJ is C1-C4 alkyl and RM, RK, and RL are independently hydrogen or C1-C4 alkyl;
(d-2) RJ is C1-C4 alkyl, RM is hydrogen or C1-C4 alkyl, and RK and RL, together with the carbon atoms to which they are attached, form a 5- to 8-membered ring;
(e-1) RJ is C1-C3 alkylcarbonyl and RM, RK, and RL are independently hydrogen or C1-C4 alkyl;
(e-2) RJ is C1-C3 alkylcarbonyl, RM is hydrogen or C1-C4 alkyl, and RK and RL, together with the carbon atoms to which they are attached, form a 5- to 8-membered ring;

(f-1) RJ is a substituted silyl group or C1-C4 alkyl, RK is optionally substituted di-C1-C4 alkylamino, and RM and RL are independently hydrogen or C1-C4 alkyl; or (f-2) RJ is a substituted silyl group or C1-C4 alkyl, RM is hydrogen or C1-C4 alkyl, and RK and RL, together with the carbon atoms to which they are attached, form a 5- to 8-membered ring comprising a nitrogen atom, wherein the 5- to 8-membered ring is optionally substituted with C1-C4 alkyl; wherein in formula 5, $R_N$, $R_{N'}$, and $R_O$ are independently hydrogen or $C_1$-$C_4$ alkyl;

wherein in formula 6, $R_P$ is a substituted silyl group; and $R_Q$ is a substituted silyl group or $C_1$-$C_4$ alkyl and $R_R$ is hydrogen, a substituted silyl group, or $C_1$-$C_4$ alkyl, or $R_Q$ and $R_R$, together with the nitrogen atom to which they are attached, form a 5- to 8-membered heterocyclic ring optionally comprising one or more additional heteroatoms;

wherein in formula 7,

X is a single bond or a carbon atom, wherein when X is a single bond, $R_S$ is absent, $R_{UA}$ and $R_R$, together with the carbon atom and nitrogen atom to which they are attached, form an optionally substituted 6-membered aromatic heterocyclic ring, and $R_{UB}$ and $R_T$, together with the carbon atom and nitrogen atom to which they are attached, form an optionally substituted 6-membered aromatic heterocyclic ring, and when X is a carbon atom, $R_{UA}$ and $R_{UB}$ are independently $C_1$-$C_4$ alkyl and $R_R$, $R_S$, and $R_T$, together with the carbon atoms to which they are attached, form the structure below:

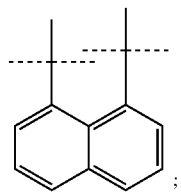

wherein in formula 8, $R_V$ is $C_1$-$C_4$ alkyl or $C_3$-$C_6$ cycloalkyl;

wherein in formula 9, $R_W$ and $R_X$ are independently $C_1$-$C_4$ alkyl or a substituted silyl group; and wherein in formula 10, $R_Y$ and $R_Z$ are independently $C_1$-$C_4$ alkyl or a substituted silyl group.

[12] The method of [11], wherein the electrophilic species scavenger is selected from the group consisting of N,O-bis(trimethylsilyl)acetamide, N,O-bis(trimethylsilyl)trifluoroacetamide, N-methyl-N-trimethylsilylacetamide, N-methyl-N-trimethylsilyltrifluoroacetamide, dimethylketene methyl trimethylsilyl acetal, isopropenyloxytrimethylsilane, 2,2,4,4-tetramethylpentanone imine, 1,1,1,3,3,3-hexamethyldisilazane (HMDS), N-trimethylsilylmorpholine, N-trimethylsilyldiethylamine, and N-tert-butyltrimethylsilylamine.

[13] The method of any one of [1] to [9] and [11] to [12], wherein per one equivalent of the protecting group to be removed or one equivalent of the resin to be removed, 1 to 5 equivalents of the silyl compound and 1 to 10 equivalents of the electrophilic species scavenger are mixed.

[14] The method of any one of [1] to [12], wherein per one equivalent of the protecting group to be removed or one equivalent of the resin to be removed, 0.1 to 0.5 equivalent of the silyl compound or acid is mixed, wherein the electrophilic species scavenger is selected from the group consisting of N,O-bis(trimethylsilyl)acetamide, N,O-bis(trimethylsilyl)trifluoroacetamide, N-methyl-N-trimethylsilylacetamide, N-methyl-N-trimethylsilyltrifluoroacetamide, dimethylketene methyl trimethylsilyl acetal, and isopropenyloxytrimethylsilane, wherein the silyl compound is selected from the group consisting of TMSOTf, TESOTf, TBSOTf, TIPSOTf, TBDPSOTf, TTMSOTf, TMSCl, TMSBr, and TMSOClO₃, and wherein the acid is represented by HX, wherein X is selected from the group consisting of —OTf, —OClO₃, Cl, Br, and I.

[15] The method of any one of [1] to [14], wherein the starting peptide compound comprises 1 to 30 amino acid residues and is linear or cyclic.

[16] The method of any one of [1] to [4] and [6] to [15], wherein the resin for solid-phase synthesis is CTC resin, Wang resin, or SASRIN resin.

[17] The method of any one of [1] to [16], wherein the method comprises mixing the starting peptide compound with the solvent, then with the electrophilic species scavenger, and subsequently with the silyl compound or acid.

[18] The method of any one of [1] to [17], wherein the solvent is selected from ethyl acetate, isopropyl acetate, 2-methyltetrahydrofuran, tetrahydrofuran, diethyl ether, methyl tert-butyl ether, dichloromethane, 1,2-dichloroethane, toluene, and acetonitrile.

[19] An amide compound represented by general formula (A) below or a salt thereof:

(A)

$$R_1'\text{-N}(CH_3)\text{-CH}(CH_2COOR_{18})\text{-CON}(R_{17A})(R_{17B})$$

wherein $R_{1'}$ is selected from the group consisting of hydrogen, Fmoc, Boc, Alloc, Cbz, Teoc, and trifluoroacetyl;

$R_{17A}$ and $R_{17B}$ are both methyl, or $R_{17A}$ and $R_{17B}$, together with the nitrogen atom to which they are attached, form piperidine or morpholine; and $R_{18}$ is hydrogen or $PG_{10}$, wherein $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl.

[20] The amide compound or salt thereof of [19], wherein the amide compound is selected from the group consisting of:

(3-1) 3-((((9H-fluoren-9-yl)methoxy)carbonyl)(methyl)amino)-4-(dimethylamino)-4-oxobutanoic acid,
(3-2) allyl 3-((((9H-fluoren-9-yl)methoxy)carbonyl)(methyl)amino)-4-(dimethylamino)-4-oxobutanoate,
(3-3) tert-butyl 3-((((9H-fluoren-9-yl)methoxy)carbonyl)(methyl)amino)-4-(dimethylamino)-4-oxobutanoate,
(3-4) benzyl 3-((((9H-fluoren-9-yl)methoxy)carbonyl)(methyl)amino)-4-(dimethylamino)-4-oxobutanoate,
(3-5) 3-((tert-butoxycarbonyl)(methyl)amino)-4-(dimethylamino)-4-oxobutanoic acid,
(3-6) allyl 3-((tert-butoxycarbonyl)(methyl)amino)-4-(dimethylamino)-4-oxobutanoate,
(3-7) tert-butyl 3-((tert-butoxycarbonyl)(methyl)amino)-4-(dimethylamino)-4-oxobutanoate,
(3-8) benzyl 3-((tert-butoxycarbonyl)(methyl)amino)-4-(dimethylamino)-4-oxobutanoate,
(3-9) 3-(((benzyloxy)carbonyl)(methyl)amino)-4-(dimethylamino)-4-oxobutanoic acid,
(3-10) allyl 3-(((benzyloxy)carbonyl)(methyl)amino)-4-(dimethylamino)-4-oxobutanoate,
(3-11) tert-butyl 3-(((benzyloxy)carbonyl)(methyl)amino)-4-(dimethylamino)-4-oxobutanoate,
(3-12) benzyl 3-(((benzyloxy)carbonyl)(methyl)amino)-4-(dimethylamino)-4-oxobutanoate,
(3-13) 3-(((allyloxy)carbonyl)(methyl)amino)-4-(dimethylamino)-4-oxobutanoic acid,
(3-14) allyl 3-(((allyloxy)carbonyl)(methyl)amino)-4-(dimethylamino)-4-oxobutanoate,
(3-15) tert-butyl 3-(((allyloxy)carbonyl)(methyl)amino)-4-(dimethylamino)-4-oxobutanoate,
(3-16) benzyl 3-(((allyloxy)carbonyl)(methyl)amino)-4-(dimethylamino)-4-oxobutanoate,
(3-17) 4-(dimethylamino)-3-(methyl((2-(trimethylsilyl)ethoxy)carbonyl)amino)-4-oxobutanoic acid,
(3-18) allyl 4-(dimethylamino)-3-(methyl((2-(trimethylsilyl)ethoxy)carbonyl)amino)-4-oxobutanoate,
(3-19) tert-butyl 4-(dimethylamino)-3-(methyl((2-(trimethylsilyl)ethoxy)carbonyl)amino)-4-oxobutanoate,
(3-20) benzyl 4-(dimethylamino)-3-(methyl((2-(trimethylsilyl)ethoxy)carbonyl)amino)-4-oxobutanoate,
(2-1) 3-((((9H-fluoren-9-yl)methoxy)carbonyl)(methyl)amino)-4-morpholino-4-oxobutanoic acid,
(2-2) allyl 3-((((9H-fluoren-9-yl)methoxy)carbonyl)(methyl)amino)-4-morpholino-4-oxobutanoate,
(2-3) tert-butyl 3-((((9H-fluoren-9-yl)methoxy)carbonyl)(methyl)amino)-4-morpholino-4-oxobutanoate,
(2-4) benzyl 3-((((9H-fluoren-9-yl)methoxy)carbonyl)(methyl)amino)-4-morpholino-4-oxobutanoate,
(2-5) 3-((tert-butoxycarbonyl)(methyl)amino)-4-morpholino-4-oxobutanoic acid,
(2-6) allyl 3-((tert-butoxycarbonyl)(methyl)amino)-4-morpholino-4-oxobutanoate,
(2-7) tert-butyl 3-((tert-butoxycarbonyl)(methyl)amino)-4-morpholino-4-oxobutanoate,
(2-8) benzyl 3-((tert-butoxycarbonyl)(methyl)amino)-4-morpholino-4-oxobutanoate,
(2-9) 3-(((benzyloxy)carbonyl)(methyl)amino)-4-morpholino-4-oxobutanoic acid,
(2-10) allyl 3-(((benzyloxy)carbonyl)(methyl)amino)-4-morpholino-4-oxobutanoate,
(2-11) tert-butyl 3-(((benzyloxy)carbonyl)(methyl)amino)-4-morpholino-4-oxobutanoate,
(2-12) benzyl 3-(((benzyloxy)carbonyl)(methyl)amino)-4-morpholino-4-oxobutanoate,
(2-13) 3-(((allyloxy)carbonyl)(methyl)amino)-4-morpholino-4-oxobutanoic acid,
(2-14) allyl 3-(((allyloxy)carbonyl)(methyl)amino)-4-morpholino-4-oxobutanoate,
(2-15) tert-butyl 3-(((allyloxy)carbonyl)(methyl)amino)-4-morpholino-4-oxobutanoate,
(2-16) benzyl 3-(((allyloxy)carbonyl)(methyl)amino)-4-morpholino-4-oxobutanoate,
(2-17) 3-(methyl((2-(trimethylsilyl)ethoxy)carbonyl)amino)-4-morpholino-4-oxobutanoic acid,
(2-18) allyl 3-(methyl((2-(trimethylsilyl)ethoxy)carbonyl)amino)-4-morpholino-4-oxobutanoate,
(2-19) tert-butyl 3-(methyl((2-(trimethylsilyl)ethoxy)carbonyl)amino)-4-morpholino-4-oxobutanoate,
(2-20) benzyl 3-(methyl((2-(trimethylsilyl)ethoxy)carbonyl)amino)-4-morpholino-4-oxobutanoate,
(4-1) 3-(methylamino)-4-oxo-4-(piperidin-1-yl)butanoic acid,
(4-2) allyl 3-(methylamino)-4-oxo-4-(piperidin-1-yl)butanoate,
(4-3) tert-butyl 3-(methylamino)-4-oxo-4-(piperidin-1-yl)butanoate,
(4-4) benzyl 3-(methylamino)-4-oxo-4-(piperidin-1-yl)butanoate,
(4-5) 3-(methylamino)-4-morpholino-4-oxobutanoic acid,
(4-6) allyl 3-(methylamino)-4-morpholino-4-oxobutanoate,
(4-7) tert-butyl 3-(methylamino)-4-morpholino-4-oxobutanoate,
(4-8) benzyl 3-(methylamino)-4-morpholino-4-oxobutanoate,
(4-9) 4-(dimethylamino)-3-(methylamino)-4-oxobutanoic acid,
(4-10) allyl 4-(dimethylamino)-3-(methylamino)-4-oxobutanoate,
(4-11) tert-butyl 4-(dimethylamino)-3-(methylamino)-4-oxobutanoate,
(4-12) benzyl 4-(dimethylamino)-3-(methylamino)-4-oxobutanoate,
(1-1) 3-((((9H-fluoren-9-yl)methoxy)carbonyl)(methyl)amino)-4-oxo-4-(piperidin-1-yl)butanoic acid,
(1-2) allyl 3-((((9H-fluoren-9-yl)methoxy)carbonyl)(methyl)amino)-4-oxo-4-(piperidin-1-yl)butanoate,
(1-3) tert-butyl 3-((((9H-fluoren-9-yl)methoxy)carbonyl)(methyl)amino)-4-oxo-4-(piperidin-1-yl)butanoate,
(1-4) benzyl 3-((((9H-fluoren-9-yl)methoxy)carbonyl)(methyl)amino)-4-oxo-4-(piperidin-1-yl)butanoate,
(1-5) 3-((tert-butoxycarbonyl)(methyl)amino)-4-oxo-4-(piperidin-1-yl)butanoic acid,
(1-6) allyl 3-((tert-butoxycarbonyl)(methyl)amino)-4-oxo-4-(piperidin-1-yl)butanoate,
(1-7) tert-butyl 3-((tert-butoxycarbonyl)(methyl)amino)-4-oxo-4-(piperidin-1-yl)butanoate,
(1-8) benzyl 3-((tert-butoxycarbonyl)(methyl)amino)-4-oxo-4-(piperidin-1-yl)butanoate,
(1-9) 3-(((benzyloxy)carbonyl)(methyl)amino)-4-oxo-4-(piperidin-1-yl)butanoic acid,
(1-10) allyl 3-(((benzyloxy)carbonyl)(methyl)amino)-4-oxo-4-(piperidin-1-yl)butanoate,
(1-11) tert-butyl 3-(((benzyloxy)carbonyl)(methyl)amino)-4-oxo-4-(piperidin-1-yl)butanoate,
(1-12) benzyl 3-(((benzyloxy)carbonyl)(methyl)amino)-4-oxo-4-(piperidin-1-yl)butanoate,
(1-13) 3-(((allyloxy)carbonyl)(methyl)amino)-4-oxo-4-(piperidin-1-yl)butanoic acid,
(1-14) allyl 3-(((allyloxy)carbonyl)(methyl)amino)-4-oxo-4-(piperidin-1-yl)butanoate,
(1-15) tert-butyl 3-(((allyloxy)carbonyl)(methyl)amino)-4-oxo-4-(piperidin-1-yl)butanoate, (1-16) benzyl 3-(((allyloxy)carbonyl)(methyl)amino)-4-oxo-4-(piperidin-1-yl)butanoate,
(1-17) 3-(methyl((2-(trimethylsilyl)ethoxy)carbonyl)amino)-4-oxo-4-(piperidin-1-yl)butanoic acid,
(1-18) allyl 3-(methyl((2-(trimethylsilyl)ethoxy)carbonyl)amino)-4-oxo-4-(piperidin-1-yl)butanoate,
(1-19) tert-butyl 3-(methyl((2-(trimethylsilyl)ethoxy)carbonyl)amino)-4-oxo-4-(piperidin-1-yl)butanoate, and
(1-20) benzyl 3-(methyl((2-(trimethylsilyl)ethoxy)carbonyl)amino)-4-oxo-4-(piperidin-1-yl)butanoate.

[21] A method of producing a peptide compound in which a protecting group removable by a silylating agent is removed, the method comprising the step of contacting a starting peptide compound comprising natural amino acid residues and/or amino acid analog residues with the silylating agent in a solvent and thereby removing the protecting group from the starting peptide compound,
wherein the silylating agent is prepared by mixing a silyl compound or acid with an electrophilic species scavenger,
wherein the starting peptide compound comprises a structure in which two amino acid residues are linked to each other, wherein the structure is represented by general formula (I) below:

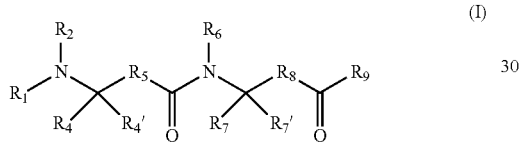

wherein
$R_1$ is hydrogen, $PG_1$, a natural amino acid residue, or an amino acid analog residue;
$R_2$ is selected from the group consisting of hydrogen and $C_1$-$C_6$ alkyl, or $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy;
except when $R_4$ and $R_{4'}$ each, together with $R_2$, forms the heterocyclic ring,
(a) $R_{4'}$ is hydrogen, and $R_4$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_2$, N-$PG_3$-indol-3-ylmethyl, 4-($PG_2$O)benzyl, $PG_2$-O-methyl, 1-($PG_2$O)ethyl, 2-($PG_2$O)ethyl, $PG_2$-OCO($CH_2$)—, $PG_2$-OCO($CH_2$)$_2$—, $PG_3$N-n-butyl, —CON($R_{14A}$)($R_{14B}$), —$CH_2$—CON($R_{14A}$)($R_{14B}$), and —($CH_2$)$_2$CON($R_{14A}$)($R_{14B}$),
(b) $R_4$ and $R_{4'}$ are independently optionally substituted $C_1$-$C_6$ alkyl, or
(c) $R_4$ and $R_{4'}$, together with the carbon atom to which they are attached, form a 3- to 7-membered alicyclic ring;
$R_5$ is a single bond or —C($R_{5A}$)($R_{5B}$)—;
$R_{5A}$ and $R_{5B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;

$R_6$ is selected from the group consisting of hydrogen and $C_1$-$C_6$ alkyl, or $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy;
except when $R_7$ and $R_{7'}$ each, together with $R_6$, forms the heterocyclic ring,
(a) $R_{7'}$ is hydrogen, and $R_7$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_4$, N-$PG_5$-indol-3-ylmethyl, 4-($PG_4$O)benzyl, $PG_4$-O-methyl, 1-($PG_4$O)ethyl, 2-($PG_4$O)ethyl, $PG_4$-OCO($CH_2$)—, $PG_4$-OCO($CH_2$)$_2$—, $PG_5$N-n-butyl, —CON($R_{15A}$)($R_{15B}$), —$CH_2$—CON($R_{15A}$)($R_{15B}$), and —($CH_2$)$_2$CON($R_{15A}$)($R_{15B}$),
(b) $R_7$ and $R_{7'}$ are independently optionally substituted $C_1$-$C_6$ alkyl, or
(c) $R_7$ and $R_{7'}$, together with the carbon atom to which they are attached, form a 3- to 7-membered alicyclic ring;
$R_8$ is a single bond or —C($R_{8A}$)($R_{8B}$)—;
$R_{8A}$ and $R_{8B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
$R_9$ is hydroxy, —O-$PG_6$, a natural amino acid residue, an amino acid analog residue, —O-RES, or —NH-RES;
RES is a resin for solid-phase synthesis;
$R_{14A}$ and $R_{14B}$ are independently hydrogen or $C_1$-$C_4$ alkyl, or $R_{14A}$ and $R_{14B}$, together with the nitrogen atom to which they are attached, form a 4- to 8-membered ring optionally comprising one or more additional heteroatoms;
$R_{15A}$ and $R_{15B}$ are independently hydrogen or $C_1$-$C_4$ alkyl, or $R_{15A}$ and $R_{15B}$, together with the nitrogen atom to which they are attached, form a 4- to 8-membered ring optionally comprising one or more additional heteroatoms;
$PG_1$ is selected from the group consisting of Fmoc, Boc, Alloc, Cbz, Teoc, and trifluoroacetyl;
$PG_2$ and $PG_4$ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;
$PG_3$ and $PG_8$ are independently selected from the group consisting of hydrogen, Fmoc, Boc, Alloc, Cbz, Teoc, methoxycarbonyl, t-Bu, trityl, cumyl, and benzyl; and
$PG_6$ is selected from the group consisting of t-Bu, trityl, cumyl, benzyl, methyl, ethyl, allyl, and 2-(trimethylsilyl)ethyl,
wherein the starting peptide compound optionally comprises additional natural amino acid residues and/or amino acid analog residues, and
wherein the starting peptide compound comprises at least one protecting group removable by the silylating agent.

[22] A method of producing a peptide compound in which a resin for solid-phase synthesis is removed, the method comprising the step of contacting a starting peptide compound comprising natural amino acid residues and/or amino acid analog residues with a silylating agent in a solvent and thereby removing the starting peptide compound from the resin for solid-phase synthesis,
wherein the silylating agent is prepared by mixing a silyl compound or acid with an electrophilic species scavenger,
wherein the starting peptide compound comprises a structure in which two amino acid residues are linked to each other, wherein the structure is represented by general formula (I) below:

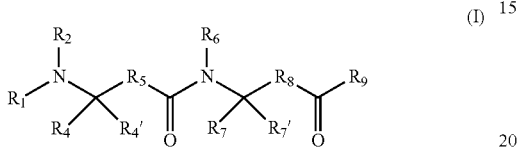

(I)

wherein
R$_1$ is hydrogen, PG$_1$, a natural amino acid residue, or an amino acid analog residue;
R$_2$ is selected from the group consisting of hydrogen and C$_1$-C$_6$ alkyl, or R$_2$ and R$_4$ or R$_2$ and R$_{4'}$, together with the nitrogen atom and carbon atom to which they are attached, form a 3- to 7-membered heterocyclic ring optionally substituted with hydroxy or C$_1$-C$_4$ alkoxy;
except when R$_4$ and R$_{4'}$ each, together with R$_2$, forms the heterocyclic ring,
(a) R$_{4'}$ is hydrogen, and R$_4$ is selected from the group consisting of hydrogen, optionally substituted C$_1$-C$_6$ alkyl, C$_3$-C$_6$ cycloalkyl, C$_3$-C$_6$ cycloalkyl-C$_1$-C$_4$ alkyl, optionally substituted phenyl, optionally substituted phenylmethyl, optionally substituted phenylethyl, 2-(methylthio)ethyl, —CH$_2$SPG$_2$, N-PG$_3$-indol-3-ylm-ethyl, 4-(PG$_2$O)benzyl, PG$_2$-O-methyl, 1-(PG$_2$O)ethyl, 2-(PG$_2$O)ethyl, PG$_2$-OCO(CH$_2$)—, PG$_2$-OCO (CH$_2$)$_2$—, PG$_3$N-n-butyl, —CON(R$_{14A}$)(R$_{14B}$), —CH$_2$—CON(R$_{14A}$)(R$_{14B}$), and —(CH$_2$)$_2$CON(R$_{14A}$) (R$_{14B}$),
(b) R$_4$ and R$_{4'}$ are independently optionally substituted C$_1$-C$_6$ alkyl, or
(c) R$_4$ and R$_{4'}$, together with the carbon atom to which they are attached, form a 3- to 7-membered alicyclic ring;
R$_5$ is a single bond or —C(R$_{5A}$)(R$_{5B}$)—;
R$_{5A}$ and R$_{5B}$ are independently selected from the group consisting of hydrogen, C$_1$-C$_6$ alkyl, optionally substituted aryl, optionally substituted heteroaryl, optionally substituted aryl-C$_1$-C$_4$ alkyl, and optionally substituted heteroaryl-C$_1$-C$_4$ alkyl;
R$_6$ is selected from the group consisting of hydrogen and C$_1$-C$_6$ alkyl, or R$_6$ and R$_7$ or R$_6$ and R$_{7'}$, together with the nitrogen atom and carbon atom to which they are attached, form a 3- to 7-membered heterocyclic ring optionally substituted with hydroxy or C$_1$-C$_4$ alkoxy;
except when R$_7$ and R$_{7'}$ each, together with R$_6$, forms the heterocyclic ring,
(a) R$_{7'}$ is hydrogen, and R$_7$ is selected from the group consisting of hydrogen, optionally substituted C$_1$-C$_6$ alkyl, C$_3$-C$_6$ cycloalkyl, C$_3$-C$_6$ cycloalkyl-C$_1$-C$_4$ alkyl, optionally substituted phenyl, optionally substituted phenylmethyl, optionally substituted phenylethyl, 2-(methylthio)ethyl, —CH$_2$SPG$_4$, N-PG$_5$-indol-3-ylm-ethyl, 4-(PG$_4$O)benzyl, PG$_4$-O-methyl, 1-(PG$_4$O)ethyl, 2-(PG$_4$O)ethyl, PG$_4$-OCO(CH$_2$)—, PG$_4$-OCO (CH$_2$)$_2$—, PG$_5$N-n-butyl, —CON(R$_{15A}$)(R$_{15B}$), —CH$_2$—CON(R$_{15A}$)(R$_{15B}$), and —(CH$_2$)$_2$CON(R$_{15A}$) (R$_{15B}$),
(b) R$_7$ and R$_{7'}$ are independently optionally substituted C$_1$-C$_6$ alkyl, or
(c) R$_7$ and R$_{7'}$, together with the carbon atom to which they are attached, form a 3- to 7-membered alicyclic ring;
R$_8$ is a single bond or —C(R$_{5A}$)(R$_{5B}$)—;
R$_{8A}$ and R$_{8B}$ are independently selected from the group consisting of hydrogen, C$_1$-C$_6$ alkyl, optionally substituted aryl, optionally substituted heteroaryl, optionally substituted aryl-C$_1$-C$_4$ alkyl, and optionally substituted heteroaryl-C$_1$-C$_4$ alkyl;
R$_9$ is hydroxy, —O-PG$_6$, a natural amino acid residue, an amino acid analog residue, —O-RES, or —NH-RES;
RES is a resin for solid-phase synthesis;
R$_{14A}$ and R$_{14B}$ are independently hydrogen or C$_1$-C$_4$ alkyl, or R$_{14A}$ and R$_{14B}$, together with the nitrogen atom to which they are attached, form a 4- to 8-membered ring optionally comprising one or more additional heteroatoms;
R$_{15A}$ and R$_{15B}$ are independently hydrogen or C$_1$-C$_4$ alkyl, or R$_{15A}$ and R$_{15B}$, together with the nitrogen atom to which they are attached, form a 4- to 8-membered ring optionally comprising one or more additional heteroatoms;
PG$_1$ is selected from the group consisting of Fmoc, Boc, Alloc, Cbz, Teoc, and trifluoroacetyl;
PG$_2$ and PG$_4$ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-C$_1$-C$_4$ alkyl, optionally substituted heteroaryl-C$_1$-C$_4$ alkyl, and 2-(trimethylsilyl)ethyl;
PG$_3$ and PG$_8$ are independently selected from the group consisting of hydrogen, Fmoc, Boc, Alloc, Cbz, Teoc, methoxycarbonyl, t-Bu, trityl, cumyl, and benzyl; and
PG$_6$ is selected from the group consisting of t-Bu, trityl, cumyl, benzyl, methyl, ethyl, allyl, and 2-(trimethylsilyl)ethyl,
wherein the starting peptide compound optionally comprises additional natural amino acid residues and/or amino acid analog residues, and
wherein the starting peptide compound comprises at least one amino acid residue bound to the resin for solid-phase synthesis.

[23] A method of producing a peptide or amide compound in which a protecting group removable by a silylating agent is removed, the method comprising the step of contacting a starting peptide or amide compound comprising natural amino acid residues and/or amino acid analog residues with the silylating agent in a solvent and thereby removing the protecting group from the starting peptide or amide compound,
wherein the silylating agent is prepared by mixing a silyl compound or acid with an electrophilic species scavenger,
wherein the starting peptide or amide compound comprises at the C-terminus an amino acid residue or a structure in which two amino acid residues are linked to each other, wherein the amino acid residue or structure is represented by general formula (II):

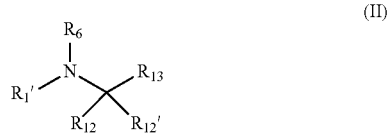

(II)

wherein $R_{1'}$ is a hydrogen atom, $PG_7$, or a group represented by formula (III) below:

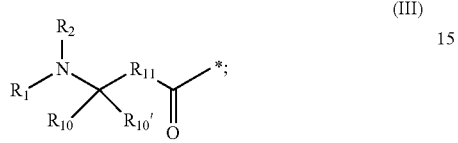

(III)

* represents the point of attachment;

$R_1$ is hydrogen, $PG_1$, a natural amino acid residue, or an amino acid analog residue;

$R_2$ is selected from the group consisting of hydrogen and $C_1$-$C_6$ alkyl, or $R_2$ and $R_{10}$ or $R_2$ and $R_{10'}$, together with the nitrogen atom and carbon atom to which they are attached, form a 3- to 7-membered heterocyclic ring optionally substituted with hydroxy or $C_1$-$C_4$ alkoxy;

except when $R_{10}$ and $R_{10'}$ each, together with $R_2$, forms the heterocyclic ring, (a) $R_{10'}$ is hydrogen, and $R_{10}$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_8$, N-$PG_9$-indol-3-ylmethyl, 4-($PG_8$O)benzyl, $PG_8$-O-methyl, 1-($PG_8$O)ethyl, 2-($PG_8$O)ethyl, $PG_8$-OCO($CH_2$)—, $PG_8$-OCO($CH_2$)$_2$—, $PG_9$N-n-butyl, —CON($R_{16A}$)($R_{16B}$), —$CH_2$—CON($R_{16A}$)($R_{16B}$), and —($CH_2$)$_2$CON($R_{16A}$)($R_{16B}$), (b) $R_{10}$ and $R_{10'}$ are independently optionally substituted $C_1$-$C_6$ alkyl, $C_3$-$C_6$ cycloalkyl, or $C_3$-$C_6$ cycloalkyl-$C_1$-$C_4$ alkyl, or (c) $R_{10}$ and $R_{10'}$, together with the carbon atom to which they are attached, form a 3 to 7-membered alicyclic ring;

$R_{11}$ is a single bond or —C($R_{11A}$)($R_{11B}$)—;

$R_{11A}$ and $R_{11B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;

$R_{12}$ and $R_{12'}$ are independently selected from the group consisting of hydrogen, $PG_{10}$-O-methyl, —($CH_2$)$_n$COO-$PG_{10}$, —($CH_2$)$_n$COO-RES, and —($CH_2$)$_n$CONH-RES;

RES is a resin for solid-phase synthesis;

n is 0, 1, or 2;

$R_6$ is selected from the group consisting of hydrogen and $C_1$-$C_6$ alkyl;

$R_{13}$ is $C_1$-$C_4$ alkyl or —($CH_2$)$_m$CON($R_{17A}$)($R_{17B}$);

m is 0, 1, or 2;

$R_{16A}$ and $R_{16B}$ are independently hydrogen or $C_1$-$C_4$ alkyl, or $R_{16A}$ and $R_{16B}$, together with the nitrogen atom to which they are attached, form a 4- to 8-membered ring optionally comprising one or more additional heteroatoms;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_1$ and $PG_7$ are independently selected from the group consisting of Fmoc, Boc, Alloc, Cbz, Teoc, and trifluoroacetyl;

$PG_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;

$PG_9$ is selected from the group consisting of hydrogen, Fmoc, Boc, Alloc, Cbz, Teoc, methoxycarbonyl, t-Bu, trityl, cumyl, and benzyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl, wherein the starting peptide compound optionally comprises additional natural amino acid residues and/or amino acid analog residues, and wherein the starting peptide or amide compound comprises at least one protecting group removal by the silylating agent.

[24] A method of producing a peptide or amide compound in which a resin for solid-phase synthesis is removed, the method comprising the step of contacting a starting peptide or amide compound comprising natural amino acid residues and/or amino acid analog residues with a silylating agent in a solvent and thereby removing the starting peptide or amide compound from the resin for solid-phase synthesis, wherein the silylating agent is prepared by mixing a silyl compound or acid with an electrophilic species scavenger, wherein the starting peptide or amide compound comprises at the C-terminus an amino acid residue or a structure in which two amino acid residues are linked to each other, wherein the amino acid residue or structure is represented by general formula (II) below:

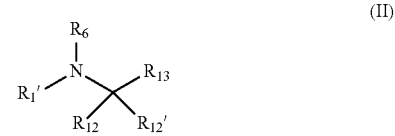

(II)

wherein $R_{1'}$ is a hydrogen atom, $PG_7$, or a group represented by the formula (III):

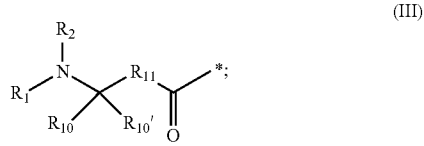

(III)

* represents the point of attachment;

$R_1$ is hydrogen, $PG_1$, a natural amino acid residue, or an amino acid analog residue;

$R_2$ is selected from the group consisting of hydrogen and $C_1$-$C_6$ alkyl, or $R_2$ and $R_{10}$ or $R_2$ and $R_{10'}$, together with the nitrogen atom and carbon atom to which they are attached, form a 3- to 7-membered heterocyclic ring optionally substituted with hydroxy or $C_1$-$C_4$ alkoxy;

except when $R_{10}$ and $R_{10'}$ each, together with $R_2$, forms the heterocyclic ring, (a) $R_{10'}$ is hydrogen, and $R_{10}$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_8$, N-$PG_9$-indol-3-ylmethyl, 4-($PG_8O$)benzyl, $PG_8$-O-methyl, 1-($PG_8O$)ethyl, 2-($PG_8O$)ethyl, $PG_8$-OCO($CH_2$)—, $PG_8$-OCO($CH_2$)$_2$—, $PG_9$N-n-butyl, —CON($R_{16A}$)($R_{16B}$), —$CH_2$—CON($R_{16A}$)($R_{16B}$), and —($CH_2$)$_2$CON($R_{16A}$)($R_{16B}$), (b) $R_{10}$ and $R_{10'}$ are independently optionally substituted $C_1$-$C_6$ alkyl, $C_3$-$C_6$ cycloalkyl, or $C_3$-$C_6$ cycloalkyl-$C_1$-$C_4$ alkyl, or (c) $R_{10}$ and $R_{10'}$, together with the carbon atom to which they are attached, form a 3- to 7-membered alicyclic ring;

R11 is a single bond or —C(R11A)(R11B)-;

R11A and R11B are independently selected from the group consisting of hydrogen, optionally substituted $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;

R12 and R12' are independently selected from the group consisting of hydrogen, $PG_{10}$-O-methyl, —($CH_2$)$_n$COO-$PG_{10}$, —($CH_2$)$_n$COO-RES, and —($CH_2$)$_n$CONH-RES;

RES is a resin for solid-phase synthesis, wherein at least one of R12 and R12' is —($CH_2$)$_n$COO-RES or —($CH_2$)$_n$CONH-RES;

RES is a resin for solid-phase synthesis;

n is 0, 1, or 2;

$R_6$ is selected from the group consisting of hydrogen and $C_1$-$C_6$ alkyl;

$R_{13}$ is $C_1$-$C_4$ alkyl or —($CH_2$)$_m$CON($R_{17A}$)($R_{17B}$);

m is 0, 1, or 2;

$R_{16A}$ and $R_{16B}$ are independently hydrogen or $C_1$-$C_4$ alkyl, or $R_{16A}$ and $R_{16B}$, together with the nitrogen atom to which they are attached, form a 4- to 8-membered ring optionally comprising one or more additional heteroatoms;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_1$ and $PG_7$ are independently selected from the group consisting of Fmoc, Boc, Alloc, Cbz, Teoc, and trifluoroacetyl;

$PG_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;

$PG_9$ is selected from the group consisting of hydrogen, Fmoc, Boc, Alloc, Cbz, Teoc, methoxycarbonyl, t-Bu, trityl, cumyl, and benzyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl, and wherein the starting peptide compound optionally comprises additional natural amino acid residues and/or amino acid analog residues.

[25] A deprotecting agent for use in removing a protecting group, comprising a silyl compound or acid and an electrophilic species scavenger.

[26] A resin removal agent for use in cleaving a peptide compound from a resin in a solid-phase reaction, comprising a silyl compound or acid and an electrophilic species scavenger.

Effects of the Invention

The present invention is advantageous over known methods in that large amounts of Bronsted acids that readily damage amide bonds are not used, the equivalents of the reagents can be reduced, the reagents used can be easily removed, and reactions in the subsequent steps are not affected. For example, 2,6-lutidine has a high boiling point (144° C.) and is therefore rarely evaporated. Although 2,6-lutidine is a basic compound and thus may be removed by acids, it is inefficient to remove excess 2,6-lutidine under acidic conditions when the target compound is a peptide compound, because the product is a compound having a basic amino group. When the 2,6-lutidine used in the previous step remains in the condensation reaction (reaction of elongating the amide bond) subsequent to the deprotection reaction, it is problematic that the condensing agent is still reacted with the remaining 2,6-lutidine, or condensation reaction still cannot be performed under desired conditions due to the presence of a base during the condensation reaction. In contrast, for example, the silylamines of the present invention are used more advantageously than 2,6-lutidine conventionally used, because the silylamines are hydrolyzed by treatment with water after reaction and converted to highly water-soluble compounds that can be easily removed, so that reagents derived from such silylamines can be easily removed by washing with aqueous solutions and do not affect peptide elongation in the subsequent step.

Among compounds used as electrophilic species scavengers such as imidates (formula 2), amides (formula 3), ketene acetals (formula 4), ketene alkoxy hemiaminals (formula 4), enol ethers (formula 4), enol esters (formula 4), imines (formula 5), amines (formula 6), diamines (formula 7), dialkylcarbodiimides (formula 8), ureas (formula 9), or urethanes (formula 10), imidates (formula 2), amides (formula 3), ketene acetals (formula 4), ketene alkoxy hemiaminals (formula 4), enol ethers (formula 4), enol esters (formula 4), or imines (formula 5) can be converted by post-reaction mild hydrolysis treatment to compounds having a low boiling point that can be easily removed. Therefore, excess reagents used for reaction can be removed much easier than excess 2,6-lutidine. Not only amide compounds (formula 3) but also imidates are converted by post-reaction mild hydrolysis treatment to compounds that can be easily removed, and thus do not affect the subsequent step. Characteristically, amines used as electrophilic species scavengers may also be secondary amines, in addition to tertiary amines as conventionally well-known, and such amines can achieve deprotection while suppressing damage to amide bonds.

In one aspect of the present invention, N-Boc groups of peptide compounds can be removed while suppressing damage to the main chains of the peptide compounds. In another aspect of the present invention, t-Bu of t-Bu esters can be removed, benzyl of benzyl esters can be removed, and trityl of trityl esters can be removed at the main-chain C-terminus and in the side chains of peptide compounds while suppressing damage to the main chains of the peptide compounds. In still another aspect of the present invention, peptide compounds can be removed from resins bound to the main-chain C-terminus or the side chains of the peptide compounds while suppressing damage to the main chains of the peptide compounds.

DESCRIPTION OF EMBODIMENTS

The abbreviations used in the present invention are listed below.
AcOEt: Ethyl acetate
Alloc: Allyloxycarbonyl
Allyl: Allyl
BEP: 2-Bromo-1-ethylpyridinium tetrafluoroborate
Bn: Benzyl
Boc: tert-Butoxycarbonyl
BSA: N,O-Bis(trimethylsilyl)acetamide
BSTFA: N,O-Bis(trimethylsilyl)trifluoroacetamide
Bu: Butyl
Cbz: Benzyloxycarbonyl
cHx: Cyclohexyl
Cl-CTC resin: 2-Chlorotrityl chloride polymer resin
CPME: Cyclopentyl methyl ether
CTC: 2-Chlorotrityl chloride
DBU: 2,3,4,6,7,8,9,10-Octahydropyrimido[1,2-a]azepine
DdZ: 3,5-Dimethoxyphenylisopropoxycarbonyl
DIC: N,N'-Diisopropylcarbodiimide
DIPEA: N,N-Diisopropylethylamine
DMA: N,N-Dimethylacetamide
DME: 1,2-Dimethoxyethane
DMF: N,N-Dimethylformamide
DMSO: Dimethyl sulfoxide
DMT-MM: 4-(4,6-Dimethoxy-1,3,5-triazin-2-yl)-4-methylmorpholinium chloride
EDCI: 1-(3-Dimethylaminopropyl)-3-ethylcarbodiimide
eq.: Equivalent
EtOH: Ethanol
Et: Ethyl
Fmoc: 9-Fluorenylmethyloxycarbonyl
HATU: 1-[Bis(dimethylamino)methylene]-1H-1,2,3-triazolo[4,5-b]pyridinium 3-oxide hexafluorophosphate
HMDS: Hexamethyldisilazane
HOAt: 3H-1,2,3-Triazolo[4,5-b]pyridin-3-ol
HOBt: 1,2,3-Benzotriazol-1-ol
HPLC: High performance liquid chromatography
i-PrOAc: Isopropyl acetate
i-Pr: Isopropyl
LCMS: Liquid chromatography mass spectrometry
MeCN: Acetonitrile
Me: Methyl
MS: Mass spectroscopy
MsOH: Methanesulfonic acid
MSTFA: N-Methyl-N-trimethylsilyltrifluoroacetamide
MTBE: Methyl tert-butyl ether
ND: Not determined
NMI: 1-Methylimidazole
NMP: N-Methylpyrrolidone
oxyma: Ethyl cyano(hydroxyimino)acetate
Pd/C: Palladium on carbon
Ph: Phenyl
pip: Piperidinyl
prep.: Preparation
T3P: Propylphosphonic anhydride
TBDPS: tert-Butyldiphenylsilyl
TBS: tert-Butyldimethylsilyl
t-Bu: tert-Butyl
TEA: Triethylamine
Teoc: 2-(Trimethylsilyl)ethoxycarbonyl
TES: Triethylsilyl
TFA: Trifluoroacetic acid
TFE: 2,2,2-Trifluoroethanol
TfOH: Trifluoromethanesulfonic acid
Tf: Trifluoromethanesulfonyl
THF: Tetrahydrofuran
2-MeTHF: 2-Methyltetrahydrofuran
TIPS: Triisopropylsilyl
TMSOTf: Trimethylsilyl trifluoromethanesulfonate
TMS: Trimethylsilyl
Tr: Trityl
TTMS: Tris(trimethylsilyl)silyl
vol.: volume
Gly: Glycine
Ala: Alanine
Ser: Serine
Thr: Threonine
Val: Valine
Leu: Leucine
Ile: Isoleucine
Phe: Phenylalanine
Tyr: Tyrosine
Trp: Tryptophan
His: Histidine
Glu: Glutamic acid
Asp: Aspartic acid
Gln: Glutamine
Asn: Asparagine
Cys: Cysteine
Met: Methionine
Lys: Lysine
Arg: Arginine
Pro: Proline
MeGly: N-Me Glycine
MeAla: N-Me Alanine
MeSer: N-Me Serine
MeThr: N-Me Threonine
MeVal: N-Me Valine
MeLeu: N-Me Leucine
MeIle: N-Me Isoleucine
MePhe: N-Me Phenylalanine
MeTyr: N-Me Tyrosine
MeTrp: N-Me Tryptophan
MeHis: N-Me Histidine
MeGlu: N-Me Glutamic acid
MeAsp: N-Me Aspartic acid
MeGln: N-Me Glutamine
MeAsn: N-Me Asparagine
MeCys: N-Me Cysteine
MeMet: N-Me Methionine
MeLys: N-Me Lysine
MeArg: N-Me Arginine
Definitions of Functional Groups The term "alkyl" as used herein refers to a monovalent group derived by removing any one hydrogen atom from an aliphatic hydrocarbon, and covers a subset of hydrocarbyl or hydrocarbon group structures that contain hydrogen and carbon atoms, but do not contain a heteroatom (which refers to an atom other than carbon and hydrogen atoms) or an unsaturated carbon-carbon bond in the skeleton. The "alkyl" includes linear or branched alkyl. The alkyl is an alkyl having 1 to 20 carbon atoms ($C_1$-$C_{20}$; hereinafter, "$C_p$-$C_q$" means that it has p to q carbon atoms), examples of which include $C_1$-$C_6$ alkyl and $C_1$-$C_4$ alkyl. Specific examples of the alkyl include methyl, ethyl, propyl, butyl, pentyl, hexyl, isopropyl, tert-butyl, and sec-butyl.

The term "cycloalkyl" as used herein refers to a saturated or partially saturated cyclic monovalent aliphatic hydrocarbon group, including single rings, bicyclo rings, and spiro rings. The cycloalkyl may be partially unsaturated. Preferred examples of the cycloalkyl include $C_3$-$C_6$ cycloalkyl, which include, for example, cyclopropyl, cyclobutyl, cyclopentyl, and cyclohexyl.

As used herein, the term "cycloalkylalkyl" refers to a group in which any hydrogen atom in the above-defined "alkyl" is replaced by the above-defined "cycloalkyl." Preferred examples of the cycloalkylalkyl include $C_{3-6}$ cycloalkyl-$C_{1-6}$ alkyl and $C_{3-6}$ cycloalkyl-$C_{1-4}$ alkyl. Specific examples include cyclopropylmethyl, cyclopropylethyl, cyclobutylmethyl, cyclopentylmethyl, and cyclohexylmethyl.

As used herein, the term "alkoxy" refers to an oxy group to which the above-defined "alkyl" is bonded. Preferred examples include $C_{1-4}$ alkoxy and $C_{1-3}$ alkoxy. Specific examples of the alkoxy include methoxy, ethoxy, 1-propoxy, 2-propoxy, n-butoxy, i-butoxy, sec-butoxy, and tert-butoxy.

As used herein, the term "alicyclic ring" refers to a monovalent non-aromatic hydrocarbon ring. The alicyclic ring may have an unsaturated bond in the ring, and may be a polycyclic ring having two or more rings. Carbon atoms constituting the ring may be oxidized to form carbonyl. The number of atoms forming the alicyclic ring is preferably 3 to 7 (3- to 7-membered alicyclic ring). Specific examples of the alicyclic ring include a cycloalkyl ring, a cycloalkenyl ring, and a cycloalkynyl ring.

As used herein, the term "heterocyclic ring" refers to a non-aromatic monovalent or divalent heterocyclic ring comprising preferably 1 to 5 heteroatoms in the ring-forming atoms. The heterocyclic ring may have a double bond and/or a triple bond in the ring, may have a carbon atom in the ring that is oxidized to form carbonyl, and may be a single ring, a fused ring, or a spiro ring. The number of the ring-forming atoms is preferably 3 to 12 (3 to 12-membered heterocyclic ring), more preferably 4 to 7 (4- to 7-membered heterocyclic ring), and still more preferably 5 to 6 (5- to 6-membered heterocyclic ring).

Specific examples of the heterocyclic ring include azetidine, piperazine, pyrrolidine, piperidine, morpholine, homomorpholine, (R)-hexahydropyrrolo[1,2-a]pyrazine, (S)-hexahydropyrrolo[1,2-a]pyrazine, 3-oxopiperazine, 2-oxopyrrolidine, azetidine, 2-oxoimidazolidine, oxetane, dihydrofuran, tetrahydrofuran, dihydropyran, tetrahydropyran, tetrahydropyridine, thiomorpholine, pyrazolidine, imidazoline, oxazolidine, isoxazolidine, thiazolidine, imidazolidine, isothiazolidine, thiadiazolidine, oxazolidone, benzodioxane, benzoxazoline, dioxolane, dioxane, and tetrahydrothiopyran.

As used herein, the term "aromatic heterocyclic ring" refers to an aromatic monovalent or divalent heterocyclic ring comprising preferably 1 to 5 heteroatoms in the ring-forming atoms. The aromatic heterocyclic ring may be partially saturated, and may be a single ring, a fused ring (such as a bicyclic aromatic heterocyclic ring in which a monocyclic aromatic heterocyclic ring is fused with a benzene ring or a monocyclic aromatic heterocyclic ring), or a spiro ring. The number of the ring-forming atoms is preferably 4 to 10 (4- to 10-membered aromatic heterocyclic ring).

Specific examples of the aromatic heterocyclic ring include furan, thiophene, pyrrole, imidazole, pyrazole, thiazole, isothiazole, oxazole, isoxazole, oxadiazole, thiadiazole, triazole, tetrazole, pyridine, pyrimidine, pyridazine, pyrazine, triazine, benzofuran, benzothiophene, benzothiadiazole, benzothiazole, benzoxazole, benzoxadiazole, benzimidazole, indole, isoindole, indazole, quinoline, isoquinoline, cinnoline, quinazoline, quinoxaline, indolizine, and imidazopyridine.

The term "aryl" as used herein refers to a monovalent aromatic hydrocarbon ring, preferred examples of which include $C_6$-$C_{10}$ aryl. Specific examples of the aryl include phenyl and naphthyl (e.g., 1-naphthyl or 2-naphthyl).

The term "heteroaryl" as used herein refers to a monovalent aromatic heterocyclic group comprising preferably 1 to 5 heteroatoms in the ring-forming atoms"". The heteroaryl may be partially saturated, and may be a single ring or fused rings (such as bicyclic heteroaryl in which heteroaryl is fused with benzene ring or monocyclic heteroaryl ring). The number of the ring-forming atoms is preferably 5 to 10 (5- to 10-membered heteroaryl).

Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, azaindolyl, indazolyl, quinolyl, isoquinolyl, cinnolinyl, quinazolinyl, quinoxalinyl, benzodioxolyl, indolizinyl, and imidazopyridyl.

As used herein, the term "heterocyclyl" refers to a non-aromatic monovalent heterocyclic group comprising preferably 1 to 5 heteroatoms in the ring-forming atoms. The heterocyclyl may have a double or triple bond in the ring, may have a carbon atom oxidized to form carbonyl, and may be a single ring or a fused ring. The number of the ring-forming atoms is preferably 3 to 10 (3- to 10-membered heterocyclyl).

Specific examples of the heterocyclyl include oxetanyl, dihydrofuryl, tetrahydrofuryl, dihydropyranyl, tetrahydropyranyl, tetrahydropyridyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, thiadiazolidinyl, azetidinyl, oxazolidone, benzodioxanyl, benzoxazolyl, dioxolanyl, and dioxanyl.

As used herein, the term "arylalkyl" refers to a group in which any hydrogen atom in the above-defined "alkyl" is replaced by the above-defined "aryl." Preferred examples of the arylalkyl include $C_6$-10 aryl-$C_1$-4 alkyl and $C_6$-10 aryl-$C_1$-3 alkyl. Specific examples include benzyl, phenylmethyl, phenethyl (phenylethyl), and naphthylmethyl.

As used herein, the term "heteroarylalkyl" refers to a group in which any hydrogen atom in the above-defined "alkyl" is replaced by the above-defined "heteroaryl." Preferred examples of the heteroarylalkyl include 5- to 10-membered heteroaryl-$C_1$-3 alkyl. Specific examples include pyrrolylmethyl, imidazolylmethyl, thienylmethyl, pyridylmethyl, pyrimidylmethyl, quinolylmethyl, and pyridylethyl.

As used herein, the term "substituted silyl" refers to a silyl group substituted with 1 to 3 substituents. The substituents may be the same or different. Such substituents are preferably $C_1$-$C_6$ alkyl, aryl, and tri-$C_1$-$C_6$ alkylsilyl. Specific examples include trimethylsilyl, triethylsilyl, triisopropylsilyl, t-butyldimethylsilyl, t-butyldiphenylsilyl, and tris(trimethylsilyl)silyl.

When the modifier "optionally substituted" is provided herein, examples of such substituents include alkyl, alkoxy, alkenyl, alkenyloxy, alkynyl, alkynyloxy, cycloalkyl, aryl, heteroaryl, heterocyclyl, arylalkyl, heteroarylalkyl, substituted silyl, halogen atoms, nitro, amino, monoalkylamino, dialkylamino, cyano, carboxyl, alkoxycarbonyl, and formyl.

As used herein, the term "deprotection/removal of a protection group" refers to converting a protected functional group back to an original functional group by removing the protecting group.

As used herein, the term "resin removal/removal of a resin" refers to cleaving a peptide compound from a resin for solid-phase synthesis that is bound to the peptide compound. The resin for solid-phase synthesis is preferably bound to the C-terminal amino acid residue of the starting peptide compound.

In one embodiment, the present invention provides methods of producing peptide pharmaceuticals comprising amino acid analogs useful for peptide pharmaceuticals. In another embodiment, the present invention provides methods of producing peptides comprising high-quality amino acid analogs for supplying pharmaceutical drug substances. In still another embodiment, the present invention provides novel amide compounds useful for producing peptide compounds.

Deprotection/Resin Removal Methods

In some aspects, the present invention relates to a method of producing a peptide compound in which a protecting group removable by a silylating agent is removed, the method comprising the step of contacting a starting peptide compound comprising natural amino acid residues and/or amino acid analog residues with the silylating agent in a solvent and thereby removing the protecting group from the starting peptide compound.

In some aspects, the present invention relates to a method of producing a peptide compound in which a resin for solid-phase synthesis is removed, the method comprising the step of contacting a starting peptide compound comprising natural amino acid residues and/or amino acid analog residues with a silylating agent in a solvent and thereby removing the starting peptide compound from the resin for solid-phase synthesis.

As used herein, the term "starting peptide compound" refers to a "peptide compound" which is a starting material to be subjected to the deprotection reaction and/or resin removal reaction of the present invention. The starting peptide compound preferably comprises at least one N-substituted amino acid residue.

"Peptide compounds" in the present invention include linear or cyclic peptide compounds comprising natural amino acid residues and/or amino acid analog residues. Cyclic peptide compounds are synonymous with "peptide compounds having a cyclic moiety."

As used in the present invention, "linear peptide compounds" are not particularly limited as long as they are peptide compounds that are formed by natural amino acids or amino acid analogs forming amide or ester bonds and that do not have a cyclic moiety. Such a linear peptide compound can be formed by a total of 1, 2, 3, 4, 5, 6, 7, 8, 9, 10, 11, 12, 13, 14, 15, 20, 25, or 30 natural amino acids or amino acid analogs. The number of amino acids constituting the linear peptide compound preferably ranges from 1 to 30, from 6 to 20, from 7 to 19, from 7 to 18, from 7 to 17, from 7 to 16, from 7 to 15, from 8 to 14, or from 9 to 13.

As used in the present invention, "peptide compounds having a cyclic moiety" are not particularly limited as long as they are peptide compounds that are formed by natural amino acids or amino acid analogs forming amide or ester bonds and that have a cyclic moiety. Such cyclic moieties are preferably formed through covalent bonds such as amide bonds, carbon-carbon bonds, S—S bonds, thioether bonds, and triazole bonds (WO2013/100132, WO2012/026566, WO2012/033154, WO2012/074130, WO2015/030014, Comb Chem High Throughput Screen. 2010; 13:75-87, Nature Chem. Bio. 2009, 5, 502, Nat Chem Biol. 2009, 5, 888-90, Bioconjugate Chem., 2007, 18, 469-476, ChemBioChem, 2009, 10, 787-798, Chemical Communications (Cambridge, United Kingdom) (2011), 47(36), 9946-9958). Compounds obtained by further chemically modifying such compounds are also included in the peptide compounds of the present invention. The peptide compounds of the present invention having a cyclic moiety may also have a linear moiety. The number of amide or ester bonds (the number or length of natural amino acids or amino acid analogs) is not particularly limited, but when the peptide compound has a linear moiety, the cyclic and linear moieties combined preferably have 30 residues or less. The total number of amino acids is more preferably 9 or more in order to achieve high metabolic stability. In addition to above, the cyclic moiety is preferably formed by 5 to 12, 6 to 12, or 7 to 12, still more preferably 7 to 11 or 8 to 11, and particularly preferably 9 to 11 (10 or 11), natural amino acids and amino acid analogs. The linear moiety preferably has 0 to 8, 0 to 7, 0 to 6, 0 to 5, or 0 to 4, and more preferably 0 to 3, amino acids and amino acid analogs. The total number of natural amino acids and amino acid analogs is preferably 1 to 30, 6 to 20, 7 to 19, 7 to 18, 7 to 17, 7 to 16, 7 to 15, 8 to 14, or 9 to 13.

Although there are no particular limitations on the types of natural amino acid residues and amino acid analog residues forming the cyclic moiety of the peptide compound of the present invention having a cyclic moiety, the cyclic moiety is preferably formed by natural amino acid residues and amino acid analog residues having a functional group with high metabolic stability. The method of cyclizing the peptide compound of the present invention having a cyclic moiety is not particularly limited as long as the method can form such a cyclic moiety. Examples of the cyclization method include amide bond formation from carboxylic acids and amines; and carbon-carbon bond formation reactions using transition metals as catalysts such as Suzuki reaction, Heck reaction, and Sonogashira reaction. Accordingly, the peptide compound of the present invention contains at least one set of functional groups allowing such bond formation reactions before cyclization. In particular, in terms of metabolic stability, it preferably contains functional groups that form an amide bond by bond formation reaction.

Preferably, the cyclic moiety formed does not include a bond that contains a heteroatom which may be readily oxidized and that hinders metabolic stability, for example. Examples of bonds produced by cyclization include amide bonds formed by active esters and amines and bonds produced by Heck reaction products from carbon-carbon double bonds and aryl halides.

The "peptide compound" of the present invention may be a linear or cyclic peptide comprising at least one N-substituted amino acid (preferably 2, 3, 4, 5, 6, 7, 8, 9, 10, 11, 12, 13, 14, 15, 20, 25, or 30, particularly preferably 5, 6, or 7, N-substituted amino acids) and at least one N-unsubstituted amino acid, under or independently of the above-described conditions of the total number of natural amino acids and amino acid analogs. The number of N-substituted amino acids is preferably within the range of 1 to 30, 6 to 20, 7 to 19, 7 to 18, 7 to 17, 7 to 16, 7 to 15, 8 to 14, or 9 to 13.

In some aspects, the starting peptide compound comprises 1 to 30 amino acid residues and is linear or cyclic. Amino acids contained in the starting peptide compound may be either "natural amino acids" or "amino acid analogs." "Amino acids", "natural amino acids", and "amino acid analogs" may be referred to herein as "amino acid residues," "natural amino acid residues," and "amino acid analog residues," respectively. The starting peptide compound may be formed by secondary amides, tertiary amides, or a mixture of secondary and tertiary amides.

The term "natural amino acid" refers to Gly, Ala, Ser, Thr, Val, Leu, Ile, Phe, Tyr, Trp, His, Glu, Asp, Gln, Asn, Cys, Met, Lys, Arg, or Pro.

"Amino acid analogs" are not particularly limited, and include β-amino acids, γ-amino acids, D-amino acids, N-substituted amino acids, α,α-disubstituted amino acids, hydroxycarboxylic acids, and unnatural amino acids (amino acids whose side chains are different from those of natural amino acids: for example, unnatural α-amino acids, β-amino acids, and γ-amino acids). An α-amino acid may be a D-amino acid, or an α,α-dialkylamino acid. In a similar manner to an α-amino acid, β-amino acid and a γ-amino acid are also allowed to have any configuration. Examples of N-substituted amino acids include amino acids of which the amino groups are substituted with any substituents. Examples of such substituents include, but are not particularly limited to, an alkyl group, an aryl group, and an aralkyl group. N-substituted amino acids include N-alkylamino acids, N-arylamino acids, and N-methylamino acids. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, and a cycloalkyl group. One or two non-adjacent methylene groups in such a group are optionally substituted with an oxygen atom, a carbonyl group (—CO—), or a sulfonyl group (—SO2-). Each group may have one, two or more substituent(s). For example, the substituents are freely selected from any functional groups including a halogen atom, an N atom, an O atom, an S atom, a B atom, an Si atom, or a P atom (i.e., an optionally substituted alkyl group, alkenyl group, alkynyl group, aryl group, heteroaryl group, aralkyl group, and cycloalkyl group).

"Natural amino acids" and "amino acid analogs" as used herein which constitute a peptide compound include all isotopes corresponding to each amino acid. The isotope of the "natural amino acid" or "amino acid analog" refers to one having at least one atom replaced with an atom of the same atomic number (number of protons) and different mass number (total number of protons and neutrons). Examples of isotopes contained in the "natural amino acid" or "amino acid analog" constituting the peptide compounds of the present invention include a hydrogen atom, a carbon atom, a nitrogen atom, an oxygen atom, a phosphorus atom, a sulfur atom, a fluorine atom, and a chlorine atom, which respectively include $^{2}H$ and $^{3}H$; $^{13}C$ and $^{14}C$; $^{15}N$; $^{17}O$ and $^{18}O$; $^{32}P$; $^{35}S$; $^{18}F$; and $^{36}Cl$.

Examples of substituents containing a halogen atom as used herein include a halogen-substituted alkyl, cycloalkyl, alkenyl, alkynyl, aryl, heteroaryl, or aralkyl. More specific examples include fluoroalkyl, difluoroalkyl, and trifluoroalkyl.

Substituents containing an O atom include groups such as hydroxy (—OH), oxy (—OR), carbonyl (—C=O—R), carboxy (—CO2H), oxycarbonyl (—C=O—OR), carbonyloxy (—O—C=O—R), thiocarbonyl (—C=O—SR), carbonylthio (—S—C=O—R), aminocarbonyl (—C=O—NHR), carbonylamino (—NH—C=O—R), oxycarbonylamino (—NH—C=O—OR), sulfonylamino (—NH—SO2-R), aminosulfonyl (—SO2-NHR), sulfamoylamino (—NH—SO2-NHR), thiocarboxyl (—C(=O)—SH), and carboxylcarbonyl (—C(=O)—CO2H).

Examples of oxy (—OR) include alkoxy, cycloalkoxy, alkenyloxy, alkynyloxy, aryloxy, heteroaryloxy, and aralkyloxy. The alkoxy is preferably $C_1$-$C_4$ alkoxy and $C_1$-$C_2$ alkoxy, and particularly preferably methoxy or ethoxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl (examples of which include $C_1$-$C_6$ or $C_1$-$C_4$ alkylaminocarbonyl, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Additional examples include compounds in which the H atom bonded to the N atom in —C=O—NHR is further replaced with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds in which the H atom bonded to the N atom in —NH—C=O—R is further replaced with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds in which the H atom bonded to the N atom in —NH—C=O—OR is further replaced with alkyl, cycloalkyl, alkenyl, alkynyl, aryl, heteroaryl, or aralkyl.

Examples of sulfonylamino (—NH—SO2-R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds in which the H atom attached to the N atom in —NH—SO2-R is further replaced with alkyl, cycloalkyl, alkenyl, alkynyl, aryl, heteroaryl, or aralkyl.

Examples of aminosulfonyl (—SO2-NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds in which the H atom attached to the N atom in —SO2-NHR is further replaced with alkyl, cycloalkyl, alkenyl, alkynyl, aryl, heteroaryl, or aralkyl.

Examples of sulfamoylamino (—NH—SO2-NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—SO2-NHR may be further replaced with substituents independently selected from the group consisting of alkyl, cycloalkyl, alkenyl, alkynyl, aryl, heteroaryl, and aralkyl, and these two substituents may form a ring.

Substituents containing an S atom include groups such as thiol (—SH), thio (—S—R), sulfinyl (—S=O—R), sulfonyl (—SO2-R), and sulfo (—SO3H).

Examples of thio (—S—R) include alkylthio, cycloalkylthio, alkenylthio, alkynylthio, arylthio, heteroarylthio, and aralkylthio.

Examples of sulfonyl (—SO2-R) include alkylsulfonyl, cycloalkylsulfonyl, alkenylsulfonyl, alkynylsulfonyl, arylsulfonyl, heteroarylsulfonyl, and aralkylsulfonyl.

Substituents containing an N atom include groups such as azido (—N3, also called "azido group"), cyano (—CN), primary amino (—NH2), secondary amino (—NH—R; also called monosubstituted amino), tertiary amino (—NR(R'); also called disubstituted amino), amidino (—C(=NH)—NH2), substituted amidino (—C(=NR)—NR'R"), guanidino (—NH—C(=NH)—NH2), substituted guanidino (—NR—C(=NR''')—NR'R"), aminocarbonylamino (—NR—CO—NR'R"), pyridyl, piperidino, morpholino, and azetidinyl.

Examples of secondary amino (—NH—R; monosubstituted amino) include alkylamino, cycloalkylamino, alkenylamino, alkynylamino, arylamino, heteroarylamino, and aralkylamino.

Examples of tertiary amino (—NR(R'); disubstituted amino) include amino groups having any two substituents each independently selected from alkyl, cycloalkyl, alkenyl, alkynyl, aryl, heteroaryl, and aralkyl, such as alkyl(aralkyl)amino, where any two such substituents may form a ring. Specific examples include dialkylamino, in particular, C1-C6 dialkylamino, C1-C4 dialkylamino, dimethylamino, and diethylamino. The term "Cp-Cq dialkylamino group" as used herein refers to an amino group substituted with two Cp-Cq alkyl groups, where the two Cp-Cq alkyl groups may be the same or different.

Examples of substituted amidino (—C(=NR)—NR'R") include groups in which three substituents R, R', and R" on the N atom are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')—NR'R") include groups in which R, R', R", and R''' are each independently selected from alkyl, cycloalkyl, alkenyl, alkynyl, aryl, heteroaryl, and aralkyl, or groups in which these substituents form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, or groups in which these substituents form a ring.

In some aspects, the starting peptide compound to be subjected to deprotection and/or resin removal comprises at least one N-substituted amino acid residue. Examples of the number of N-substituted amino acid residues contained in the starting peptide compound include 1, 2, 3, 4, 5, 6, 7, 8, 9, 10, 11, 12, 13, 14, 15, 20, 25, or 30. The number of N-substituted amino acid residues is preferably within the range of 6 to 20, 7 to 19, 7 to 18, 7 to 17, 7 to 16, 7 to 15, 8 to 14, or 9 to 13. Two or more N-substituted amino acid residues may be linked to each other in the starting peptide compound.

In some aspects, half or more of the amino acids constituting the peptide compound of the present invention (for example, n or more amino acids (where n is an integer) when the peptide compound is constituted by 2n amino acids, or n+1 or more amino acids when the peptide compound is constituted by 2n+1 amino acids) are preferably N-substituted amino acids.

As used herein, the term "N-substitution" in N-substituted amino acids refers to, but is not limited to, replacement of a hydrogen atom attached to an N atom with a methyl group, an ethyl group, a propyl group, a butyl group, or a hexyl group. Preferred N-substituted amino acids include amino acids in which amino groups contained in natural amino acids are N-methylated, N-ethylated, N-propylated, N-butylated, and N-pentylated. Such amino acids are called N-methylamino acid, N-ethylamino acid, N-propylamino acid, N-butylamino acid, and N-pentylamino acid.

When the starting peptide compound comprises at least one N-substituted amino acid residue (for example, when the starting peptide compound comprises one or more partial structures in which an N-substituted amino acid residue is linked to the adjacent amino acid residue, more specifically, one or more partial structures each comprising at least two amino acid residues, which structure is represented by general formulas (I) and/or (II)), conventional deprotection/resin removal methods easily cause main-chain damage such as amide bond cleavage or peptide main-chain rearrangement. Even in case of such starting peptide compounds, use of the methods of the present invention is able to remove protecting groups of interest efficiently in high yield and purity without involving main-chain damage, and to cleave peptide compounds from resins in solid-phase reactions efficiently in high yield and purity.

In some embodiments, the starting peptide compound of the present invention may not comprise N-substituted amino acid residues or a partial structure in which an N-substituted amino acid residue is linked to the adjacent amino acid residue.

In some aspects, the starting peptide compound to be subjected to deprotection and/or resin removal comprises at least one partial structure in which at least two amino acid residues are linked to each other, wherein the structure is represented by general formula (I) below.

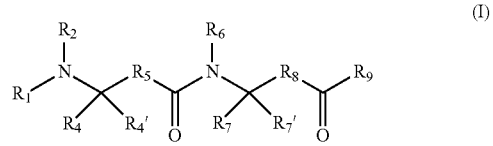

In formula (I), $R_1$ is hydrogen, $PG_1$, a natural amino acid residue, or an amino acid analog residue.

When the structure represented by formula (I) is at the N-terminus of the starting peptide compound, $R_1$ is preferably hydrogen or $PG_1$. On the other hand, when the structure represented by formula (I) is at a position other than the N-terminus of the starting peptide compound, R1 is preferably a natural amino acid residue or an amino acid analog residue.

In formula (I), $R_2$ is selected from the group consisting of hydrogen and $C_1$-$C_6$ alkyl, or $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy.

In some aspects, when $R_2$ is $C_1$-$C_6$ alkyl, the $C_1$-$C_6$ alkyl is preferably methyl, ethyl, propyl, butyl, or pentyl.

In some aspects, when $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy, the 3- to 7-membered heterocyclic ring formed is preferably an azetidine ring, a pyrrolidine ring, or a piperidine ring. $R_{4'}$ is hydrogen when $R_2$ and $R_4$ together form the heterocyclic ring, and $R_4$ is hydrogen when $R_2$ and $R_{4'}$ together form the heterocyclic ring.

In formula (I), except when $R_2$ and $R_4$ or $R_2$ and $R_{4'}$ together form the heterocyclic ring,
 (a) $R_{4'}$ is hydrogen, and $R_4$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_2$, N-$PG_3$-indol-3-ylmethyl, 4-($PG_2$O)benzyl, $PG_2$-O-methyl (i.e., —$CH_2$—O-$PG_2$), 1-($PG_2$O)ethyl, 2-($PG_2$O)ethyl, $PG_2$-OCO($CH_2$)—, $PG_2$-OCO($CH_2$)$_2$—, $PG_3$N-n-butyl, —CON($R_{14A}$)($R_{14B}$), —$CH_2$—CON($R_{14A}$)($R_{14B}$), and —($CH_2$)$_2$CON($R_{14A}$)($R_{14B}$),
 (b) $R_4$ and $R_{4'}$ are independently optionally substituted $C_1$-$C_6$ alkyl, or
 (c) $R_4$ and R4', together with the carbon atom to which they are attached, form a 3- to 7-membered alicyclic ring.

Combinations of $R_4$ and $R_{4'}$ are preferably a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, cyclopentyl and a hydrogen atom, cyclohexyl and a hydrogen atom, optionally substituted phenyl and a hydrogen atom, optionally substituted phenylmethyl and a hydrogen atom, optionally substituted phenylethyl and a hydrogen atom, 2-(methylthio)ethyl and a hydrogen atom, —$CH_2SPG_2$ and a hydrogen atom, N-$PG_3$-indol-3-ylmethyl and a hydrogen atom, 4-($PG_2$O)benzyl and a hydrogen atom, $PG_2$-O-methyl and a hydrogen atom, 1-($PG_2$O)ethyl and a hydrogen atom, 2-($PG_2$O)ethyl and a hydrogen atom, $PG_2$-OCO($CH_2$)— and a hydrogen atom, $PG_2$-OCO($CH_2$)$_2$— and a hydrogen atom, $PG_3$N-n-butyl and a hydrogen atom, —CON($R_{14A}$)($R_{14B}$) and a hydrogen atom, —$CH_2$—CON($R_{14A}$)($R_{14B}$) and a hydrogen atom, —($CH_2$)$_2$CON($R_{14A}$)($R_{14B}$) and a hydrogen atom, methyl and methyl, and methyl and ethyl. When $R_4$ and $R_{4'}$, together with the carbon atom to which they are attached, form a 3- to 7-membered alicyclic ring, the alicyclic ring is preferably a cyclopropyl ring, a cyclobutyl ring, a cyclopentyl ring, or a cyclohexyl ring.

In formula (I), $R_5$ is a single bond or —$C(R_{5A})(R_{5B})$—; and $R_{5A}$ and $R_{5B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl.

$R_5$ is preferably a single bond or —$C(R_{5A})(R_{5B})$— where the combinations of $R_{5A}$ and $R_{5B}$ is a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, optionally substituted phenyl and a hydrogen atom, optionally substituted phenylmethyl and a hydrogen atom, optionally substituted phenylethyl and a hydrogen atom, methyl and methyl, or methyl and ethyl.

In formula (I), $R_6$ is selected from the group consisting of hydrogen and $C_1$-$C_6$ alkyl, or $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy.

In some aspects, when $R_6$ is $C_1$-$C_6$ alkyl, the $C_1$-$C_6$ alkyl is preferably methyl, ethyl, propyl, butyl, or pentyl.

In some aspects, when $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy, the 3- to 7-membered heterocyclic ring formed is preferably an azetidine ring, a pyrrolidine ring, or a piperidine ring. R7' is hydrogen when R6 and R7 together form the heterocyclic ring, and R7 is hydrogen when R6 and R7' together form the heterocyclic ring.

In formula (I), preferably, either or both of R2 and R6 are other than hydrogen, and more preferably, either or both of R2 and R6 are $C_1$-$C_6$ alkyl.

In formula (I), except when $R_6$ and $R_7$, or $R_6$ and $R_{7'}$ together form the heterocyclic ring,
 (a) $R_{7'}$ is hydrogen, and $R_7$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_4$, N-$PG_5$-indol-3-ylmethyl, 4-($PG_4$O)benzyl, $PG_4$-O-methyl (i.e., —$CH_2$—O-$PG_4$), 1-($PG_4$O)ethyl, 2-($PG_4$O)ethyl, $PG_4$-OCO($CH_2$)—, $PG_4$-OCO($CH_2$)$_2$—, $PG_5$N-n-butyl, —CON($R_{15A}$)($R_{15B}$), —$CH_2$—CON($R_{15A}$)($R_{15B}$), and —($CH_2$)$_2$CON($R_{15A}$)($R_{15B}$),
 (b) $R_7$ and $R_{7'}$ are independently optionally substituted $C_1$-$C_6$ alkyl, or
 (c) $R_7$ and $R_{7'}$, together with the carbon atom to which they are attached, form a 3- to 7-membered alicyclic ring.

Combinations of $R_7$ and $R_{7'}$ are preferably a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, cyclopentyl and a hydrogen atom, cyclohexyl and a hydrogen atom, optionally substituted phenyl and a hydrogen atom, optionally substituted phenylmethyl and a hydrogen atom, optionally substituted phenylethyl and a hydrogen atom, 2-(methylthio)ethyl and a hydrogen atom, —$CH_2SPG_4$ and a hydrogen atom, N-$PG_5$-indol-3-ylmethyl and a hydrogen atom, 4-($PG_4$O)benzyl and a hydrogen atom, $PG_4$-O-methyl and a hydrogen atom, 1-($PG_4$O)ethyl and a hydrogen atom, 2-($PG_4$O)ethyl and a hydrogen atom, $PG_4$-OCO($CH_2$)— and a hydrogen atom, $PG_4$-OCO($CH_2$)$_2$— and a hydrogen atom, $PG_5$N-n-butyl and a hydrogen atom, —CON($R_{15A}$)($R_{15B}$) and a hydrogen atom, —$CH_2$—CON($R_{15A}$)($R_{15B}$) and a hydrogen atom, —(CH$_2$)$_2$CON(R$_{15A}$)(R$_{15B}$) and a hydrogen atom, methyl and methyl, and methyl and ethyl. When R$_7$ and R$_7$', together with the carbon atom to which they are attached, form a 3- to 7-membered alicyclic ring, the alicyclic ring is preferably a cyclopropyl ring, a cyclobutyl ring, a cyclopentyl ring, or a cyclohexyl ring.

In formula (I), R$_8$ is a single bond or —C(R$_{8A}$)(R$_{8B}$)—; and R$_{8A}$ and R$_{8B}$ are independently selected from the group consisting of hydrogen, C$_1$-C$_6$ alkyl, optionally substituted aryl, optionally substituted heteroaryl, optionally substituted aryl-C$_1$-C$_4$ alkyl, and optionally substituted heteroaryl-C$_1$-C$_4$ alkyl.

R$_8$ is preferably a single bond or —C(R$_{8A}$)(R$_{8B}$)— where the combination of R$_{8A}$ and R$_{8B}$ is a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, optionally substituted phenyl and a hydrogen atom, optionally substituted phenylmethyl and a hydrogen atom, optionally substituted phenylethyl and a hydrogen atom, methyl and methyl, or methyl and ethyl.

In formula (I), R$_9$ is hydroxy, —O-PG$_6$, a natural amino acid residue, an amino acid analog residue, —O—RES, or —NH-RES, where RES is a resin for solid-phase synthesis.

When the structure represented by formula (I) is at the C-terminus of the starting peptide compound, R$_9$ is preferably hydroxy, —O-PG$_6$, —O—RES, or —NH-RES. On the other hand, when the structure represented by formula (I) is at a position other than the C-terminus of the starting peptide compound, R$_9$ is preferably a natural amino acid residue or an amino acid analog residue.

In formula (I), R$_{14A}$ and R$_{14B}$ are independently hydrogen or C$_1$-C$_4$ alkyl, or R$_{14A}$ and R$_{14B}$, together with the nitrogen atom to which they are attached, form a 4- to 8-membered ring optionally comprising one or more additional heteroatoms. When R$_{14A}$ and/or R$_{14B}$ are C$_1$-C$_4$ alkyl, the C$_1$-C$_4$ alkyl is preferably methyl, ethyl, or propyl. When R$_{14A}$ and R$_{14B}$, together with the nitrogen atom to which they are attached, form a 4- to 8-membered ring optionally comprising one or more additional heteroatoms, the 4- to 8-membered ring is preferably an azetidine ring, a pyrrolidine ring, a piperidine ring, a piperazine ring, or a morpholine ring.

In formula (I), R$_{15A}$ and R$_{15B}$ are independently hydrogen or C$_1$-C$_4$ alkyl, or R$_{15A}$ and R$_{15B}$, together with the nitrogen atom to which they are attached, form a 4- to 8-membered ring optionally comprising one or more additional heteroatoms. When R$_{15A}$ and/or R$_{15B}$ are C$_1$-C$_4$ alkyl, the C$_1$-C$_4$ alkyl is preferably methyl, ethyl, or propyl. When R$_{15A}$ and R$_{15B}$, together with the nitrogen atom to which they are attached, form a 4- to 8-membered ring optionally comprising one or more additional heteroatoms, then the 4- to 8-membered ring is preferably an azetidine ring, a pyrrolidine ring, a piperidine ring, a piperazine ring, or a morpholine ring.

In formula (I), PG$_1$ is selected from the group consisting of Fmoc, Boc, Alloc, Cbz, Teoc, and trifluoroacetyl.

PG$_1$ is preferably Fmoc, Boc, or Cbz.

In formula (I), PG$_2$ and PG$_4$ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-C$_1$-C$_4$ alkyl, optionally substituted heteroaryl-C$_1$-C$_4$ alkyl, and 2-(trimethylsilyl)ethyl.

PG$_2$ and PG$_4$ are preferably methyl, allyl, t-Bu, trityl, methoxytrityl, cumyl, THP, optionally substituted aryl, optionally substituted aryl-C$_1$-C$_4$ alkyl, or optionally substituted heteroaryl-C$_1$-C$_4$ alkyl.

In formula (I), PG$_3$ and PG$_8$ are independently selected from the group consisting of hydrogen, Fmoc, Boc, Alloc, Cbz, Teoc, methoxycarbonyl, t-Bu, trityl, cumyl, and benzyl.

PG$_3$ and PG$_8$ are preferably Fmoc, Boc, Cbz, t-Bu, or trityl.

In formula (I), PG$_6$ is selected from the group consisting of t-Bu, trityl, cumyl, benzyl, methyl, ethyl, allyl, and 2-(trimethylsilyl)ethyl.

PG$_6$ is preferably t-Bu, trityl, cumyl, benzyl, methyl, or allyl.

Structures represented by general formula (I), in which at least two amino acid residues are linked to each other, include many such structures easily cleaved or damaged when known deprotection or resin removal conditions are used. Only the protecting groups of interest or resins for solid-phase synthesis can be selectively and efficiently removed without such cleavage or damage by using the reaction conditions of the present invention.

In some aspects, structures represented by general formula (I), in which at least two amino acid residues are linked to each other, include those in which one N-substituted amino acid is linked to one N-unsubstituted amino acid and those in which two N-substituted amino acids are linked to each other. Specific examples of such amino acid residues include structures represented by general formula (I'), in which two amino acid residues are linked to each other, wherein R$_5$ and R$_8$ in general formula (I) are single bonds.

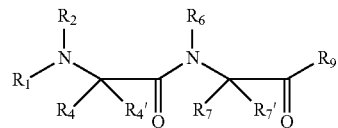

(I')

Each group in formula (I') may be the same as that in formula (I) above.

In some aspects, in formula (I'), R1 is preferably hydrogen, PG1, a natural amino acid residue, or an amino acid analog residue.

In some aspects, in formula (I'), preferably, either or both of R2 and R6 are other than hydrogen, and more preferably, either or both of R2 and R6 are C1-C6 alkyl.

In some aspects, in formula (I'), R2 and R6 may be independently C1-C6 alkyl, which is preferably methyl, ethyl, propyl, butyl, or pentyl.

In some aspects, in formula (I'), R2 and R4 or R2 and R4', or R6 and R7 or R6 and R7' may each independently, together with the nitrogen atom and carbon atom to which they are attached, form a 3- to 7-membered heterocyclic ring optionally substituted with hydroxy or C1-C4 alkoxy. R4' is hydrogen when R2 and R4 together form the heterocyclic ring, and R4 is hydrogen when R2 and R4' together form the heterocyclic ring. R7' is hydrogen when R6 and R7 together form the heterocyclic ring, and R7 is hydrogen when R6 and R7' together form the heterocyclic ring.

In some aspects, in formula (I'), R9 is hydroxy, —O-PG6, a natural amino acid residue, an amino acid analog residue, —O—RES, or —NH-RES, where RES is a resin for solid-phase synthesis.

In some aspects, in formula (I'), R4 and R4', or R7 and R7' may each be C$_1$-C$_6$ alkyl, or R4 and R4', or R7 and R7' may, together with the carbon atom to which they are attached, form a 3- to 7-membered alicyclic ring.

In some aspects, in formula (I'), R4' may be hydrogen, and R4 may be selected from the group consisting of hydrogen, optionally substituted C1-C6 alkyl, C3-C6 cycloalkyl, C3-C6 cycloalkyl-C1-C4 alkyl, optionally substituted phenyl, optionally substituted phenylmethyl, optionally substituted phenylethyl, 2-(methylthio)ethyl, —CH2SPG2, N-PG3-indol-3-ylmethyl, 4-(PG2O)benzyl, PG2-O-methyl, 1-(PG2O)ethyl, 2-(PG2O)ethyl, PG2-OCO(CH2)-, PG2-OCO(CH2)2-, PG3N-n-butyl, —CON(R14A)(R14B), —CH2-CON(R14A)(R14B), and —(CH2)2CON(R14A)(R14B).

In some aspects, in formula (I'), R7' may be hydrogen, and R7 may be selected from the group consisting of hydrogen, optionally substituted C1-C6 alkyl, C3-C6 cycloalkyl, C3-C6 cycloalkyl-C1-C4 alkyl, optionally substituted phenyl, optionally substituted phenylmethyl, optionally substituted phenylethyl, 2-(methylthio)ethyl, —CH2SPG4, N-PG5-indol-3-ylmethyl, 4-(PG4O)benzyl, PG4-O-methyl, 1-(PG4O)ethyl, 2-(PG4O)ethyl, PG4-OCO(CH2)-, PG4-OCO(CH2)2-, PG5N-n-butyl, —CON(R15A)(R15B), —CH2-CON(R15A)(R15B), and —(CH2)2CON(R15A)(R15B).

More preferably, in the structure represented by general formula (I'), $R_1$ is hydrogen, $PG_1$, a natural amino acid residue, or an amino acid analog residue;

$R_2$ and $R_6$ are methyl or ethyl; and/or $R_2$ and $R_4$ or $R_2$ and $R_4$', or $R_6$ and $R_7$ or $R_6$ and $R_7$', each independently, together with the nitrogen atom and carbon atom to which they are attached, form a 4- to 6-membered heterocyclic ring optionally substituted with hydroxy or $C_1$-$C_4$ alkoxy. $R_4$' is hydrogen when $R_2$ and $R_4$ together form the heterocyclic ring, and $R_4$ is hydrogen when $R_2$ and $R_4$', together form the heterocyclic ring. $R_7$' is hydrogen when $R_6$ and $R_7$ together form the heterocyclic ring, and $R_7$ is hydrogen when $R_6$ and $R_7$' together form the heterocyclic ring.

$R_9$ may be —O-$PG_6$, a natural amino acid residue, an amino acid analog residue, or —O-RES, where RES is a solid-phase synthesis CTC, Wang, or SASRIN resin. $R_4$ and $R_4$', or $R_7$ and $R_7$', may be each independently methyl or ethyl, and $R_4$ and $R_4$' or $R_7$ and $R_7$' may, together with the nitrogen atom and carbon atom to which they are attached, form a 5- or 6-membered alicyclic ring.

When $R_4$' and $R_7$' are hydrogen, $R_4$ and $R_7$ may be each independently hydrogen, or alkyl selected from the group consisting of methyl, ethyl, isopropyl, isobutyl, and sec-butyl, or optionally substituted phenylmethyl, optionally substituted phenylethyl, benzyloxymethyl, 1-benzyloxyethyl, 2-benzyloxyethyl, tert-butoxycarbonylmethyl, methoxycarbonylmethyl, tert-butoxycarbonylethyl, methoxycarbonylethyl, tert-butoxycarbamoylbutyl, N,N-dimethylaminocarbonyl, piperidylcarbonyl, pyrrolidylcarbonyl, N,N-dimethylaminocarbonylmethyl, piperidylcarbonylmethyl, pyrrolidylcarbonylmethyl, N,N-dimethylaminocarbonylethyl, piperidylcarbonylethyl, or pyrrolidylcarbonylethyl.

In some aspects, the starting peptide compound may comprise one or more additional natural amino acid residues and/or amino acid analog residues, in addition to one or more structures represented by general formula (I).

In some aspects, the starting peptide compound comprises at least one protecting group removable by the method of the present invention. Such a protecting group may be contained in a structure represented by general formula (I), or may be contained in an amino acid residue other than the structure represented by general formula (I).

In some aspects, the starting peptide compound comprises at least one resin for solid-phase synthesis that is removable by the method of the present invention. Such a resin may be contained in a structure represented by general formula (I), or may be contained in an amino acid residue other than the structure represented by general formula (I).

In some aspects, the resin for solid-phase synthesis is bound to the carboxyl group contained in the C-terminal amino acid residue of the starting peptide compound.

In some aspects, the starting peptide compound to be subjected to deprotection and/or resin removal comprises at the C-terminus a structure in which at least two amino acid residues are linked to each other, wherein the structure is represented by general formula (II) below.

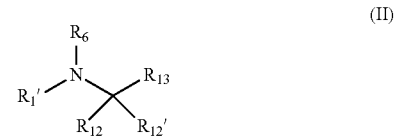

(II)

$R_{1'}$ is a group represented by formula (III):

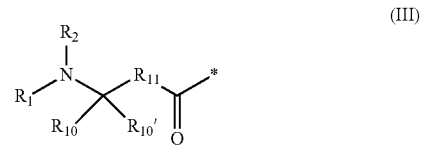

(III)

wherein * represents the point of attachment.

In formula (III), R1 is hydrogen, PG1, a natural amino acid residue, or an amino acid analog residue.

In formula (III), R2 is selected from the group consisting of hydrogen and C1-C6 alkyl, or R2 and R10 or R2 and R10', together with the nitrogen atom and carbon atom to which they are attached, form a 3- to 7-membered heterocyclic ring optionally substituted with hydroxy or C1-C4 alkoxy. R10' is hydrogen when $R_2$ and $R_{10}$ together form the heterocyclic ring, or $R_{10}$ is hydrogen when $R_2$ and $R_{10'}$ together form the heterocyclic ring.

In some aspects, when $R_2$ is $C_1$-$C_6$ alkyl, the $C_1$-$C_6$ alkyl is preferably methyl, ethyl, propyl, butyl, or pentyl.

In some aspects, when $R_2$ and $R_{10}$, or $R_2$ and $R_{10'}$, together with the nitrogen atom and carbon atom to which they are attached, form a 3- to 7-membered heterocyclic ring optionally substituted with hydroxy or $C_1$-$C_4$ alkoxy, the 3- to 7-membered heterocyclic ring formed is preferably an azetidine ring, a pyrrolidine ring, or a piperidine ring.

In formula (III), except when $R_2$ and $R_{10}$ or $R_2$ and $R_{10'}$ together form the heterocyclic ring, (a) $R_{10'}$ is hydrogen, and $R_{10}$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_8$, N-$PG_9$-indol-3-ylmethyl, 4-($PG_8$O)benzyl, $PG_8$-O-methyl (i.e., —$CH_2$—O-$PG_8$), 1-($PG_8$O)ethyl, 2-($PG_8$O)ethyl, $PG_8$-OCO($CH_2$)—, $PG_8$-OCO($CH_2$)$_2$—, $PG_9$N-n-butyl, —CON($R_{16A}$)($R_{16B}$), —$CH_2$—CON($R_{16A}$)($R_{16B}$), and —($CH_2$)$_2$CON($R_{16A}$)($R_{16B}$), (b) $R_{10}$ and $R_{10'}$ are independently optionally substituted $C_1$-$C_6$ alkyl, $C_3$-$C_6$ cycloalkyl, or $C_3$-$C_6$ cycloalkyl-$C_1$-$C_4$ alkyl, or (c) $R_{10}$ and $R_{10'}$, together with the carbon atom to which they are attached, form a 3- to 7-membered alicyclic ring.

The combination of $R_{10}$ and $R_{10'}$ is preferably a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, optionally substituted phenyl and a hydrogen atom, optionally substituted phenylmethyl and a hydrogen atom, optionally substituted phenylethyl and a hydrogen atom, 2-(methylthio) ethyl and a hydrogen atom, —$CH_2SPG_8$ and a hydrogen atom, N-$PG_9$-indol-3-ylmethyl and a hydrogen atom, 4-($PG_8O$)benzyl and a hydrogen atom, $PG_8$-O-methyl and a hydrogen atom, 1-($PG_8O$)ethyl and a hydrogen atom, 2-($PG_8O$)ethyl and a hydrogen atom, $PG_8$-OCO($CH_2$)— and a hydrogen atom, $PG_8$-OCO($CH_2$)$_2$— and a hydrogen atom, $PG_9$N-n-butyl and a hydrogen atom, —CON($R_{16A}$)($R_{16B}$) and a hydrogen atom, —$CH_2$—CON($R_{16A}$)($R_{16B}$) and a hydrogen atom, —($CH_2$)$_2$CON($R_{16A}$)($R_{16B}$) and a hydrogen atom, methyl and methyl, or methyl and ethyl. When $R_{10}$ and $R_{10'}$, together with the carbon atom to which they are attached, form a 3- to 7-membered alicyclic ring, the alicyclic ring is preferably a cyclopropyl ring, a cyclobutyl ring, a cyclopentyl ring, or a cyclohexyl ring.

In formula (III), $R_1$ is a single bond or —C($R_{11A}$)($R_{11B}$)—; and $R_{11A}$ and $R_{11B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl.

$R_{11}$ is preferably a single bond or —C($R_{11A}$)($R_{11B}$)— where the combination of $R_{11A}$ and $R_{11B}$ is a hydrogen atom and a hydrogen atom, methyl and a hydrogen atom, ethyl and a hydrogen atom, isopropyl and a hydrogen atom, isobutyl and a hydrogen atom, cyclopropyl and a hydrogen atom, cyclopropylmethyl and a hydrogen atom, optionally substituted phenyl and a hydrogen atom, optionally substituted phenylmethyl and a hydrogen atom, optionally substituted phenylethyl and a hydrogen atom, methyl and methyl, or methyl and ethyl.

In formula (II), $R_{12}$ and $R_{12'}$ are independently selected from the group consisting of hydrogen, $PG_{10}$-O-methyl (i.e., —$CH_2$—O-$PG_{10}$), —($CH_2$)$_n$COO-$PG_{10}$, —($CH_2$)$_n$COO—RES, and —($CH_2$)$_n$CONH-RES. RES is a resin for solid-phase synthesis, and n is 0, 1, or 2.

In some aspects, when used for the resin removal method of the present invention, either one of R12 and R12' is preferably selected from —(CH2)nCOO—RES and —(CH2)nCONH—RES.

In formula (II), R6 is selected from the group consisting of hydrogen and C1-C6 alkyl. In some aspects, when R6 is C1-C6 alkyl, the C1-C6 alkyl is preferably methyl, ethyl, propyl, butyl, or pentyl.

In formulas (II) and (III), preferably, either or both of R2 and R6 are other than hydrogen, and more preferably, either or both of R2 and R6 are C1-C6 alkyl.

In formula (II), R13 is C1-C4 alkyl or —(CH2)mCON(R17A)(R17B), wherein m is 0, 1, or 2, and R17A and R17B are independently hydrogen or C1-C4 alkyl, or R17A and R17B, together with the nitrogen atom to which they are attached, form a 4- to 8-membered ring optionally comprising one or more additional heteroatoms.

In some aspects, when R13 is C1-C4 alkyl, the C1-C4 alkyl is preferably methyl or ethyl.

In some aspects, when R17A and R17B, together with the nitrogen atom to which they are attached, form a 4- to 8-membered ring optionally comprising one or more additional heteroatoms, the ring formed is preferably an azetidine ring, a pyrrolidine ring, a piperidine ring, a piperazine ring, or a morpholine ring.

In formula (II), R16A and R16B are independently hydrogen or C1-C4 alkyl, or R16A and R16B, together with the nitrogen atom to which they are attached, form a 4- to 8-membered ring optionally comprising one or more additional heteroatoms.

When R16A and R16B are C1-C4 alkyl, the C1-C4 alkyl is preferably methyl, ethyl, or propyl.

When R16A and R16B, together with the nitrogen atom to which they are attached, form a 4- to 8-membered ring optionally comprising one or more additional heteroatoms, the 4- to 8-membered ring is preferably an azetidine ring, a pyrrolidine ring, a piperidine ring, a piperazine ring, or a morpholine ring.

PG1 is selected from the group consisting of Fmoc, Boc, Alloc, Cbz, Teoc, and trifluoroacetyl.

$PG_1$ is preferably Fmoc, Boc, or Cbz.

In formula (II), $PG_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl.

$PG_8$ is preferably methyl, allyl, t-Bu, trityl, methoxytrityl, cumyl, THP, optionally substituted aryl, optionally substituted aryl-$C_1$-$C_4$ alkyl, or optionally substituted heteroaryl-$C_1$-$C_4$ alkyl.

In formula (II), PG9 is selected from the group consisting of hydrogen, Fmoc, Boc, Alloc, Cbz, Teoc, methoxycarbonyl, t-Bu, trityl, cumyl, and benzyl. PG9 is preferably Fmoc, Boc, Cbz, t-Bu, or trityl.

In formula (II), PG10 is selected from the group consisting of t-Bu, trityl, cumyl, benzyl, methyl, ethyl, allyl, optionally substituted aryl, optionally substituted aryl-C1-C4 alkyl, optionally substituted heteroaryl-C1-C4 alkyl, and 2-(trimethylsilyl)ethyl. PG10 is preferably t-Bu, trityl, cumyl, benzyl, methyl, or allyl.

In some aspects, PG1 to PG10 that can be comprised in general formulas (I) to (III) may be each independently a protecting group that can be removed by the deprotection method of the present invention. Such protecting groups include t-Bu, triphenylmethyl, 2-(trimethylsilyl)-ethyl, Boc, Teoc, Cbz, methoxycarbonyl, tetrahydropyranyl, and 1-ethoxyethyl.

In some aspects, PG1 to PG10 may be each independently a protecting group that cannot be removed by the deprotection method of the present invention. Such protecting groups include Fmoc and Alloc.

In some aspects, PG1 to PG10 may be each independently a group that does not function as a protecting group, for example, a group that cannot be removed or can be structurally transformed. Examples of such protecting groups include those described in Greene's "Protective Groups in Organic Synthesis" (5th ed., John Wiley & Sons 2014).

Structures represented by general formula (II), in which at least two amino acid residues are linked to each other, include many such structures easily subjected to cleavage or rearrangement when known deprotection or resin removal conditions are used. Such cleavage and rearrangement may be called damage. Only the protecting groups of interest or resins for solid-phase synthesis can be selectively and efficiently removed without such damage using the reaction conditions of the present invention.

In some aspects, structures represented by general formula (II), in which two amino acid residues are linked to each other, include those in which one N-substituted amino acid is linked to one N-unsubstituted amino acid and those in which two N-substituted amino acids are linked to each other. Specific examples of such structures include structures in which R1' of general formula (II) is represented by general formula (III) and in which $R_{11}$ of formula (III) is —C($R_{11A}$)($R_{11B}$)— (formula IV) or $R_{11}$ of formula (III) is a single bond (formula V).

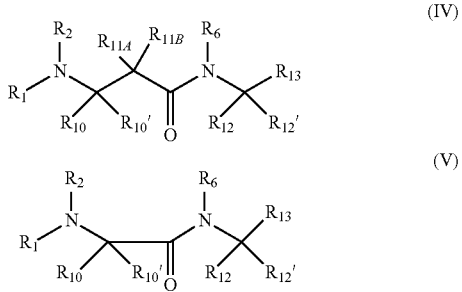

Each group in formulas (IV) and (V) may be the same as that in formulas (II) and (III) above.

In some aspects, in formulas (IV) and (V), R1 is hydrogen, PG1, a natural amino acid residue, or an amino acid analog residue.

In some aspects, in formulas (IV) and (V), R1 is hydrogen, PG1, a natural amino acid residue, or an amino acid analog residue, and R2 and R10 are preferably methyl, ethyl, propyl, butyl, or pentyl.

In some aspects, in formulas (IV) and (V), R1 is hydrogen, PG1, a natural amino acid residue, or an amino acid analog residue, and R2 and R10 or R2 and R10' preferably each independently, together with the nitrogen atom and carbon atom to which they are attached, form a 3- to 7-membered heterocyclic ring optionally substituted with hydroxy or C1-C4 alkoxy. R10' is hydrogen when R2 and R10 together form the heterocyclic ring, and R10 is hydrogen when R2 and R10' together form the 3- to 7-membered heterocyclic ring.

In some aspects, in formulas (IV) and (V), R10' may be hydrogen, and R10 may be selected from the group consisting of hydrogen, optionally substituted C1-C6 alkyl, C3-C6 cycloalkyl, C3-C6 cycloalkyl-C1-C4 alkyl, optionally substituted phenyl, optionally substituted phenylmethyl, optionally substituted phenylethyl, 2-(methylthio)ethyl, —CH2SPG8, N-PG9-indol-3-ylmethyl, 4-(PG8O)benzyl, PG8-O-methyl, 1-(PG8O)ethyl, 2-(PG8O)ethyl, PG8-OCO (CH2)-, PG8-OCO(CH2)2-, PG9N-n-butyl, —CON(R16A) (R16B), —CH2-CON(R16A)(R16B), and —(CH2)2CON (R16A)(R16B).

In some aspects, in formulas (IV) and (V), preferably, R6 may be C1-C6 alkyl, which is preferably methyl, ethyl, propyl, butyl, or pentyl.

In some aspects, in formulas (IV) and (V), R13 may be C1-C4 alkyl, which is preferably methyl, ethyl, propyl, or butyl, and more preferably methyl or ethyl.

In some aspects, in formulas (IV) and (V), R13 may be —(CH$_2$)$_m$CON($R_{17A}$)($R_{17B}$), and m is 0, 1, or 2. In this case, $R_{17A}$ and/or $R_{17B}$ may be independently $C_1$-$C_4$ alkyl, and the $C_1$-$C_4$ alkyl is preferably methyl or ethyl. $R_{17A}$ and $R_{17B}$ may, together with the nitrogen atom to which they are attached, form a 4- to 8-membered ring optionally comprising one or more additional heteroatoms, and the 4- to 8-membered ring is preferably an azetidine ring, a pyrrolidine ring, a piperidine ring, a piperazine ring, or a morpholine ring.

In some aspects, in formulas (IV) and (V), R12 and R12' are independently selected from the group consisting of hydrogen, PG10-O-methyl, —(CH2)nCOO—PG10, —(CH2)nCOO—RES, and —(CH2)nCONH—RES. When R12 and R12' is PG10-O-methyl, —(CH2)nCOO—PG10, —(CH2)nCOO—RES, or —(CH2)nCONH—RES, n is 0, 1, or 2, and PG10 is preferably t-Bu, trityl, cumyl, benzyl, methyl, or allyl. RES is a resin for solid-phase synthesis, and preferably CTC resin or Wang resin.

In some aspects, when used for the resin removal method of the present invention, either one of R12 and R12' is preferably selected from —(CH2)nCOO—RES and —(CH2)nCONH—RES.

In some aspects, in formulas (IV) and (V), more preferably, R1 is hydrogen, $PG_1$, a natural amino acid residue, or an amino acid analog residue;

$R_2$ is methyl and ethyl; and/or $R_2$ and $R_{10}$, together with the nitrogen atom and carbon atom to which they are attached, form a 4- to 6-membered heterocyclic ring optionally substituted with hydroxy or $C_1$-$C_4$ alkoxy.

$R_{10}$ and $R_{10'}$ may be each independently selected from methyl or ethyl, or $R_{10}$ and $R_{10'}$ may together form a 5- or 6-membered alicyclic ring. Alternatively, $R_{10'}$ may be hydrogen, and $R_{10}$ may be hydrogen, or alkyl selected from methyl, ethyl, isopropyl, isobutyl, and sec-butyl, or optionally substituted phenylmethyl, optionally substituted phenylethyl, benzyloxymethyl, 1-benzyloxyethyl, 2-benzyloxyethyl, tert-butoxycarbonylmethyl, methoxycarbonylmethyl, tert-butoxycarbonylethyl, methoxycarbonylethyl, tert-butoxycarbamoylbutyl, N,N-dimethylaminocarbonyl, piperidylcarbonyl, pyrrolidylcarbonyl, N,N-dimethylaminocarbonylmethyl, piperidylcarbonylmethyl, pyrrolidylcarbonylmethyl, N,N-dimethylaminocarbonylethyl, piperidylcarbonylethyl, or pyrrolidylcarbonylethyl.

$R_6$ may be methyl or ethyl, and $R_{13}$ may be methyl or —(CH$_2$)$_m$CON($R_{17A}$)($R_{17B}$). When R13 is —(CH$_2$)$_m$CON($R_{17A}$)($R_{17B}$), $R_{17A}$ and $R_{17B}$, together with the nitrogen atom to which they are attached, form a piperidine ring.

$R_{12}$ and $R_{12'}$ are independently selected from the group consisting of hydrogen, $PG_{10}$-O-methyl, —(CH$_2$)$_n$ COO—$PG_{10}$, —(CH$_2$)$_n$COO—RES, and —(CH$_2$)$_n$ CONH—RES.

In some aspects, the starting peptide compound may comprise one or more additional natural amino acid residues and/or amino acid analog residues, in addition to a structure represented by general formula (II). The starting peptide compound may comprise one or more structures represented by general formula (I), may comprise a structure represented by general formula (II) at the C-terminus, and optionally may further comprise one or more additional natural amino acid residues and/or amino acid analog residues. The peptide compound may be formed by secondary amides, tertiary amides, or a mixture of secondary and tertiary amides.

In some aspects, the starting peptide compound comprises at least one protecting group removable by the method of the present invention. Such a protecting group may be contained in a structure represented by general formula (II), or may be contained in an amino acid residue other than the structure represented by general formula (II).

In some aspects, the starting peptide compound comprises at least one resin for solid-phase synthesis that is removable by the method of the present invention. When the starting peptide compound comprises a structure represented by general formula (II), such a resin is included in the structure represented by general formula (II).

In some aspects, the present invention relates to a method of producing an amide compound in which a protecting group removable by a silylating agent is removed, the method comprising the step of contacting a starting amide compound with the silylating agent in a solvent and thereby removing the protecting group from the starting amide compound.

In some aspects, the present invention relates to a method of producing an amide compound in which a resin for solid-phase synthesis is removed, the method comprising the step of contacting a starting amide compound with a silylating agent in a solvent and thereby removing the starting amide compound from the resin for solid-phase synthesis In some aspects, the starting amide compound to be subjected to deprotection/resin removal is represented by general formula (II).

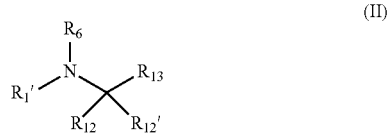

(II)

In formula (II), $R_{1'}$ is a hydrogen atom or $PG_7$, and the other groups are the same as defined above. $R_6$ is preferably $C_1$-$C_6$ alkyl. $PG_7$ is selected from the group consisting of Fmoc, Boc, Alloc, Cbz, Teoc, and trifluoroacetyl and is preferably Fmoc, Boc, or Cbz.

Starting amide compounds represented by general formula (II), in particular, N-substituted compounds are susceptible to damage such as rearrangement when known deprotection or resin removal conditions are used. Only the protecting groups of interest or resin for solid-phase synthesis can be selectively and efficiently removed without such damage using the reaction conditions of the present invention.

Herein, the "silylating agent" is not particularly limited as long as it can be used for the deprotection or resin removal reaction of the present invention, and the term refers to an agent that can function as a deprotecting agent or reagent and/or a resin-removing agent or reagent. Herein, "silylating agents" may be called deprotecting agents or reagents and/or resin-removing agents or reagents. The silylating agent can be prepared, for example, by mixing the silyl compound with an electrophilic species scavenger or mixing an acid with an electrophilic species scavenger having a silyl group in a solvent. The mixing of the silyl compound with an electrophilic species scavenger or the mixing of an acid with an electrophilic species scavenger having a silyl group may be performed previously, or in a solvent, or in the presence or absence of the starting peptide compound.

Examples of the "silyl compound" as used herein include silyl compounds having a leaving group (X) represented by formula 1:

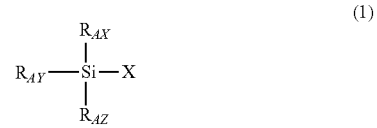

(1)

wherein $R_{AX}$, $R_{AY}$, and $R_{AZ}$ are independently $C_1$-$C_4$ alkyl or phenyl, and X is selected from the group consisting of —OTf, —OClO$_3$, Cl, Br, and I.

Preferably, $R_{AX}$, $R_{AY}$, and $R_{AZ}$ may be independently selected from methyl, ethyl, i-propyl, t-butyl, and phenyl.

More specific examples of such silyl compounds include TMSOTf, TESOTf, TBSOTf, TIPSOTf, TBDPSOTf, TTMSOTf, TMSCl, TMSBr, TMSOClO$_3$, and TMSI.

The "acid" that can be used herein for preparing a silylating agent is not particularly limited as long as it can generate the silyl compound, and examples thereof include acids represented by HX (wherein X is as defined for X of formula (1)).

As used herein, the term "electrophilic species scavenger" refers to a compound that can form an adduct or salt with a proton or is reactive with a cationic species and that is less susceptible to silylation. Such electrophilic species scavengers include imidates (formula 2), amides (formula 3), ketene acetals (formula 4), ketene alkoxy hemiaminals (formula 4), enol ethers (formula 4), enol esters (formula 4), imines (formula 5), amines (formula 6), diamines (formula 7), dialkylcarbodiimides (formula 8), ureas (formula 9), or urethanes (formula 10). They may have a substituted silyl group, specific examples of the substituted silyl group include TMS (trimethylsilyl), TES (triethylsilyl), TBS (tributylsilyl), TIPS (triisopropylsilyl), and TBDPS (t-butyldimethylsilyl).

The imidates are represented by formula 2:

(2)

wherein $R_B$ is a substituted silyl group and $R_C$ is a substituted silyl group, or $R_B$ and $R_C$, together with the nitrogen atom and carbon atom to which they are attached, form a 5- to 7-membered ring; and $R_D$ is $C_1$-$C_4$ alkyl optionally substituted with one or more fluorine atoms or is optionally substituted methylene, wherein when $R_D$ is optionally substituted methylene, formula 2 is dimerized to form a compound represented by the formula below:

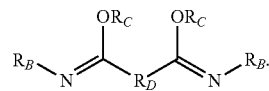

Preferred imidates include N-silyl imidates represented by formula 2-1 and bisoxazolines represented by formula 2-2 below:

(2-1)
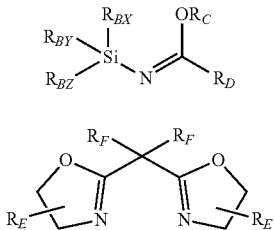

(2-2)
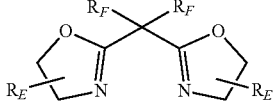

(2-2-1-1)
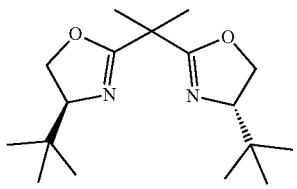

wherein
$R_{BX}$, $R_{BY}$, and $R_{BZ}$ are independently $C_1$-$C_4$ alkyl or phenyl, $R_C$ and $R_D$ are as defined above; and $R_E$ and $R_F$ are independently $C_1$-$C_4$ alkyl.

Preferably, $R_{BX}$, $R_{BY}$, and $R_{BZ}$ may be independently selected from methyl, ethyl, i-propyl, t-butyl, and phenyl.

Preferred N-silyl imidates include N,O-bis(trimethylsilyl)acetamides represented by formula 2-1-1. Preferred bisoxazolines include 4-substituted bisoxazolines represented by formula 2-2-1.

(2-1-1)
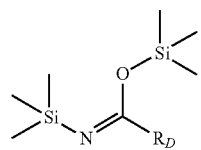

(2-2-1)
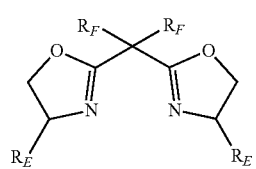

More preferred N-silyl imidates include N,O-bis(trimethylsilyl)acetamide represented by formula 2-1-1-1 and N,O-bis(trimethylsilyl)trifluoroacetamide represented by formula 2-1-1-2. More preferred bisoxazolines include N,O-bis(trimethylsilyl)trifluoroacetamide 2,2'-isopropylidenebis[(4S)-4-tert-butyl-2-oxazoline] represented by formula 2-2-1-1.

(2-1-1-1)
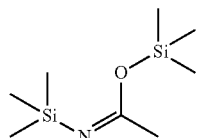

(2-1-1-2)
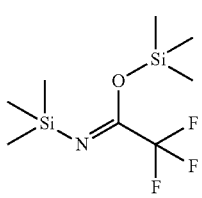

The amides are represented by formula 3:

(3)
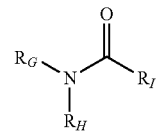

wherein
$R_G$ is a silyl group substituted with one or more $C_1$-$C_4$ alkyl;
$R_H$ is hydrogen or $C_1$-$C_4$ alkyl; and
$R_I$ is hydrogen, or $C_1$-$C_4$ alkyl optionally substituted with one or more fluorine atoms.

Preferred amides include N-silylamides represented by formula 3-1:

(3-1)
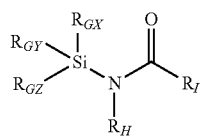

wherein
RGX, RGY, and RGZ are independently $C_1$-$C_4$ alkyl or phenyl; and
$R_H$ and $R_I$ are as defined above.

Preferably, $R_{GX}$, $R_{GY}$, and $R_{GZ}$ may be independently selected from methyl, ethyl, i-propyl, t-butyl, and phenyl.

Preferred N-silylamides include N-trimethylsilylacetamides represented by formula 3-1-1:

(3-1-1)
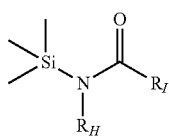

wherein RH and RI are as defined above.

More preferably, N-trimethylsilylacetamides include N-methyl-N-trimethylsilylacetamide represented by formula 3-1-1-1 and N-methyl-N-trimethylsilyltrifluoroacetamide represented by formula 3-1-1-2.

(3-1-1-1)
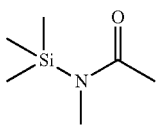

-continued (3-1-1-2)

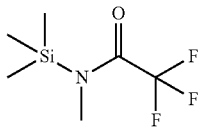

The ketene acetals, ketene alkoxy hemiaminals, enol ethers, and enol esters are each represented by formula 4:

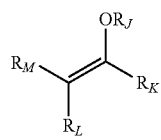

(4)

wherein
(a-1) RJ is a substituted silyl group, RK is C1-C4 alkoxy, and RM and RL are independently hydrogen or $C_1$-$C_4$ alkyl;
(a-2) $R_J$ is a substituted silyl group, $R_M$ is hydrogen or $C_1$-$C_4$ alkyl, and $R_K$ and $R_L$, together with the carbon atoms to which they are attached, form a 5- to 8-membered ring comprising an oxygen atom;
(b-1) $R_J$ is a substituted silyl group, $R_K$ is $C_1$-$C_4$ alkyl, and $R_M$ and $R_L$ are independently hydrogen or $C_1$-$C_4$ alkyl;
(b-2) $R_J$ is a substituted silyl group, $R_M$ is hydrogen or $C_1$-$C_4$ alkyl, and $R_K$ and $R_L$, together with the carbon atoms to which they are attached, form a 5- to 8-membered ring;
(c-1) $R_J$ and $R_M$, together with the carbon atoms to which they are attached, form a 5- to 7-membered ring comprising an oxygen atom, $R_K$ is hydrogen or $C_1$-$C_4$ alkyl, and $R_L$ IS $C_1$-$C_4$ alkyl;
(c-2) $R_J$ and $R_M$, together with the carbon atoms to which they are attached, form a 5- to 7-membered ring comprising an oxygen atom, and $R_K$ and $R_L$, together with the carbon atoms to which they are attached, form a 5- to 8-membered ring;
(d-1) $R_J$ is $C_1$-$C_4$ alkyl and $R_M$, $R_K$, and $R_L$ are independently hydrogen or $C_1$-$C_4$ alkyl;
(d-2) $R_J$ is $C_1$-$C_4$ alkyl, $R_M$ is hydrogen or $C_1$-$C_4$ alkyl, and $R_K$ and $R_L$, together with the carbon atoms to which they are attached, form a 5- to 8-membered ring;
(e-1) $R_J$ is $C_1$-$C_3$ alkylcarbonyl and $R_M$, $R_K$, and $R_L$ are independently hydrogen or $C_1$-$C_4$ alkyl;
(e-2) $R_J$ is $C_1$-$C_3$ alkylcarbonyl, RM is hydrogen or $C_1$-$C_4$ alkyl, and RK and RL, together with the carbon atoms to which they are attached, form a 5- to 8-membered ring;
(f-1) RJ is a substituted silyl group or $C_1$-$C_4$ alkyl, RK is optionally substituted di-$C_1$-$C_4$ alkylamino, and RM and RL are independently hydrogen or $C_1$-$C_4$ alkyl; or
(f-2) RJ is a substituted silyl group or $C_1$-$C_4$ alkyl, RM is hydrogen or $C_1$-$C_4$ alkyl, and RK and RL, together with the carbon atoms to which they are attached, form a 5- to 8-membered ring comprising a nitrogen atom, and the 5- to 8-membered ring is optionally substituted with $C_1$-$C_4$ alkyl.

Here, preferred examples of the $C_1$-$C_4$ alkyl include methyl, ethyl, n-propyl, isopropyl, n-butyl, i-butyl, and t-butyl. Preferred examples of the $C_1$-$C_3$ alkylcarbonyl include acetyl and propionyl.

Preferred ketene acetals include silylketene acetals represented by formula 4-1:

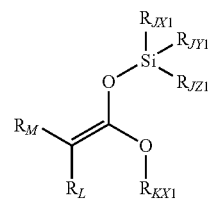

(4-1)

wherein
$R_{JX1}$, $R_{JY1}$, and $R_{JZ1}$ are independently $C_1$-$C_4$ alkyl or phenyl;
$R_{KX1}$ is $C_1$-$C_4$ alkyl; and
$R_L$ and $R_M$ are as defined above.

Here, preferred examples of the $C_1$-$C_4$ alkyl include methyl, ethyl, n-propyl, isopropyl, n-butyl, i-butyl, and t-butyl.

Preferably, $R_{JX1}$, $R_{JY1}$, and $R_{JZ1}$ may be independently selected from methyl, ethyl, i-propyl, t-butyl, and phenyl.

Preferred ketene silyl acetals include ketene trimethylsilyl acetals represented by formula 4-1-1:

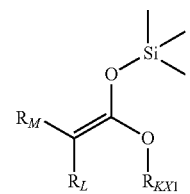

(4-1-1)

wherein $R_{KX1}$, $R_L$, and $R_M$ are as defined above.

Preferred $R_{KX1}$, $R_L$, and $R_M$ include methyl, ethyl, n-propyl, isopropyl, n-butyl, i-butyl, and t-butyl.

Preferred ketene trimethylsilyl acetals include dimethylketene methyl trimethylsilyl acetal represented by formula 4-1-1-1.

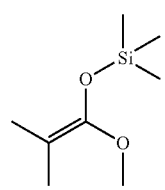

(4-1-1-1)

Preferred enol ethers include silylenol ethers represented by formula 4-2:

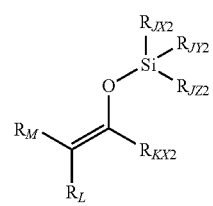

(4-2)

wherein $R_{JX2}$, $R_{JY2}$, and $R_{JZ2}$ are independently $C_1$-$C_4$ alkyl or phenyl;

$R_{KX2}$ is hydrogen or $C_1$-$C_4$ alkyl; and $R_L$ and $R_M$ are as defined above.

Preferred $C_1$-$C_4$ alkyl of $R_{KX1}$, $R_L$, and $R_M$ include methyl, ethyl, n-propyl, isopropyl, n-butyl, i-butyl, and t-butyl.

Preferably, $R_{JX2}$, $R_{JY2}$, and $R_{JZ2}$ are independently selected from the group consisting of methyl, ethyl, i-propyl, t-butyl, and phenyl.

Preferred silyl enol ethers include trimethylsilyl enol ethers represented by formula 4-2-1:

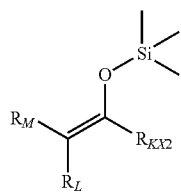

(4-2-1)

wherein $R_{KX2}$, $R_L$, and $R_M$ are as defined above.

Preferred trimethylsilyl enol ethers include isopropenyloxytrimethylsilane represented by formula 4-2-1-1.

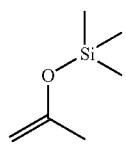

4-2-1-1

In another embodiment, preferred enol ethers include cyclic enol ethers represented by formula 4-3:

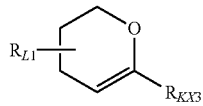

(4-3)

wherein $R_{KX3}$ and RU are independently hydrogen or $C_1$-$C_4$ alkyl.

Preferred cyclic enol ethers include dihydropyran represented by formula 4-3-1.

(4-3-1)

In another embodiment, preferred enol ethers include linear enol ethers, and preferred linear enol ethers include ethyl vinyl ether represented by formula 4-4.

(4-4)

The imines are represented by formula 5:

(5)

wherein $R_N$, $R_{N'}$, and $R_O$ are independently hydrogen or $C_1$-$C_4$ alkyl.

Preferred $C_1$-$C_4$ alkyl of $R_N$, $R_{N'}$, and $R_O$ include methyl, ethyl, n-propyl, isopropyl, n-butyl, i-butyl, and t-butyl.

Preferred imines include ketimines represented by formula 5-1:

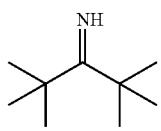

(5-1)

wherein $R_N$ is as defined above.

Preferred $R_N$ and $R_{N'}$ include methyl, ethyl, n-propyl, isopropyl, n-butyl, i-butyl, and t-butyl.

Preferred ketimines include 2,2,4,4-tetramethylpentanone imine represented by formula 5-1-1.

(5-1-1)

The amines are represented by formula 6:

(6)

wherein $R_P$ is a substituted silyl group; and $R_Q$ is a substituted silyl group or $C_1$-$C_4$ alkyl and $R_R$ is hydrogen, a substituted silyl group, or $C_1$-$C_4$ alkyl, or $R_Q$ and $R_R$, together with the nitrogen atom to which they are attached, form a 5- to 8-membered heterocyclic ring comprising an oxygen atom.

Preferred amines include disilylamines represented by formula 6-1:

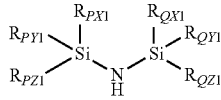
(6-1)

wherein $R_{PX1}$, $R_{PY1}$, $R_{PZ1}$, $R_{QX1}$, $R_{QY1}$, and $R_{QZ1}$ are independently $C_1$-$C_4$ alkyl or phenyl.

Preferably, $R_{PX1}$, $R_{PY1}$, $R_{PZ1}$, $R_{QX1}$, $R_{QY1}$, and $R_{QZ1}$ are independently selected from the group consisting of methyl, ethyl, i-propyl, t-butyl, and phenyl.

Preferred disilylamines include 1,1,1,3,3,3-hexamethyldisilazane (HMDS) represented by formula 6-1-1.

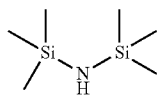
(6-1-1)

In another embodiment, preferred amines include N-dialkyl-N-silylamines represented by formula 6-2:

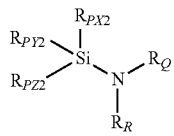
(6-2)

wherein $R_{PX2}$, $R_{PY2}$, and $R_{PZ2}$ are independently $C_1$-$C_4$ alkyl or phenyl; and $R_Q$ and $R_R$ are as defined above.

Preferred $C_1$-$C_4$ alkyl of $R_{PX2}$, $R_{PY2}$, and $R_{PZ2}$ include methyl, ethyl, n-propyl, isopropyl, n-butyl, i-butyl, and t-butyl.

Preferably, $R_{PX2}$, $R_{PY2}$, and $R_{PZ2}$ are independently selected from the group consisting of methyl, ethyl, i-propyl, t-butyl, and phenyl.

Preferred N-dialkyl-N-silylamines include N-dialkyl-N-trimethylsilylamines represented b formula 6-2-1:

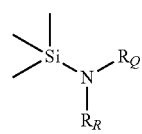
(6-2-1)

wherein $R_Q$ and $R_R$ are as defined above.

Preferred N-dialkyl-N-trimethylsilylamines include N-trimethylsilylmorpholine represented by formula 6-2-1-1 and N-trimethylsilyldiethylamine represented by formula 6-2-1-2.

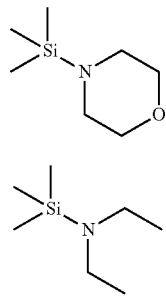
(6-2-1-1)

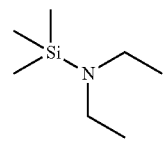
(6-2-1-2)

In another embodiment, preferred amines include N-alkyl-N-disilylamines represented by formula 6-3:

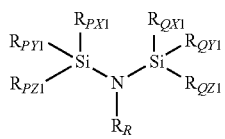
(6-3)

wherein $R_{QX3}$, $R_{QY3}$, $R_{QZ3}$, $R_{RX1}$, $R_{RY1}$, and $R_{RZ1}$ are independently $C_1$-$C_4$ alkyl or phenyl; and $R_R$ is $C_1$-$C_4$ alkyl.

Specifically, for example, $R_{QX3}$, $R_{QY3}$, $R_{QZ3}$, $R_{RX1}$, $R_{RY1}$, and $R_{RZ1}$ may be independently selected from methyl, ethyl, i-propyl, t-butyl, and phenyl.

Preferred $C_1$-$C_4$ alkyl of $R_R$ include methyl, ethyl, n-propyl, isopropyl, n-butyl, i-butyl, and t-butyl.

Preferred N-alkyl-N-disilylamines include N-alkyl-N-bistrimethylsilylamines represented by formula 6-3-1:

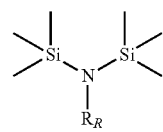
(6-3-1)

wherein $R_R$ is $C_1$-$C_4$ alkyl.

Preferred $C_1$-$C_4$ alkyl of $R_R$ include methyl, ethyl, n-propyl, isopropyl, n-butyl, i-butyl, and t-butyl.

In another embodiment, preferred amines include N-alkyl-N-silylamines represented by formula 6-4:

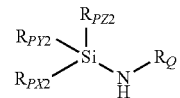
(6-4)

wherein $R_{PX2}$, $R_{PY2}$, and $R_{PZ2}$ are independently $C_1$-$C_4$ alkyl or phenyl; and $R_Q$ is $C_1$-$C_4$ alkyl.

Preferably, $R_{PX2}$, $R_{PY2}$, and $R_{PZ2}$ are independently selected from the group consisting of methyl, ethyl, i-propyl, t-butyl, and phenyl.

Preferred $C_1$-$C_4$ alkyl of $R_Q$ include methyl, ethyl, n-propyl, isopropyl, n-butyl, i-butyl, and t-butyl.

Preferred N-alkyl-N-silylamines include N-alkyl-N-trimethylsilylamines represented by formula 6-4-1:

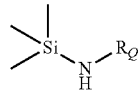

(6-4-1)

wherein $R_Q$ is $C_1$-$C_4$ alkyl.

Preferred $C_1$-$C_4$ alkyl of $R_Q$ include methyl, ethyl, n-propyl, isopropyl, n-butyl, i-butyl, and t-butyl.

Preferred N-alkyl-N-trimethylsilylamines include N-tert-butyltrimethylsilylamine represented by formula 6-4-1-1.

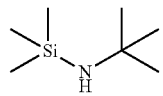

(6-4-1-1)

The diamines are represented by formula 7:

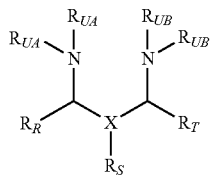

(7)

wherein
X is a single bond or a carbon atom,
wherein when X is a single bond, $R_S$ is absent, $R_{UA}$ and $R_R$, together with the carbon atom and nitrogen atom to which they are attached, form an optionally substituted 6-membered aromatic heterocyclic ring, and $R_{UB}$ and $R_T$, together with the carbon atom and nitrogen atom to which they are attached, form an optionally substituted 6-membered aromatic heterocyclic ring, and when X is a carbon atom, $R_{UA}$ and $R_{UB}$ are independently $C_1$-$C_4$ alkyl and $R_R$, $R_S$, and $R_T$, together with the carbon atoms to which they are attached, form the structure below:

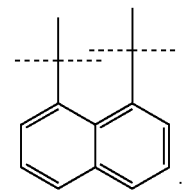

When X in formula 7 is a carbon atom, preferred diamines include tetraalkylnaphthalenediamines represented by formula 7-1:

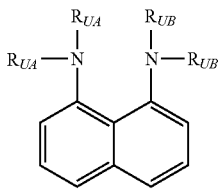

(7-1)

wherein $R_{UA}$ and $R_{UB}$ are independently $C_1$-$C_4$ alkyl.

Preferred tetraalkylnaphthalenediamines include N,N,N',N'-tetramethyl-1,8-naphthalenediamine represented by formula 7-1-1.

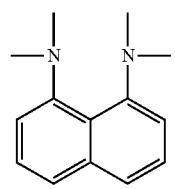

(7-1-1)

In another embodiment, when X in formula 7 is a single bond, preferred diamines include 2,2'-bipyridine represented by formula 7-2-1.

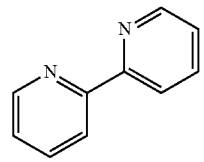

(7-2-1)

The dialkylcarbodiimides are represented by formula 8:

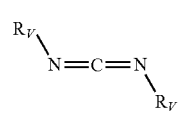

(8)

wherein $R_V$ is $C_1$-$C_4$ alkyl or $C_3$-$C_6$ cycloalkyl.

Preferred $C_1$-$C_4$ alkyl of $R_V$ include methyl, ethyl, n-propyl, isopropyl, n-butyl, i-butyl, t-butyl, and cyclohexyl.

Preferred dialkylcarbodiimides include diisopropylcarbodiimide represented by formula 8-1.

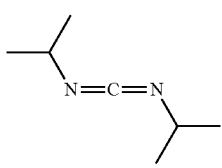

(8-1)

The ureas are represented by formula 9:

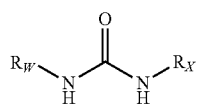

(9)

wherein $R_W$ and $R_X$ are independently $C_1$-$C_4$ alkyl or a substituted silyl group.

Preferred ureas include N,N'-bis(trimethylsilyl)urea represented by formula 9-1.

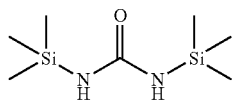

(9-1)

The urethanes are represented by formula 10:

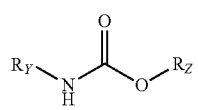

(10)

wherein $R_Y$ and $R_Z$ are independently $C_1$-$C_4$ alkyl or a substituted silyl group.

Preferred urethanes include N,O-bis(trimethylsilyl)urea represented by formula 10-1.

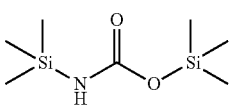

Formula 10-1

In some aspects, silylating agents can be prepared by mixing a peptide compound, a solvent, an electrophilic species scavenger, and a silyl compound or acid in any order. It is preferred to mix the peptide compound with the solvent, then with the electrophilic species scavenger, and subsequently with the silyl compound or acid.

In some aspects, the solvent used may be an aprotic solvent, examples of which include esters, ethers, alkylnitriles, halogenated hydrocarbons, and hydrocarbons. Among them, ethyl acetate, isopropyl acetate, 2-methyltetrahydrofuran, tetrahydrofuran, diethyl ether, methyl tert-butyl ether, dichloromethane, 1,2-dichloroethane, toluene, or acetonitrile is preferred, ethyl acetate, isopropyl acetate, 2-methyltetrahydrofuran, tetrahydrofuran, or 1,2-dichloroethane is more preferred, and ethyl acetate or 2-methyltetrahydrofuran is particularly preferred.

In some aspects, a stoichiometric amount or more of a silyl compound, and an electrophilic species scavenger can be used in order to produce a silylating agent in the present invention to remove a protecting group and/or remove a resin from a peptide compound. In this case, 1 to 5 equivalents, preferably 2 to 4 equivalents, of a silyl compound and 1 to 10 equivalents, preferably 1 to 8 equivalents, of an electrophilic species scavenger can be used for one equivalent of the protecting group to be removed or one equivalent of the resin to be removed which is contained in a peptide, for example.

In some aspects, a silylating agent can be prepared by combining an electrophilic species scavenger with a catalytic amount of, for example, 0.1 to 0.5 equivalent, preferably 0.3 to 0.4 equivalent, of a silyl compound, per one equivalent of the protecting group to be removed or one equivalent of the resin to be removed. In this case, TMSOTf, TESOTf, TBSOTf, TIPSOTf, TBDPSOTf, TTMSOTf, TMSCl, TMSBr, or TMSOClO$_3$ is preferably used as such a silylating agent, and N,O-bis(trimethylsilyl)acetamide, N,O-bis(trimethylsilyl)trifluoroacetamide, N-methyl-N-trimethylsilylacetamide, N-methyl-N-trimethylsilyltrifluoroacetamide, dimethylketene methyl trimethylsilyl acetal, or isopropenyloxytrimethylsilane is preferably used as such an electrophilic species scavenger. In this case, 1 to 10 equivalents, preferably 1 to 8 equivalents, of the electrophilic species scavenger can be used per one equivalent of the protecting group to be removed or one equivalent of the resin to be removed.

In some aspects, a silylating agent can be prepared by combining an electrophilic species scavenger with a catalytic amount of, for example, 0.1 to 0.5 equivalent, preferably 0.3 to 0.4 equivalent, of an acid per one equivalent of the protecting group to be removed or one equivalent of the resin to be removed. In this case, TfOH, HOClO$_3$, HCl, HBr, or HI is preferably used, and TfOH is more preferably used as such an acid. N-silyl imidates (formula 2-1), N-silylamides (formula 3-1), ketene silyl acetals (formula 4-1), and silyl enol ethers (formula 4-2) are preferably used, and N,O-bis(trimethylsilyl)acetamide (formula 2-1-1-1), N,O-bis(trimethylsilyl)trifluoroacetamide (formula 2-1-1-2), N-methyl-N-trimethylsilylacetamide (formula 3-1-1-1), N-methyl-N-trimethylsilyltrifluoroacetamide (formula 3-1-1-2), dimethylketene methyl trimethylsilyl acetal (formula 4-1-1-1), and isopropenyloxytrimethylsilane (formula 4-2-1-1) are more preferably used as such electrophilic species scavengers. Among them, N,O-bis(trimethylsilyl)trifluoroacetamide and N-methyl-N-trimethylsilyltrifluoroacetamide are particularly preferred. In this case, 1 to 10 equivalents, preferably 1 to 8 equivalents, of the electrophilic species scavenger can be used per one equivalent of the protecting group to be removed or one equivalent of the resin to be removed.

In some aspects, the "protecting group removable by a silylating agent" is not particularly limited, as long as the protecting group can be removed by the silylating agent. Specific examples of such protecting groups include protecting groups for carboxyl groups, such as t-Bu, benzyl, triphenylmethyl, cumyl, and 2-(trimethylsilyl)-ethyl; protecting groups for amino groups, such as Boc, Teoc, Cbz, methoxycarbonyl, and cumyl; protecting groups for hydroxy groups, such as tetrahydropyranyl and 1-ethoxyethyl; and protecting groups for SH groups, such as triphenylmethyl and methoxytrityl.

Chemical synthesis methods for start peptide compounds herein include, for example, liquid phase synthesis methods, solid phase synthesis methods using Fmoc synthesis, Boc synthesis, or such, and combinations thereof. In Fmoc synthesis, an amino acid in which the main chain amino group is protected with an Fmoc group, the side-chain functional groups are protected when necessary with protecting groups that are not cleaved by a base such as piperidine, and the main chain carboxylic acid group is not protected, is used as a basic unit. The basic unit is not particularly limited and may be any other combination as long as it has an Fmoc-protected amino group and a carboxylic acid group. For example, a dipeptide may be used as a basic unit. The basic unit to be positioned at the N terminus may be one that is not an Fmoc amino acid. For example, it may be a Boc amino acid, or a carboxylic acid analog that does not have an amino group. The main chain carboxylic acid group is immobilized onto a solid phase by a chemical reaction with a functional group on a solid-phase carrier. Next, the Fmoc group is deprotected by a base such as piperidine or DBU, and the newly generated amino group and a subsequently added basic unit, i.e. a protected amino acid carrying a carboxylic acid, are subjected to a condensation reaction to generate an amide bond. In the condensation reaction, various combinations such as DIC and HOBt, DIC and HOAt, and HATU and DIPEA are possible. Repeating the Fmoc group deprotection and the subsequent amide bond-forming reaction enables generation of the desired peptide sequence. After the desired sequence is obtained, removal of the resin from the solid phase is performed, and the protecting groups introduced as necessary to the side-chain functional groups are deprotected. The deprotection and resin removal methods of the present invention can be provided for removal from solid-phase resins and removal of protecting groups from side chain functional groups. Steps such as cyclization may also be conducted during the solid-phase resin removal step or the deprotection step or finally. For example, side chain carboxylic acids may be condensed with N-terminal amino groups of main chains, and side chain amino groups may be condensed with C-terminal carboxylic acids of main chains. In this case, reaction orthogonality is needed between the C-terminal carboxylic acid and the side chain carboxylic acid to be cyclized, or between the N-terminal amino or hydroxy group of the main chain and the side chain amino group to be cyclized, and the protecting group is selected taking orthogonality of the protecting group into consideration. Reaction products thus obtained can be purified by reverse phase columns, molecular sieve columns, or the like. The details are described in Solid-Phase Synthesis Handbook published by Merck K. K. on May 1, 2002, for example.

Herein, the "resin for solid-phase synthesis" is not particularly limited, as long as it can be used for the synthesis of peptide compounds by the solid-phase method and can be removed by the silylating agent of the present invention. Specific examples of such resins for solid-phase synthesis include those removable under acidic conditions, such as CTC resins, Wang resins, SASRIN resins, trityl chloride resins (Trt resins), 4-methyltrityl chloride resins (Mtt resins), and 4-methoxytrityl chloride resins (Mmt). The resin can be appropriately selected according to the functional group on the amino acid to be used. For example, when using a carboxylic acid (main-chain carboxylic acid or side-chain carboxylic acid represented by Asp or Glu) or a hydroxy group on an aromatic ring (phenol group represented by Tyr) as the functional group on the amino acid, use of trityl chloride resin (Trt resin) or 2-chlorotritylchloride resin (CTC resin) as the resin is preferred. When using an aliphatic hydroxy group (aliphatic alcohol group represented by Ser or Thr) as the functional group on the amino acid, use of tritylchloride resin (Trt resin), 2-chlorotritylchloride resin (CTC resin), or 4-methyltritylchloride resin (Mtt resin) as the resin is preferred.

Furthermore, the types of polymers constituting the resins are also not particularly limited. For resins composed of polystyrenes, either 100 to 200 mesh or 200 to 400 mesh may be used. The cross-link percentage is also not particularly limited, but those cross-linked with 1% divinylbenzene (DVB) are preferred. Types of the polymer forming the resin include Tentagel or Chemmatrix.

In some aspects, the deprotection reaction and/or resin removal reaction of the present invention can be performed at a reaction temperature of −50 to 100° C., preferably −20 to 50° C., and more preferably 0 to 30° C.

In some aspects, the deprotection reaction and/or resin removal reaction of the present invention can be performed for a reaction time of 10 minutes to one week, preferably 10 minutes to 6 hours, and more preferably 1 to 3 hours.

In some aspects, in the deprotection reaction and/or resin removal reaction of the present invention, a target product can be obtained by adding an alcohol or water to a reaction solution to quench the reaction, and causing the target product to precipitate or washing an organic layer with water or saline and then concentrating the organic layer under reduced pressure. The alcohol is not particularly limited, but is preferably a water-soluble and low-boiling alcohol, and particularly preferably methanol. The water used for quenching the reaction is not particularly limited, but is preferably alkaline water, and particularly preferably aqueous sodium bicarbonate or dipotassium hydrogenphosphate. When the organic layer is washed, the saline is not particularly limited in terms of concentration, but is preferably brine or 5% saline.

In some aspects, when a starting peptide compound comprises both a protecting group that can be removed by the method of the present invention and a resin for solid-phase synthesis that can be removed by the method of the present invention, deprotection and resin removal reactions can be conducted at the same time. Specifically, the present invention also relates to a method of producing a peptide compound in which a protecting group removable by a silylating agent is removed from a starting peptide compound comprising natural amino acid residues and/or amino acid analog residues and in which a resin for solid-phase synthesis that is removable by the silylating agent is removed from the starting peptide compound, the method comprising the step of contacting the starting peptide compound with the silylating agent in a solvent.

In some aspects, the present invention relates to an amide compound represented by formula (A) below or a salt thereof:

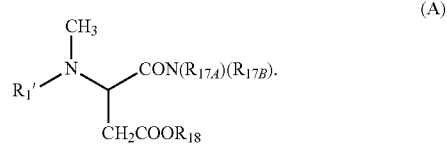

(A)

In formula (A), $R_{1'}$ is selected from the group consisting of hydrogen, Fmoc, Boc, Alloc, Cbz, Teoc, and trifluoroacetyl. $R_{1'}$ is preferably hydrogen, Fmoc, Boc, or Cbz.

In formula (A), $R_{17A}$ and $R_{17B}$ are both methyl, or $R_{17A}$ and $R_{17B}$, together with the nitrogen atom to which they are attached, form piperidine or morpholine.

In formula (A), $R_{18}$ is hydrogen or $PG_{10}$. $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl. $R_{18}$ is preferably a hydrogen atom, t-Bu, benzyl, or allyl.

Preferred combinations of $R_1$ and $R_{18}$ in formula (A) include Fmoc and a hydrogen atom, Fmoc and allyl, Fmoc and t-Bu, Fmoc and benzyl, Boc and a hydrogen atom, Boc and allyl, Boc and t-Bu, Boc and benzyl, Cbz and a hydrogen atom, Cbz and allyl, Cbz and t-Bu, Cbz and benzyl, Alloc and a hydrogen atom, Alloc and allyl, Alloc and t-Bu, Alloc and benzyl, Teoc and a hydrogen atom, Teoc and allyl, Teoc and t-Bu, Teoc and benzyl, a hydrogen atom and a hydrogen atom, a hydrogen atom and allyl, a hydrogen atom and t-Bu, and a hydrogen atom and benzyl.

Specific examples of the amide compound represented by formula (A) include the following compounds:

(1-1) 3-((((9H-fluoren-9-yl)methoxy)carbonyl)(methyl)amino)-4-oxo-4-(piperidin-1-yl)butanoic acid,
(1-2) allyl 3-((((9H-fluoren-9-yl)methoxy)carbonyl)(methyl)amino)-4-oxo-4-(piperidin-1-yl)butanoate,
(1-3) tert-butyl 3-((((9H-fluoren-9-yl)methoxy)carbonyl)(methyl)amino)-4-oxo-4-(piperidin-1-yl)butanoate,
(1-4) benzyl 3-((((9H-fluoren-9-yl)methoxy)carbonyl)(methyl)amino)-4-oxo-4-(piperidin-1-yl)butanoate,
(1-5) 3-((tert-butoxycarbonyl)(methyl)amino)-4-oxo-4-(piperidin-1-yl)butanoic acid,
(1-6) allyl 3-((tert-butoxycarbonyl)(methyl)amino)-4-oxo-4-(piperidin-1-yl)butanoate,
(1-7) tert-butyl 3-((tert-butoxycarbonyl)(methyl)amino)-4-oxo-4-(piperidin-1-yl)butanoate,
(1-8) benzyl 3-((tert-butoxycarbonyl)(methyl)amino)-4-oxo-4-(piperidin-1-yl)butanoate,
(1-9) 3-(((benzyloxy)carbonyl)(methyl)amino)-4-oxo-4-(piperidin-1-yl)butanoic acid,
(1-10) allyl 3-(((benzyloxy)carbonyl)(methyl)amino)-4-oxo-4-(piperidin-1-yl)butanoate,
(1-11) tert-butyl 3-(((benzyloxy)carbonyl)(methyl)amino)-4-oxo-4-(piperidin-1-yl)butanoate,
(1-12) benzyl 3-(((benzyloxy)carbonyl)(methyl)amino)-4-oxo-4-(piperidin-1-yl)butanoate,
(1-13) 3-(((allyloxy)carbonyl)(methyl)amino)-4-oxo-4-(piperidin-1-yl)butanoic acid,
(1-14) allyl 3-(((allyloxy)carbonyl)(methyl)amino)-4-oxo-4-(piperidin-1-yl)butanoate,
(1-15) tert-butyl 3-(((allyloxy)carbonyl)(methyl)amino)-4-oxo-4-(piperidin-1-yl)butanoate,
(1-16) benzyl 3-(((allyloxy)carbonyl)(methyl)amino)-4-oxo-4-(piperidin-1-yl)butanoate,
(1-17) 3-(methyl((2-(trimethylsilyl)ethoxy)carbonyl)amino)-4-oxo-4-(piperidin-1-yl)butanoic acid,
(1-18) allyl 3-(methyl((2-(trimethylsilyl)ethoxy)carbonyl)amino)-4-oxo-4-(piperidin-1-yl)butanoate,
(1-19) tert-butyl 3-(methyl((2-(trimethylsilyl)ethoxy)carbonyl)amino)-4-oxo-4-(piperidin-1-yl)butanoate,
(1-20) benzyl 3-(methyl((2-(trimethylsilyl)ethoxy)carbonyl)amino)-4-oxo-4-(piperidin-1-yl)butanoate,
(2-1) 3-((((9H-fluoren-9-yl)methoxy)carbonyl)(methyl)amino)-4-morpholino-4-oxobutanoic acid,
(2-2) allyl 3-((((9H-fluoren-9-yl)methoxy)carbonyl)(methyl)amino)-4-morpholino-4-oxobutanoate,
(2-3) tert-butyl 3-((((9H-fluoren-9-yl)methoxy)carbonyl)(methyl)amino)-4-morpholino-4-oxobutanoate,
(2-4) benzyl 3-((((9H-fluoren-9-yl)methoxy)carbonyl)(methyl)amino)-4-morpholino-4-oxobutanoate,
(2-5) 3-((tert-butoxycarbonyl)(methyl)amino)-4-morpholino-4-oxobutanoic acid,
(2-6) allyl 3-((tert-butoxycarbonyl)(methyl)amino)-4-morpholino-4-oxobutanoate,
(2-7) tert-butyl 3-((tert-butoxycarbonyl)(methyl)amino)-4-morpholino-4-oxobutanoate,
(2-8) benzyl 3-((tert-butoxycarbonyl)(methyl)amino)-4-morpholino-4-oxobutanoate,
(2-9) 3-(((benzyloxy)carbonyl)(methyl)amino)-4-morpholino-4-oxobutanoic acid,
(2-10) allyl 3-(((benzyloxy)carbonyl)(methyl)amino)-4-morpholino-4-oxobutanoate,
(2-11) tert-butyl 3-(((benzyloxy)carbonyl)(methyl)amino)-4-morpholino-4-oxobutanoate,
(2-12) benzyl 3-(((benzyloxy)carbonyl)(methyl)amino)-4-morpholino-4-oxobutanoate,
(2-13) 3-(((allyloxy)carbonyl)(methyl)amino)-4-morpholino-4-oxobutanoic acid,
(2-14) allyl 3-(((allyloxy)carbonyl)(methyl)amino)-4-morpholino-4-oxobutanoate,
(2-15) tert-butyl 3-(((allyloxy)carbonyl)(methyl)amino)-4-morpholino-4-oxobutanoate,
(2-16) benzyl 3-(((allyloxy)carbonyl)(methyl)amino)-4-morpholino-4-oxobutanoate,
(2-17) 3-(methyl((2-(trimethylsilyl)ethoxy)carbonyl)amino)-4-morpholino-4-oxobutanoic acid,
(2-18) allyl 3-(methyl((2-(trimethylsilyl)ethoxy)carbonyl)amino)-4-morpholino-4-oxobutanoate,
(2-19) tert-butyl 3-(methyl((2-(trimethylsilyl)ethoxy)carbonyl)amino)-4-morpholino-4-oxobutanoate,
(2-20) benzyl 3-(methyl((2-(trimethylsilyl)ethoxy)carbonyl)amino)-4-morpholino-4-oxobutanoate,
(3-1) 3-((((9H-fluoren-9-yl)methoxy)carbonyl)(methyl)amino)-4-(dimethylamino)-4-oxobutanoic acid,
(3-2) allyl 3-((((9H-fluoren-9-yl)methoxy)carbonyl)(methyl)amino)-4-(dimethylamino)-4-oxobutanoate,
(3-3) tert-butyl 3-((((9H-fluoren-9-yl)methoxy)carbonyl)(methyl)amino)-4-(dimethylamino)-4-oxobutanoate,
(3-4) benzyl 3-((((9H-fluoren-9-yl)methoxy)carbonyl)(methyl)amino)-4-(dimethylamino)-4-oxobutanoate,
(3-5) 3-((tert-butoxycarbonyl)(methyl)amino)-4-(dimethylamino)-4-oxobutanoic acid,
(3-6) allyl 3-((tert-butoxycarbonyl)(methyl)amino)-4-(dimethylamino)-4-oxobutanoate,
(3-7) tert-butyl 3-((tert-butoxycarbonyl)(methyl)amino)-4-(dimethylamino)-4-oxobutanoate,
(3-8) benzyl 3-((tert-butoxycarbonyl)(methyl)amino)-4-(dimethylamino)-4-oxobutanoate,
(3-9) 3-(((benzyloxy)carbonyl)(methyl)amino)-4-(dimethylamino)-4-oxobutanoic acid,
(3-10) allyl 3-(((benzyloxy)carbonyl)(methyl)amino)-4-(dimethylamino)-4-oxobutanoate,
(3-11) tert-butyl 3-(((benzyloxy)carbonyl)(methyl)amino)-4-(dimethylamino)-4-oxobutanoate,
(3-12) benzyl 3-(((benzyloxy)carbonyl)(methyl)amino)-4-(dimethylamino)-4-oxobutanoate,
(3-13) 3-(((allyloxy)carbonyl)(methyl)amino)-4-(dimethylamino)-4-oxobutanoic acid,
(3-14) allyl 3-(((allyloxy)carbonyl)(methyl)amino)-4-(dimethylamino)-4-oxobutanoate,
(3-15) tert-butyl 3-(((allyloxy)carbonyl)(methyl)amino)-4-(dimethylamino)-4-oxobutanoate,
(3-16) benzyl 3-(((allyloxy)carbonyl)(methyl)amino)-4-(dimethylamino)-4-oxobutanoate,
(3-17) 4-(dimethylamino)-3-(methyl((2-(trimethylsilyl)ethoxy)carbonyl)amino)-4-oxobutanoic acid,
(3-18) allyl 4-(dimethylamino)-3-(methyl((2-(trimethylsilyl)ethoxy)carbonyl)amino)-4-oxobutanoate,
(3-19) tert-butyl 4-(dimethylamino)-3-(methyl((2-(trimethylsilyl)ethoxy)carbonyl)amino)-4-oxobutanoate,
(3-20) benzyl 4-(dimethylamino)-3-(methyl((2-(trimethylsilyl)ethoxy)carbonyl)amino)-4-oxobutanoate,
(4-1) 3-(methylamino)-4-oxo-4-(piperidin-1-yl)butanoic acid,
(4-2) allyl 3-(methylamino)-4-oxo-4-(piperidin-1-yl)butanoate, (4-3) tert-butyl 3-(methylamino)-4-oxo-4-(piperidin-1-yl)butanoate,
(4-4) benzyl 3-(methylamino)-4-oxo-4-(piperidin-1-yl)butanoate,
(4-5) 3-(methylamino)-4-morpholino-4-oxobutanoic acid,
(4-6) allyl 3-(methylamino)-4-morpholino-4-oxobutanoate,
(4-7) tert-butyl 3-(methylamino)-4-morpholino-4-oxobutanoate,
(4-8) benzyl 3-(methylamino)-4-morpholino-4-oxobutanoate,
(4-9) 4-(dimethylamino)-3-(methylamino)-4-oxobutanoic acid,
(4-10) allyl 4-(dimethylamino)-3-(methylamino)-4-oxobutanoate,
(4-11) tert-butyl 4-(dimethylamino)-3-(methylamino)-4-oxobutanoate, or
(4-12) benzyl 4-(dimethylamino)-3-(methylamino)-4-oxobutanoate.

The amide compound of the present invention represented by formula (A) can be synthesized according to the following scheme, for example.

organic base salts include diethylamine salts, diethanolamine salts, meglumine salts, and N,N-dibenzylethylenediamine salts.

Examples of the acidic amino acid salts include aspartates and glutamates. Examples of the basic amino acid salts include arginine salts, lysine salts, and ornithine salts.

The compounds of the present invention may absorb water to form hydrates when left in the air, for example. Such hydrates are also included in the present invention.

Further, the compounds of the present invention may absorb certain other solvents to form solvates. Such solvates are also included in the present invention.

Herein, although structural formulas of the compounds of the present invention may represent certain isomers for convenience, the present invention includes all isomers and mixtures of isomers possible in terms of compound structure, such as geometric isomers, optical isomers, and tautomers, and the compounds are not limited to the formulas described for convenience. For example, when the compounds have an asymmetric carbon atom in the molecule and exist as optically active isomers and racemates, both are included in the present invention.

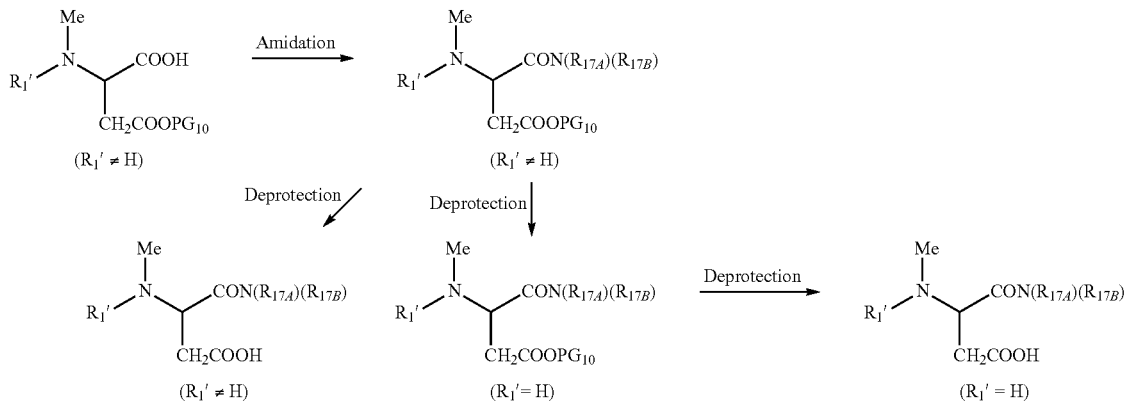

The amidation step in the above scheme can be achieved by condensing any amine $((R_{17A})(R_{17B})NH)$ with a carboxyl group using a dehydration condensation agent such as a carbodiimide compound according to Solid-Phase Synthesis Handbook (publisher: Merck K. K., date of publication: May 1, 2002) or the method of Albert et al. (Synthesis, 1987, 7, 635-637), for example.

The deprotection step in the above scheme can be achieved using the method described in Greene's "Protective Groups in Organic Synthesis" (5th ed., John Wiley & Sons 2014) or the deprotection method described herein, for example.

The compounds of the present invention may be either free forms or salts thereof, both of which are included in the present invention. Examples of such "salts" include inorganic acid salts, organic acid salts, inorganic base salts, organic base salts, and acidic or basic amino acid salts.

Examples of the inorganic acid salts include hydrochlorides, hydrobromides, sulfates, nitrates, and phosphates. Examples of the organic acid salts include acetates, succinates, fumarates, maleates, tartrates, citrates, lactates, stearates, benzoates, methanesulfonates, benzenesulfonates, and p-toluenesulfonates.

Examples of the inorganic base salts include alkali metal salts such as sodium salts and potassium salts, alkaline earth metal salts such as calcium salts and magnesium salts, aluminum salts, and ammonium salts. Examples of the All prior art references cited herein are incorporated by reference into this description.

EXAMPLE

The present invention will be further illustrated with reference to the following Examples but is not limited thereto.

Solvents such as methylene chloride, ethyl acetate, 2-MeTHF, dichloroethane, or DMF used in the practice of the present invention were those from commercial suppliers, used without purification. Solvents such as dehydrated solvents, ultradehydrated solvents, or anhydrous solvents used for reactions without addition of water as a solvent were those from commercial suppliers, used without purification.

Unless otherwise stated, silyl compounds such as TMSOTf used in the practice of the present invention, or reagents like electrophilic species scavengers such as BSA and BSTFA used in the practice of the present invention were those from commercial suppliers, used without purification.

Unless otherwise stated, starting peptide or amide compounds used in the practice of the present invention were those from commercial suppliers, used without purification. As necessary, such compounds were produced by known methods and used.

In the following examples, analysis was performed by any one or more of the HPLC methods 1 to 4 or methods A, B, C, D, E, F, G, or H.

Analysis: HPLC (reaction conversion rate, purity)
HPLC method 1
Instrument: Waters ACQUITY UPLC H-Class
Column: Ascentis Express C18 (2.7 μm, 4.6 mm×50 mm), Supelco
Eluent: A) 0.05% TFA/water, B) 0.05% TFA/CH$_3$CN
Gradient (B): 5% (0 min.)⇒100% (6 min.)⇒5% (7 min.)⇒5% (9 min.)
Flow rate: 1.0 mL/min.
Detection: 210 nm
Injection vol.: 5 μL
Sample prep.: 5 μL/1.00 mL
HPLC method 2
Instrument: Waters LCT Premier
Column: Ascentis Express C18 (2.7 μm, 4.6 mm×50 mm), Supelco
Column temp.: 35 deg.
Eluent: A) 0.05% TFA/water, B) 0.05% TFA/CH$_3$CN
Gradient (B): 50% (0 min.)⇒100% (6 to 11 min.)⇒50% (11 min.)⇒50% (13 min.)
Flow rate: 1.0 mL/min.
Detection: 210 nm
Injection vol.: 5 μL
Sample prep.: 5 μL/1.00 mL
HPLC method 3
Instrument: Waters ACQUITY UPLC H-Class
Column: Ascentis Express C18, (2.7 μm, 2.1 mm×50 mm), Supelco
Column temp.: 35 deg.
Eluent: A) 0.05% TFA/water, B) 0.05% TFA/CH$_3$CN
Gradient (A): 95%(0 min)→0%(4.0 min)→0%(4.5 min)→95%(4.6 min)→95%(6 min)
Flow rate: 0.25 mL/min
Detection: PDA 210 nm (200-400 nm PDA total)
Injection vol.: 0.3 μL
Sample prep.: 50 μL/10 mL
HPLC method 4
Instrument: Waters ACQUITY UPLC H-Class
Column: CAPCELL CORE ADME, (2.7 μm, 3.0 mm×150 mm)
Column temp.: 30 deg.
Solvents: A) 0.05% TFA/water, B) 0.05% TFA/CH$_3$CN
Gradient (A): 70%(0 min)→30%(20.0 min)→0%(20.1 min)→0%(22.0 min)→70%(22.1 min)→70%(24 min)
Flow rate: 0.3 mL/min
Detection: PDA 254 nm (200-400 nm PDA total)
Injection vol.: 0.3 μL
Sample prep.: amorphous 10.0 mg in CH$_3$CN 10 ml; this solution 0.3 mL/0.7 mL CH$_3$CN A. Boc Removal Reaction Experiments Example 1

Boc Removal Reaction of Boc-MeAla-MePhe-Leu-MeLeu-Thr(OBn)-MeGly-OAllyl (Compound 3a) (6-Mer: TfOH-BSTFA Method)

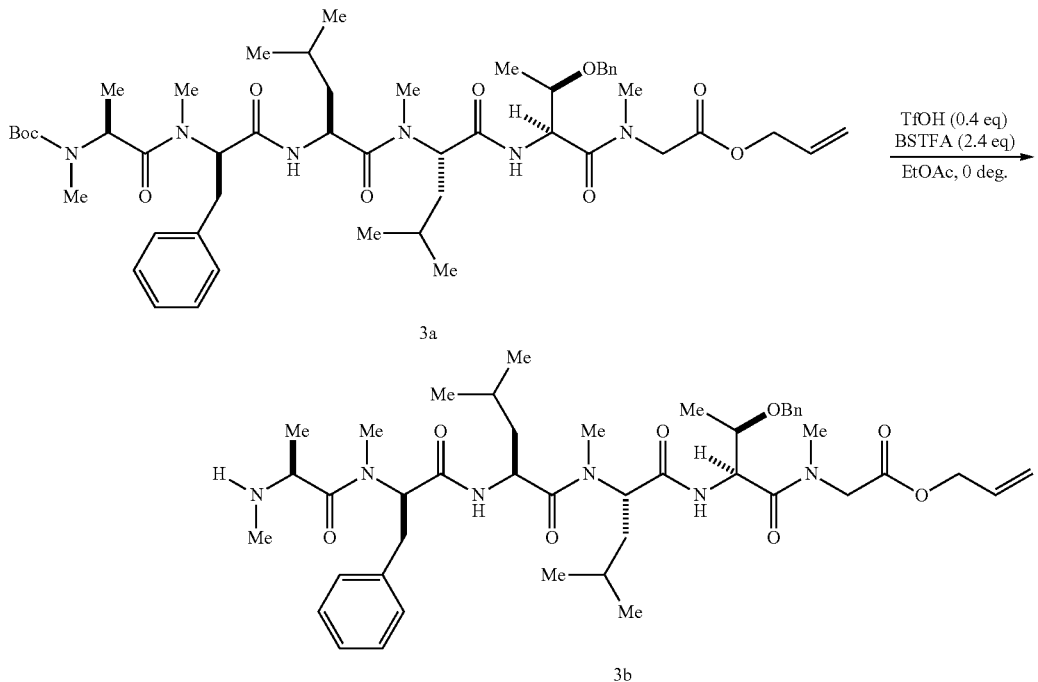

77.7 mg of the raw material was weighed into a reaction vessel and dissolved in 5 v/w of ethyl acetate, and the reaction vessel was cooled with ice. After 10 minutes, 0.055 ml (2.4 eq) of BSTFA and 3.0 μl (0.4 eq) of TfOH were sequentially added under a nitrogen atmosphere, and the reaction solution was stirred. Three hours after the addition of the reagents, the reaction was analyzed by LCMS and the raw material was confirmed to disappear.

The reaction was quenched with saturated aqueous sodium bicarbonate. The organic layer was washed with saturated aqueous sodium bicarbonate and 5% saline. The resulting organic layer was concentrated under reduced pressure to give 77.3 mg of a deprotected product quantitatively.

Amide bond cleavage was not confirmed.

TABLE 1

|  | Weight (mg) | Yield (%) |
|---|---|---|
| Raw material (Compound 3a) | 77.7 | — |
| Product (Compound 3b) | 77.3 | Quantitative |

TABLE 2

| Analysis (HPLC method 1) | | | |
|---|---|---|---|
| MW | m/z | rt | Purity LC A % |
| Raw material (Compound 3a) 906.55 | 807.55 ([M − Boc + H]+) | 5.976 | 93.83 |
| Product (Compound 3b) 806.49 | 807.49 ([M + H]+) | 3.968 | 94.36 |

Example 2

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-Mer: TMSOTf-HMDS Method)

two layers were separated. The organic layer was washed with a mixture of 1 ml of saturated aqueous sodium bicarbonate and 1 ml of brine. The resulting organic layer was concentrated to give 68.0 mg of a deprotected product in 90% yield as a transparent film.

TABLE 3

|  | Weight (mg) | Yield (%) |
|---|---|---|
| Raw material (Compound 1a) | 81.0 | — |
| Product (Compound 1b) | 68.0 | 90 |

TABLE 4

| Analysis (HPLC method 1: Determination of purities of the raw material and target product) | | | |
|---|---|---|---|
| MW | m/z | rt | Purity LC A % |
| Raw material (Compound 1a) 1560.96 | 1242.05 | 6.519 | 96.680 |
| Product (Compound 1b) 1460.90 | 731.78 | 4.635 | 98.003 |

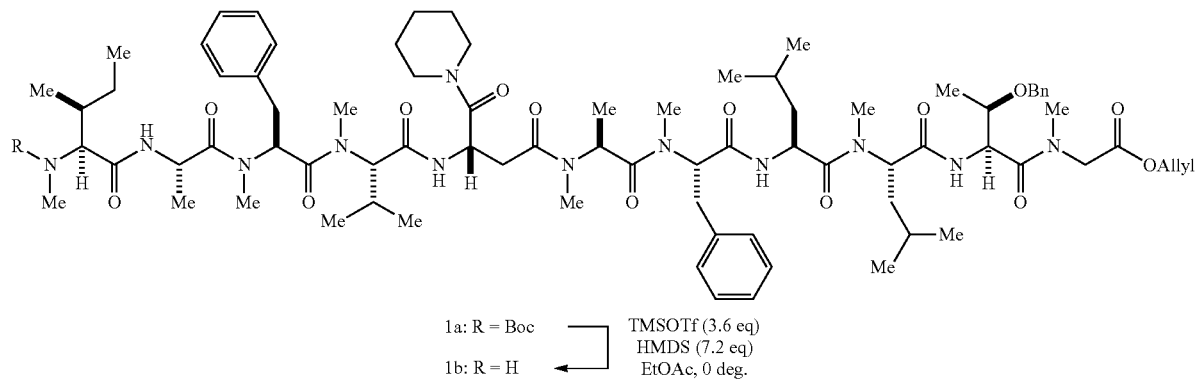

1a: R = Boc
1b: R = H
TMSOTf (3.6 eq)
HMDS (7.2 eq)
EtOAc, 0 deg.

0.0810 g of the raw material was weighed into a reaction vessel and dissolved in 10 v/w of ethyl acetate, and the reaction vessel was cooled with ice. After 10 minutes, 0.079 ml (7.2 eq) of HMDS and 34 μl (3.6 eq) of TMSOTf were sequentially added under a nitrogen atmosphere, and the reaction solution was stirred. Four hours after the addition of the reagents, the reaction was analyzed by LCMS and the raw material was confirmed to disappear. Amide bond cleavage was not confirmed.

After confirming the disappearance of the raw material, the reaction solution was stirred for another one hour and the reaction was analyzed by LCMS. Also at this time, amide bond cleavage was not confirmed.

To the reaction vessel was added 1 ml of brine to quench the reaction. 5 ml of ethyl acetate was then added and the

TABLE 5

| Analysis (HPLC method 2: Mass spectroscopy) | | | |
|---|---|---|---|
| MW | m/z | rt |
| Raw material (Compound 1a) 1560.96 | 1561.4097 ([M + H]+) | 5.883 |
| Product (Compound 1b) 1460.90 | 1461.5303 ([M + H]+) | 4.817 |

Example 3

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-Mer: TMSOTf-HMDS Method)

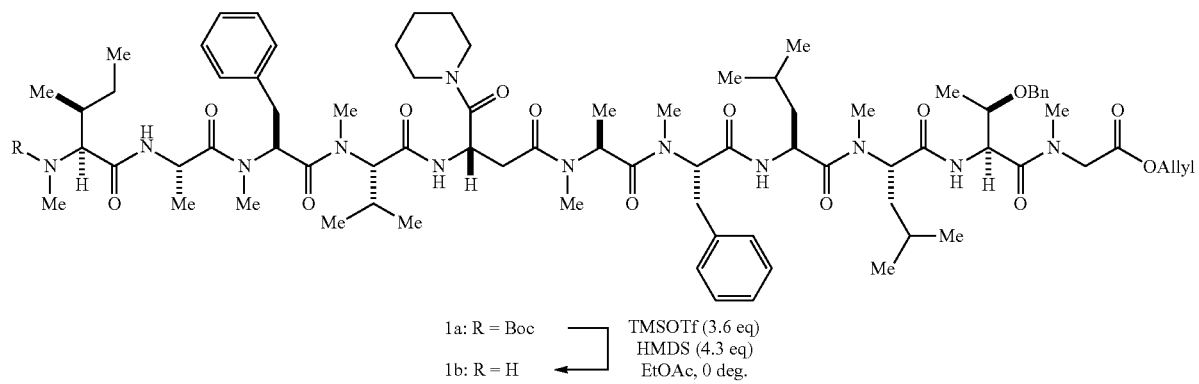

1a: R = Boc  →  TMSOTf (3.6 eq), HMDS (4.3 eq), EtOAc, 0 deg.
1b: R = H

The reaction was carried out according to Example 2. 19 hours after the reaction was started, the reaction was analyzed by LCMS. However, decomposition of the product was not confirmed.

TABLE 6

|  | Weight (mg) | Yield (%) |
|---|---|---|
| Raw material (Compound 1a) | 21.7 | — |
| Product (Compound 1b) | Not isolated | Not isolated |

TABLE 7

Analysis (HPLC method 1: Determination of purities of the raw material and target product)

|  | MW | m/z | rt | Purity LC A % |
|---|---|---|---|---|
| Raw material (Compound 1a) | 1560.96 | 1241.89 | 6.476 | 98.408 |
| Product (Compound 1b) | 1460.90 | 731.76 | 4.562 | 97.256 |

Example 4

Boc Removal Reaction of Boc-MeAla-MePhe-Leu-MeLeu-Thr(OBn)-MeGly-MeIle-Ala-MePhe-MeVal-Asp(OBn)-pip (Compound 2a) (11-Mer: TfOH-BSTFA Method)

The reaction was carried out according to Example 1.

TABLE 9

|  | Weight (mg) | Yield (%) |
|---|---|---|
| Raw material (Compound 2a) | 48.1 | — |
| Product (Compound 2b) | Not isolated | Not isolated |

TABLE 10

Analysis (HPLC method 1: Determination of purities of the raw material and target product)

|  | MW | m/z | rt | Purity LC A % |
|---|---|---|---|---|
| Raw material (Compound 2a) | 1610.97 | ND | 6.492 | 84.00 |
| Product (Compound 2b) | 1510.92 | ND | 4.776 | 81.54 |

TABLE 11

Analysis (HPLC method 2: Mass spectroscopy)

|  | MW | m/z | rt |
|---|---|---|---|
| Raw material (Compound 2a) | 1610.97 | 1611.43 ( [M + H]+) | 5.96 |
| Product (Compound 2b) | 1510.92 | 1511.53 ( [M + H]+) | 2.84 |

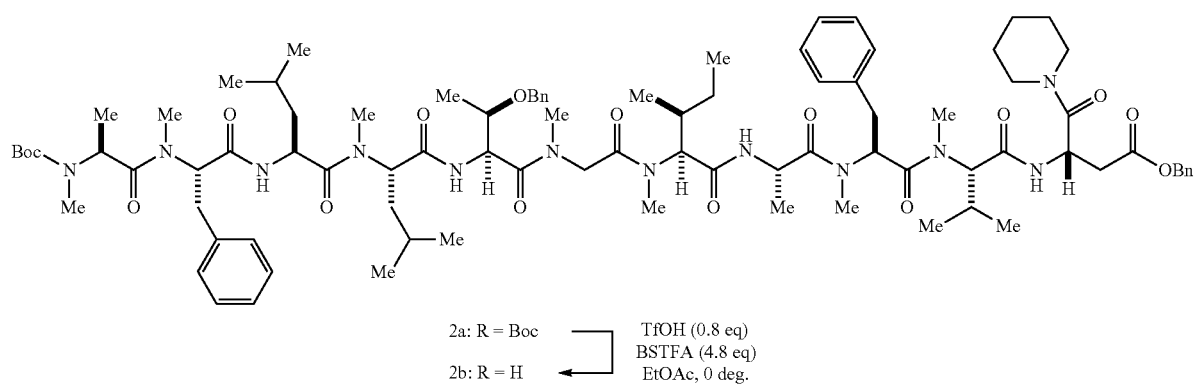

2a: R = Boc  →  TfOH (0.8 eq), BSTFA (4.8 eq), EtOAc, 0 deg.
2b: R = H

Example 5

Boc Removal Reaction of Boc-MePhe-Leu-MeLeu-Thr(OBn)-MeGly-OAllyl (Compound 4a) (5-mer: TfOH-BSTFA Method)

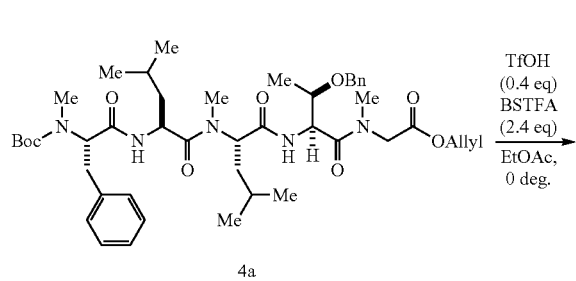

The reaction was carried out according to Example 1.

TABLE 12

| | Weight (mg) | Yield (%) |
|---|---|---|
| Raw material (Compound 4a) | 98.5 | — |
| Product (Compound 4b) | 78.7 | 91 |

TABLE 13

Analysis (HPLC method 1)

| | MW | m/z | rt | Purity LC Area % |
|---|---|---|---|---|
| Raw material (Compound 4a) | 821.49 | 844.4 ( [M + Na]+) | 6.033 | 90.51 |
| Product (Compound 4b) | 721.44 | 722.46 ( [M + H]+) | 3.879 | 93.30 |

Example 6

Reactions for Boc Removal of Boc-MeLeu-Thr(OBn)-MeGly-OAllyl (Compound 8a) and its Elongation to Form Boc-Leu-MeLeu-Thr(OBn)-MeGly-OAllyl (3 mer: TfOH-BSTFA Method)

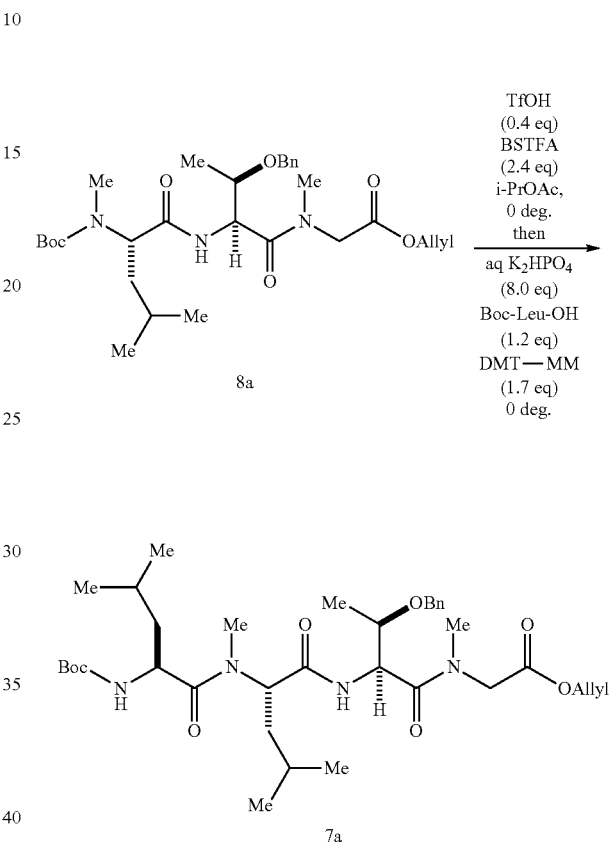

73.3 mg of the starting material was weighed into a reaction vessel and dissolved in 5 v/w of isopropyl acetate. After cooling the reaction vessel with ice, 0.085 ml of BSTFA and 0.0047 ml of TfOH were added and the reaction solution was stirred for two hours. After confirming by LC that deprotection was completed without main chain cleavage, 5 v/w of water and 186.9 mg of dipotassium hydrogenphosphate were added. 40.1 mg of Boc-Leu-OH monohydrate and 63.1 mg of DMT-MM were then added and the reaction solution was stirred with ice-cooling. 17 hours after the addition of the reagents, completion of the reaction was confirmed by LC. The reaction was quenched by adding 5 v/w of a 1 N aqueous sodium hydroxide solution. The organic layer was separated by liquid separation treatment, then washed once with a 1 N aqueous sodium hydroxide solution, twice with a 5% aqueous potassium bisulfate solution, and once with a 5% aqueous sodium chloride solution, and subsequently concentrated under reduced pressure. 82.0 mg (93% yield) of a crude product was obtained as an oily liquid.

TABLE 14

|  | Weight (mg) | Yield (%) |
|---|---|---|
| Raw material (Compound 8a) | 73.3 | — |
| Product (Compound 7a) | 82.0 | 93 |

TABLE 15

Analysis of deprotection reaction (HPLC method 1)

|  | MW | m/z | rt | Purity LC A % |
|---|---|---|---|---|
| Raw material (Compound 8a) | 547.33 | 448.30 ( [M − Boc + H]+) | 5.513 | 96.17 |
| Boc-removed product | 447.27 | ND | 2.938 | 95.95 |

TABLE 16

Analysis of elongation reaction (HPLC method 1)

|  | MW | m/z | rt | Purity LC A % |
|---|---|---|---|---|
| Product (Compound 8b) | 660.85 | 561.28 ( [M − Boc + H]+) | 5.657 | 95.36 |

Example 6a

Reactions for Teoc Removal of Teoc-MeLeu-Thr(OBn)-MeGly-OAllyl (Compound 80b) and its Elongation to form Boc-Leu-MeLeu-Thr(OBn)-MeGly-OAllyl (7a) (3-mer: TfOH-BSTFA Method)

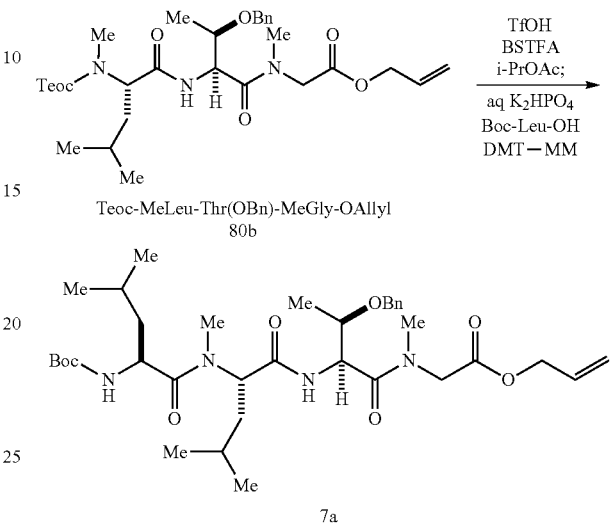

Compound 7a can be obtained without main chain cleavage by removing the Teoc group in the same operation as in Example 6 and then reacting with Boc-Leu-OH.

Example 7

Boc Removal Reaction of Boc-MeIle-Ala-MePhe-MeVal-Asp(OBn)-pip (Compound 5a) (5-mer: TfOH-BSTFA Method)

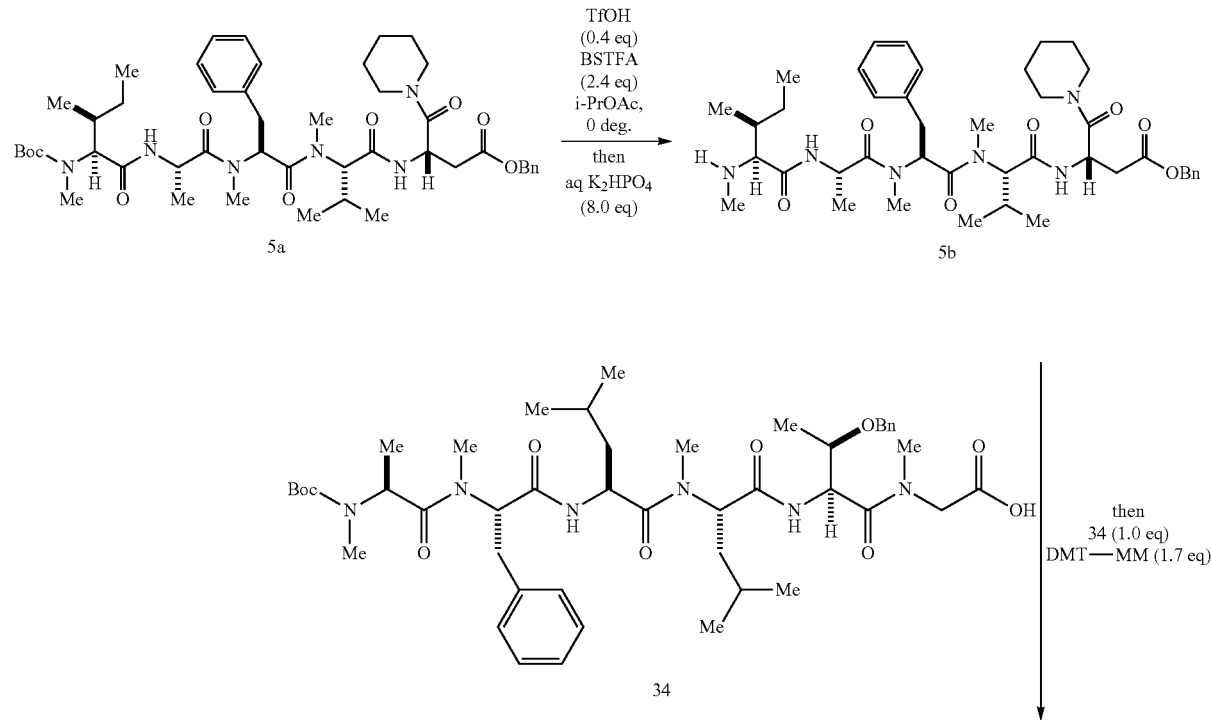

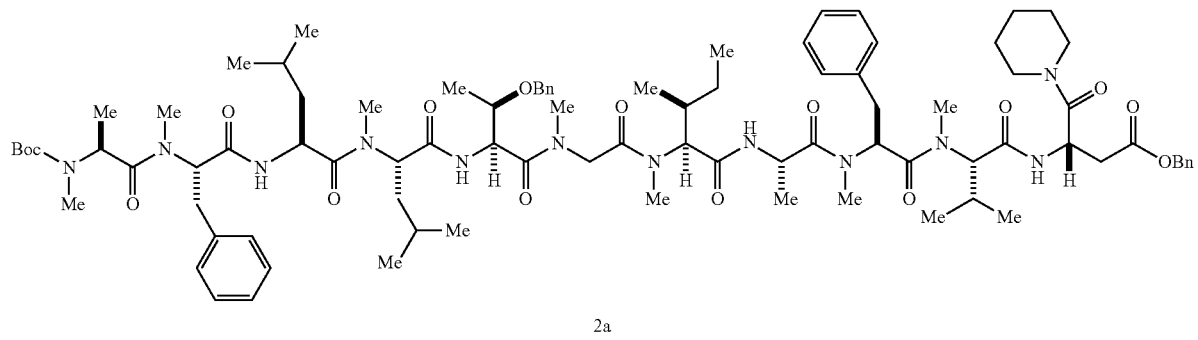

2a

Deprotection and elongation reactions were performed in a one-pot operation according to the experimental method described in Example 6.

TABLE 17

|  | Weight (mg) | Yield (%) |
| --- | --- | --- |
| Raw material (Compound 5a) | 105.3 | — |
| Product (Compound 2a) | 153.6 | 78% |

TABLE 18

Analysis of deprotection reaction (HPLC method 1)

|  | MW | m/z | rt | Purity LC A % |
| --- | --- | --- | --- | --- |
| Raw material (Compound 5a) | 862.52 | 573.33 | 5.978 | 95.01 |
| Deprotected product (Compound 5b) | 762.47 | 763.47 ([M + H]+) | 3.779 | 94.05 |

TABLE 19

Analysis of the product after elongation (HPLC method 1: Determination of purities of the raw material and target product)

|  | MW | m/z | rt | Purity LC A % |
| --- | --- | --- | --- | --- |
| Product (Compound 2a) | 1610.97 | ND | 6.699 | 85.93 |

TABLE 20

Analysis of the product after elongation (HPLC method 2: Mass spectroscopy)

|  | MW | m/z | rt |
| --- | --- | --- | --- |
| Product (Compound 2a) | 1610.97 | 1611.43 ([M + H]+) | 5.96 |

Example 8

Boc Removal and Elongation Reactions of Boc-Ala-MePhe-MeVal-Asp(OBn)-pip (Compound 6a) (4-mer: TfOH-BSTFA Method)

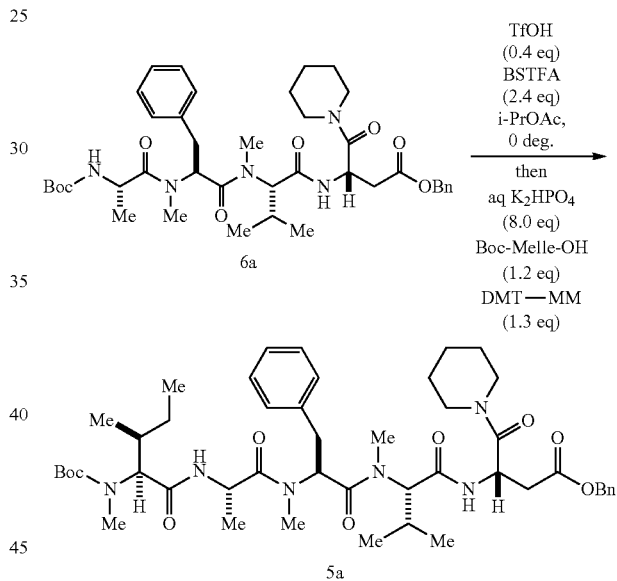

Deprotection and elongation reactions were performed in a one-pot operation according to the experimental method described in Example 6.

TABLE 21

|  | Weight (mg) | Yield (%) |
| --- | --- | --- |
| Raw material (Compound 6a) | 277 | — |
| Product (Compound 5a) | 308.9 | 95% |

TABLE 22

Analysis of the deprotected product (HPLC method 1)

|  | MW | m/z | rt | Purity LC A % |
| --- | --- | --- | --- | --- |
| Raw material (Compound 6a) | 735.42 | 758.4 ([M + Na]+) | 5.357 | 98.921 |

TABLE 22-continued

Analysis of the deprotected product (HPLC method 1)

| | MW | m/z | rt | Purity LC A % |
|---|---|---|---|---|
| Deprotected product (Compound 6b) | 635.37 | 636.40 ([M + H]+) | 3.383 | 97.893 |

TABLE 23

Analysis after elongation reaction (HPLC method 1)

| | MW | m/z | rt | Purity LC A % |
|---|---|---|---|---|
| Product (Compound 5a) | 862.52 | 573.33 | 5.978 | 96.938 |

Example 9

Boc Removal Reaction of Boc-Leu-MeLeu-Thr(OBn)-MeGly-OAllyl (Compound 7a) (4-mer: TfOH-BSTFA Method)

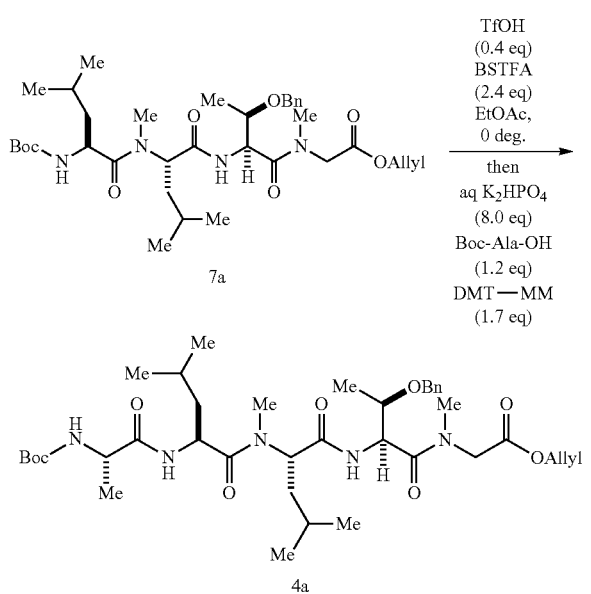

Deprotection and elongation reactions were performed in a one-pot operation according to the experimental method described in Example 6.

TABLE 24

| | Weight (mg) | Yield (%) |
|---|---|---|
| Raw material (Compound 7a) | 82.0 | — |
| Product (Compound 4a) | 98.5 | 97 |

TABLE 25

Analysis (HPLC method 1)

| | MW | m/z | rt | Purity LC A % |
|---|---|---|---|---|
| Raw material (Compound 7a) | 660.41 | 561.28 ([M − 100 + H]+) | 5.657 | 95.36 |
| Intermediate (Compound 7b) | 560.36 | 561.40 ([M + H]+) | 3.545 | 94.04 |

TABLE 26

Analysis (HPLC method 1)

| | MW | m/z | rt | Purity LC A % |
|---|---|---|---|---|
| Product (Compound 4a) | 821.49 | 844.4 ([M + Na]+) | 6.034 | 90.36 |

Example 10

Boc Removal Reaction of Boc-Leu-MeLeu-Thr(OBn)-MeGly-OAllyl (Compound 7a) Under Known Conditions (4-mer: HCl Method) (Russ. J. Bioorg. Chem., 2016, 42, 143)

18.7 mg of the raw material was weighed into a reaction vessel and dissolved in 10 v/w of trifluoroethanol. 8.5 μl (1.2 eq) of 4 N HCl (ethyl acetate solution) was then added and the reaction solution was stirred. Two hours after the addition of the reagent, the reaction was analyzed by LCMS (HPLC method 1) and the conversion rate (=target product/(target product+starting material)) was confirmed to be 81%. At this time, 0.861% of H-Thr(OBn)-MeGly-OAllyl (Compound 7c) and 1.275% of H-Leu-MeLeu-Thr(OBn)-OH (Compound 7d) were respectively detected as compounds in which amide bonds were cleaved.

TABLE 27

Analysis (HPLC method 1)

| | MW | m/z | rt | LC A % |
|---|---|---|---|---|
| Raw material (Compound 7a) | 660.41 | 561.28 ([M − Boc + H]+) | 5.657 | 18.437 |
| Product (Compound 7b) | 560.36 | 561.40 ([M + H]+) | 3.363 | 79.258 |
| Cleaved product (Compound 7c) | 320.17 | 321.08 ([M + H]+) | 2.500 | 0.861% |
| Cleaved product (Compound 7d) | 449.29 | 450.17 ([M + H]+) | 2.759 | 1.275% |

Example 11

Reactions for Deprotection of Boc-MePhe-MeVal-Asp(OBn)-pip (Compound 9a) and its Elongation to Form Boc-Ala-MePhe-MeVal-Asp(OBn)-pip (3-mer: TMSOTf-BSTFA Method)

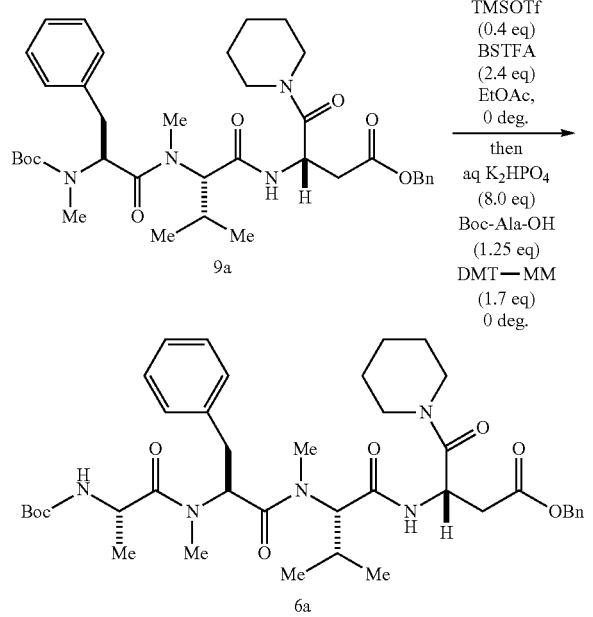

Deprotection and elongation reactions were performed in a one-pot operation according to the experimental method described in Example 6.

TABLE 28

| | Weight (mg) | Yield (%) |
|---|---|---|
| Raw material (Compound 9a) | 253.2 | — |
| Product (Compound 6a) | 319.4 | Quantitative |

TABLE 29

Analysis of deprotection reaction (HPLC method 1)

| | MW | m/z | rt | Purity LC A % |
|---|---|---|---|---|
| Raw material (Compound 9a) | 664.38 | 687.5 ([M + Na]+) | 5.647 | 99.206 |
| Deprotected product | 564.33 | 565.31 ([M + H]+) | 3.338 | 98.885 |

TABLE 30

Analysis of elongation reaction (HPLC method 1)

| | MW | m/z | rt | Purity LC A % |
|---|---|---|---|---|
| Product (Compound 6a) | 735.92 | 758.4 ([M + Na]+) | 5.377 | 99.538 |

Example 12

Deprotection of Boc-MePhe-MeVal-Asp(OBn)-pip (Compound 9a) (3-mer: TMSOTf-MSTFA Method)

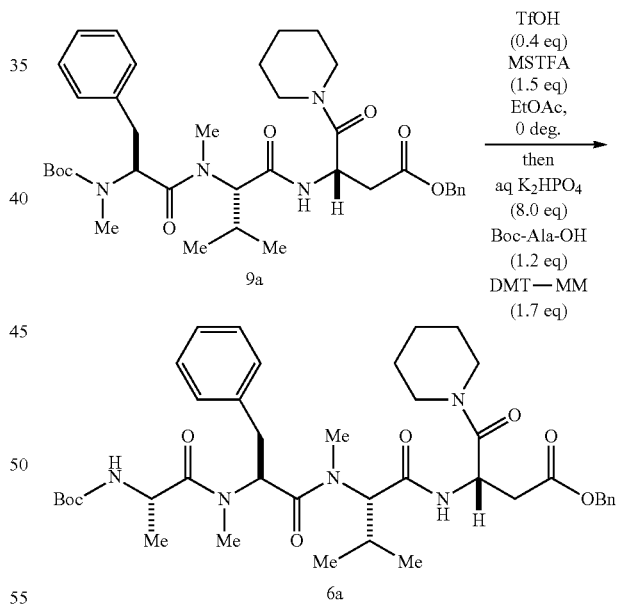

Deprotection and elongation reactions were performed in a one-pot operation according to the experimental method described in Example 6.

TABLE 31

| | Weight (mg) | Yield (%) |
|---|---|---|
| Raw material (Compound 9a) | 200.6 | — |
| Product (Compound 6a) | 220.6 | 95 |

TABLE 32

Analysis of deprotection reaction (HPLC method 1)

| | MW | m/z | rt | Purity LC A % |
|---|---|---|---|---|
| Raw material (Compound 9a) | 664.38 | 687.5 ([M + Na]+) | 5.647 | 99.206 |
| Deprotected product (Compound 9b) | 564.33 | 565.31 ([M + H]+) | 3.338 | 97.921 |

TABLE 33

Analysis of elongation reaction (HPLC method 1)

| | MW | m/z | rt | Purity LC A % |
|---|---|---|---|---|
| Product (Compound 6a) | 735.92 | 758.4 ([M + Na]+) | 5.308 | 99.279 |

Example 13

Deprotection of Boc-MePhe-MeVal-Asp(OBn)-pip (Compound 9a) (3-mer: TMSOTf-BSA Method, TMSOTf 2.4 eq, BSA 2.4 eq)

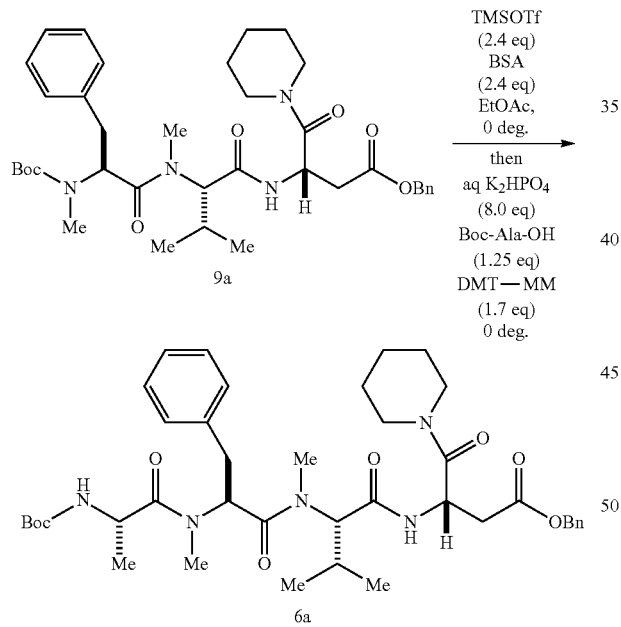

Deprotection and elongation reactions were performed in a one-pot operation according to the experimental method described in Example 6.

TABLE 34

| | Weight (mg) | Yield (%) |
|---|---|---|
| Raw material (Compound 9a) | 204.6 | — |
| Product (Compound 6a) | 219.0 | 97 |

TABLE 35

Analysis of deprotection reaction (HPLC method 1)

| | MW | m/z | rt | Purity LC A % |
|---|---|---|---|---|
| Raw material (Compound 9a) | 664.38 | 687.5 ([M + Na]+) | 5.647 | 99.206 |
| Deprotected product (Compound 9b) | 564.33 | 565.31 ([M + H]+) | 3.338 | 98.970 |

TABLE 36

Analysis of elongation reaction (HPLC method 1)

| | MW | m/z | rt | Purity LC A % |
|---|---|---|---|---|
| Product (Compound 6a) | 735.92 | 758.5 ([M + Na]+) | 5.301 | 99.573 |

Example 14

Deprotection of Boc-MePhe-MeVal-Asp(OBn)-pip (Compound 9a) (3-mer: TMSOTf-HMDS Method)

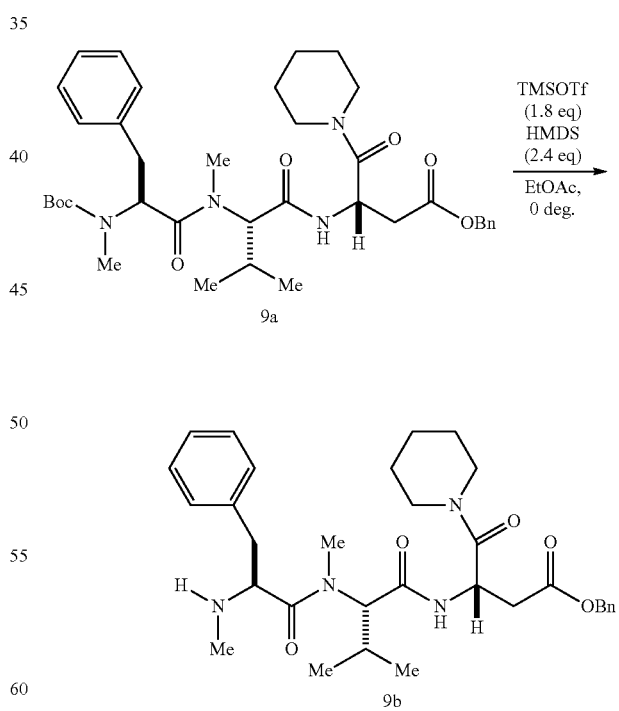

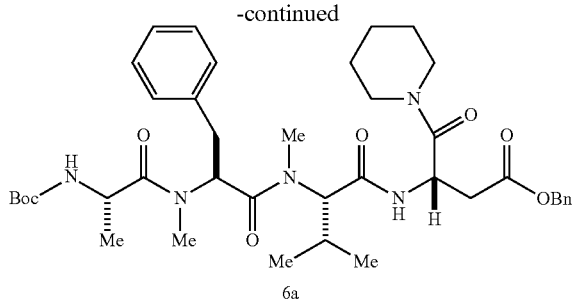

6a 107.4 mg of the raw material was weighed into a reaction vessel and dissolved in 5 v/w of ethyl acetate, and the reaction vessel was cooled with ice. After 10 minutes, 0.085 ml (2.4 eq) of HMDS (1,1,1,3,3,3-hexamethyldisilazane) and 35 μl (1.2 eq) of TMSOTf were sequentially added under a nitrogen atmosphere, and the reaction solution was stirred. Two hours after the addition of the reagents, the reaction was analyzed by LCMS to find that the conversion rate was 55.8%. Therefore, 20 μl (0.69 eq) of TMOSTf was further added. One hour after the further addition of the reagent, the raw material was confirmed to disappear by LCMS. Amide bond cleavage was not confirmed.

To the reaction vessel was added 373.4 mg (13.3 eq) of dipotassium hydrogenphosphate, after which 0.89 ml of water was added and the reaction solution was stirred for 20 minutes.

To the reaction vessel was then added 3 ml of ethyl acetate, and the two layers were separated. The organic layer was washed with a mixture of 1 ml of saturated aqueous sodium bicarbonate and 1 ml of brine. The resulting organic layer was concentrated.

The resulting oily liquid was then dissolved in 1 ml of ethyl acetate, and 251.0 mg of dipotassium hydrogenphosphate was added. After adding 0.89 ml of water, the reaction vessel was cooled with ice. 36.8 mg of Boc-Ala-OH and 79.5 mg DMT-MM were added, and the reaction solution was stirred overnight in an ice bath. After 15.5 hours, the raw material was confirmed to disappear by LCMS and liquid separation treatment was then conducted. The resulting organic layer was washed twice with 5% potassium carbonate, once with water, twice with 5% potassium bisulfate, and once with brine, and concentrated. 0.1075 g (90% yield) of a crude product was obtained as a white solid.

TABLE 37

|  | Weight (mg) | Yield (%) |
| --- | --- | --- |
| Raw material (Compound 9a) | 107.4 | — |
| Product (Compound 6a) | 107.5 | 90 |

TABLE 38

Analysis of deprotection reaction (HPLC method 1)

|  | MW | m/z | rt | Purity LC A % |
| --- | --- | --- | --- | --- |
| Raw material (Compound 9a) | 664.38 | 687.5 ([M + Na]+) | 5.647 | 99.206 |
| Intermediate (Compound 9b) | 564.33 | 565.31 ([M + H]+) | 3.360 | 98.783 |

TABLE 39

Analysis of elongation reaction (HPLC method 1)

|  | MW | m/z | rt | Purity LC A % |
| --- | --- | --- | --- | --- |
| Product (Compound 9a) | 735.42 | 758.4 ([M + Na]+) | 5.268 | 98.031 |

B. Screening of Electrophilic Species Scavengers

Example 15

Deprotection of Boc-MePhe-MeVal-Asp(OBn)-pip (Compound 9a)
(Base: N-(Trimethylsilyl)diethylamine)

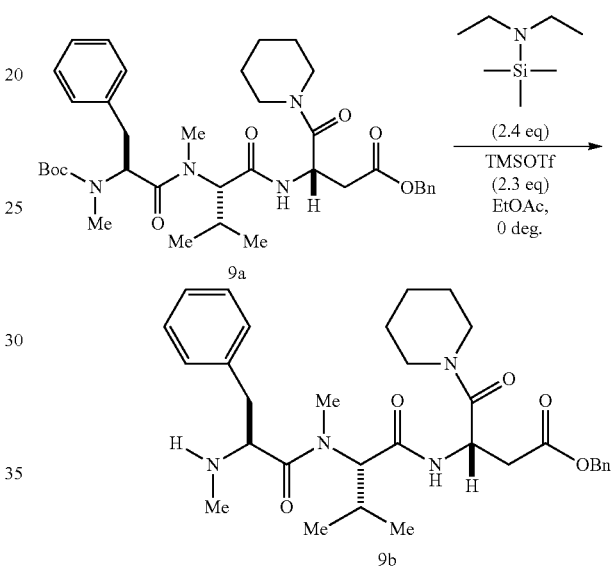

99.5 mg of the raw material was weighed into a reaction vessel and dissolved in 5 v/w of ethyl acetate, and the reaction vessel was cooled with ice. 0.070 ml (2.4 eq) of N-((trimethylsilyl)diethylamine) and 0.032 ml (1.2 eq) of TMSOTf were sequentially added under a nitrogen atmosphere, and the reaction solution was stirred. 1.5 hours after the addition of the reagents, the reaction was analyzed by LCMS to find that the conversion rate was 30%. Therefore, 0.029 ml (1.1 eq) of TMOSTf was further added. Four hours after the start of the reaction, the reaction was analyzed by LCMS and the raw material was confirmed to disappear. At this time, amide bond cleavage was not confirmed. The reaction solution was stirred overnight, and 20 hours after the start of the reaction, the reaction was analyzed again by LCMS. Also at this time, amide bond cleavage was not confirmed.

21 hours after the start of the reaction, 0.2032 g of dipotassium hydrogenphosphate and 0.50 mL of water were added to the reaction solution which was then stirred for 30 min. The reaction solution was diluted with 4 ml of ethyl acetate, and the two layers were then separated to provide an organic layer. The resulting organic layer was washed twice with a mixed solvent of 0.5 ml of brine and 0.5 ml of saturated aqueous sodium bicarbonate. The organic layer was then washed with 0.5 ml of brine and concentrated. The residue was dissolved in 4 ml of isopropyl acetate and washed twice with a mixed solvent of 1 ml of 0.5 M aqueous sodium hydroxide and 0.5 ml of brine. Then, the organic layer was washed with 0.5 ml of 10% saline and concentrated under reduced pressure to give 81.7 mg of a deprotected product in 97% yield.

TABLE 40

|  | Weight (mg) | Yield (%) |
|---|---|---|
| Raw material (Compound 9a) | 99.5 | — |
| Product (Compound 9b) | 81.7 | 97 |

TABLE 41

| Analysis (HPLC method 1) | | | | |
|---|---|---|---|---|
|  | MW | m/z | rt | Purity LC A % |
| Raw material (Compound 9a) | 664.38 | 687.5 ([M + Na]+) | 5.647 | 99.206 |
| Product (Compound 9b) | 564.33 | 565.27 ([M + H]+) | 3.364 | 95.547 |

Example 16

Deprotection of Boc-MePhe-MeVal-Asp(OBn)-pip (Compound 9a)

(Base: N-(Trimethylsilyl)morpholine)

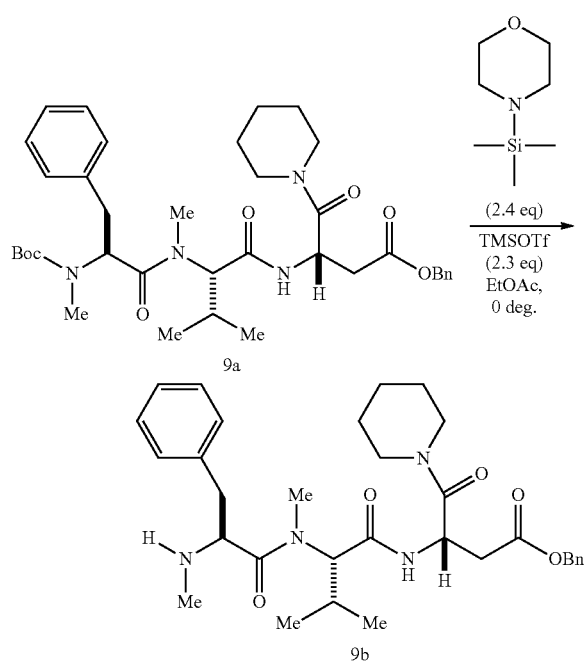

The experiment was performed according to the method described in Example 15.

TABLE 42

|  | Weight (mg) | Yield (%) |
|---|---|---|
| Raw material (Compound 9a) | 98.4 | — |
| Product (Compound 9b) | 117.8 | Quantitative |

TABLE 43

| Analysis (HPLC method 1) | | | | |
|---|---|---|---|---|
|  | MW | m/z | rt | Purity LC A % |
| Raw material (Compound 9a) | 664.38 | 687.5 ([M + Na]+) | 5.647 | 99.206 |
| Product (Compound 9b) | 564.33 | 565.30 ([M + H]+) | 3.350 | 98.652 |

Example 17

Deprotection of Boc-MePhe-MeVal-Asp(OBn)-pip (Compound 9a)

(Base: N-tert-Butyltrimethylsilylamine)

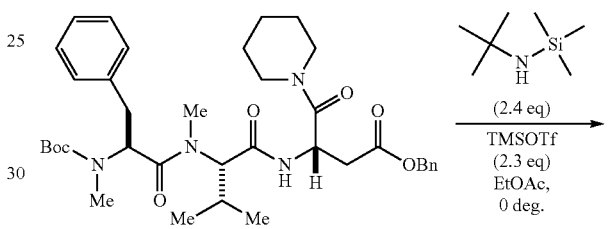

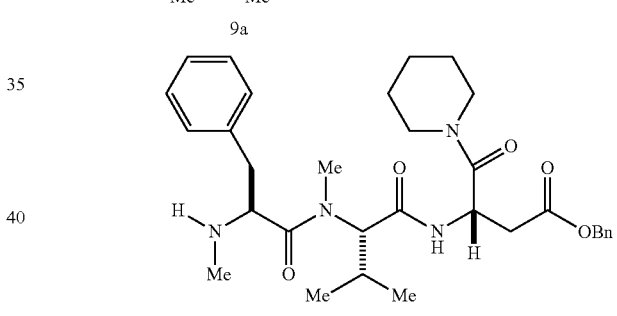

The experiment was performed according to the method described in Example 15.

TABLE 44

|  | Weight (mg) | Yield (%) |
|---|---|---|
| Raw material (Compound 9a) | 100.9 | — |
| Product (Compound 9b) | 128.6 | Quantitative |

TABLE 45

| Analysis (HPLC method 1) | | | | |
|---|---|---|---|---|
|  | MW | m/z | rt | Purity LC A % |
| Raw material (Compound 9a) | 664.38 | 687.5 ([M + Na]+) | 5.647 | 99.206 |
| Product (Compound 9b) | 564.33 | 565.28 ([M + H]+) | 3.354 | 98.631 |

Example 18

Deprotection of Boc-MePhe-MeVal-Asp(OBn)-pip (Compound 9a)
(Base: 2,2,4,4-Tetramethylpentanoneimine)

Example 19

Deprotection of Boc-MePhe-MeVal-Asp(OBn)-pip (Compound 9a)
(Base: Isopropenyloxytrimethylsilane)

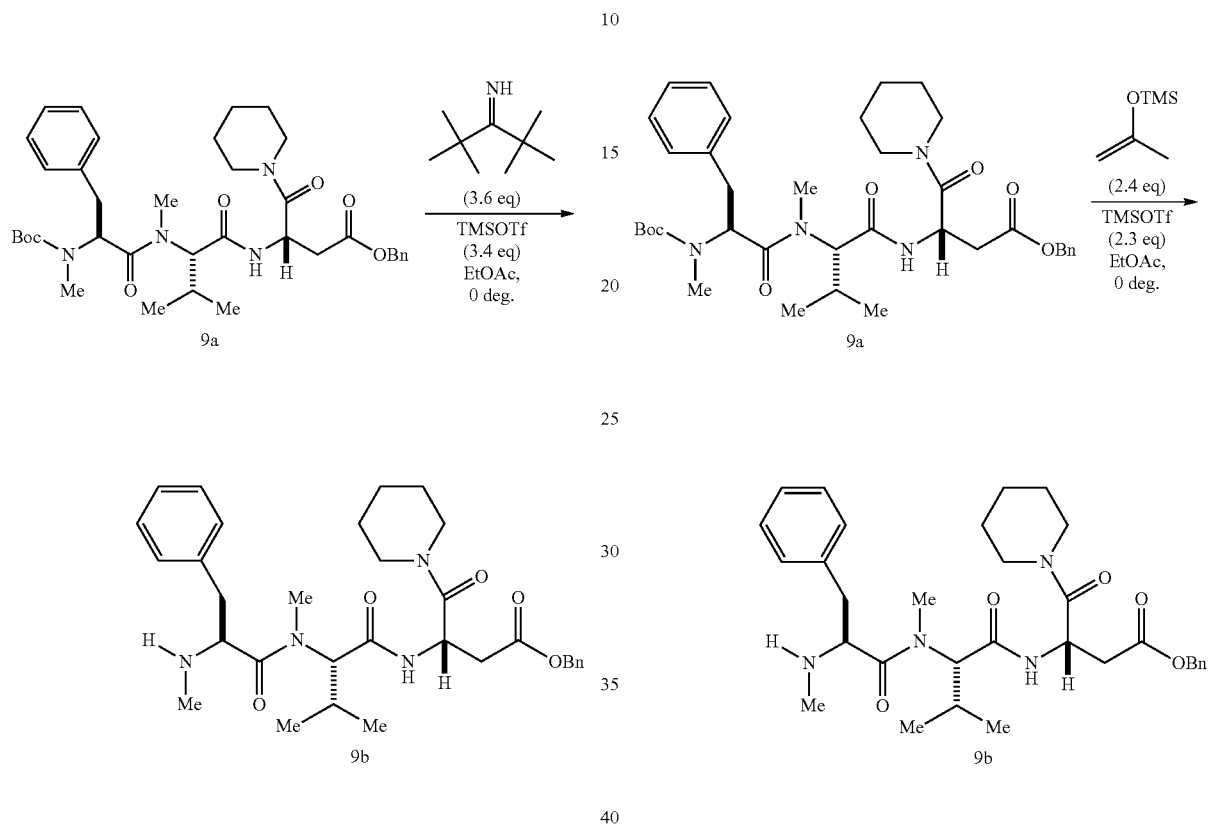

The experiment was performed according to the method described in Example 15.

TABLE 46

|  | Weight (mg) | Yield (%) |
|---|---|---|
| Raw material (Compound 9a) | 88.0 | — |
| Product (Compound 9b) | 102.5 | Quantitative |

TABLE 47

| Analysis (HPLC method 1) | | | | |
|---|---|---|---|---|
|  | MW | m/z | rt | Purity LC A % |
| Raw material (Compound 9a) | 664.38 | 687.5 ([M + Na]+) | 5.647 | 99.206 |
| Product (Compound 9b) | 564.33 | 565.28 ([M + H]+) | 3.338 | 98.433 |

The experiment was performed according to the method described in Example 15.

TABLE 48

|  | Weight (mg) | Yield (%) |
|---|---|---|
| Raw material (Compound 9a) | 44.3 | — |
| Product (Compound 9b) | 44.2 | Quantitative |

TABLE 49

| Analysis (HPLC method 1) | | | | |
|---|---|---|---|---|
|  | MW | m/z | rt | Purity LC A % |
| Raw material (Compound 9a) | 664.38 | 687.5 ([M + Na]+) | 5.647 | 99.206 |
| Product (Compound 9b) | 564.33 | 565.27 ([M + H]+) | 3.340 | 97.587 |

Example 20

Deprotection of Boc-MePhe-MeVal-Asp(OBn)-pip (Compound 9a)
(Base: Dimethylketene methyl trimethylsilyl acetal)

Example 21

Deprotection of Boc-MePhe-MeVal-Asp(OBn)-pip (Compound 9a)
(Base: 3,4-Dihydro-2H-pyran)

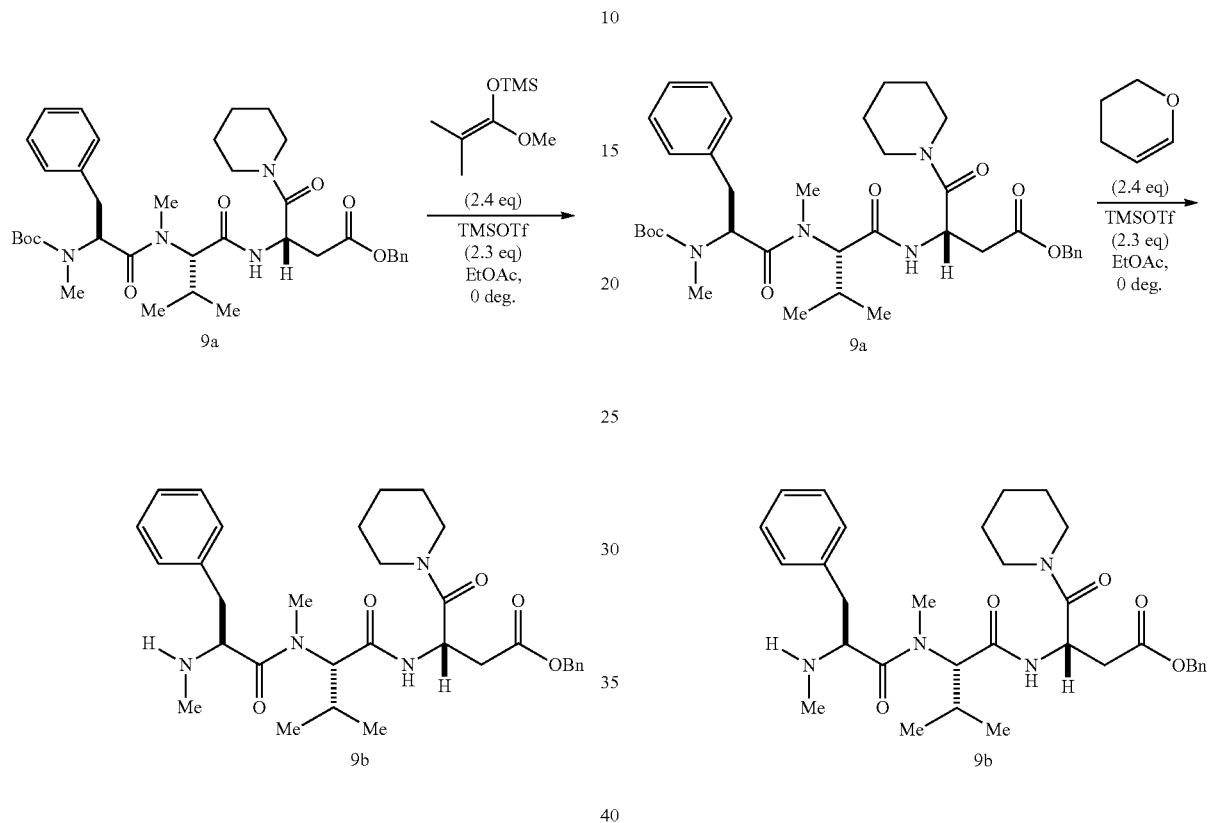

The experiment was performed according to the method described in Example 15.

TABLE 50

|  | Weight (mg) | Yield (%) |
|---|---|---|
| Raw material (Compound 9a) | 44.9 | — |
| Product (Compound 9b) | 44.7 | Quantitative |

TABLE 51

Analysis (HPLC method 1)

|  | MW | m/z | rt | Purity LC A % |
|---|---|---|---|---|
| Raw material (Compound 9a) | 664.38 | 687.5 ([M + Na]+) | 5.647 | 99.206 |
| Product (Compound 9b) | 564.33 | 565.27 ([M + H]+) | 3.348 | 98.352 |

The experiment was performed according to the method described in Example 15.

TABLE 52

|  | Weight (mg) | Yield (%) |
|---|---|---|
| Raw material (Compound 9a) | 53.7 | — |
| Product (Compound 9b) | 69.2 | Quantitative |

TABLE 53

Analysis (HPLC method 1)

|  | MW | m/z | rt | Purity LC A % |
|---|---|---|---|---|
| Raw material (Compound 9a) | 664.38 | 687.5 ([M + Na]+) | 5.647 | 99.206 |
| Product (Compound 9b) | 564.33 | 565.27 ([M + H]+) | 3.325 | 98.503 |

Example 22

Deprotection of Boc-MePhe-MeVal-Asp(OBn)-pip (Compound 9a)

(Base: N,N,N',N'-Tetramethyl-1,8-naphthalenediamine)

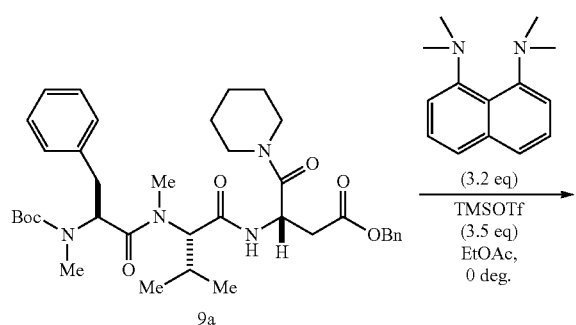

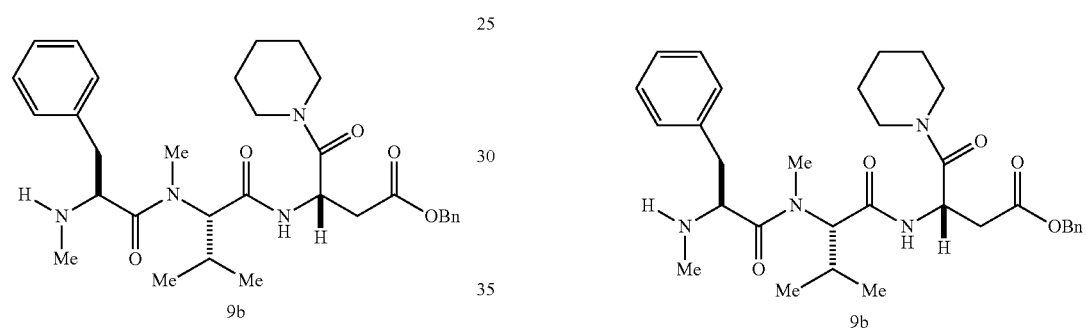

The experiment was performed according to the method described in Example 15.

TABLE 54

|  | Weight (mg) | Yield (%) |
| --- | --- | --- |
| Raw material (Compound 9a) | 50.6 | — |
| Product (Compound 9b) | 57.6 | Quantitative |

TABLE 55

Analysis (HPLC method 1)

|  | MW | m/z | rt | Purity LC A % |
| --- | --- | --- | --- | --- |
| Raw material (Compound 9a) | 664.38 | 687.5 ([M + Na]+) | 5.647 | 99.206 |
| Product (Compound 9b) | 564.33 | 565.28 ([M + H]+) | 3.353 | 98.409 |

(LCA % of the product described above is a value obtained by excluding the base remaining after post-treatment.)

Example 23

Deprotection of Boc-MePhe-MeVal-Asp(OBn)-pip (Compound 9a)

(Base: 2,2'-Isopropylidenebis[(4S)-4-tert-butyl-2-oxazoline])

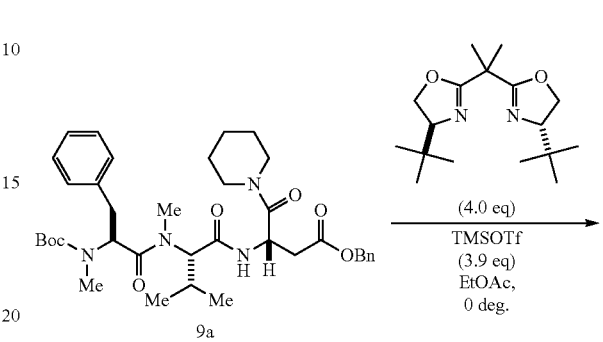

The experiment was performed according to the method described in Example 15.

TABLE 56

|  | Weight (mg) | Yield (%) |
| --- | --- | --- |
| Raw material (Compound 9a) | 45.7 | — |
| Product (Compound 9b) | 128.5 | Quantitative |

TABLE 57

Analysis (HPLC method 1)

|  | MW | m/z | rt | LC A % |
| --- | --- | --- | --- | --- |
| Raw material (Compound 9a) | 664.38 | 687.5 ([M + Na]+) | 5.647 | 99.206 |
| Product (Compound 9b) | 564.33 | 565.28 ([M + H]+) | 3.353 | 90.099 |

(LCA % of the product described above is a value obtained by excluding the base remaining after post-treatment.)

Example 24

Deprotection of Boc-MePhe-MeVal-Asp(OBn)-pip (Compound 9a)
(Base: Diisopropylcarbodiimide)

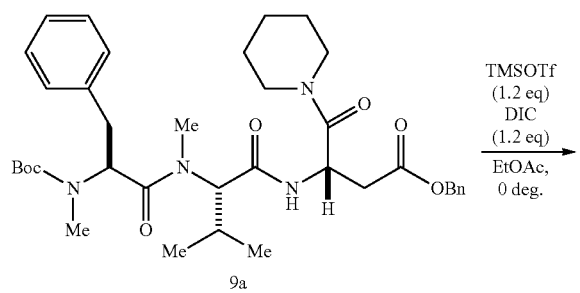

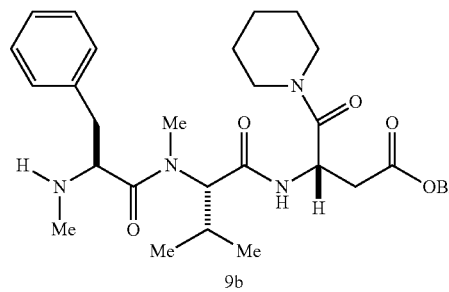

The experiment was performed according to the method described in Example 15.

TABLE 58

| | Weight (mg) | Yield (%) |
|---|---|---|
| Raw material (Compound 9a) | 36.8 | — |
| Product (Compound 9b) | 31.2 | 85 |

TABLE 59

| Analysis (HPLC method 1) | | | | |
|---|---|---|---|---|
| | MW | m/z | rt | LC A % |
| Raw material (Compound 9a) | 664.38 | 687.5 ([M + Na]+) | 5.647 | 99.206 |
| Product (Compound 9b) | 564.33 | 565.28 ([M + H]+) | 3.347 | 89.920 |

(LCA % of the product described above is a value obtained by excluding the base remaining after post-treatment.)

C. Screening of Electrophilic Species Scavengers (Experiments in 11-Mer Peptides)

Example 25

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-BSTFA Method)

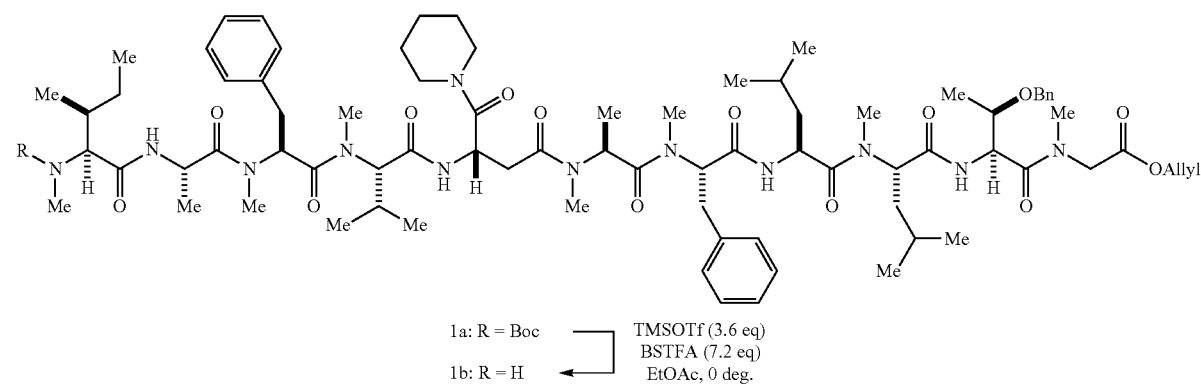

The experiment was performed according to Example 2.

TABLE 60

| | Weight (mg) | Yield (%) |
|---|---|---|
| Raw material (Compound 1a) | 19.7 | — |
| Product (Compound 1b) | 14.8 | 80 |

TABLE 61

| Analysis (HPLC method 1: Determination of purities of the raw material and target product) | | | | |
|---|---|---|---|---|
| | MW | m/z | rt | Purity LC A % |
| Raw material (Compound 1a) | 1560.96 | 1242.05 | 6.519 | 96.680 |
| Product (Compound 1b) | 1460.90 | 731.67 | 4.638 | 96.275 |

Example 26

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-BSA Method)

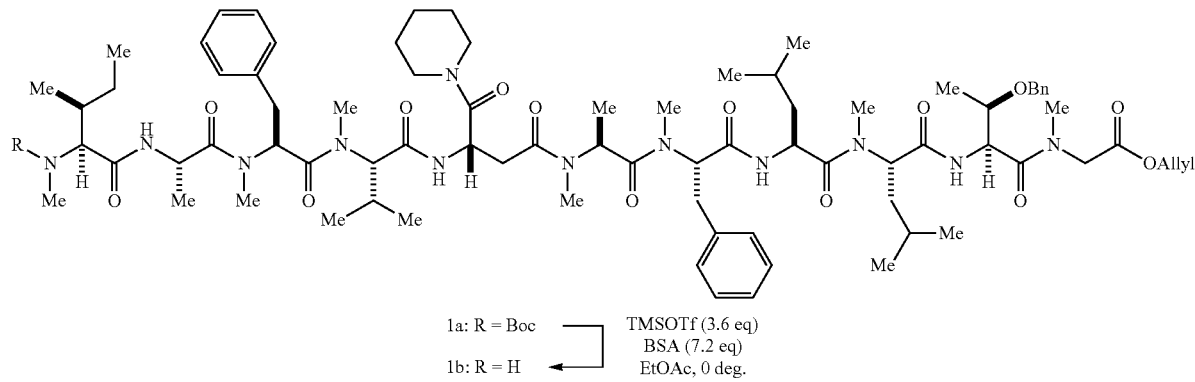

1a: R = Boc
1b: R = H

TMSOTf (3.6 eq)
BSA (7.2 eq)
EtOAc, 0 deg.

The experiment was performed according to Example 2.

TABLE 62

|  | Weight (mg) | Yield (%) |
|---|---|---|
| Raw material (Compound 1a) | 18.0 | — |
| Product (Compound 1b) | 11.8 | 70 |

TABLE 63

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.67 | 4.633 | 94.636 |

Example 27

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-silylamine Method)

The experiment was performed according to Example 2.

TABLE 64

|  | Weight (mg) | Yield (%) |
|---|---|---|
| Raw material (Compound 1a) | 19.3 | — |
| Product (Compound 1b) | 16.1 | 89 |

TABLE 65

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.68 | 4.627 | 96.267 |

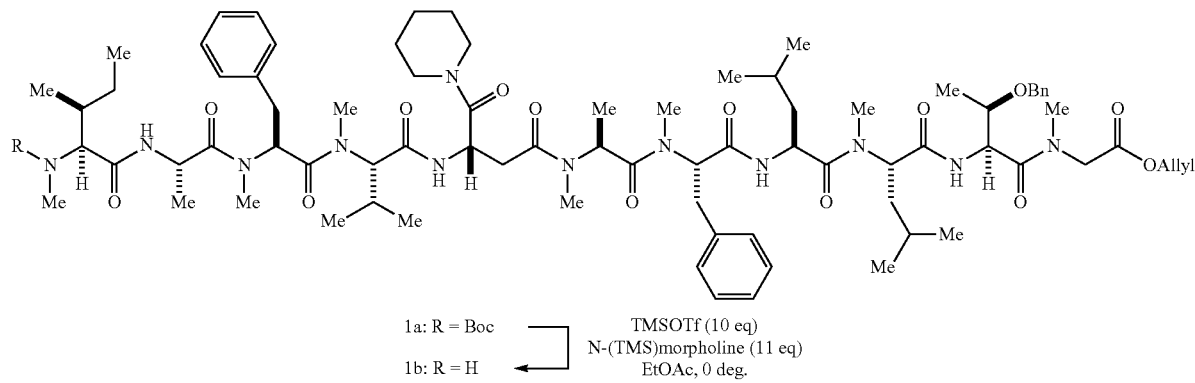

1a: R = Boc
1b: R = H

TMSOTf (10 eq)
N-(TMS)morpholine (11 eq)
EtOAc, 0 deg.

Example 28

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-silylamine Method)

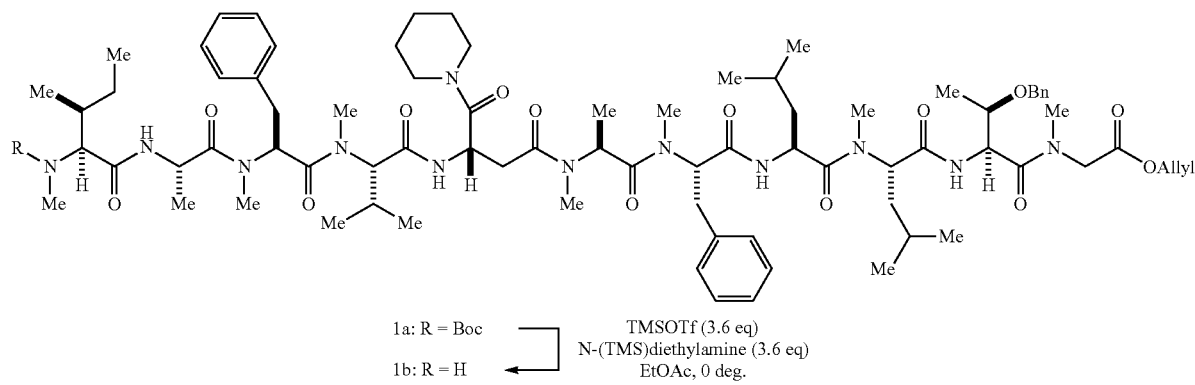

1a: R = Boc
1b: R = H

TMSOTf (3.6 eq)
N-(TMS)diethylamine (3.6 eq)
EtOAc, 0 deg.

The experiment was performed according to Example 2.

TABLE 66

|  | Weight (mg) | Yield (%) |
|---|---|---|
| Raw material (Compound 1a) | 20.2 | — |
| Product (Compound 1b) | 15.3 | 81 |

TABLE 67

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.65 | 4.626 | 97.574 |

Example 29

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-imine Method)

The experiment was performed according to Example 2.

TABLE 68

|  | Weight (mg) | Yield (%) |
|---|---|---|
| Raw material (Compound 1a) | 18.7 | — |
| Product (Compound 1b) | 15.7 | 90 |

TABLE 69

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.70 | 4.631 | 97.089 |

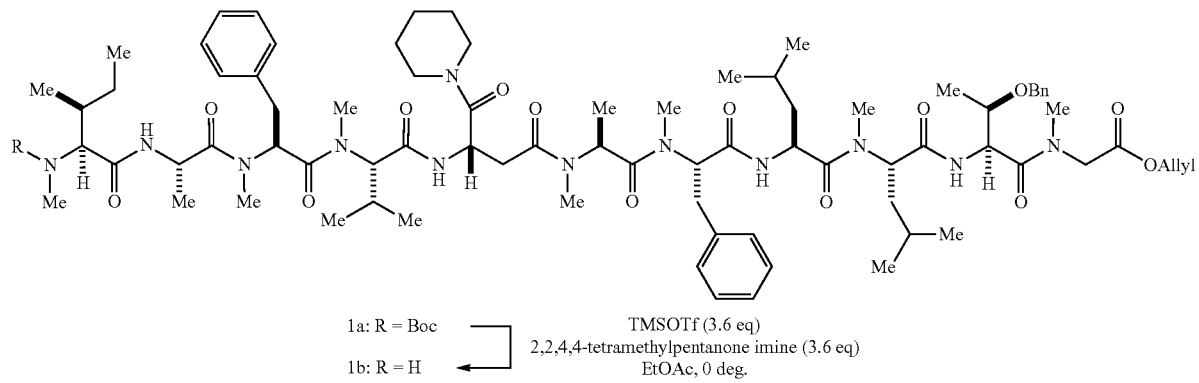

1a: R = Boc
1b: R = H

TMSOTf (3.6 eq)
2,2,4,4-tetramethylpentanone imine (3.6 eq)
EtOAc, 0 deg.

Example 30

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-MSTFA Method)

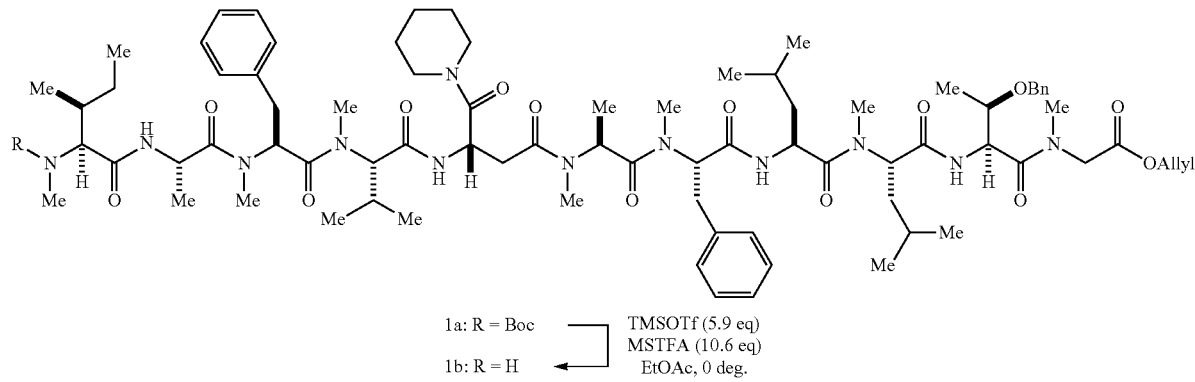

The experiment was performed according to Example 2.

TABLE 70

| | Weight (mg) | Yield (%) |
|---|---|---|
| Raw material (Compound 1a) | 21.7 | — |
| Product (Compound 1b) | 15.7 | 77 |

TABLE 71

Analysis (HPLC method 1: Determination of purities of the raw material and target product)

| | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.61 | 4.616 | 96.490 |

Example 31

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-silylamine Method)

The experiment was performed according to Example 2.

TABLE 72

| | Weight (mg) | Yield (%) |
|---|---|---|
| Raw material (Compound 1a) | 17.5 | — |
| Product (Compound 1b) | 13.5 | 81 |

TABLE 73

Analysis (HPLC method 1: Determination of purities of the raw material and target product)

| | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.71 | 4.629 | 97.390 |

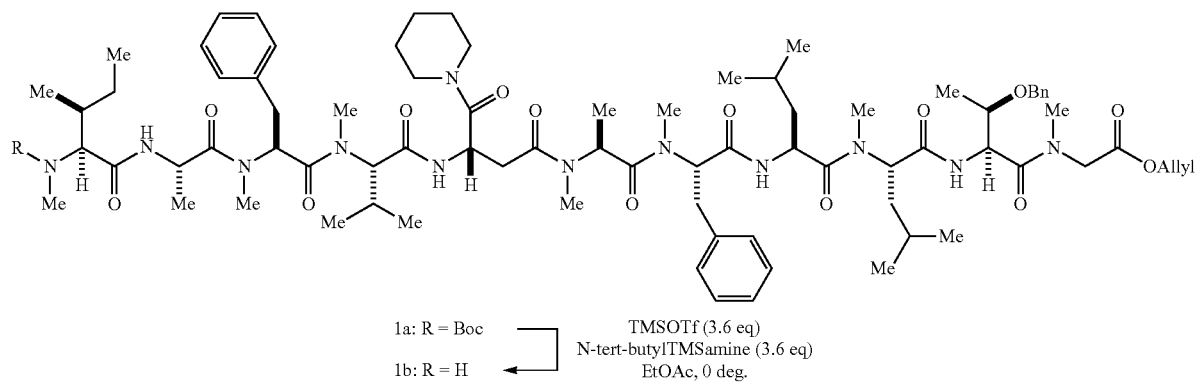

Example 32

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-ketene silyl acetal Method)

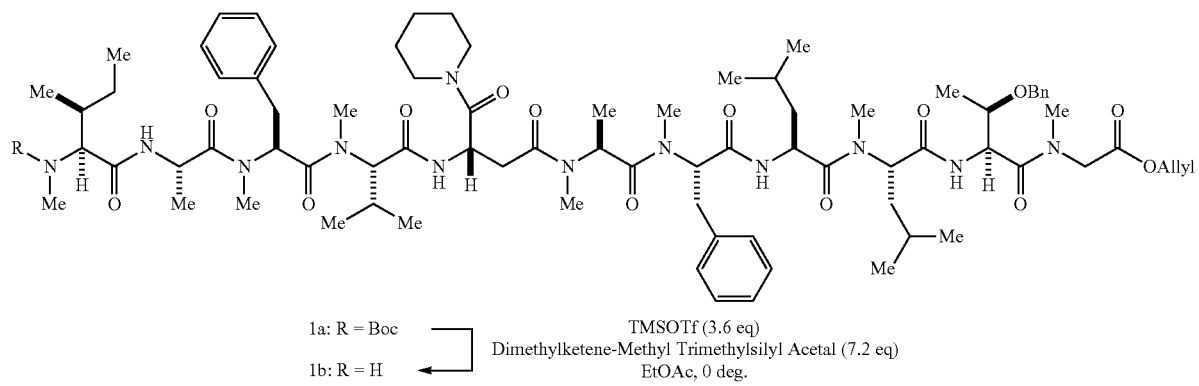

The experiment was performed according to Example 2.

TABLE 74

|  | Weight (mg) | Yield (%) |
|---|---|---|
| Raw material (Compound 1a) | 23.6 | — |
| Product (Compound 1b) | 19.8 | 90 |

TABLE 75

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.63 | 4.620 | 97.488 |

Example 33

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-proton Sponge Method)

The experiment was performed according to Example 2.

TABLE 76

|  | Weight (mg) | Yield (%) |
|---|---|---|
| Raw material (Compound 1a) | 17.5 | — |
| Product (Compound 1b) | 16.2 | 97 |

(The base remains even after post-treatment.)

TABLE 77

Analysis (HPLC method 1: Determination of purities of the raw material and target product)

|  | MW | m/z | rt | Purity LC A % |
|---|---|---|---|---|
| Raw material (Compound 1a) | 1560.96 | 1242.05 | 6.519 | 96.680 |
| Product (Compound 1b) | 1460.90 | 731.68 | 4.628 | 96.025 |

(LC A % of the product described above is a value obtained by excluding the base remaining after post-treatment.)

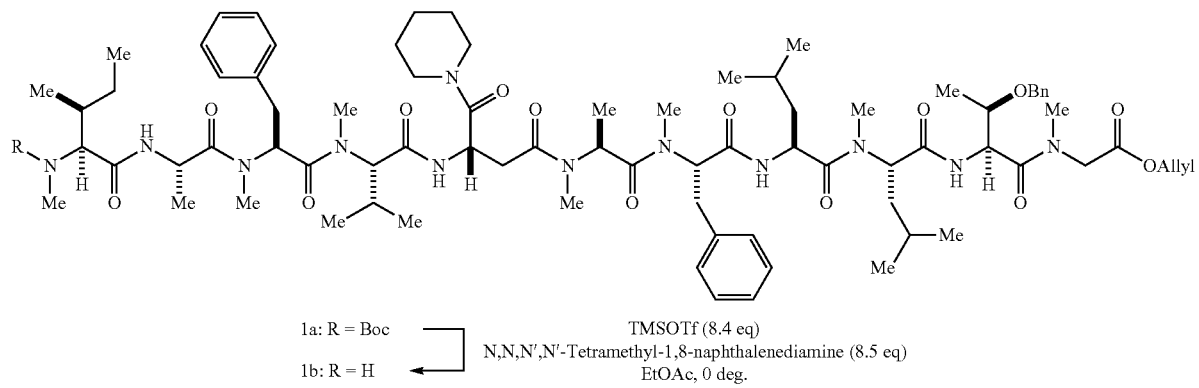

Example 34

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-lutidine Method)

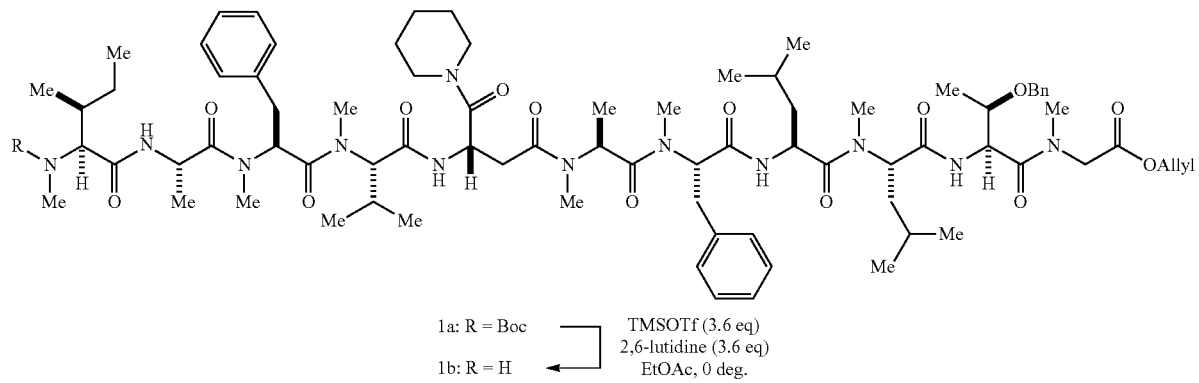

18.8 mg of the raw material was weighed into a reaction vessel and dissolved in 10 v/w of ethyl acetate. 0.005 ml (3.6 eq) of 2,6-lutidine and 0.0078 ml (3.6 eq) of TMSOTf were then added and the reaction solution was stirred. Four hours after the addition of the reagents, the reaction was analyzed by LCMS (HPLC method 1) and the conversion rate (=target product/(target product+starting material)) was confirmed to be 14%. Next, the reaction was analyzed by LCMS 19 hours after the addition of the reagents to find that the conversion rate was still 14%. Amide bond cleavage was not confirmed.

TABLE 78

|  | Weight (mg) | Yield (%) |
|---|---|---|
| Raw material (Compound 1a) | 18.8 | — |
| Product (Compound 1b) | Not isolated | Not isolated |

TABLE 79

Analysis (HPLC method 1: Determination of purity of the raw material)

|  | MW | m/z | rt | Purity LC A % |
|---|---|---|---|---|
| Raw material (Compound 1a) | 1560.96 | 1242.05 | 6.519 | 96.680 |

TABLE 80

Analysis (HPLC method 1: Determination of conversion rate)

|  | MW | m/z | rt | LC A % |
|---|---|---|---|---|
| Raw material (Compound 1a) | 1560.96 | 1242.05 | 6.519 | 75.059 |
| Product (Compound 1b) | 1460.90 | 731.67 | 4.620 | 11.831 |

Example 35

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-lutidine Method)

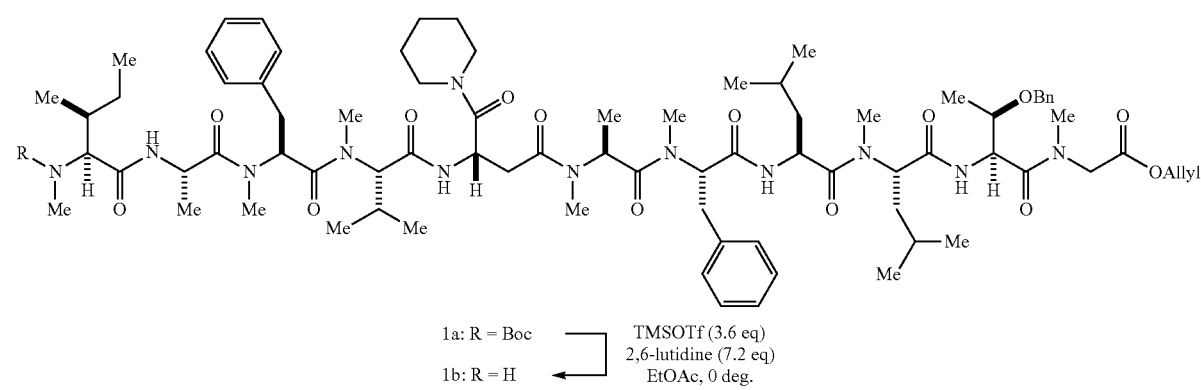

89.3 mg of the raw material was weighed into a reaction vessel and dissolved in 1 ml of ethyl acetate. 0.016 ml (2.4 eq) of 2,6-lutidine and 0.012 ml (1.2 eq) of TMSOTf were then added and the reaction solution was stirred. 1.25 hours after the addition of the reagents, the reaction was analyzed by LCMS (HPLC method 1) to find that the conversion rate (=target product/(target product+starting material)) was 0%. Therefore, 0.032 ml (4.8 eq) of 2,6-lutidine and 0.024 ml (2.4 eq) of TMSOTf were further added. The reaction was analyzed by LCMS, 1.25 hours and 14 hours after the further addition of the reagents, respectively, to find that the conversion rate was still 0%. Amide bond cleavage was not confirmed.

TABLE 81

|  | Weight (mg) | Yield (%) |
| --- | --- | --- |
| Raw material (Compound 1a) | 89.3 | — |
| Product (Compound 1b) | Not isolated | Not isolated |

TABLE 82

Analysis (HPLC method 1: Determination of purity of the raw material)

|  | MW | m/z | rt | Purity LC A % |
| --- | --- | --- | --- | --- |
| Raw material (Compound 1a) | 1560.96 | 1242.05 | 6.545 | 89.564 |

TABLE 83

Analysis (HPLC method 1: Determination of conversion rate)

|  | MW | m/z | rt | LC A % |
| --- | --- | --- | --- | --- |
| Raw material (Compound 1a) | 1560.96 | 1242.05 | 6.571 | 89.649 |
| Product (Compound 1b) | 1460.90 | ND | ND | 0 |

Example 36

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-2,6-di-tert-butylpyridine Method)

14.9 mg of the raw material was weighed into a reaction vessel and dissolved in 0.2 ml of ethyl acetate. 0.011 ml (5.4 eq) of 2,6-di-t-butylpyridine and 0.0062 ml (3.6 eq) of TMSOTf were then added and the reaction solution was stirred. Four hours after the addition of the reagents, the reaction was analyzed by LCMS (HPLC method 1) to find that the conversion rate (=target product/(target product+starting material)) was 59%. The reaction was analyzed again by LCMS 22 hours after the start of the reaction to find that the conversion rate was still 59%. Amide bond cleavage was not confirmed.

TABLE 84

|  | Weight (mg) | Yield (%) |
| --- | --- | --- |
| Raw material (Compound 1a) | 14.9 | — |
| Product (Compound 1b) | Not isolated | Not isolated |

TABLE 85

Analysis (HPLC method 1: Determination of purity of the raw material)

|  | MW | m/z | rt | Purity LC A % |
| --- | --- | --- | --- | --- |
| Raw material (Compound 1a) | 1560.96 | 1242.05 | 6.545 | 96.680 |

TABLE 86

Analysis (HPLC method 1: Determination of conversion rate)

|  | MW | m/z | rt | LC A % |
| --- | --- | --- | --- | --- |
| Raw material (Compound 1a) | 1560.96 | 1242.05 | 6.571 | 26.863 |
| Product (Compound 1b) | 1460.90 | 731.67 | 4.620 | 38.429 |
| Ethyl acetate |  |  | 1.850 | 12.893 |
| 2,6-di(tBu)pyridine |  |  | 3.844 | 19.629 |

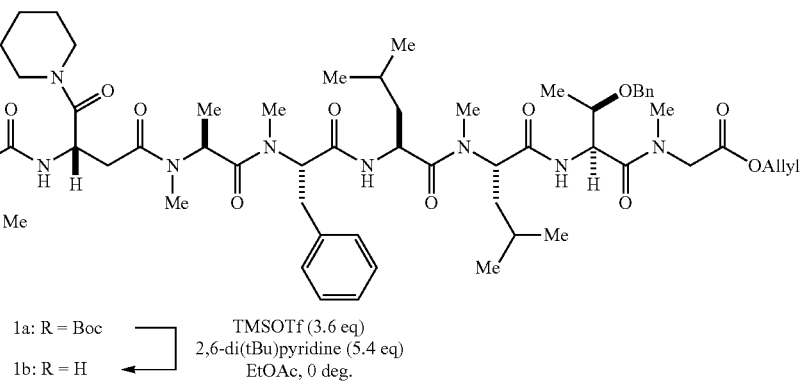

Example 37

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-tert-amine Method)

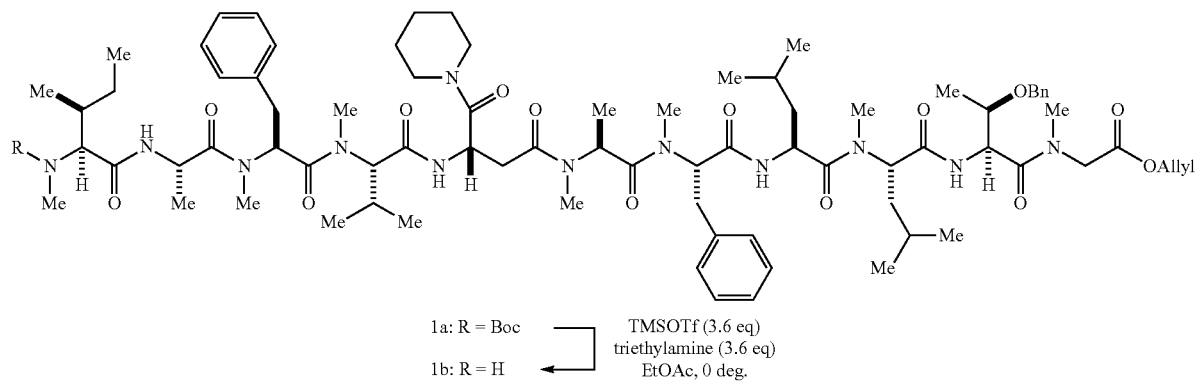

1a: R = Boc
1b: R = H
TMSOTf (3.6 eq)
triethylamine (3.6 eq)
EtOAc, 0 deg.

17.7 mg of the raw material was weighed into a reaction vessel and dissolved in 0.20 ml of ethyl acetate. 0.0057 ml (3.6 eq) of triethylamine and 0.0074 ml (3.6 eq) of TMSOTf were then added and the reaction solution was stirred. The reaction was analyzed by LCMS (HPLC method 1) one hour and four hours after the addition of the reagents to find that the conversion rate (=target product/(target product+starting material)) was merely 0.7% at each time. Amide bond cleavage was not confirmed.

TABLE 87

| | Weight (mg) | Yield (%) |
|---|---|---|
| Raw material (Compound 1a) | 17.7 | — |
| Product (Compound 1b) | Not isolated | Not isolated |

TABLE 88

Analysis (HPLC method 1: Determination of purity of the raw material)

| | MW | m/z | rt | Purity LC A % |
|---|---|---|---|---|
| Raw material (Compound 1a) | 1560.96 | 1242.05 | 6.519 | 96.680 |

TABLE 89

Analysis (HPLC method 1: Determination of conversion rate)

| | MW | m/z | rt | LC A % |
|---|---|---|---|---|
| Raw material (Compound 1a) | 1560.96 | 1242.05 | 6.579 | 84.391 |
| Product (Compound 1b) | 1460.90 | 731.67 | 4.639 | 0.599 |
| Ethyl acetate (Solvent) | | | 1.844 | 13.474 |

Example 38

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-tert-amine Method)

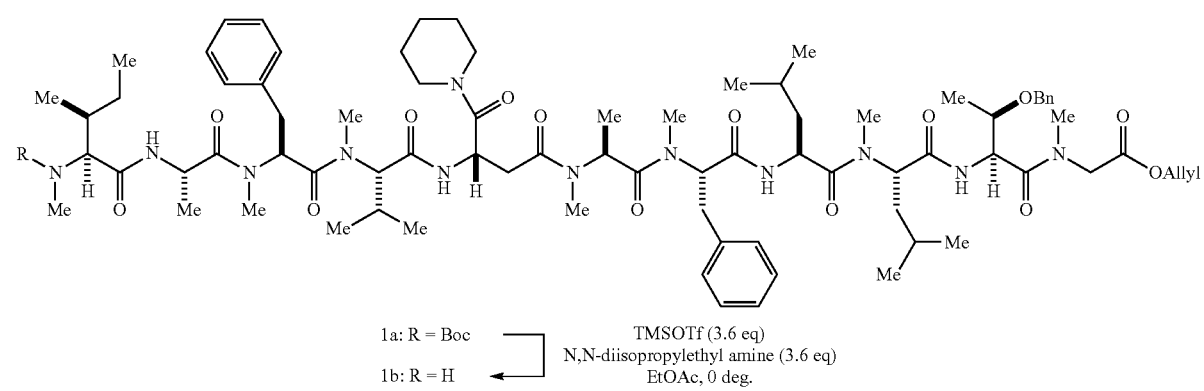

1a: R = Boc
1b: R = H
TMSOTf (3.6 eq)
N,N-diisopropylethyl amine (3.6 eq)
EtOAc, 0 deg.

19.1 mg of the raw material was weighed into a reaction vessel and dissolved in 0.20 ml of ethyl acetate. 0.0074 ml (3.6 eq) of diisopropylethylamine and 0.0077 ml (3.6 eq) of TMSOTf were then added and the reaction solution was stirred. The reaction was analyzed by LCMS (HPLC method 2) two hours and four hours after the addition of the reagents to find that the conversion rate (=target product/(target product+starting material)) was merely 0.8% or less at each time. Amide bond cleavage was not confirmed.

TABLE 90

|  | Weight (mg) | Yield (%) |
| --- | --- | --- |
| Raw material (Compound 1a) | 19.1 | — |
| Product (Compound 1b) | Not isolated | Not isolated |

TABLE 91

| Analysis (HPLC method 1: Determination of purity of the raw material) | | | |
| --- | --- | --- | --- |
| | MW | m/z | rt | Purity LC A % |
| Raw material (Compound 1a) | 1560.96 | 1242.05 | 6.519 | 96.680 |

TABLE 92

| Analysis (HPLC method 1: Determination of conversion rate) | | | |
| --- | --- | --- | --- |
| | MW | m/z | rt | LC A % |
| Raw material (Compound 1a) | 1560.96 | 1241.79 | 6.568 | 85.820 |
| Product (Compound 1b) | 1460.90 | 731.68 | 4.629 | 0.458 |
| Ethyl acetate (Solvent) | | | 1.836 | 12.495 |

Example 39

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TMSOTf-tert-amine Method)

92.9 mg of the raw material was weighed into a reaction vessel and dissolved in 1 ml of ethyl acetate, and the reaction vessel was then cooled with ice. 0.015 ml (2.4 eq) of diisopropylethylamine and 0.013 ml (1.2 eq) of TMSOTf were then added under a nitrogen atmosphere, and the reaction solution was stirred. The reaction was analyzed two hours after the addition of the reagents to find that the conversion rate (=target product/(target product+starting material)) was 0%. Therefore, 0.030 ml (4.8 eq) of diisopropylethylamine and 0.026 ml (2.4 eq) of TMSOTf were further added three hours after the addition of the reagents. Three hours after the further addition of the reagents, the reaction was analyzed again to find that the conversion rate was 0%. Amide bond cleavage was not confirmed.

TABLE 93

|  | Weight (mg) | Yield (%) |
| --- | --- | --- |
| Raw material (Compound 1a) | 92.9 | — |
| Product (Compound 1b) | Not isolated | Not isolated |

TABLE 94

| Analysis (HPLC method 1: Determination of purity of the raw material) | | | |
| --- | --- | --- | --- |
| | MW | m/z | rt | Purity LC A % |
| Raw material (Compound 1a) | 1560.96 | 1241.93 | 6.538 | 89.465 |

TABLE 95

| Analysis (HPLC method 1: Determination of conversion rate) | | | |
| --- | --- | --- | --- |
| | MW | m/z | rt | LC A % |
| Raw material (Compound 1a) | 1560.96 | 1242.05 | 6.568 | 89.432 |
| Product (Compound 1b) | 1460.90 | ND | ND | 0 |

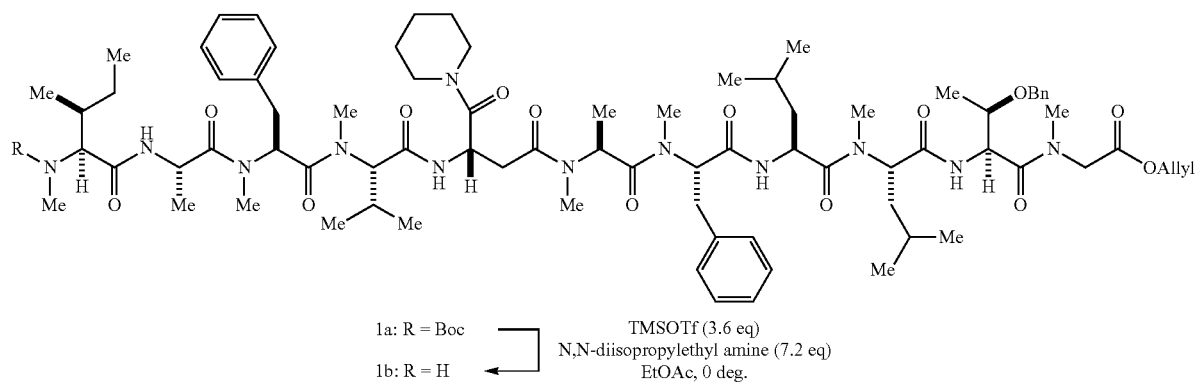

Example 40

Boc removal reaction of Boc-MeIle-Ala-MePhe-MeVal-Asp(pip)-MeAla-MePhe-Leu-MeLeu-Thr(OBn)-MeGly-OAllyl (Compound 1a) (11-mer: conducted using only TMSOTf in the absence of an organic base.)

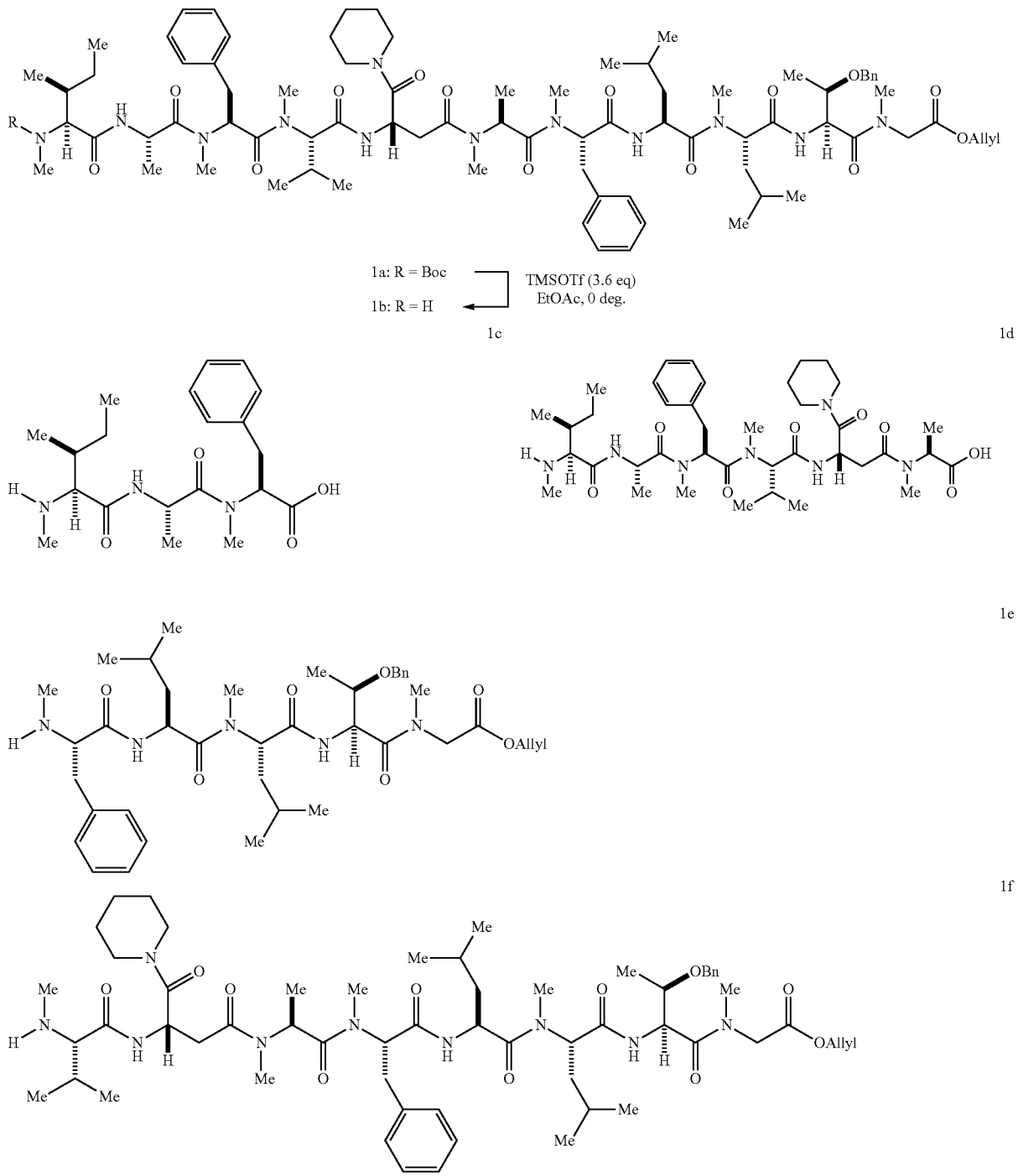

18.3 mg of the raw material was weighed into a reaction vessel and dissolved in 0.2 ml of ethyl acetate, and the reaction vessel was then cooled with ice. 0.0077 ml (3.6 eq) of TMSOTf was then added under a nitrogen atmosphere, and the reaction solution was stirred. The reaction was analyzed 1.5 hours after the addition of the reagent to confirm that multiple amide bond-cleaved products were produced at a conversion rate (=target product/(target product+starting material)) of 68%.

TABLE 96

| | Weight (mg) | Yield (%) |
|---|---|---|
| Raw material (Compound 1a) | 18.3 | — |
| Product (Compound 1b) | Not isolated | Not isolated |

TABLE 97

Analysis (HPLC method 1: Determination of purity of the raw material)

| | MW | m/z | rt | Purity LC A % |
|---|---|---|---|---|
| Raw material (Compound 1a) | 1560.96 | 1242.05 | 6.519 | 96.680 |

TABLE 98

Analysis (HPLC method 1: Determination of conversion rate and rates of production of by-products)

| | MW | m/z | rt | LC A % |
|---|---|---|---|---|
| Raw material (Compound 1a) | 1560.96 | 1241.77 | 6.575 | 15.543 |
| Product (Compound 1b) | 1460.90 | 731.72 | 4.630 | 32.712 |
| Cleaved product (Compound 1c) | 377.23 | 378.22 ([M + H]+) | 2.269 | 0.986 |
| Cleaved product (Compound 1d) | 757.47 | 758.40 ([M + H]+) | 2.758 | 9.731 |
| Cleaved product (Compound 1e) | 721.44 | 722.43 ([M + H]+) | 3.893 | 15.859 |
| Cleaved product (Compound 1f) | 1101.68 | 1102.56 ([M + H]+) | 4.220 | 4.701 |
| Cleaved product (Compound 1g) | Unknown | 573.27 | 4.788 | 4.808 |
| Ethyl acetate | | | 1.840 | 15.660 |

The structure of Compound 1g is unknown.

Example 41

Boc removal reaction of Boc-MeIle-Ala-MePhe-MeVal-Asp(pip)-MeAla-MePhe-Leu-MeLeu-Thr(OBn)-MeGly-OAllyl (Compound 1a) (11-mer: conducted with TMSOTf and triisopropylsilane in the absence of an organic base.)

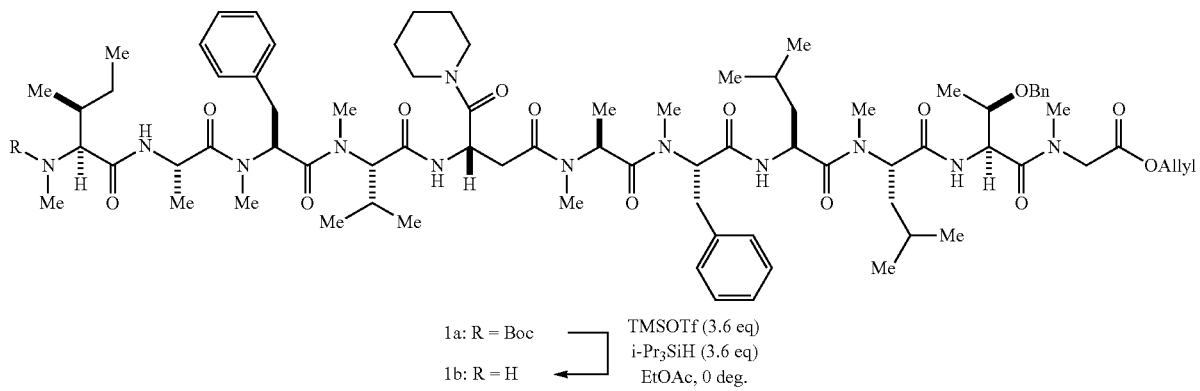

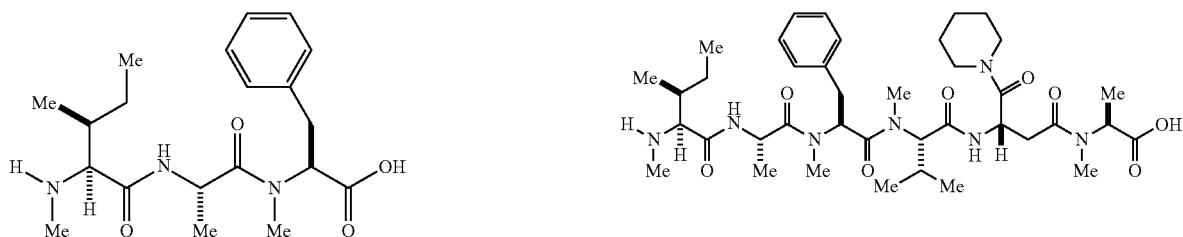

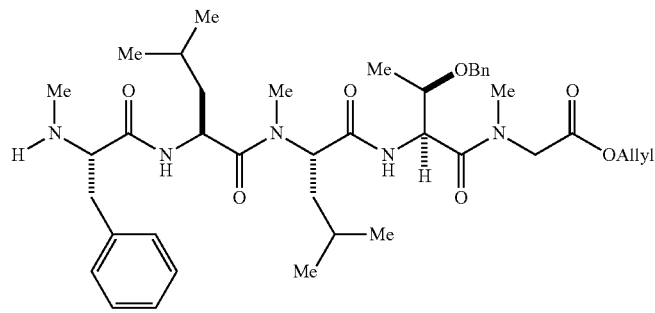

1e

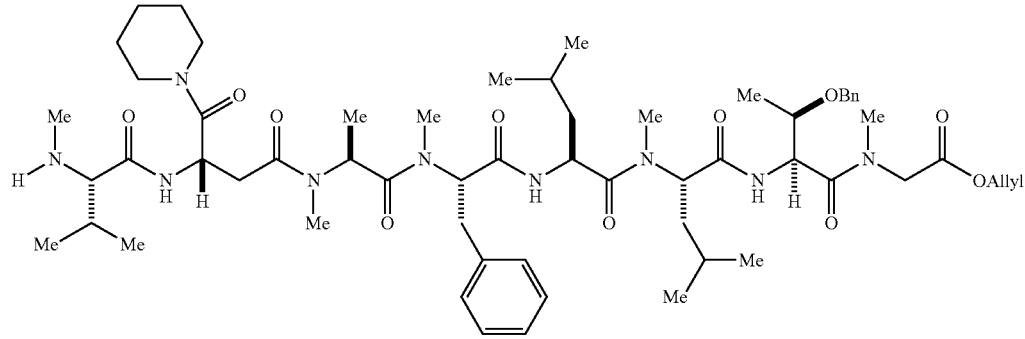

1f 20.5 mg of the raw material was weighed into a reaction vessel and dissolved in 0.2 ml of ethyl acetate, and the reaction vessel was then cooled with ice. 0.0097 ml (3.6 eq) of triisopropylsilane and 0.0085 ml (3.6 eq) of TMSOTf were then added under a nitrogen atmosphere, and the reaction solution was stirred. The reaction was analyzed one hour after the addition of the reagents to confirm that multiple amide bond-cleaved products were produced at a conversion rate (=target product/(target product+starting material)) of 43%.

TABLE 99

|  | Weight (mg) | Yield (%) |
|---|---|---|
| Raw material (Compound 1a) | 20.5 | — |
| Product (Compound 1b) | Not isolated | Not isolated |

TABLE 100

| Analysis (HPLC method 1: Determination of purity of the raw material) | | | | |
|---|---|---|---|---|
|  | MW | m/z | rt | Purity LC A % |
| Raw material (Compound 1a) | 1560.96 | 1242.05 | 6.538 | 96.680 |

TABLE 101

| Analysis (HPLC method 1: Determination of conversion rate and rates of production of by-products) | | | | |
|---|---|---|---|---|
|  | MW | m/z | rt | LC A % |
| Raw material (Compound 1a) | 1560.96 | 1241.77 | 6.575 | 28.216 |
| Product (Compound 1b) | 1460.90 | 731.59 | 4.624 | 20.995 |
| Cleaved product (Compound 1c) | 377.23 | 378.24 ([M + H]+) | 2.259 | 0.479 |
| Cleaved product (Compound 1d) | 757.47 | 758.44 ([M + H]+) | 2.750 | 5.875 |

TABLE 101-continued

| Analysis (HPLC method 1: Determination of conversion rate and rates of production of by- products) | | | | |
|---|---|---|---|---|
| | MW | m/z | rt | LC A % |
| Cleaved product (Compound 1e) | 721.44 | 722.36 ([M + H]+) | 3.885 | 15.802 |
| Cleaved product (Compound 1f) | 1101.68 | 1102.55 ([M + H]+) | 4.212 | 5.239 |
| Impurity (Compound 1g) | Unknown | 573.24 | 4.780 | 8.178 |
| Ethyl acetate | | | 1.836 | 14.570 |

The structure of Compound 1g is unknown.

Example 42

Boc Removal Reaction of Boc-MeIle-Ala-MePhe-MeVal-Asp(pip)-MeAla-MePhe-Leu-MeLeu-Thr(OBn)-MeGly-OAllyl (Compound 1a) (11-mer: TFA Method)

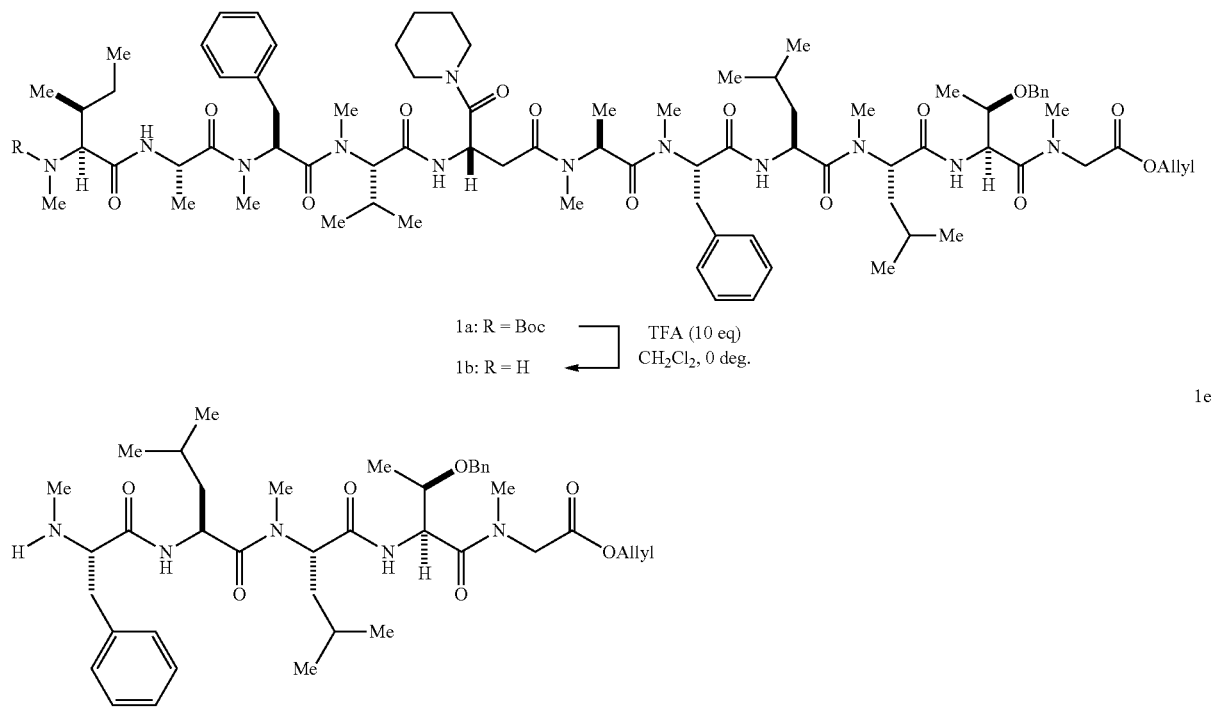

35.3 mg of the raw material was weighed into a reaction vessel and dissolved in 10 v/w of methylene chloride, and the reaction vessel was then cooled with ice. 0.004 ml (2.3 eq) of trifluoroacetic acid was then added under a nitrogen atmosphere, and the reaction solution was stirred. The reaction was analyzed 10 minutes after the addition of the reagent to find that the conversion rate (=target product/(target product+starting material)) was 0%. Therefore, 0.004 ml (2.3 eq) of trifluoroacetic acid was further added. The reaction was analyzed again 10 minutes after the further addition of the reagent to find that the conversion rate was 0%. Therefore, 0.0094 ml (5.4 eq) of trifluoroacetic acid was further added. 10 minutes after the further addition of the reagent, the reaction solution was warmed to room temperature and continued to be stirred. Four hours after warming to room temperature, the reaction was analyzed to confirm that an amide bond-cleaved product 1e was produced at a conversion rate of 2%.

TABLE 102

| | Weight (mg) | Yield (%) |
|---|---|---|
| Raw material (Compound 1a) | 35.3 | — |
| Product (Compound 1b) | Not isolated | Not isolated |

TABLE 103

| Analysis (HPLC method 1: Determination of purity of the raw material) | | | | |
|---|---|---|---|---|
| | MW | m/z | rt | Purity LC A % |
| Raw material (Compound 1a) | 1560.96 | 1242.05 | 6.519 | 96.680 |

TABLE 104

Analysis (HPLC method 1: Determination of conversion rate and rates of production of by-products)

|  | MW | m/z | rt | LC A % |
|---|---|---|---|---|
| Raw material (Compound 1a) | 1560.96 | 1242.05 | 6.568 | 93.488 |
| Product (Compound 1b) | 1460.90 | 731.67 | 4.637 | 2.048 |
| Cleaved product (Compound 1e) | 721.44 | 722.47 ([M + H]+) | 3.900 | 0.880 |
| Impurity (Compound 1g) | Unknown | 573.29 | 4.789 | 1.020 |
| Methylene chloride |  |  | 2.375 | 1.059 |

The structure of Compound 1g is unknown.

Example 43

Boc removal reaction of Boc-MeIle-Ala-MePhe-MeVal-Asp(pip)-MeAla-MePhe-Leu-MeLeu-Thr(OBn)-MeGly-OAllyl (Compound 1a) (11-mer: TFA-TIPS-H₂O-PhOH method) Reference: J. Am. Chem. Soc., 2015, 137, 13488

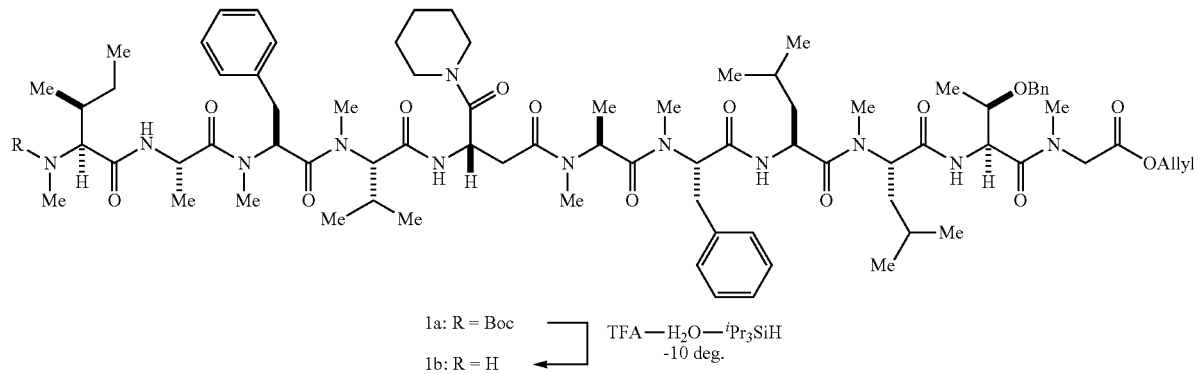

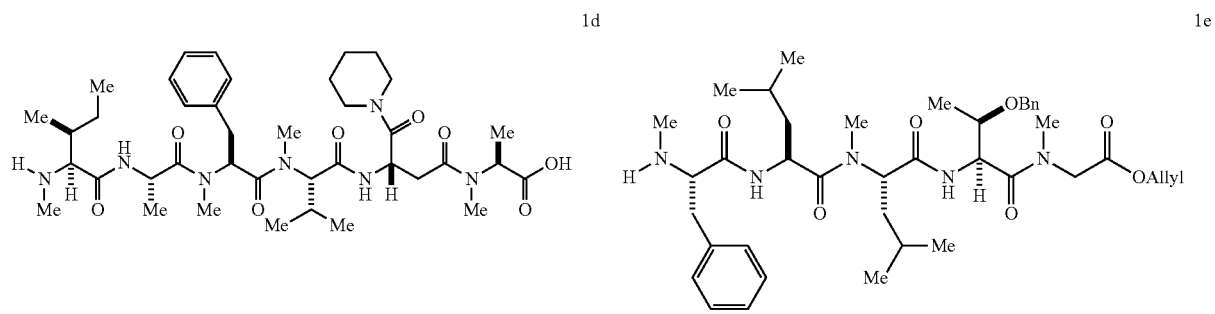

15.9 mg of the raw material was weighed into a reaction vessel, 0.0125 ml of water and 0.0125 ml of triisopropylsilane were added, and the reaction vessel was cooled to −10° C. 0.48 ml of trifluoroacetic acid was then added and the reaction solution was stirred. The reaction was analyzed two hours after the addition of the reagent to confirm that amide bond-cleaved products 1d and 1e were produced at a conversion rate (=target product/(target product+starting material)) of 89%. The reaction was analyzed again 14.5 hours after the addition of the reagent to confirm that the raw material was consumed and the amide bond-cleaved products 1d and 1e were increasingly produced.

TABLE 105

|  | Weight (mg) | Yield (%) |
|---|---|---|
| Raw material (Compound 1a) | 15.9 | — |
| Product (Compound 1b) | Not isolated | Not isolated |

TABLE 106

Analysis (HPLC method 1: Determination of purity of the raw material)

| | MW | m/z | rt | Purity LC A % |
|---|---|---|---|---|
| Raw material (Compound 1a) | 1560.96 | 1242.05 | 6.519 | 96.680 |

TABLE 107

Analysis (HPLC method 1: Determination of conversion rate and rates of production of by-products at two hours after the reaction)

| | MW | m/z | rt | LC A % |
|---|---|---|---|---|
| Raw material (Compound 1a) | 1560.96 | 1241.57 | 6.527 | 9.531 |
| Product (Compound 1b) | 1460.90 | 731.67 | 4.629 | 77.361 |
| Cleaved product (Compound 1d) | 757.47 | 758.41 ([M + H]+) | 2.761 | 5.716 |
| Impurity (Compound 1e) | 721.44 | 722.47 ([M + H]+) | 3.902 | 7.392 |

TABLE 108

Analysis (HPLC method 1: Rates of production of the target product and by-products at 14.5 hours after the reaction)

| | MW | m/z | rt | LC A % |
|---|---|---|---|---|
| Raw material (Compound 1a) | 1560.96 | ND | ND | 0 |
| Product (Compound 1b) | 1460.90 | 731.67 | 4.631 | 29.383 |
| Cleaved product (Compound 1d) | 757.47 | 758.39 ([M + H]+) | 2.757 | 37.117 |
| Cleaved product (Compound 1e) | 721.44 | 722.41 ([M + H]+) | 3.892 | 32.950 |

Example 44

Boc removal reaction of Boc-MeIle-Ala-MePhe-MeVal-Asp(pip)-MeAla-MePhe-Leu-MeLeu-Thr(OBn)-MeGly-OAllyl (Compound 1a) (11-mer: TFA-TIPS-$H_2$O-PhOH method) Reference: J. Am. Chem. Soc., 2012, 134, 13244

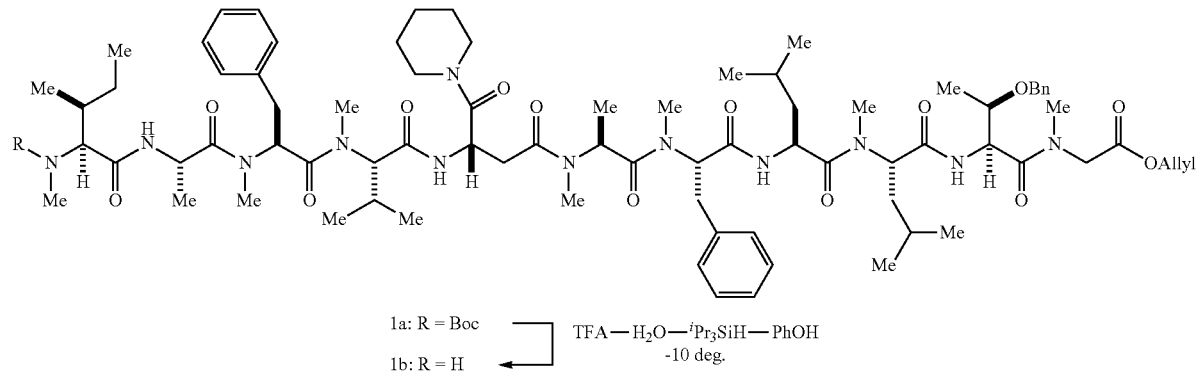

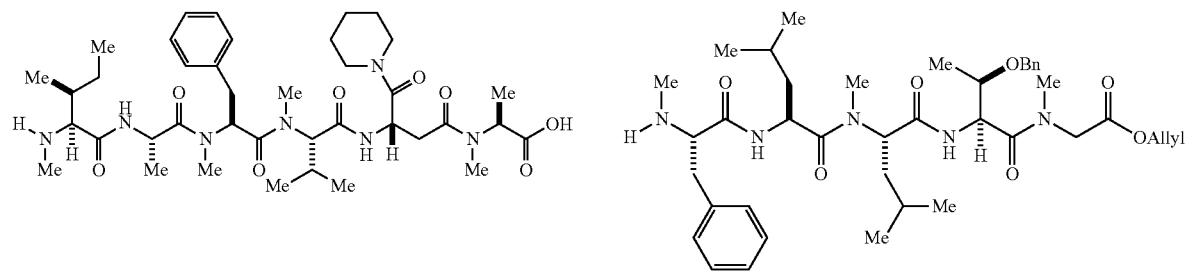

10.3 mg of phenol was weighed into a reaction vessel, 0.034 ml of water and 0.025 ml of triisopropylsilane were added, and the reaction vessel was cooled to −10° C. 0.50 ml of trifluoroacetic acid was then added. Six minutes after the addition, 13.4 mg of the raw material was added and the reaction solution was stirred. The reaction was analyzed two hours after the addition of the raw material to confirm that amide bond-cleaved products 1d and 1e were produced at a conversion rate (=target product/(target product+starting material)) of 82%. The reaction was analyzed again seven hours after the addition of the raw material to confirm that the raw material was consumed and the amide bond-cleaved products 1d and 1e were increasingly produced.

TABLE 109

|  | Weight (mg) | Yield (%) |
|---|---|---|
| Raw material (Compound 1a) | 10.3 | — |
| Product (Compound 1b) | Not isolated | Not isolated |

TABLE 110

Analysis (HPLC method 1: Determination of purity of the raw material)

|  | MW | m/z | rt | Purity LC A % |
|---|---|---|---|---|
| Raw material (Compound 1a) | 1560.96 | 1242.05 | 6.538 | 96.680 |

TABLE 111

Analysis (HPLC method 1: Determination of conversion rate and rates of production of by-products at two hours after the reaction)

|  | MW | m/z | rt | LC A % |
|---|---|---|---|---|
| Raw material (Compound 1a) | 1560.96 | 1242.05 | 6.523 | 6.500 |
| Product (Compound 1b) | 1460.90 | 731.67 | 4.628 | 30.640 |
| Cleaved product (Compound 1d) | 757.47 | 758.38 ([M + H]+) | 2.769 | 1.583 |
| Cleaved product (Compound 1e) | 721.44 | 722.37 ([M + H]+) | 3.884 | 2.659 |
| Phenol |  |  | 2.172 | 58.619 |

TABLE 112

Analysis (HPLC method 1: Rates of production of the target product and by-products at five hours after the reaction)

|  | MW | m/z | rt | LC A % |
|---|---|---|---|---|
| Raw material (Compound 1a) | 1560.96 | ND | ND | 0 |
| Product (Compound 1b) | 1460.90 | 731.67 | 4.633 | 25.258 |
| Cleaved product (Compound 1d) | 757.47 | 758.40 ([M + H]+) | 2.769 | 8.506 |
| Cleaved product (Compound 1e) | 721.44 | 722.39 ([M + H]+) | 3.884 | 8.035 |
| Phenol |  |  | 2.172 | 58.200 |

As shown in Examples 2, 3, and 26 to 44, it was found that imidates, amides, ketene acetals, enol ethers, imines, amines, diamines, and dialkylcarbodiimides are excellent as electrophilic species scavengers, suppress main chain damage, and allow efficient progress of Boc removal reaction of peptides having a long main chain such as 11-mers.

D. Experiment of Comparison Between the TFA Method and the TMSOTf-HMDS Method in tBu Removal Reactions (Table 113)

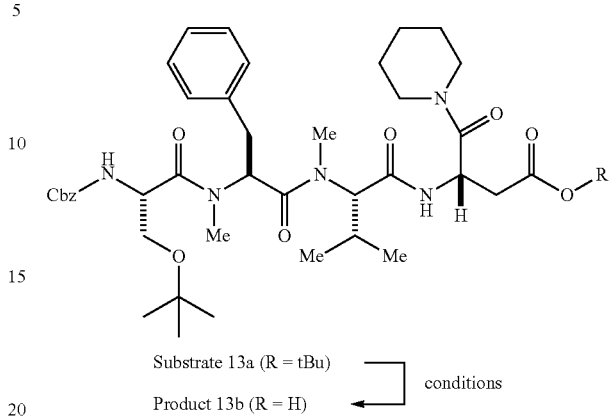

Substrate 13a (R = tBu)
Product 13b (R = H)
conditions

Example 45 t-Bu Removal Reaction of Compound 13a (TFA Method)

29.8 mg of Substrate 13a was weighed into a reaction vessel and dissolved in 10 v/w of dichloromethane. To the solution was added TFA (10 eq.) at room temperature. Four hours after the addition of the reagent, TFA (10 eq.) was further added. 1.5 hours after the further addition of the reagent, the reaction was analyzed by LCMS to find that the reaction conversion rate was 52%. The purity was reduced by 22%, while 10% of a by-product due to amide bond cleavage was observed.

Example 46 t-Bu Removal Reaction of Compound 13a (TMSOTf-HMDS Method)

30.0 mg of Substrate 13a was weighed into a reaction vessel and dissolved in 10 v/w of ethyl acetate. HMDS (3.0 eq.) and TMSOTf (2.0 eq) were sequentially added to the solution at 0° C. Two hours after the addition of the reagents, the reaction solution was warmed to room temperature. 2.5 hours after warming, HMDS (3 eq.) and TMSOTf (2 eq.) were further added. 30 minutes after the further addition of the reagents, the reaction was analyzed by LCMS to confirm that the conversion rate was 99% or more. At this time, amide bond cleavage was not confirmed.

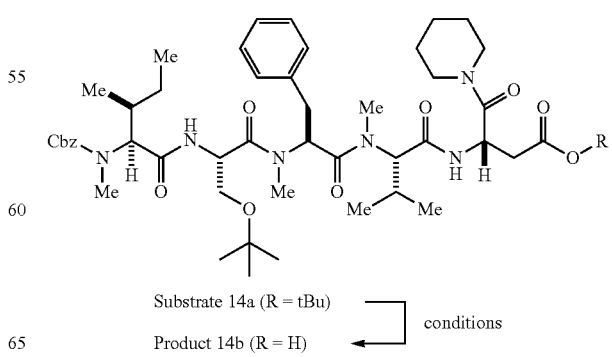

Substrate 14a (R = tBu)
Product 14b (R = H)
conditions

Example 47 t-Bu Removal Reaction of Compound 14a (TFA Method)

29.7 mg of Substrate 14a was weighed into a reaction vessel and dissolved in 10 v/w of dichloromethane. To the solution was added TFA (20 eq.) at room temperature. Seven hours after the addition of the reagent, the reaction was analyzed by LCMS to find that the reaction conversion rate was 92%. The purity was reduced by 46%, while 24% of a by-product due to amide bond cleavage was observed.

Example 48 t-Bu Removal Reaction of Compound 14a (TMSOTf-HMDS Method)

30.0 mg of Substrate 14a was weighed into a reaction vessel and dissolved in 10 v/w of ethyl acetate. HMDS (3.0 eq.) and TMSOTf (2.0 eq) were sequentially added to the solution at 0° C. Six hours after the addition of the reagents, the reaction was analyzed by LCMS and the raw material was confirmed to disappear. At this time, amide bond cleavage was not confirmed. After confirming the completion of the reaction, 44.5 mg (8.0 eq) of potassium hydrogenphosphate and 0.30 mL of water were added to the reaction solution, which was then stirred for 30 minutes with ice-cooling. 1 mL of ethyl acetate was added to the reaction solution, which was then washed with 0.30 mL of brine. The organic layer was filtered through celite, then concentrated, and dried under reduced pressure to give 26.8 mg of 2b in a purity of 99%.

Example 49 t-Bu Removal Reaction of Compound 15a (TFA Method)

29.9 mg of Substrate 15a was weighed into a reaction vessel and dissolved in 10 v/w of dichloromethane. To the solution was added TFA (20 eq.) at room temperature. 5.5 hours after the addition of the reagent, the reaction was analyzed by LCMS to find that the reaction conversion rate was 50%. 28% of a by-product due to amide bond cleavage was observed.

Example 50 t-Bu Removal Reaction of Compound 15a (TMSOTf-HMDS Method)

30.0 mg of Substrate 15a was weighed into a reaction vessel and dissolved in 10 v/w of ethyl acetate. HMDS (3.6 eq) and TMSOTf (2.4 eq) were sequentially added to the solution at room temperature. Five hours after the addition of the reagents, HMDS (1.8 eq.) and TMSOTf (1.2 eq.) were further added. One hour after the further addition of the reagents, the reaction was analyzed by LCMS and the raw material was confirmed to disappear. At this time, amide bond cleavage was not confirmed.

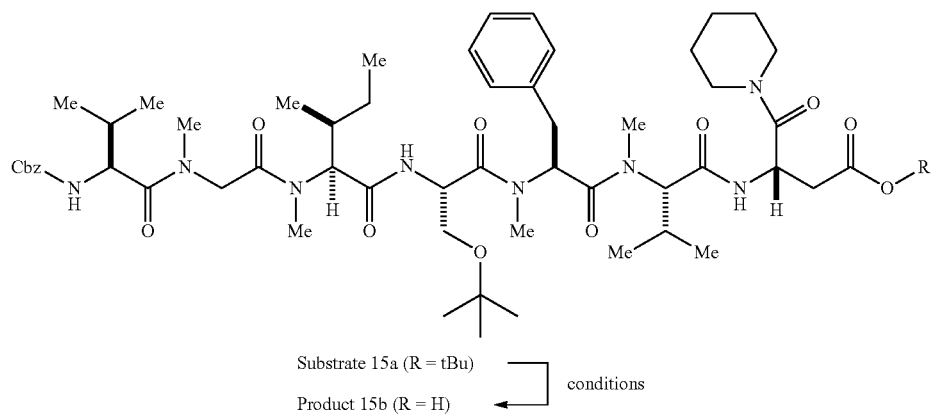

Substrate 15a (R = tBu)
Product 15b (R = H)
conditions

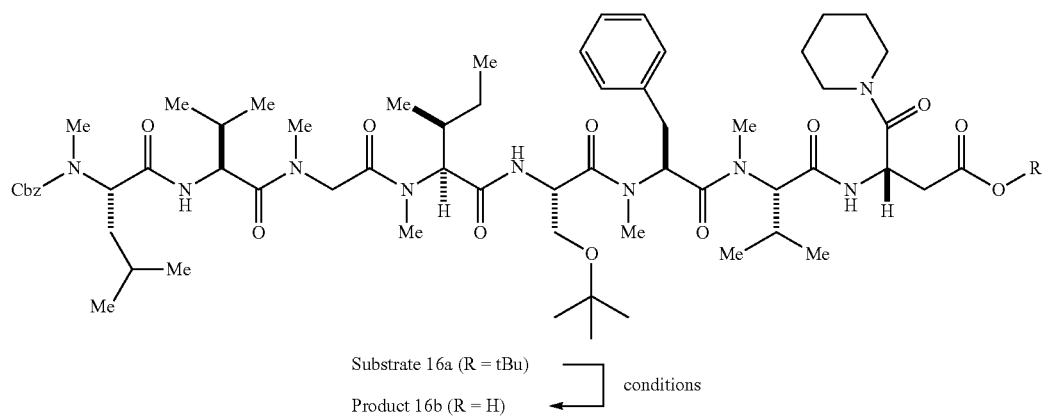

Substrate 16a (R = tBu)
Product 16b (R = H) ⟵ conditions

Example 51 t-Bu Removal Reaction of Compound 16a (TFA Method)

30.2 mg of Substrate 16a was weighed into a reaction vessel and dissolved in 10 v/w of dichloromethane. To the solution was added TFA (20 eq.) at room temperature. 4.5 hours after the addition of the reagent, TFA (10 eq.) was further added. One hour after the further addition of the reagent, the reaction was analyzed by LCMS to find that the reaction conversion rate was 65%. 7.0% of a by-product due to amide bond cleavage was observed.

Example 52 t-Bu Removal Reaction of Compound 16a (TMSOTf-HMDS Method)

29.9 mg of Substrate 16a was weighed into a reaction vessel and dissolved in 10 v/w of ethyl acetate. HMDS (3.6 eq) and TMSOTf (2.4 eq) were sequentially added to the solution at room temperature. Four hours after the addition of the reagents, the reaction was analyzed by LCMS and the raw material was confirmed to disappear. At this time, amide bond cleavage was not confirmed.

Example 53 t-Bu Removal Reaction of Compound 17a (TFA Method)

50.0 mg of Substrate 17a was weighed into a reaction vessel and dissolved in 10 v/w of dichloromethane. To the solution was added TFA (5 eq.) at 0° C. Two hours after the addition of the reagent, TFA (5 eq.) was added. After another 15.5 hours, the reaction solution was warmed to room temperature. Three hours after warming, TFA (10 eq.) was added. After another 1.5 hours, TFA (20 eq.) was added. 1.5 hours after the further addition of the reagent, the reaction was analyzed by LCMS to find that the reaction conversion rate was 54%. 26% of a by-product due to amide bond cleavage was observed.

Example 54 t-Bu Removal Reaction of Compound 17a (TMSOTf-HMDS Method)

30.0 mg of Substrate 17a was weighed into a reaction vessel and dissolved in 10 v/w of ethyl acetate. HMDS (5.4 eq.) and TMSOTf (3.6 eq) were sequentially added to the solution at 0° C. Four hours after the addition of the

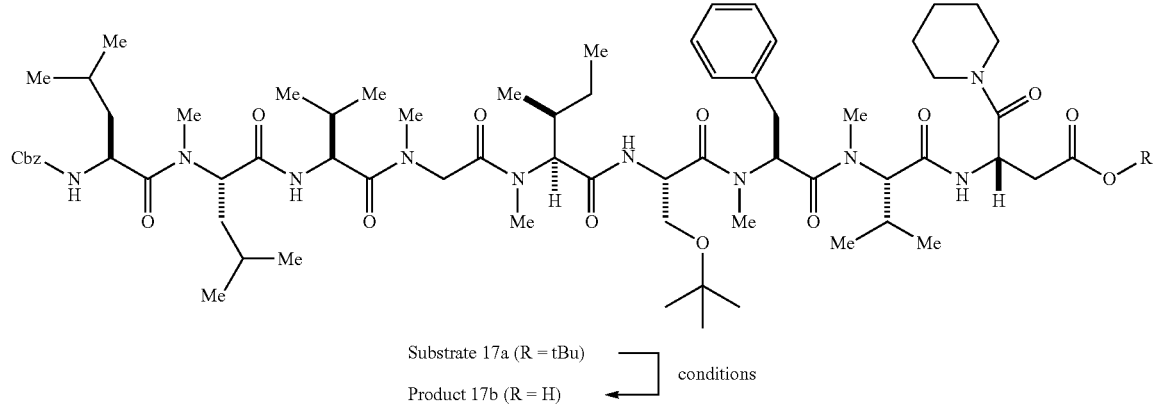

Substrate 17a (R = tBu)
Product 17b (R = H) ⟵ conditions reagents, the reaction solution was warmed to room temperature. Three hours after warming, the reaction was analyzed by LCMS and the raw material was confirmed to disappear. At this time, amide bond cleavage was not confirmed.

Example 57 t-Bu Removal Reaction of Compound 19a (TFA Method)

50.0 mg of Substrate 19a was weighed into a reaction vessel and dissolved in 10 v/w of dichloromethane. To the

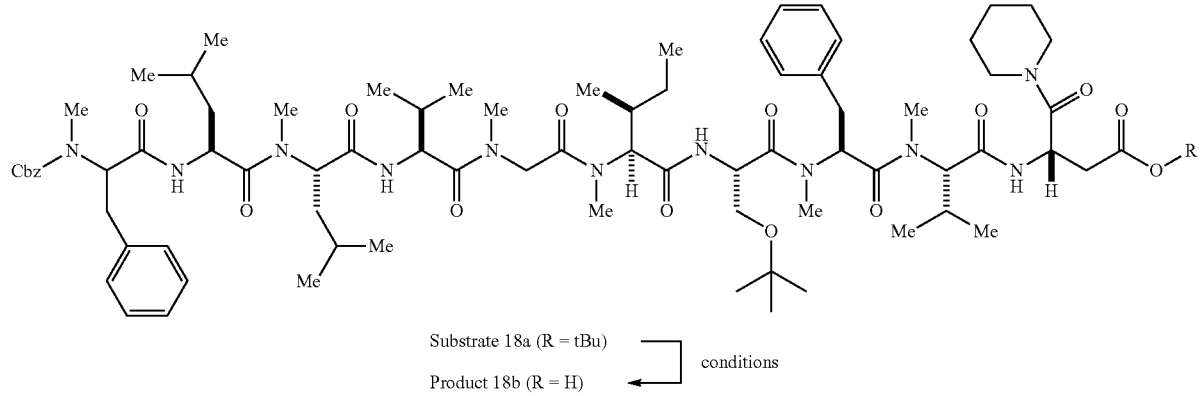

Substrate 18a (R = tBu)
Product 18b (R = H) ← conditions

Example 55 t-Bu Removal Reaction of Compound 18a (TFA Method)

29.9 mg of Substrate 18a was weighed into a reaction vessel and dissolved in 10 v/w of dichloromethane. To the solution was added TFA (20 eq.) at 0° C. 4.5 hours after the addition of the reagent, TFA (10 eq.) was further added and the reaction solution was warmed to room temperature. Two hours after the further addition of the reagent, the reaction was analyzed by LCMS to find that the reaction conversion rate was 82%. 34% of a by-product due to amide bond cleavage was observed.

Example 56 t-Bu Removal Reaction of Compound 18a (TMSOTf-HMDS Method)

29.8 mg of Substrate 18a was weighed into a reaction vessel and dissolved in 10 v/w of ethyl acetate. HMDS (7.2 eq.) and TMSOTf (4.8 eq) were sequentially added to the solution at 0° C. Three hours after the addition of the reagents, the reaction solution was warmed to room temperature. 3.5 hours after warming, the reaction was analyzed by LCMS and the raw material was confirmed to disappear. At this time, amide bond cleavage was not confirmed.

solution was added TFA (5 eq.) at 0° C. Two hours after the addition of the reagent, TFA (5 eq.) was added. After another 15.5 hours, the reaction solution was warmed to room temperature. Three hours after warming, TFA (10 eq.) was added. After another 1.5 hours, TFA (20 eq.) was added. 1.5 hours after the further addition of the reagent, the reaction was analyzed by LCMS to find that the reaction conversion rate was 82%. 14% of a by-product due to amide bond cleavage was observed.

Example 58 t-Bu Removal Reaction of Compound 19a (TMSOTf-HMDS Method)

30.0 mg of Substrate 19a was weighed into a reaction vessel and dissolved in 10 v/w of ethyl acetate. HMDS (3.6 eq.) and TMSOTf (2.4 eq) were sequentially added to the solution at 0° C. 3.5 hours after the addition of the reagents, the reaction solution was warmed to room temperature and HMDS (3.6 eq.) and TMSOTf (2.4 eq.) were further added. One hour after the further addition of the reagents, the reaction was analyzed by LCMS and the raw material was confirmed to disappear. At this time, amide bond cleavage was not confirmed.

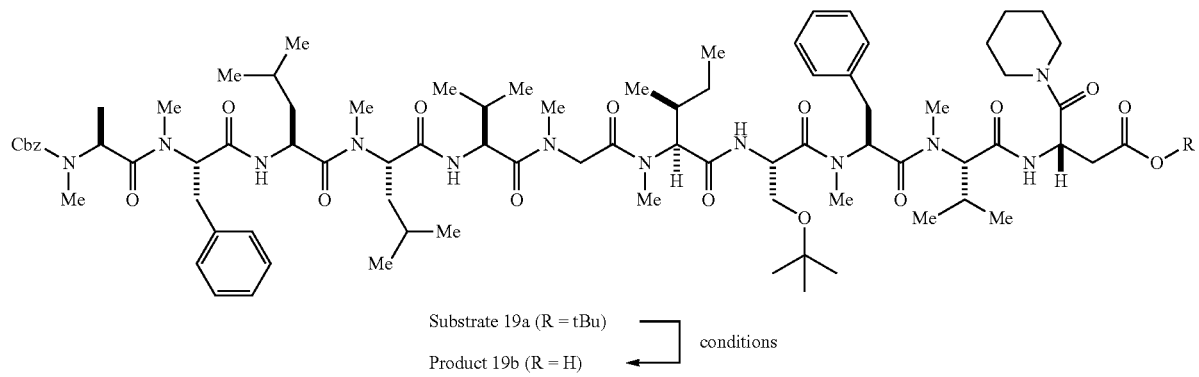

Substrate 19a (R = tBu)
Product 19b (R = H) ← conditions

As shown in Examples 45 to 58, it was found that in tBu removal reactions, the TMSOTf-HMDS method using a combination of silylating agents and electrophilic species scavengers does not cause main chain damage and allows deprotection reactions to proceed more efficiently, as compared with the conventional TFA method.

TABLE 113

Reaction conditions and experimental results

| Substrate | Example No. | Reaction condition | Conversion rate | Purity reduction (LCMS Area %) | Main chain cleavage (LCMS Area %) |
|---|---|---|---|---|---|
| 13a | 45 | TFA (10 to 20 eq.)<br>$CH_2Cl_2$ (10 v/w)<br>rt, 6 h | 52% | 22% | MePhe-MeVal: 10.0% |
|  | 46 | TMSOTf (2.4 to 4.8 eq.)<br>HMDS (3.6 to 7.2 eq.)<br>EtOAc (10 v/w %)<br>0° C. to rt, 5 h | >99% | 1.2% | Not detected. |
| 14a | 47 | TFA (20 eq.)<br>$CH_2Cl_2$ (10 v/w)<br>rt, 7 h | 92% | 46% | MePhe-MeVal: 22.0%<br>MeVal-Asp(pip): 1.5% |
|  | 48 | TMSOTf (2 eq.)<br>HMDS (3 eq.)<br>EtOAc (10 v/w %)<br>0° C., 6 h | 100% | 0.7% | Not detected. |
| 15a | 49 | TFA (20 eq.)<br>$CH_2Cl_2$ (10 v/w)<br>rt, 6 h | 50% | 33% | MeIle-Ser(tBu): 6.4%<br>MePhe-MeVal: 16.3%<br>MeVal-Asp(pip): 5.0% |
|  | 50 | TMSOTf (2.4 to 3.6 eq.)<br>HMDS (3.6 to 5.4 eq.)<br>EtOAc (10 v/w %)<br>rt, 6 h | 100% | 0.2% | Not detected. |
| 16a | 51 | TFA (20 to 30 eq.)<br>$CH_2Cl_2$ (10 v/w)<br>rt, 6 h | 65% | 26% | MeIle-tBuSer: 7.0% |
|  | 52 | TMSOTf (2.4 eq.)<br>HMDS (3.6 eq.)<br>EtOAc (10 v/w %)<br>rt, 4 h | 100% | ≈0% | Not detected. |
| 17a | 53 | TFA (5 to 40 eq.)<br>$CH_2Cl_2$ (10 v/w)<br>0° C. to rt, 24 h | 54% | 25% | MeIle-Ser(tBu): 5.8%<br>MeVal-Asp(pip): 20.5% |
|  | 54 | TMSOTf (3.6 eq.)<br>HMDS (5.4 eq.)<br>EtOAc (10 v/w %)<br>0° C. to rt, 7 h | 100% | 2.6% | Not detected. |
| 18a | 55 | TFA (20 to 30 eq.)<br>$CH_2Cl_2$ (10 v/w)<br>0° C. to rt, 7 h | 82% | 33% | MePhe-MeVal: 15.1%<br>MeVal-Asp(pip): 12.3%<br>MeLeu-Val: 6.9% |
|  | 56 | TMSOTf (4.8 eq.)<br>HMDS (7.2 eq.)<br>EtOAc (10 v/w %)<br>0° C. to rt, 7 h | 100% | 2.7% | Not detected. |
| 19a | 57 | TFA (5 to 40 eq.)<br>$CH_2Cl_2$ (10 v/w)<br>0° C. to rt, 24 h | 54% | 17% | MeIle-Ser(tBu): 0.8%<br>MePhe-Leu: 5.4%<br>MePhe-MeVal: 6.6%<br>MeLeu-Val: 1.6% |
|  | 58 | TMSOTf (2.4 to 4.8 eq.)<br>HMDS (3.6 to 7.2 eq.)<br>EtOAc (10 v/w %)<br>0° C. to rt, 5 h | 100% | 0.6% | Not detected. |

Identification of Products

TABLE 114

(HPLC method 1)
MS (major peaks) and retention times of the target products
(in Examples of the TMSOTf/HMDS method)

| Example No. | Compound No. | Compound data | | Retention time (min) |
|---|---|---|---|---|
| | | MW | m/z | |
| 45, 46 | 13b | 751.92 | 752.42 ([M + H]+) | 4.723 |
| 47, 48 | 14b | 879.11 | 879.52 ([M + H]+) | 5.313 |
| 49, 50 | 15b | 1049.32 | 1049.63 ([M + H]+) | 4.985 |
| 51, 52 | 16b | 1176.51 | 1198.67 ([M + Na]+) | 5.527 |
| 53, 54 | 17b | 1275.64 | 1089.62 | 5.652 |
| 55, 56 | 18b | 1450.87 | 536.23 | 5.964 |
| 57, 58 | 19b | 1535.98 | 1222.41 | 6.183 |

TABLE 115

MS and retention times of decomposed products

| Example No. | Compound No. | Compound data | | Retention time (min) |
|---|---|---|---|---|
| | | MW | m/z | |
| 45 | 13c + its isomer | 456.54 | 457.28 ([M + H]+) | 4.504 |
| | | | 439.30 ([M—H2O + H]+) | 4.894 |
| | 13d + its isomer | 369.51 | 370.29 ([M + H]+) | 2.691 |
| | | | 370.31 ([M + H]+) | 2.731 |
| 47 | 14c | 696.89 | 679.35 ([M—H2O + H]+) | 4.935 |
| | 14d + its isomer | 583.73 | 584.20 ([M + H]+) | 5.118 |
| | | | 566.19 ([M—H2O + H]+) | 5.477 |
| 49 | 15c + its isomer | 449.55 | 432.28 ([M—H2O + H]+) | 5.287 |
| | | | 450.30 ([M + H]+) | 3.928 |
| | 15d | 673.90 | 674.40 ([M + H]+) | 3.792 |
| | 15e | 753.94 | 754.29 ([M + H]+) | 4.863 |
| | 15f + its isomer | 697.83 | 698.35 ([M + H]+) | 4.101 |
| | | 736.93 | 736.30 ([M—H2O + H]+) | 5.123 |
| | 15g + its isomer | 810.99 | 793.37 ([M—H2O + H]+) | 4.487 |
| | | | 793.40 ([M—H2O + H]+) | 5.444 |
| 51 | 16c | 673.90 | 674.48 ([M + H]+) | 3.591 |
| | 16d + its isomer | 576.74 | 577.32 ([M + H]+) | 4.500 |
| | | | 559.28 ([M—H2O + H]+) | 5.267 |
| 53 | 17c + its isomers | 689.90 | 690.45 ([M + H]+) | 4.764 |
| | | | 672.38 ([M—H2O + H]+) | 5.432 |
| | | | 672.59 ([M—H2O + H]+) | 5.463 |
| | 17d + its isomer | 1107.45 | 1129.61 ([M + Na]+) | 5.627 |
| | 17e + its isomers | 1051.34 | 1033.66 ([M—H2O + H]+) | 5.116 |
| | | | 1033.77 ([M—H2O + H]+) | 5.944 |
| | | | 1033.64 ([M—H2O + H]+) | 5.985 |
| 55 | 18c | 553.70 | 536.31 ([M—H2O + H]+) | 5.199 |
| | 18d | 1212.54 | 1194.58 ([M—H2O + H]+) | 5.469 |
| | 18e + its isomers | 1155.49 | 1177.57 ([M + Na]+) | 5.746 |
| | | | 1177.39 ([M + Na]+) | 5.788 |
| | | | 1137.73 ([M—H2O + H]+) | 5.904 |
| 57 | 19c | 673.90 | 674.38 ([M + H]+) | 3.633 |
| | 19d + its isomer | 1155.53 | 1155.73 ([M + H]+) | 3.863, 3.906 |
| | 19e | 1211.64 | 1211.65 ([M + H]+) | 4.619 |
| | 19f | 398.46 | 381.16 ([M—H2O + H]+) | 4.898 |
| | 19g | 638.81 | 621.31 ([M—H2O + H]+) | 5.246 |
| | 19h + its isomers | 1240.60 | 1240.51 ([M + H]+) | 5.794, 5.831 |
| | | | 1222.59 ([M—H2O + H]+) | 5.953 |

The structures of Compounds 13c to 19h are provided below.
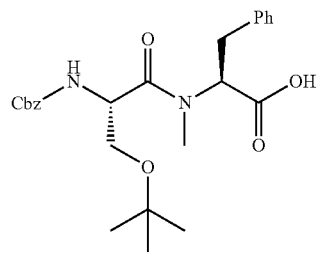 13c
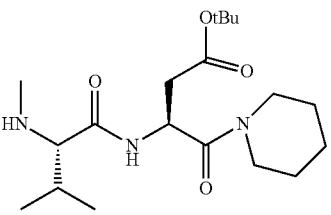 13d
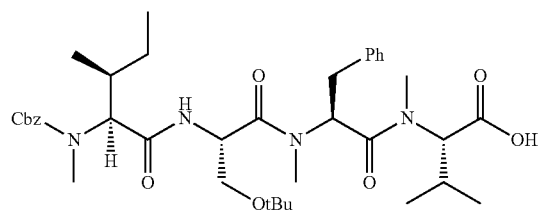 14c
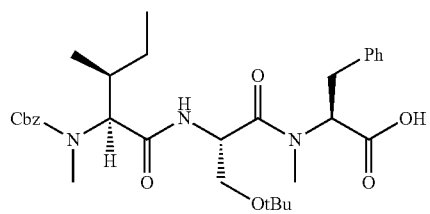 14d
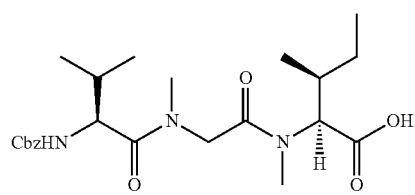 15c
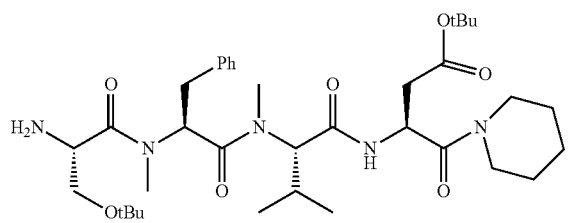 15d
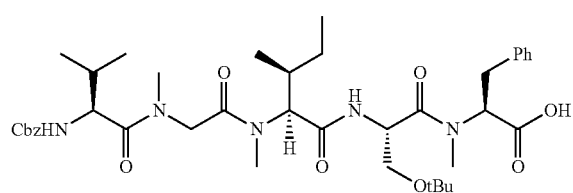 15e
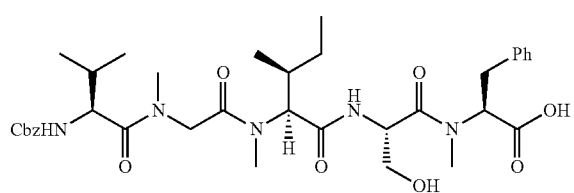 15f
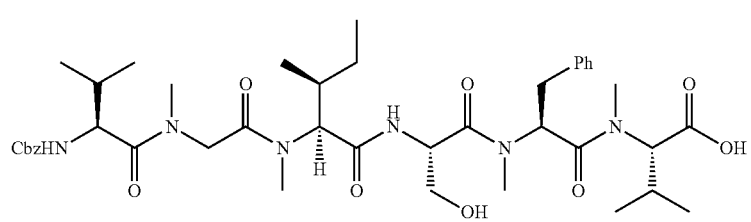 15g
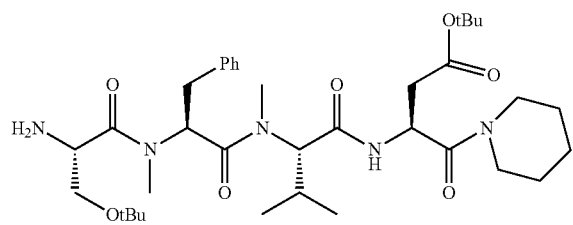 16c
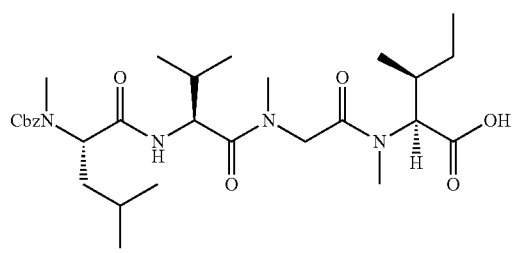 16d -continued
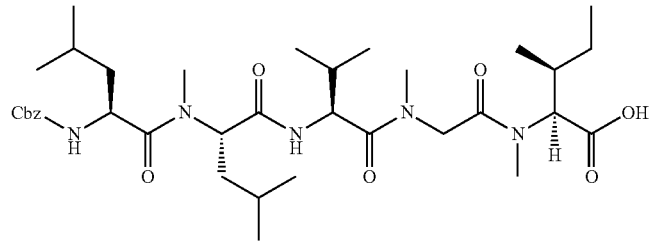
17c
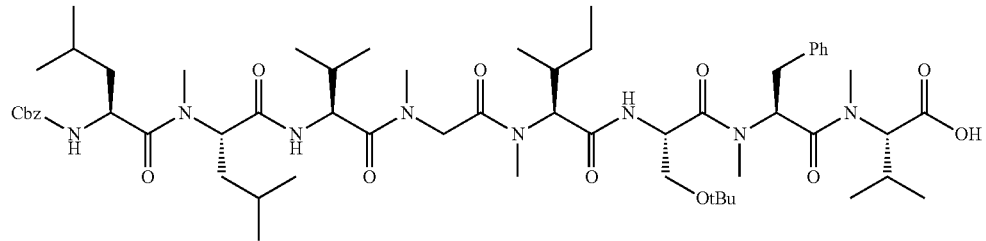
17d
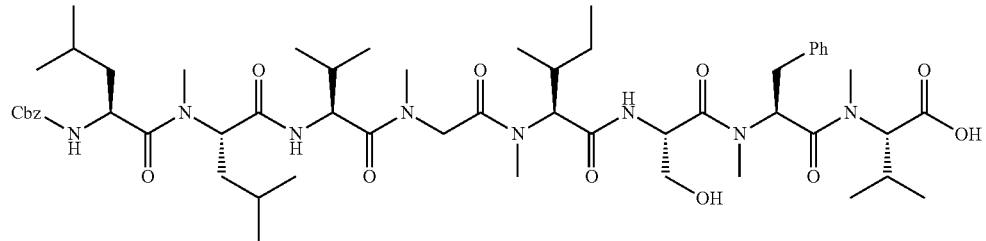
17e
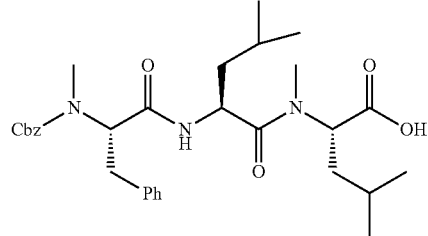
18c
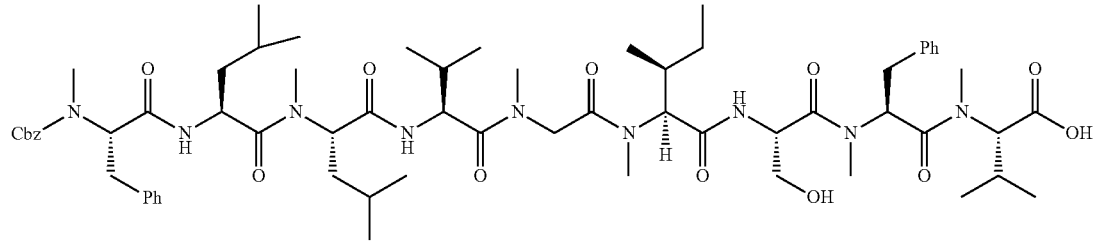
18d
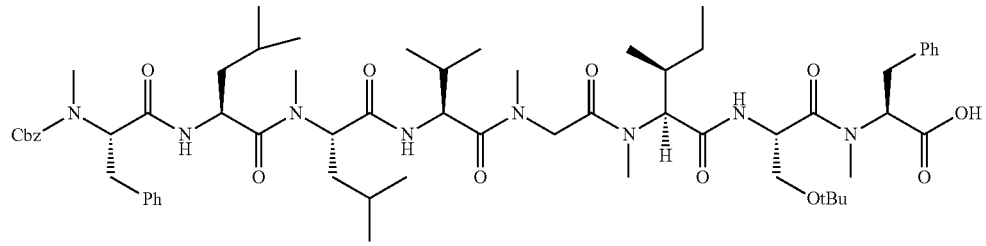
18e -continued
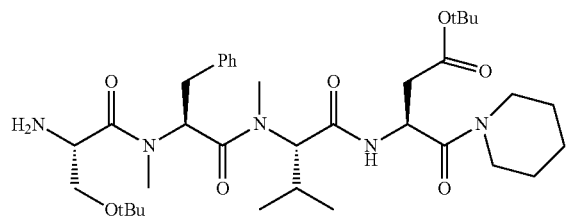
19c
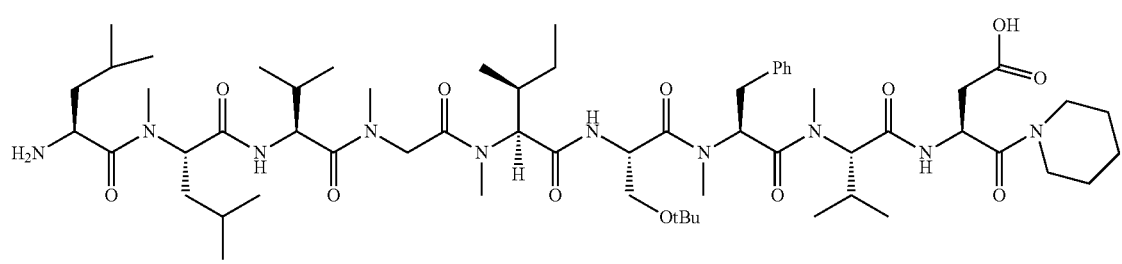
19d
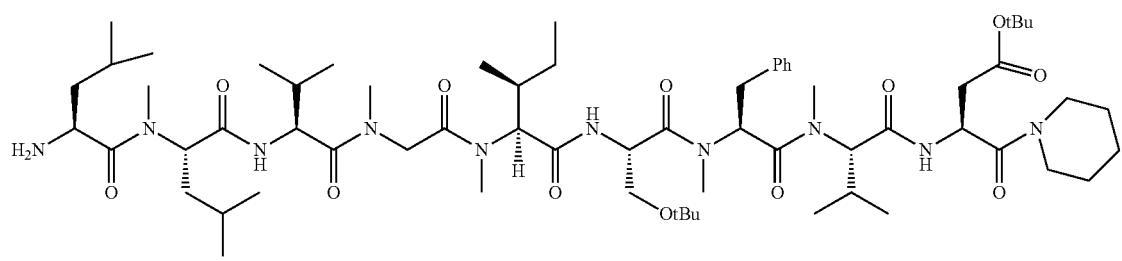
19e
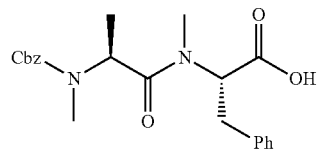
19f
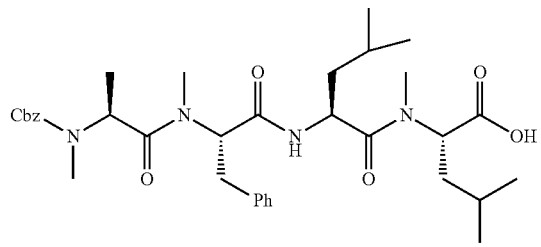
19g
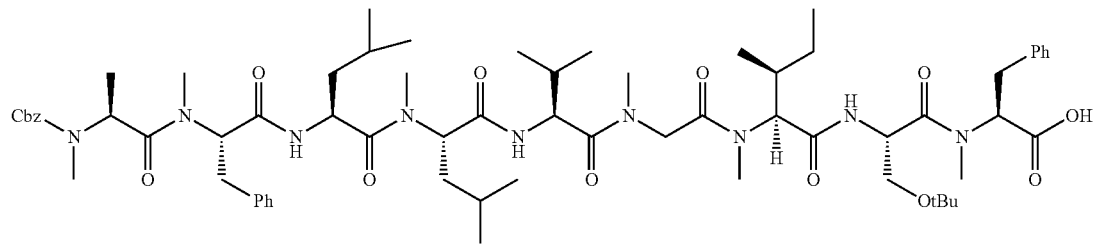
19h

Example 59 t-Bu Removal Reaction of Fmoc-MeAsp(OtBu)-Pip (Compound 12a) (1-Mer: TFA Method)

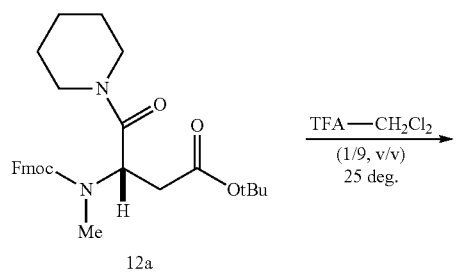

48.0 mg of the raw material was weighed into a reaction vessel and dissolved in 9 v/w of dichloromethane. 1 v/w of trifluoroacetic acid was then added and the reaction solution was stirred. 19 hours after the addition of the reagents, the reaction was analyzed by LCMS (HPLC method 4) and the conversion rate (=target product/(target product+starting material)) was confirmed to be 77%. At this time, a rearrangement product 12c and a hydrolysate 12d were observed as compounds in which amide bonds were damaged. Impurities of unknown structure were also produced.

TABLE 116

|  | Weight (mg) | Yield (%) |
| --- | --- | --- |
| Raw material (Compound 12a) | 48.0 | — |
| Product (Compound 12b) | Not isolated | Not isolated |

Raw Material Purity Analysis (HPLC Method 1)

TABLE 117

| Analysis (HPLC method 1) | | | | |
| --- | --- | --- | --- | --- |
|  | MW | m/z | rt | Purity LC A % |
| Raw material (Compound 12a) | 492.26 | 493.24 ([M + H]+) | 5.527 | 98.268 |

TABLE 118

| Analysis (HPLC method 4) | | | | |
| --- | --- | --- | --- | --- |
|  | MW | m/z | rt | Purity LC A % |
| Raw material (Compound 12a) | 492.26 | 437.25 ([M-tBu + H]+) | 23.660 | 98.268 |
| Product (Compound 12b) | 436.20 | 437.22 ([M + H]+) | 15.194 | 53.776 |
| Rearrangement product (Compound 12c) | 436.20 | 437.28 ([M + H]+) | 15.553 | 1.474 |
| Hydrolysate (Compound 12d) | 369.12 | 250.91 | 10.522 | 0.901 |
| Impurity of unknown structure (12e) |  | 102.07 | 17.949 | 28.043 |

Example 60 t-Bu Removal Reaction of Fmoc-MeAsp(OtBu)-pip (Compound 12a) (1-Mer: TMSOTf-HMDS Method)

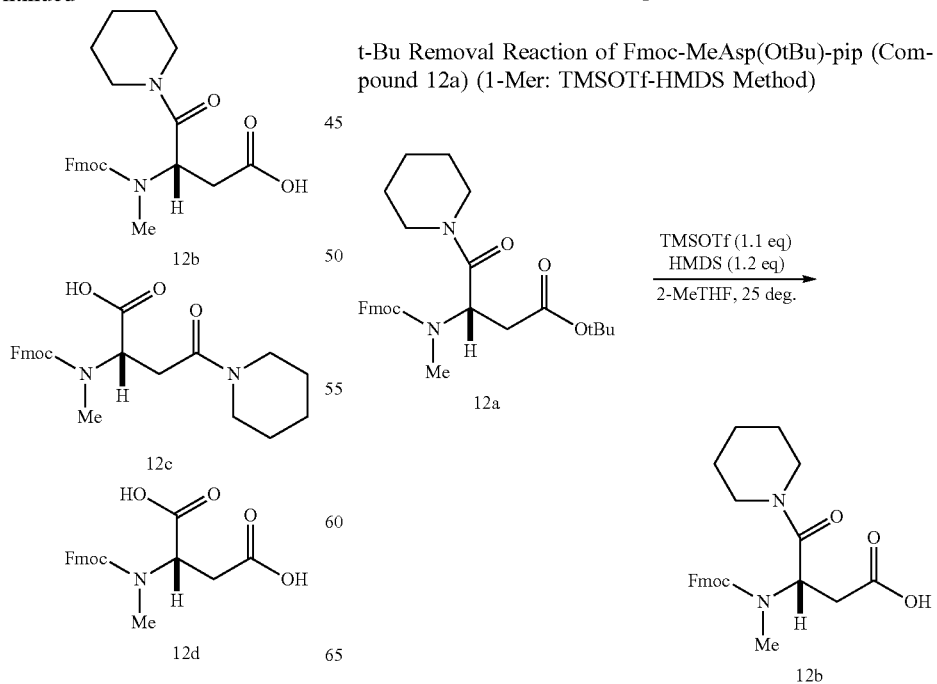

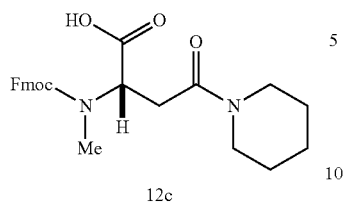

12c

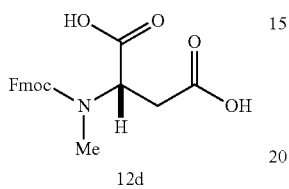

12d

The experiment was performed according to Example 2.

TABLE 119

| | Weight (g) | Yield (%) |
|---|---|---|
| Raw material (Compound 12a) | 59.9 | — |
| Product (Compound 12b) | 55.8 | Quantitative |

TABLE 120

| Analysis (HPLC method 1) | | | |
|---|---|---|---|
| | MW | m/z | rt | Purity LC A % |
| Raw material (Compound 12a) | 492.26 | 493.24 ([M + H]+) | 5.527 | 98.268 |

TABLE 121

| Analysis (HPLC method 4) | | | |
|---|---|---|---|
| | MW | m/z | rt | Purity LC A % |
| Product (Compound 12b) | 436.20 | 437.22 ([M + H]+) | 15.194 | 98.999 |
| Rearrangement product (Compound 12c) | 436.20 | 437.28 ([M + H]+) | 15.553 | 0.379 |
| Hydrolysate (Compound 12d) | 369.12 | 250.91 | 10.522 | 0.15 |
| Impurity of unknown structure (12e) | | 102.07 | 17.949 | 0.474 |

E. Experiment of Comparison Between the TFA Method and the TMSOTf-HMDS Method in t-Bu Removal Reactions (Table 122)

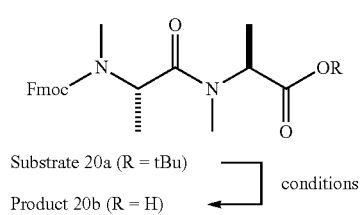

Substrate 20a (R = tBu)
Product 20b (R = H)
conditions

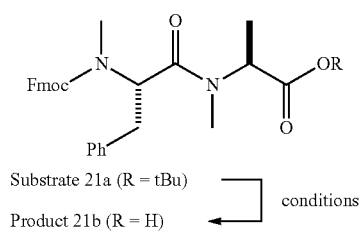

Substrate 21a (R = tBu)
Product 21b (R = H)
conditions

Example 61 t-Bu Removal Reaction of Compound 20a (TFA Method)

27.1 mg of Substrate 20a was weighed into a reaction vessel and dissolved in 10 v/w of dichloromethane. To the solution was added TFA (10 eq.) at room temperature. Eight hours after the addition of the reagent, the reaction was analyzed by LCMS to find that the reaction conversion rate was 76%. The purity was reduced by 11%, while 8.1% of a by-product due to amide bond cleavage was confirmed. The same reaction was performed for Substrate 21a (Table 122).

Example 62 t-Bu Removal Reaction of Compound 20a (TMSOTf-HMDS Method)

27.6 mg of Substrate 20a was weighed into a reaction vessel and dissolved in 10 v/w of ethyl acetate. HMDS (2.4 eq) and TMSOTf (2.4 eq) were sequentially added to the solution at room temperature. Two hours after the addition of the reagents, the reaction was analyzed by LCMS and the raw material was confirmed to disappear. At this time, amide bond cleavage was not confirmed.

The same reaction was performed for Substrate 21a (Table 122).

TABLE 122

| Substrate | Example No. | Raw material | Reaction time | Conversion rate | Purity reduction (LCMS Area %) | Amide bond cleavage (LCMS Area %) |
|---|---|---|---|---|---|---|
| 20a | 61 | 27.1 mg | 8 h | 76% | 11% | 8.1% |
|  | 62 | 27.6 mg | 2 h | 100% | 0% | Not detected. |
| 21a | 63 | 26.0 mg | 8 h | 76% | 9% | 2.7% |
|  | 64 | 26.2 mg | 2 h | 100% | 0% | Not detected. |

Identification of Products

TABLE 123

(HPLC method 1)
Major peaks and retention times of products and target products

| Example No. | Compound | MW | m/z | Retention time (min) |
|---|---|---|---|---|
| 61 | 20b | 410.47 | 433.16 ([M + Na]+) | 3.858 |
|  | 20c | 325.36 | 104.01 ([M-Fmoc + H]+)* | 3.976 |
| 63 | 21b | 486.57 | 487.17 ([M + Na]+) | 4.485 |
|  | 21c | 401.46 | 180.02 ([M-Fmoc + H]+)** | 4.594 |

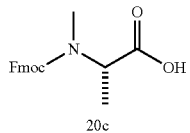

20c

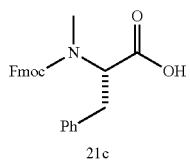

21c

F. Experiment of Comparison Between the TFA Method and the TMSOTf-HMDS Method in Resin Removal Reactions (Table 124)

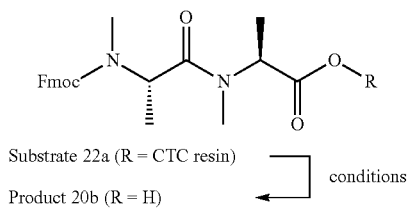

Substrate 22a (R = CTC resin)
Product 20b (R = H)
conditions

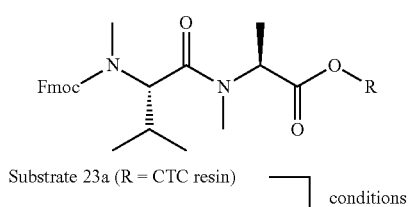

Substrate 23a (R = CTC resin)
Product 23b (R = H)
conditions

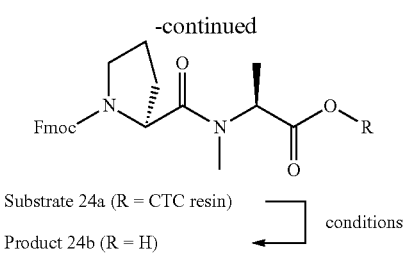

Substrate 24a (R = CTC resin)
Product 24b (R = H)
conditions

Example 65

Resin Removal Reaction of Resin 22a (TFA Method)

30.2 mg of Resin 22a was weighed into a reaction vessel, and the resin was swollen by adding 10 v/w of dichloromethane. After removing the dichloromethane from the reaction solution, 10 v/w % of TFA (5% dichloromethane solution) was added at room temperature and the vessel was shaken at 25° C. One hour after the shaking started, the reaction was analyzed by LCMS to find that 7.8% of a by-product due to amide bond cleavage was produced. The same reaction was performed for Resins 23a to 24a (Table 124).

Example 66

Resin Removal Reaction of Resin 22a (TMSOTf-HMDS Method)

23.0 mg of Substrate 22a was weighed into a reaction vessel, and the resin was swollen by adding 10 v/w of 1,2-dichloroethane. After removing the 1,2-dichloroethane from the reaction solution, a solution of HMDS (3.6 eq.) and TMSOTf (2.4 eq.) in 10 v/w of 1,2-dichloroethane was added to the reaction vessel. After stirring at 25° C. for four hours, the reaction was analyzed by LCMS and no amide bond cleavage was confirmed. The same reaction was performed for Resins 23a to 24a (Table 124).

TABLE 124

| Substrate | Example No. | Raw material | Reagent amount | Reaction time | Amide bond cleavage (LCMS Area %) |
|---|---|---|---|---|---|
| 22a | 65 | 30.2 mg | 5% TFA in $CH_2Cl_2$ (10 v/w) | 1 h | 7.9% |
|  | 66 | 23.0 mg | TMSOTf (2.4 eq.) HMDS (4.8 eq.) | 4 h | 0% |
| 23a | 67 | 30.0 mg | 5% TFA in $CH_2Cl_2$ (10 v/w) | 1 h | 2.3% |
|  | 68 | 24.0 mg | TMSOTf (2.4 eq.) HMDS (4.8 eq.) | 4 h | 0% |
| 24a | 69 | 30.3 mg | 5% TFA in $CH_2Cl_2$ (10 v/w) | 1 h | 0.3% |
|  | 70 | 23.6 mg | TMSOTf (2.4 eq.) HMDS (4.8 eq.) | 4 h | 0% |

Identification of Products
HPLC method A
Instrument: Waters ACQUITY UPLC H-Class
Column: Ascentis Express C18 (2.7 μm, 4.6 mm×50 mm), Supelco
Eluent: A) 0.05% TFA/water, B) 0.05% TFA/$CH_3CN$
Gradient (B): 5% (0 min.)⇒100% (4 min.)⇒100% (4.5 min.)⇒5% (4.6 min.)⇒5% (6 min.)
Flow rate: 1.0 mL/min.
Detection: 210 nm
Injection vol.: 5 μL
Sample prep.: 25 μL/0.975 mL MeCN
HPLC method B
Instrument: Waters ACQUITY UPLC H-Class
Column: Ascentis Express C18 (2.7 μm, 4.6 mm×50 mm), Supelco
Eluent: A) 0.05% TFA/water, B) 0.05% TFA/$CH_3CN$
Gradient (B): 5% (0 min.)⇒100% (4 min.)⇒100% (4.5 min.)⇒5% (4.6 min.)⇒5% (6 min.)
Flow rate: 1.0 mL/min.
Detection: 210 nm
Injection vol.: 5 μL
Sample prep.: 5 μL/1.00 mL (MeCN 0.950 ml+0.1 M phosphate buffer (pH 8.0) 0.050 ml)
HPLC method C
Instrument: Waters ACQUITY UPLC H-Class
Column: Ascentis Express C18 (2.7 μm, 4.6 mm×50 mm), Supelco
Eluent: A) 0.05% TFA/water, B) 0.05% TFA/CH3CN
Gradient (B): 5% (0 min.)⇒100% (4 min.)⇒100% (4.5 min.)⇒5% (4.6 min.)⇒5% (6 min.)
Flow rate: 1.0 mL/min.
Detection: 210 nm
Injection vol.: 5 μL
Sample prep.: 5 μL/1.00 mL MeCN
HPLC method D
Instrument: Shimadzu LCMS-2020
Column: Ascentis Express C18 (2.7 μm, 2.1 mm×50 mm), Supelco
Eluent: A) 0.1% FA/water, B) 0.1% FA/CH3CN
Gradient (B): 5% (0 min.)⇒100% (4.5 min.)⇒100% (5 min.)
Flow rate: 1.0 mL/min.
Detection: 210 nm-400 nm
Injection vol.: 1 μL
HPLC method E
Instrument: SHIMADZU LCMS-2020
Column: Ascentis Express C18 2.1 mm×50 mm, Supelco
Eluent: A) 0.1% FA/water, B) 0.1% FA/CH3CN
Gradient (B): 5% (0 min.)⇒100% (1.5 min.)⇒100% (2 min.)
Flow rate: 1.0 mL/min.
Detection: PDA 210 nm-400 nm
Injection vol.: 1 μL
HPLC method F
Instrument: Waters Acquity UPLC/SQD2
Column: Ascentis Express C18 (2.7 μm, 2.1 mm×50 mm), Supelco
Eluent: A) 0.1% FA/water, B) 0.1% FA/CH3CN
Gradient (B): 5% (0 min.)⇒100% (1 min.)⇒100% (1.4 min.)
Flow rate: 1.0 mL/min.
Detection: 210 nm-400 nm
Injection vol.: 1 μL
HPLC method G
Instrument: Waters Acquity UPLC/SQD2
Column: Ascentis Express C18 (2.7 μm, 2.1 mm×50 mm), Supelco
Eluent: A) 0.1% FA/water, B) 0.1% FA/CH3CN
Gradient (B): 5% (0 min.)⇒100% (1 min.)⇒100% (1.4 min.)
Flow rate: 1.0 mL/min.
Detection: 210 nm-400 nm
Injection vol.: 1 μL
HPLC method H
Instrument: Waters Acquity UPLC/SQD
Column: Ascentis Express C18 (2.7 μm, 2.1 mm×50 mm), Supelco
Eluent: A) 0.1% FA/water, B) 0.1% FA/CH3CN
Gradient (B): 5% (0 min.)⇒100% (4.5 min.)⇒100% (5.0 min.)
Flow rate: 1.0 mL/min.
Detection: 210 nm-400 nm
Injection vol.: 2 μL

TABLE 125

| Example No. | HPLC method | Compound | MW | m/z | Retention time (min) |
|---|---|---|---|---|---|
| 65, | A | 20b | 410.47 | 411.18 ([M + H]+) | 3.034 |
| 66 | A | 22c | 339.39 | 118.01 ([M-Fmoc + H]+) | 3.648 |
| 67, | A | 23b | 438.52 | 439.24 ([M + H]+) | 3.310 |
| 68 | A | 23c | 353.42 | 354.16 ([M + H]+) | 3.472 |
| 69, | B | 24b | 422.48 | 423.19 ([M + H]+) | 2.898 |
| 70 | B | 24c | 337.38 | 116.01 ([M-Fmoc + H]+) | 3.049 |

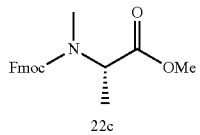

22c

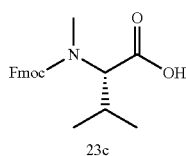

23c

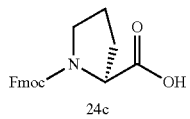

24c

G. Experiment of Comparison Between the TFA Method and the TMSOTf-HMDS Method in Resin Removal Reactions (Table 126)

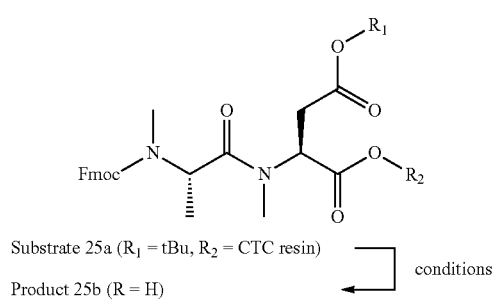

Substrate 25a ($R_1$ = tBu, $R_2$ = CTC resin)
Product 25b (R = H)

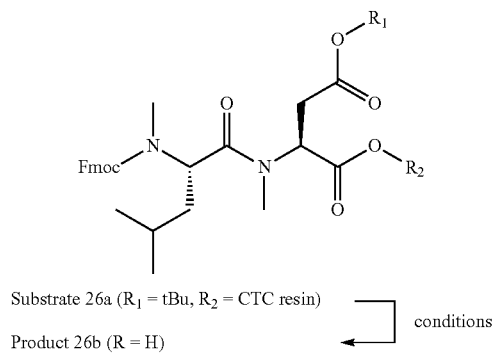

Substrate 26a ($R_1$ = tBu, $R_2$ = CTC resin)
Product 26b (R = H)

Example 71

CTC Resin Removal and t-Bu Removal Reactions of Resin 25a (TFA Method)

20.0 mg of Resin 25a was weighed into a reaction vessel, and the resin was swollen by adding 10 v/w of dichloromethane. After removing the dichloromethane from the reaction solution, 10 v/w % of TFA (10% dichloromethane solution) was added at room temperature and the vessel was shaken at 25° C. One hour after the shaking started, the reaction was analyzed by LCMS to find that the reaction conversion rate was 17%. 3.8% of a by-product due to amide bond cleavage was produced. The same reaction was performed for Resin 26a (Table 126).

Example 72

CTC Resin Removal and tBu Deprotection Reactions of Resin 25a (TMSOTf-HMDS Method)

23.0 mg of Substrate 25a was weighed into a reaction vessel, and the resin was swollen by adding 10 v/w of 1,2-dichloroethane. After removing the 1,2-dichloroethane from the reaction solution, a solution of HMDS (10.7 eq.) and TMSOTf (7.1 eq.) in 10 v/w of 1,2-dichloroethane was added to the reaction vessel. After shaking at 25° C. for four hours, the reaction was analyzed by LCMS and the t-Bu ester was confirmed to disappear. The same reaction was performed for Resin 26a (Table 126).

TABLE 126

| Substrate | Example No. | Raw material | Reagent | Reaction time | Conversion rate | Amide bond cleavage (LCMS Area %) |
|---|---|---|---|---|---|---|
| 25a | 71 | 20.0 mg | 10% TFA in CH$_2$Cl$_2$ (10 v/w) | 1 h | 17% | 3.8% |
| | 72 | 20.3 mg | TMSOTf (7.1 eq.) HMDS (10.7 eq.) | 4 h | 100% | 0% |
| 26a | 73 | 19.8 mg | 10% TFA in CH$_2$Cl$_2$ (10 v/w) | 1 h | 13% | 1.1% |
| | 74 | 20.0 mg | TMSOTf (7.1 eq.) HMDS (14.2 eq.) | 3 h | 100% | 0% |

Identification of Products

TABLE 127

(HPLC method 1)
Major peaks and retention times of products and target products

| | | Compound data | | |
|---|---|---|---|---|
| Example No. | Compound | MW | m/z | Retention time (min) |
| 71, 72 | 25b | 454.48 | 477.10 ([M + Na]+) | 2.649 |
| | 25c | 339.39 | 118.07 ([M-Fmoc + H]+) | 3.560 |
| 73, 74 | 26b | 496.56 | 497.24 ([M + H]+) | 3.117 |
| | 26c | 367.45 | 146.00 ([M-Fmoc + H]+) | 3.661 |

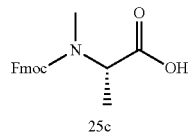

25c

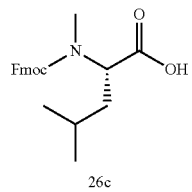

26c

H. Synthesis of Raw Materials for Boc Removal, t-Bu Removal, and Resin Removal Reactions

Example 75

Synthesis of 3-Mer Raw Material for Boc Removal Reaction (Boc-Asp(OBn)-pip)

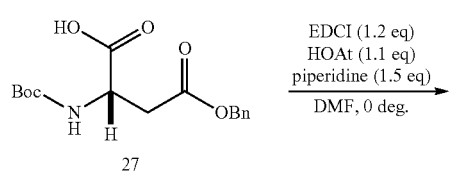

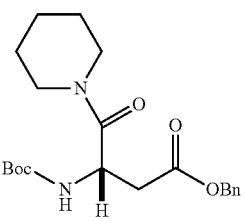

28

The synthesis was performed according to Example 88.

TABLE 128

| | Weight (g) | Yield (%) |
|---|---|---|
| Raw material (27) | 34.6 | — |
| Product (28) | 37.6 | 90 |

TABLE 129

| Analysis (HPLC method 1) | | | |
|---|---|---|---|
| MW | m/z | rt | Purity LC A % |
| Product (28) 390.48 | 291.19 ([M-Boc + H]+) | 4.530 | 97.619 |

Example 76

Synthesis of 2-mer (Boc-MeVal-Asp(OBn)-pip)

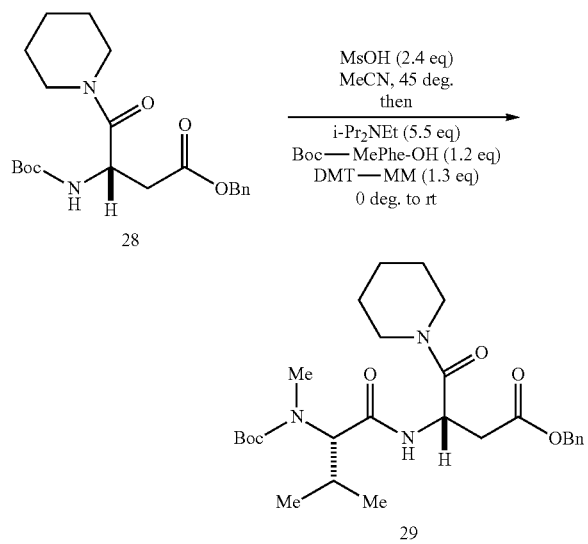

5.714 g of the raw material was weighed into a reaction vessel and 29 ml of MeCN was added. After adding 2.3 ml of methanesulfonic acid, the oil bath was set at 45° C. and the reaction vessel was heated. After 70 minutes, the reaction vessel was brought back to room temperature and then immersed in an ice bath. To the reaction solution was added 14 ml of diisopropylethylamine, followed by addition of 4.046 g of Boc-MeVal-OH and 5.284 g of DMT-MM. One hour after the addition of the reagents, the reaction solution was concentrated. The reaction was quenched by adding ethyl acetate and 5% aqueous potassium carbonate to the concentrate. The organic layer was separated by liquid separation treatment and then washed twice with a 5% aqueous potassium carbonate solution, once with water, three times with a 5% aqueous potassium bisulfate solution, once with a 10% aqueous sodium chloride solution, and once with brine. The organic layer was concentrated under reduced pressure to give 7.055 g (96% yield) of a pale yellow solid.

TABLE 130

| | Weight (g) | Yield (%) |
|---|---|---|
| Raw material (28) | 5.714 | — |
| Product (29) | 7.055 | 96 |

TABLE 131

| Analysis (HPLC method 1) | | | |
|---|---|---|---|
| MW | m/z | rt | Purity LC A % |
| Product (29) 503.64 | 526.29 ([M + Na]+) | 5.178 | 96.889 |

Example 77

Synthesis of 3-mer (Boc-MePhe-MeVal-Asp(OBn)-pip)

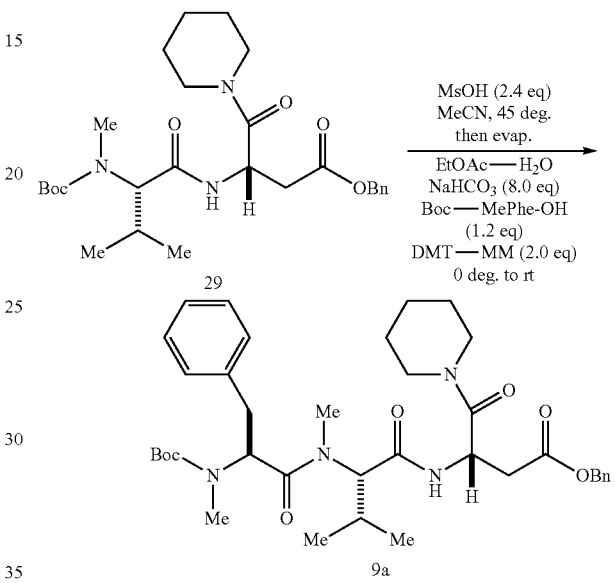

7.055 g of the raw material was weighed into a reaction vessel and 35 ml of MeCN was added. After adding 2.2 ml of methanesulfonic acid, the oil bath was set at 45° C. and the reaction vessel was heated. After 70 minutes, the reaction vessel was brought back to room temperature and then the reaction solution was concentrated. After the concentration, 35 ml of ethyl acetate was added, the reaction vessel was immersed in an ice bath, and 9.466 g of sodium bicarbonate was then added. 35 ml of water was then added, followed by addition of 4.61 g of Boc-MePhe-OH and 7.73 g of DMT-MM. After six hours, the reaction was followed by LCMS to confirm that the raw material consumption rate was 99%. One hour after the analysis, liquid separation treatment was conducted by adding ethyl acetate and water to give an organic layer. The organic layer was washed three times with a 5% aqueous potassium carbonate solution, once with water, three times with a 5% aqueous potassium bisulfate solution, and once with brine. The organic layer was concentrated under reduced pressure and the resulting crude product was purified by silica gel column chromatography to provide 6.9757 g (75% yield) of the target product as a white solid.

TABLE 132

| | Weight (g) | Yield (%) |
|---|---|---|
| Raw material (29) | 7.055 | — |
| Product (9a) | 6.9757 | 75 |

TABLE 133

| | Analysis (HPLC method 1) | | | |
|---|---|---|---|---|
| | MW | m/z | rt | Purity LC A % |
| Product (9a) | 664.84 | 687.43 ([M + Na]+) | 5.684 | 99.206 |

Example 78

Synthesis of Boc-MeGly-OAllyl

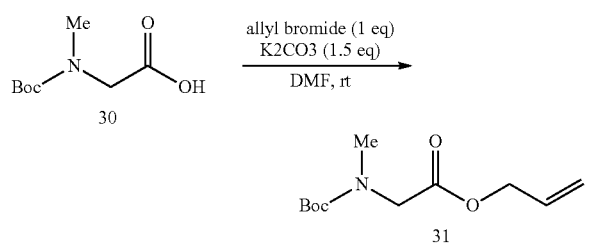

9.286 g of the raw material was weighed into a reaction vessel and 46 ml of DMF was added. The reaction vessel was cooled with ice, and 10.20 g of potassium carbonate and 4.15 ml of allyl bromide were then added. After 15 minutes, the reaction vessel was brought back to room temperature and then stirred overnight. To the reaction vessel was added MTBE, and the reaction was quenched with water. After liquid separation, the organic layer was washed once with brine. The organic layer was dried over magnesium sulfate, filtered, and concentrated under reduced pressure. The resulting crude product was purified by silica gel column chromatography to provide 10.083 g (90% yield) of the target product 31 as a transparent oily liquid.

TABLE 134

| | Weight (g) | Yield (%) |
|---|---|---|
| Raw material (30) | 9.286 | — |
| Product (31) | 10.083 | 90 |

Example 79

Synthesis of Boc-Thr(OBn)-MeGly-OAllyl

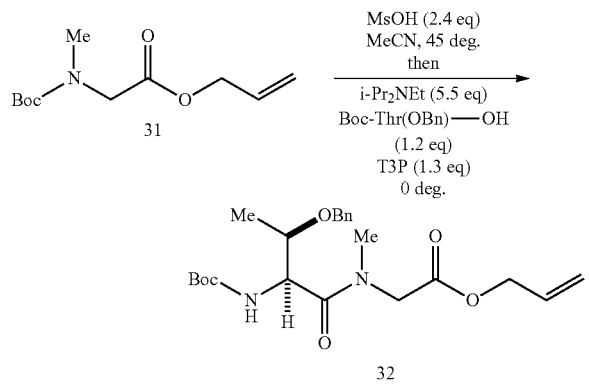

Deprotection and condensation reactions were performed according to Example 76.

TABLE 135

| | Weight (g) | Yield (%) |
|---|---|---|
| Raw material (31) | 6.5224 | — |
| Product (32) | 13.5594 | Quantitative |

TABLE 136

| | Analysis (HPLC method 1) | | | |
|---|---|---|---|---|
| | MW | m/z | rt | Purity LC A % |
| Product (Compound 32) | 420.51 | 321.10 ([M-Boc + H]+) | 4.770 | 98.54 |

Example 80

Synthesis of Boc-MeLeu-Thr(OBn)-MeGly-OAllyl

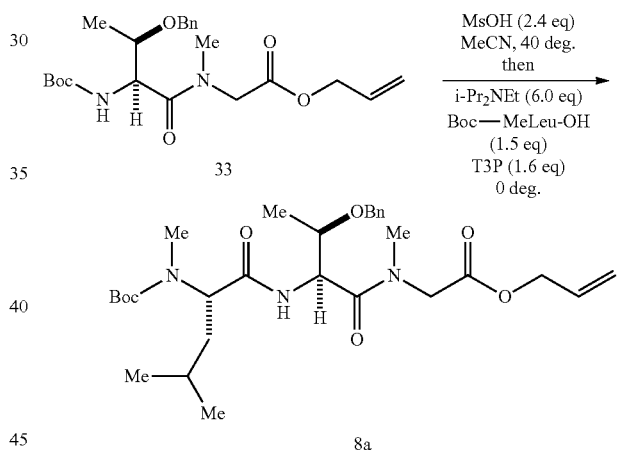

Deprotection and condensation reactions were performed by the same method as described above.

Example 80a

Synthesis of Teoc-MeLeu-OPfp by Esterification Reaction of Teoc-MeLeu-OH with Pentafluorophenol (Pfp-OH)

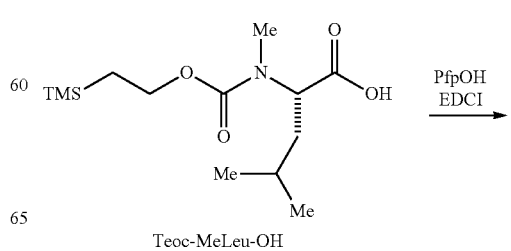

Teoc-MeLeu-OH

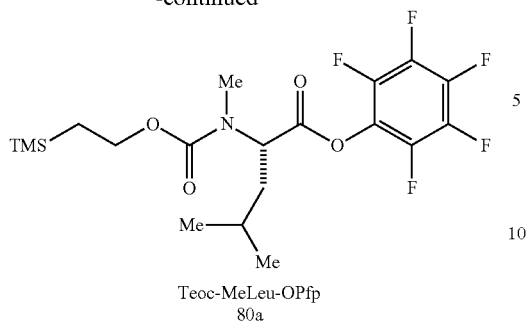

Teoc-MeLeu-OPfp
80a 926 mg of the raw material and 736 mg of pentafluorophenol (Pfp-OH) were respectively weighed into a reaction vessel, and 7.8 mL of isopropyl acetate was added. 767 mg of EDCI hydrochloride was added and the reaction solution was stirred at room temperature for two hours. The organic layer was washed twice with 8 mL of 0.5 N hydrochloric acid and twice with 8 mL of a 5% aqueous potassium carbonate solution, and 2 g of sodium sulfate was added to the organic layer. The solid was removed by filtration and the organic layer was concentrated under reduced pressure to give the target product as a transparent oily liquid. The obtained compound is used for the next reaction without purification.

TABLE 137

| | Analysis (HPLC method G) | | |
|---|---|---|---|
| | MW | m/z | Retention time (min) |
| Product (Compound 80a) | 455.16 | 428.3 ([M—C2H4 + H]+) | 1.19 |

Example 80b

Synthesis of Teoc-MeLeu-Thr(OBn)-MeGly-OAllyl

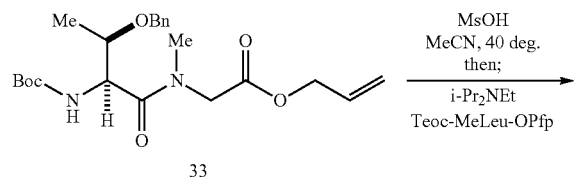

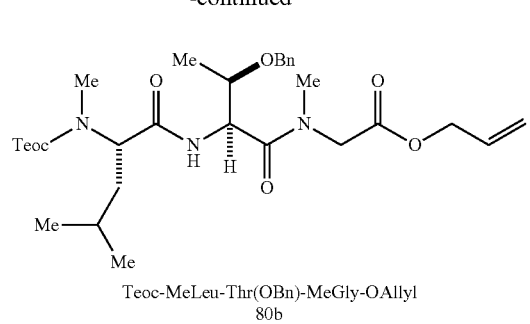

Teoc-MeLeu-Thr(OBn)-MeGly-OAllyl
80b

Compound 80b can be synthesized by condensation reaction using the method of Meneses et al. (J. Org. Chem., 2010, 75, 564-569) in which the terminal protecting group of Compound 33 is removed and then reacted with pentafluorophenyl ester (Compound 80a) to form an amide bond.

TABLE 138

| | Weight (g) | Yield (%) |
|---|---|---|
| Raw material (33) | 13.4338 | — |
| Product (8a) | 15.5319 | 100 |

TABLE 139

| | Analysis (HPLC method 1) | | | |
|---|---|---|---|---|
| | MW | m/z | rt | Purity LC A % |
| Product (8a) | 660.41 | 561.28 ([M-Boc + H]+) | 5.657 | 95.36 |

Example 81

Synthesis of Boc-MeAla-MePhe-Leu-MeLeu-Thr(OBn)-MeGly-OAllyl

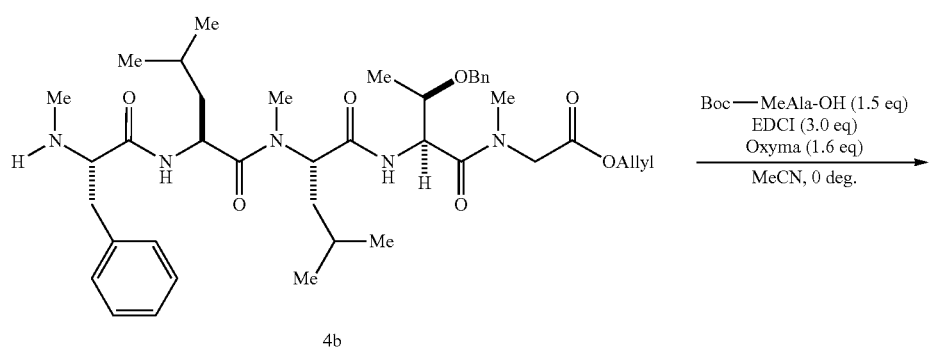

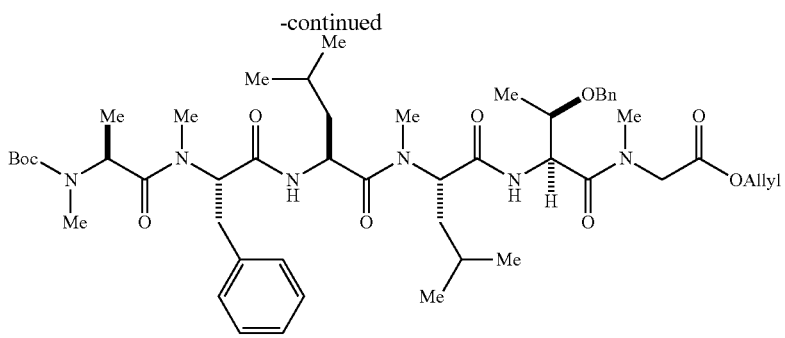
3a
The reaction was performed according to Example 88.
TABLE 140
| | Weight (g) | Yield (%) |
|---|---|---|
| Raw material (4b) | 5.0118 | — |
| Product (3a) | 5.68 | 90 |
TABLE 141
| | Analysis (HPLC method 1) | | | |
|---|---|---|---|---|
| | MW | m/z | rt | Purity LC A % |
| Product (3a) | 906.55 | 807.58 ([M-Boc] + H)+ | 5.974 | 93.06 |
Example 82
Synthesis of Boc-MeAla-MePhe-Leu-MeLeu-Thr(OBn)-MeGly-OH
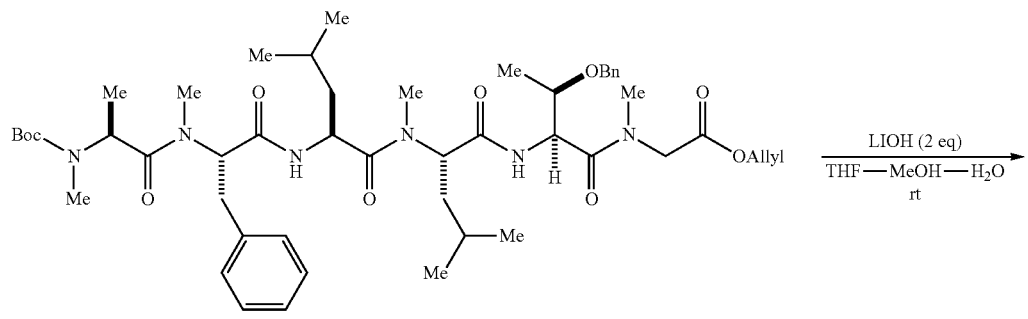
3a
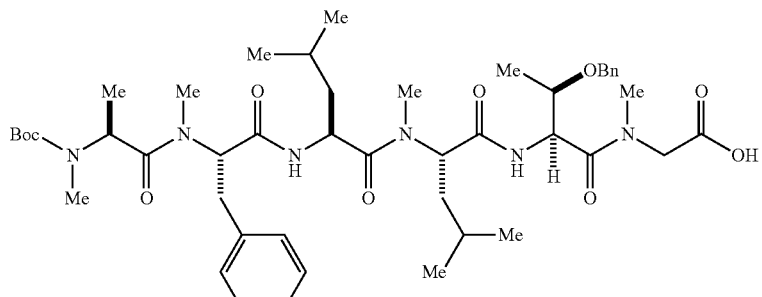
34

1.1180 g of the raw material was weighed into a reaction vessel and 2.2 ml each of THF, methanol, and water were added. 102.8 mg of lithium hydroxide monohydrate was then added and the reaction solution was stirred at room temperature for five hours. The completion of the reaction was confirmed by LC, and the reaction solution was then concentrated under reduced pressure. After adding ethyl acetate to the concentrate, 0.5 N hydrochloric acid was added to quench the reaction. The organic layer was separated by liquid separation treatment and then washed twice with 0.5 N hydrochloric acid and twice with a 5% aqueous sodium chloride solution. The solvent was evaporated by concentration under reduced pressure to give 918.8 mg (86% yield) of a white solid.

TABLE 142

|  | Weight (g) | Yield (%) |
|---|---|---|
| Raw material (3a) | 1.1180 | — |
| Product (34) | 0.9188 | 86 |

TABLE 143

| Analysis (HPLC method 1) | | | |
|---|---|---|---|
| MW | m/z | rt | Purity LC A % |
| Product (34) 866.52 | 767.5 ([M-Boc] + H)+ | 5.361 | 92.03 |

Example 83

Synthesis of Fmoc-Asp(OtBu)-pip

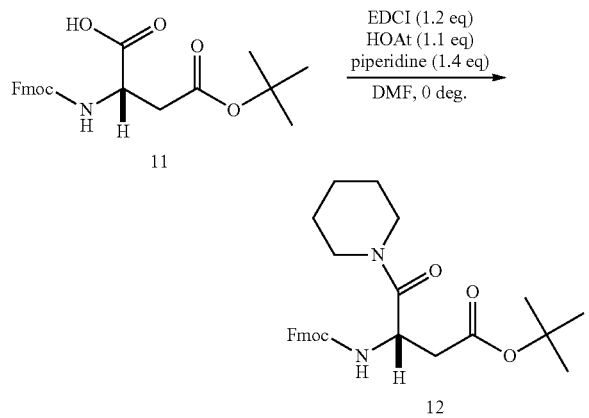

The reaction was performed according to Example 88.

TABLE 144

|  | Weight (g) | Yield (%) |
|---|---|---|
| Raw material (11) | 40 | — |
| Product (12) | 47 | Quantitative |

TABLE 145

| Analysis (HPLC method 1) | | | |
|---|---|---|---|
| MW | m/z | rt | Purity LC A % |
| Product (12) 478.25 | 423.24 ([M-tBu] + H)+ | 4.019 | 99.318 |

Example 84

Synthesis of FmocAsp(OH)pip

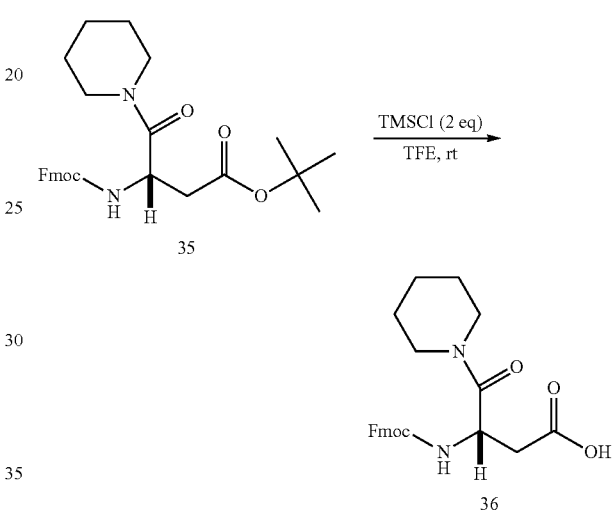

45.4 g of the raw material was weighed into a reaction vessel and 454 ml of trifluoroethanol was added. 24 ml of chlorotrimethylsilane was then added and the reaction solution was stirred at room temperature. Two and a half hours after the start of the reaction, 910 ml of water was added in two portions and crystals were allowed to precipitate. The crystals were filtered and then dried to give 25.8 g (61% yield) of the target product 36.

TABLE 146

|  | Weight (g) | Yield (%) |
|---|---|---|
| Raw material (35) | 40 | — |
| Product (36) | 25.8 | 61 |

TABLE 147

| Analysis (HPLC method 1) | | | |
|---|---|---|---|
| MW | m/z | rt | Purity LC A % |
| Product (36) 422.18 | 423.21 ([M] + H)+ | 3.101 | 98.259 |

Example 85

Loading of Fmoc-Asp(OH)-pip onto CTC Resin

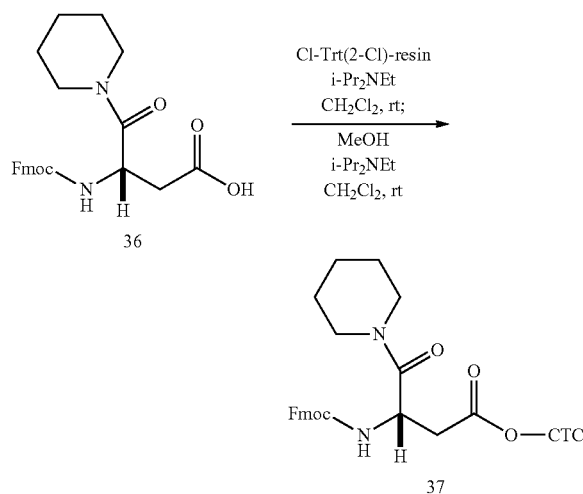

The same loading step as in the method described in Example 112 was conducted. The product was analyzed after 5-mer elongation and the following resin removal step.

TABLE 148

| | Weight (g) |
|---|---|
| Raw material (36) | 4.09 |

Example 86

Solid-Phase Synthesis (2-Mer Elongation)

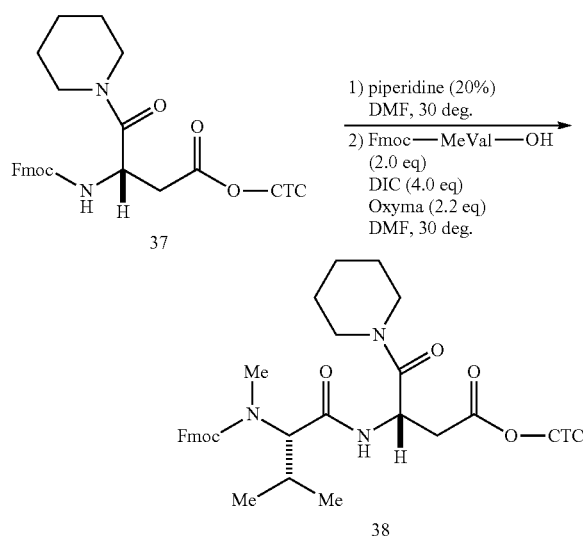

The reactions were performed in a solid-phase synthesis column.

1) Deprotection step: To Fmoc-MeAla-OCTC resin (37, theoretical amino acid loading amount: 9.49 mmol) was added DMF (104 mL). A 20% solution of piperidine in DMF (104 mL) was added at 30° C., and the column was shaken at 30° C. for 15 minutes. After the solution was discharged, a 20% solution of piperidine in DMF (104 mL) was added again and the column was shaken at 30° C. for 15 minutes. After the solution was discharged, the resin was washed with DMF (130 ml) for 2 min×7.

2) Elongation step: In a reaction vessel separate from the solid-phase column, 6.62 g of Fmoc-MeVal-OH and 2.93 g of Oxyma were dissolved in 52 ml of DMF, and 5.87 ml of DIC was then added. The vessel was shaken at 30° C. for 30 minutes. This solution was added to the solid-phase synthesis column, which was then shaken at 30° C. for two hours. After the solution was discharged, the resin was washed with DMF (130 ml) for 2 min×6.

Example 87

Solid-Phase Synthesis (Sequential Elongation from 2-Mer to 5-Mer and Resin Removal Reaction)

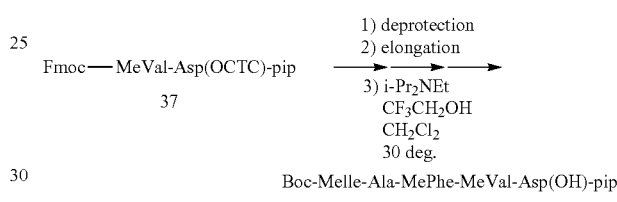

Deprotection and elongation steps were repeated according to the method described in Example 86 to provide Boc-MeIle-Ala-MePhe-MeVal-Asp(OCTC)-pip. To the resulting resin was added 147 ml of a mixed solvent of diisopropylethylamine, trifluoroethanol, and methylene chloride (2% diisopropylethylamine, solvent volume ratio 1:1), followed by shaking at 30° C. for two and a half hours. The discharged and resin-removed peptide solution was collected. After the resin removal solution was discharged, the resin was washed twice with 25 ml of a mixed solvent of trifluoroethanol and methylene chloride (volume ratio 1:1), and the solutions were concentrated. The concentrate was dissolved in 130 ml of ethyl acetate and washed twice with an aqueous potassium carbonate solution, twice with potassium bisulfate, and once with an aqueous sodium chloride solution, and the organic layer was then concentrated under reduced pressure. After drying, 4.9821 g (69% yield) of a white solid was obtained.

TABLE 149

| | Weight (g) | Yield (%) |
|---|---|---|
| Fmoc-MeAsp(OH)-pip (37) | 4.09 | — |
| Product (38) | 4.9821 | 69 |

TABLE 150

| Analysis (HPLC method 1) | | | | |
|---|---|---|---|---|
| | MW | m/z | rt | Purity LC A % |
| Product (38) | 772.47 | 795.5 ([M + Na]+) | 4.856 | 96.471 |

Example 88

Synthesis of Fmoc-MeAsp(OtBu)-pip

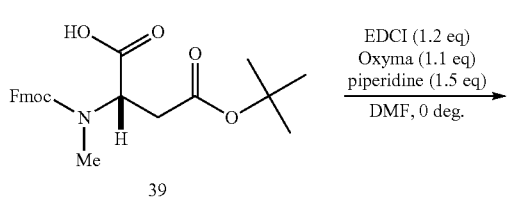

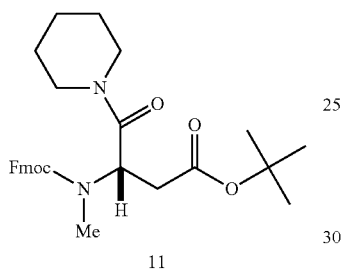

49.6 g of EDCI hydrochloride was weighed into a reaction vessel and 400 ml of DMF was added. The reaction vessel was cooled to 0° C., and 100.050 g of Fmoc-MeAsp(OtBu)-OH was then added. Next, a solution of 40.1 g of Oxyma in 100 ml of DMF was added, followed by 34.9 ml of piperidine, using a dropping funnel. Four hours and 30 minutes after the dropwise addition of piperidine was completed, the reaction was analyzed by LCMS and the raw material was confirmed to disappear. The reaction solution was diluted with ethyl acetate, and 500 ml of 0.5 N hydrochloric acid was then added to quench the reaction. The organic layer was separated and then washed twice with water, twice with a 5% aqueous sodium carbonate solution, and twice with a 5% aqueous sodium chloride solution. The resulting organic layer was concentrated under reduced pressure. The resulting crude product was recrystallized from ethyl acetate and heptane to give 86.230 g (75% yield) of the target product.

TABLE 151

| | Analysis (HPLC method 1) | | | |
| --- | --- | --- | --- | --- |
| | MW | m/z | rt | Purity LC A % |
| Product (Compound 11) | 492.26 | 493.24 ([M + H]+) | 5.527 | 98.268 |

Example 89

Synthesis of Synthetic Intermediate (Cbz-Asp(OtBu)-pip (41)) for 11-Residue Peptide (tBu Form, Cbz-MeAla-MePhe-Leu-MeLeu-Val-MeGly-MeIle-Ser(OtBu)-MePhe-MeVal-Asp(OtBu)-pip (22))

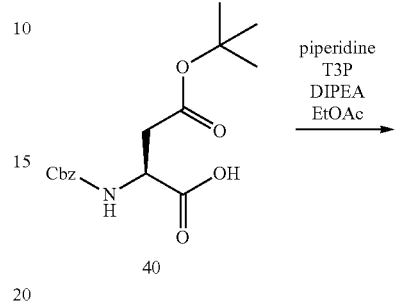

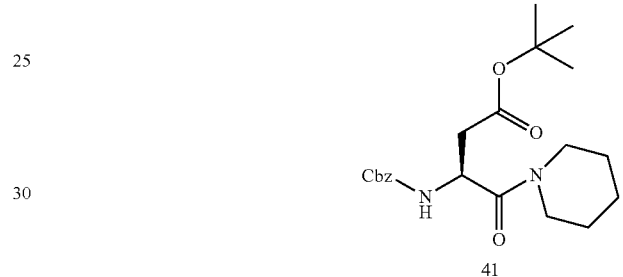

17.5 g of Cbz-Asp(OtBu)-OH was weighed into a reaction vessel and 175 mL of ethyl acetate was added. After cooling the reaction solution to 0° C., piperidine (3 eq.), diisopropylethylamine (6 eq.), and a 1.7 M solution of T3P in ethyl acetate (3 eq.) were added, respectively. The reaction solution was warmed to room temperature and stirred at room temperature for 10 minutes, and 175 mL of a 5% aqueous potassium carbonate solution was then added. The aqueous layer was removed, and the organic layer was then washed twice with 175 mL of a 5% aqueous potassium bisulfate solution. The resulting organic layer was concentrated and dried under reduced pressure to afford 20 g of Cbz-Asp(OtBu)-pip (41) in 100% yield.

Example 90

Synthesis of H-Asp(OtBu)-pip (42)

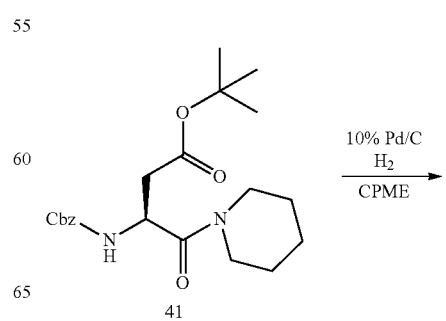

-continued

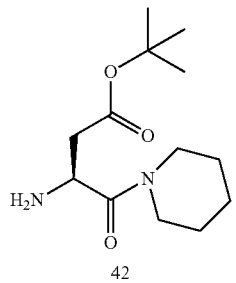
42

9.5 g of Cbz-Asp(OtBu)-pip (41) was weighed into each of two reaction vessels, and 50 mL of CPME was added to each vessel. 10% Pd/C (20 w/w %) was added to both vessels and then reacted at 30° C. under a 3 bar hydrogen atmosphere. Three hours after the start of the reaction, the two reaction solutions were mixed, filtered, and washed with 100 mL of CPME. The resulting mixture was concentrated and dried under reduced pressure to afford 12.3 g of H-Asp(OtBu)-pip (42) in 99% yield.

11-mer (22) was synthesized from H-Asp(OtBu)-pip (42) by the 19 steps described below. The synthesized intermediates are provided as follows.

H-Asp(OtBu)-pip (42)

Cbz-MeVal-Asp(OtBu)-pip (43)

H-MeVal-Asp(OtBu)-pip (44)

Cbz-MePhe-MeVal-Asp(OtBu)-pip (45)

H-MePhe-MeVal-Asp(OtBu)-pip (46)

Cbz-Ser(OtBu)-MePhe-MeVal-Asp(OtBu)-pip (13)

H-Ser(OtBu)-MePhe-MeVal-Asp(OtBu)-pip (47)

Cbz-MeIle-Ser(OtBu)-MePhe-MeVal-Asp(OtBu)-pip (14)

H-MeIle-Ser(OtBu)-MePhe-MeVal-Asp(OtBu)-pip (48)

Cbz-MeGly-MeIle-Ser(OtBu)-MePhe-MeVal-Asp(OtBu)-pip (49)

H-MeGly-MeIle-Ser(OtBu)-MePhe-MeVal-Asp(OtBu)-pip (50)

Cbz-Val-MeGly-MeIle-Ser(OtBu)-MePhe-MeVal-Asp(OtBu)-pip (15)

H-Val-MeGly-MeIle-Ser(OtBu)-MePhe-MeVal-Asp(OtBu)-pip (51)

Cbz-MeLeu-Val-MeGly-MeIle-Ser(OtBu)-MePhe-MeVal-Asp(OtBu)-pip (16)

H-MeLeu-Val-MeGly-MeIle-Ser(OtBu)-MePhe-MeVal-Asp(OtBu)-pip (52)

Cbz-Leu-MeLeu-Val-MeGly-MeIle-Ser(OtBu)-MePhe-MeVal-Asp(OtBu)-pip (17)

H-Leu-MeLeu-Val-MeGly-MeIle-Ser(OtBu)-MePhe-MeVal-Asp(OtBu)-pip (53)

Cbz-MePhe-Leu-MeLeu-Val-MeGly-MeIle-Ser(OtBu)-MePhe-MeVal-Asp(OtBu)-pip (18)

H-MePhe-Leu-MeLeu-Val-MeGly-MeIle-Ser(OtBu)-MePhe-MeVal-Asp(OtBu)-pip (54)

Cbz-MeAla-MePhe-Leu-MeLeu-Val-MeGly-MeIle-Ser(OtBu)-MePhe-MeVal-Asp(OtBu)-pip (19)

Example 91

Elongation of Peptide Chain (Elongation Method A)

8.6 g of 42 was weighed into a reaction vessel and 108 mL of CPME was added. Cbz-MeVal-OH (1.1 eq.) and diisopropylethylamine (3 eq.) were added, and a solution of BEP (1.5 eq.) in 21.5 mL of MeCN was then added. After stirring at room temperature for three minutes, 15 mL of a 10% aqueous sodium bisulfate solution was added. The aqueous layer was removed, and 15 mL of a 5% aqueous potassium carbonate solution and trimethylamine hydrochloride (3 eq.) were then added to the organic layer at room temperature. The mixture was warmed to 40° C. and then stirred at 40° C. for 90 minutes. After cooling to room temperature, the aqueous layer was removed and the resulting organic layer was then washed with 15 mL of a 5% aqueous potassium carbonate solution. The resulting organic layer was concentrated and dried under reduced pressure to give 17 g of 43 quantitatively.

Example 92

Removal of N-Terminal Cbz (Deprotection Method A)

9.5 g of 43 was weighed into each of two reaction vessels, and 50 mL of CPME was added to each vessel. 10% Pd/C (20 w/w %) was added to both vessels and then reacted at 35° C. under a 3 bar hydrogen atmosphere. Two hours after the start of the reaction, the two reaction solutions were mixed, filtered, and washed with 100 mL of CPME. The resulting mixture was concentrated and dried under reduced pressure to give 14 g of 44 in 100% yield.

Example 93

Elongation of Peptide Chain (Elongation Method B)

14 g of 44 was weighed into a reaction vessel, and 126 mL of CPME and 14 mL of acetonitrile were added, respectively. Cbz-MePhe-OH (1.1 eq.), diisopropylethylamine (8 eq.), and a 1.7 M solution of T3P in ethyl acetate (3 eq.) was sequentially added at room temperature. After stirring at room temperature for one hour, 140 mL of a 5% aqueous potassium bisulfate solution was added. The aqueous layer was removed, and 140 mL of a 5% aqueous potassium carbonate solution and trimethylamine hydrochloride (3 eq.) were then added at room temperature. After stirring at room temperature for 30 minutes, the aqueous layer was removed. The resulting organic layer was then washed with 140 mL of a 5% aqueous potassium carbonate solution. The resulting organic layer was concentrated and dried under reduced pressure to give 24.1 g of 45 in 96% yield.

Example 94

Removal of N-Terminal Cbz (Deprotection Method B)

9.2 g of 15a was weighed into each of two reaction vessels, and 46 mL of CPME was added to each vessel. 10% Pd/C (20 w/w %) was added to both vessels and then reacted at 35° C. under a 5 bar hydrogen atmosphere. Six hours after the start of the reaction, the reaction vessels were cooled to room temperature and stored at room temperature overnight under an air atmosphere. Further reaction was performed at 45° C. for four hours under a 5 bar hydrogen atmosphere. The two reaction solutions were mixed, filtered, and washed with 92 mL of CPME. The resulting mixture was concentrated and dried under reduced pressure to give 15.9 g of 51 in 98% yield.

The peptides of 2-mer to 11-mer were synthesized by the same technique. The reaction conditions different from those described above, except for the reaction time and the mass of the raw material used, are further described in the column "Reaction method."

TABLE 152

(HPLC method 1)

| Example No. | Product | Reaction method | Raw material | Reaction time | Product amount | Yield | Purity (LCMS Area %) |
|---|---|---|---|---|---|---|---|
| 91 | 43 | Elongation A | 8.6 g | 3 min | 17 g | Quantitative | 99.7% |
| 92 | 44 | Deprotection A | 9.5 g × 2 | 2 h | 14 g | 100% | ND |
| 93 | 45 | Elongation B | 14 g | 30 min | 24.1 g | 96% | 99.6% |
| 95 | 46 | Deprotection A | 11.5 g × 2 | 2 h | 18.1 g | 99% | ND |
| 96 | 13 | Elongation B | 17.3 g | 15 min | 26.5 g | Quantitative | 98.9% |
| 97 | 47 | Deprotection A | 12 g × 2 | 4 h | 19.5 g | 97% | ND |
| 98 | 14 | Elongation A | 16 g | 5 min | 22.2 g | 100% | 99.4% |
| 99 | 48 | Deprotection A | 9.5 g × 2 | 2 h | 15.6 g | 96% | ND |
| 100 | 49 | Elongation B | 15.3 g | 15 min | 19.5 g | Quantitative | 99.6% |
| 101 | 50 | Deprotection A (5 bar) | 9.5 g × 2 | 3 h | 16.3 g | 99% | ND |
| 102 | 15 | Elongation B | 16 g | 30 min | 20 g | 99% | 99.6% |
| 94 | 51 | Deprotection B | 9.2 g × 2 | 10 h | 15.9 g | 98% | ND |
| 103 | 16 | Elongation A (40° C.) | 14.5 g | 1 min | 18.0 g | 98% | 96.0% |
| 104 | 52 | Deprotection A (45° C., 5 bar) | 8 g × 2 | 4 h | 14.3 g | 100% | ND |
| 105 | 17 | Elongation B | 13 g | 30 min | 15.6 g | 98% | 97.2% |
| 106 | 53 | Deprotection A (45° C., 5 bar) | 10 g | 4 h | 8.9 g | 99% | ND |
| 107 | 18 | Elongation A | 7 g | 3 min | 8.6 g | 99% | 97.0% |
| 108 | 54 | Deprotection A (45° C., 5 bar) | 7.6 g | 4 h | 6.8 g | 98% | ND |
| 109 | 19 | Elongation B | 500 mg | 2 h | 555 mg | 96% | 95.3% |

Among the synthesized intermediates, 13a, 14a, 15a, 16a, 17a, 18a, and 19a were used for tBu removal experiments. The compounds used for tBu removal reactions were analyzed by LCMS as described in Table 153.

TABLE 153

Analysis

| Example No. | Compound | HPLC Method | MW | m/z | Retention time (min) |
|---|---|---|---|---|---|
| 46 | 13a | 1 | 808.03 | 808.49 ([M + H]+) | 5.938 |
| 48 | 14a | 1 | 935.22 | 935.59 ([M + H]+) | 6.233 |
| 50 | 15a | 1 | 1105.43 | 1105.69 ([M + H]+) | 5.924 |
| 52 | 16a | 1 | 1232.62 | 1232.79 ([M + H]+) | 6.374 |
| 54 | 17a | 1 | 1345.78 | 1369 ([M + Na]+) | 6.727 |
| 56 | 18a | 1 | 1506.98 | 1530 ([M + Na]+) | 7.096 |
| 58 | 19a | 1 | 1592.09 | 1615 ([M + Na]+) | 6.987 |

I. Synthesis of C-Terminal tBu-Protected Dipeptides

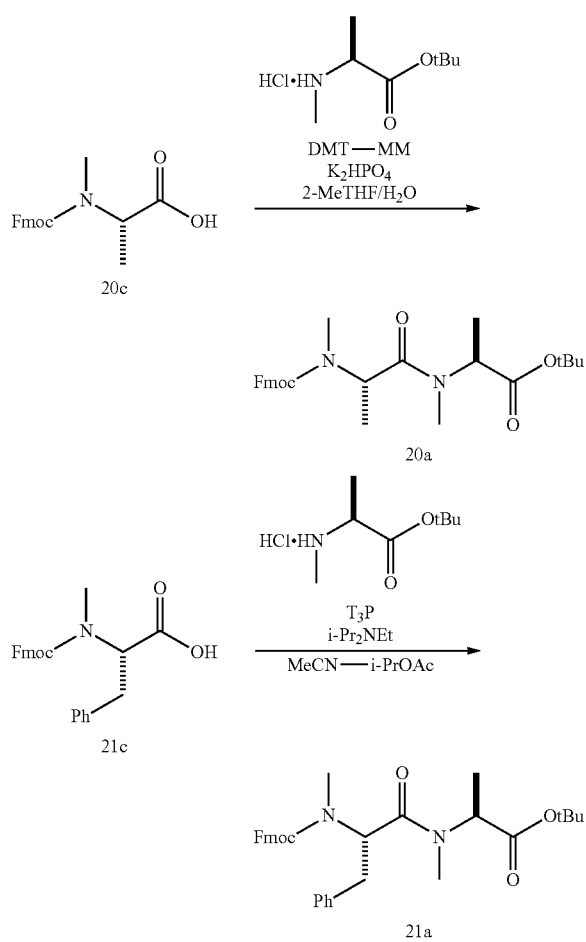

Example 110

Synthesis of Fmoc-MeAla-MeAla-OtBu (20a)

99.7 mg of H-MeAla-OtBu hydrochloride and 710 mg of dipotassium hydrogenphosphate were weighed in a reaction vessel, respectively, and 10 v/w each of 2-MeTHF and water relative to H-MeAla-OtBu hydrochloride were added. Fmoc-MeAla-OH (167 mg) and DMT-MM (211 mg) were sequentially added at 0° C. and the reaction solution was then warmed to room temperature. After shaking at room temperature for 16 hours, the reaction was analyzed by LCMS and Fmoc-MeAla-OH was confirmed to disappear. The reaction solution was transferred to a separatory funnel using 4 mL of water and 6 mL of 2-MeTHF, and the aqueous layer was then removed. The resulting organic layer was washed with brine (3 mL), 15% aqueous sodium bisulfate (3 mL), and 5% aqueous sodium carbonate (3 mL), respectively, and the solvent was then removed by concentration under reduced pressure. The resulting crude product was purified by silica gel column chromatography using the conditions described below, and the fractions containing the target product were then concentrated and dried under reduced pressure to provide 227.6 mg of 20a in a yield of 96% and a purity of 99.5%.

Example 111

Synthesis of Fmoc-MePhe-MeAla-OtBu(21a)

H-MeAla-OtBu hydrochloride (99.8 mg) and Fmoc-MePhe-OH (205 mg) were weighed into a reaction vessel, respectively, and 8 v/w of isopropyl acetate and 2 v/w of acetonitrile relative to H-MeAla-OtBu hydrochloride as well as diisopropylethylamine (4 eq.) were sequentially added. A 1.7 M solution of T3P in ethyl acetate (2.5 eq.) was added at room temperature. After stirring at room temperature for four hours, a 1.7 M solution of T3P in ethyl acetate (0.5 eq.) and diisopropylethylamine (0.8 eq.) were added. 30 minutes after the addition of the reagents, the reaction was analyzed by LCMS to find that the reaction conversion rate was 98.5%. NMI (2 eq.) was added at room temperature, and the reaction solution was then stirred at 50° C. for five minutes. The reaction solution was transferred to a separatory funnel using 6 mL of ethyl acetate, and the aqueous layer was then removed. The resulting organic layer was washed with a 5% aqueous sodium carbonate solution (3 mL), a 5% aqueous potassium bisulfate solution (3 mL), and a 5% aqueous sodium carbonate solution (3 mL), respectively. The organic layer was dehydrated with sodium sulfate for 30 minutes, then filtered, and concentrated under reduced pressure to remove the solvent. The resulting crude product was purified by silica gel column chromatography using the conditions described below, and the fractions containing the target product were then concentrated and dried under reduced pressure to provide 227.6 mg of 21a in a yield of 96% and a purity of 99.5%.

TABLE 154

| | Analysis (HPLC method 1) | | | |
|---|---|---|---|---|
| | Compound data | | | |
| Example No. | Compound | MW | m/z | Retention time (min) |
| 110 | 20a | 466.58 | 489.2 ([M + Na]+) | 5.243 |
| 111 | 21a | 542.68 | 543.2 ([M + H]+) | 5.754 |

J. Synthesis of CTC Resin-Loaded Dipeptides

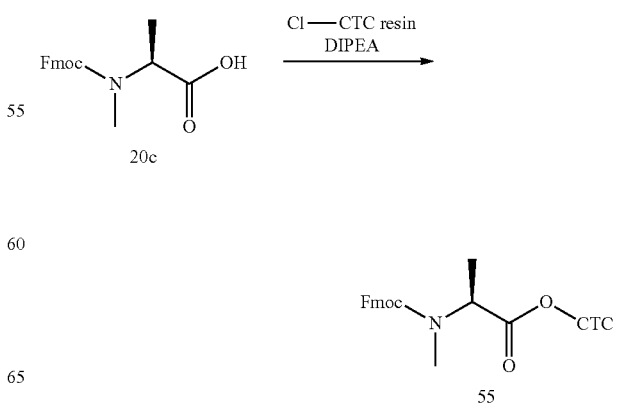

-continued

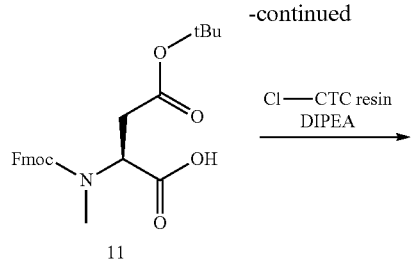

Example 112

Loading of Fmoc-MeAla-OH onto CTC Resin 4.47 g of Cl-CTC resin was weighed into a reaction column, dichloromethane (36 mL) was added, and the column was shaken at 30° C. for 60 minutes. After discharging the dichloromethane, a solution of Fmoc-MeAla-OH (1.24 g) and diisopropylethylamine (1.4 mL) in dichloromethane (36 mL) was added at room temperature. After stirring at 30° C. for three hours, the reaction was analyzed by LCMS to find that the reaction conversion rate was 96.0%. After discharging the reaction solution, a solution of methanol (3.6 mL) and diisopropylethylamine (1.8 mL) in DMF (30 mL) was added at room temperature. After shaking at 30° C. for 1.5 hours, the reaction solution was discharged. The resin was washed with 36 mL of DMF four times and then dried under reduced pressure to give 4.80 g of 55. 56 was also synthesized by the same technique. The products were analyzed in the next step.

TABLE 155

Analysis (HPLC method 1)

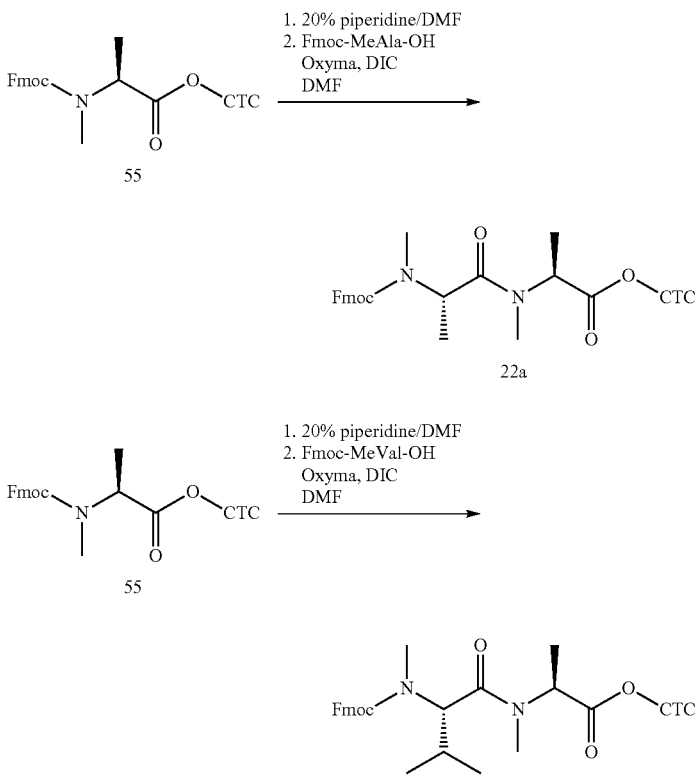

TABLE 155-continued

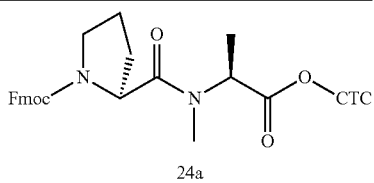

24a

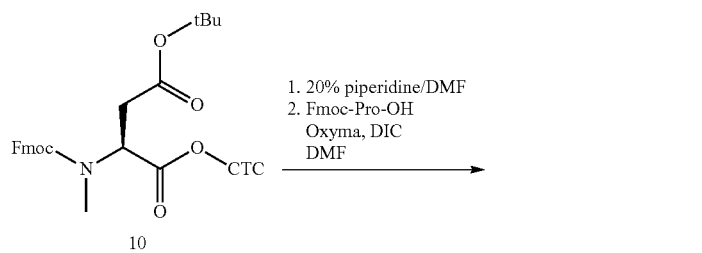

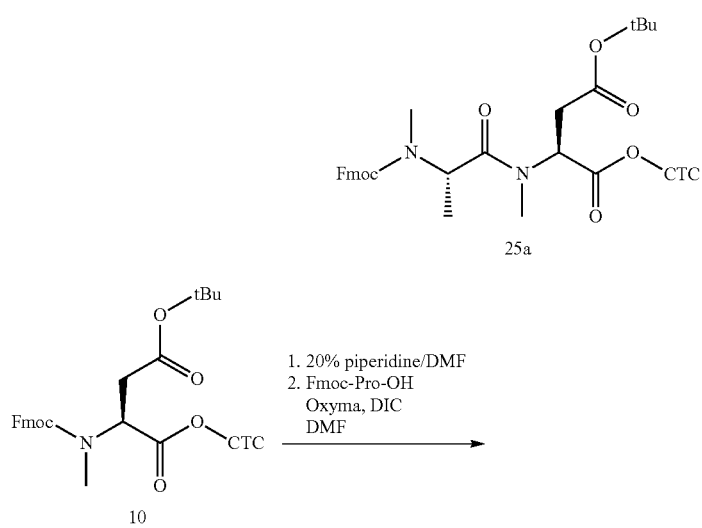

| Example No. | Product | Cl-CTC resin | Amino acid | Reaction conversion rate | Product amount |
|---|---|---|---|---|---|
| 112 | 55 | 4.47 g | 1.24 g | 96% | 4.80 g |
| 113 | 10 | 10.0 g | 3.41 g | 99% | 12.4 g |

Example 114

Synthesis of Fmoc-MeAla-MeAla-OCTC (22a), Fmoc-Me-Val-MeAla-OCTC (23a), and Fmoc-Pro-MeAla-OCTC (24a)

Dipeptides 22a to 24a were simultaneously synthesized using a solid-phase peptide synthesizer Prelude X. 676 mg, 687 mg, and 705 mg of resin Fmoc-MeAla-OCTC (55) were weighed into three reaction vessels, respectively. DMF (8 mL) was added thereto, and the resin was swollen by allowing to stand at room temperature for one hour. After the DMF was discharged, a 20% solution of piperidine in DMF (8 mL) was added and the vessels were shaken at room temperature for 15 minutes. After the solution was discharged, a 20% solution of piperidine in DMF (8 mL) was added again and the vessels were shaken at room temperature for 15 minutes. The cocktails 1 to 3 described below were added to RV 1 to RV 3, respectively, and a 12.5% solution of DIC in DMF (4 eq.) was then added. The vessels were shaken at room temperature for three hours with nitrogen bubbling. After discharging the solution, the resin was washed with DMF (8 v/w) for 2 min×5 and with MTBE (8 v/w) for 2 min×4, which each wash was carried out by shaking at room temperature. The resulting resin was dried under reduced pressure to provide 30a, 31a, and 32a, respectively. The obtained compounds were identified by the resin removal reactions in Examples 65, 67, and 69.

About 20 mg each of the obtained three resins were weighed into three reaction vessels, a 20% solution of piperidine in DMF (100 mL) was added to each vessel, and the reaction solution was stirred at room temperature for two hours. Dibenzofulvene was quantitatively determined from the absorbance of the solution to calculate the loading rate of each dipeptide (Table 156).

Example 115

Synthesis of Fmoc-MeAla-MeAsp(OtBu)-OCTC (25a) and Fmoc-MeLeu-MeAsp(OtBu)-OCTC (26a)

Dipeptides 25a to 26a were simultaneously synthesized using a solid-phase peptide synthesizer Prelude X. 340 mg of resin Fmoc-MeAsp(OtBu)-OCTC (10) was weighed into each of two reaction vessels. DMF (8 mL) was added thereto, and the resin was swollen by allowing to stand at room temperature for 30 minutes. After the DMF was discharged, a 20% solution of piperidine in DMF (8 v/w) was added and the vessels were shaken at room temperature for 5 minutes. After the solution was discharged, a 20% solution of piperidine in DMF (8 v/w) was added again and the vessels were shaken at room temperature for 20 minutes. After discharging the solution, the cocktails 1 and 2 described below were added to the corresponding reaction vessels, respectively, a 12.5% solution of DIC in DMF (4 eq.) was then added, and the vessels were shaken at room temperature for three hours with nitrogen bubbling. After discharging the solution, the resin was washed with DMF (8 v/w) for 2 min×4 and with MTBE (8 v/w) for 2 min×4, which each wash was carried out by shaking at room temperature. The resulting resin was dried under reduced pressure to provide 994 mg of 25a and 1.00 g of 26a, respectively. The obtained compounds were identified by the resin removal reactions in Examples 71 and 73.

About 20 mg each of the obtained two resins were weighed into two reaction vessels, a 20% solution of piperidine in DMF (100 mL) was added to each vessel, and the reaction solution was stirred at room temperature for two hours. Dibenzofulvene was quantitatively determined from the absorbance of the solution to calculate the loading rate of each dipeptide (Table 156).

TABLE 156

| | Analysis (HPLC method 1) | | | |
|---|---|---|---|---|
| Example No. | Product | Raw material | Reaction conversion rate | Loading rate |
| 114 | 22a | 676 mg | 100% | 0.41 mmol/g |
| | 23a | 687 mg | 100% | 0.31 mmol/g |
| | 24a | 705 mg | 100% | 0.42 mmol/g |
| 115 | 25a | 340 mg | 100% | 0.27 mmol/g |
| | 26a | 340 mg | 100% | 0.27 mmol/g |

Example 116

Synthesis of Fmoc-MeAsp(OAllyl)-Mor

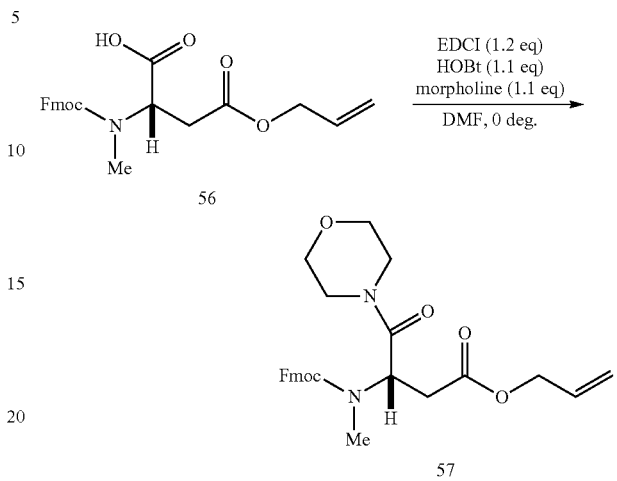

Fmoc-MeAsp(OAllyl)-OH (56, 87.9 g) was added to a reaction vessel and dissolved in DMF (430 ml). HOBt (31.9 g) and EDCI hydrochloride (49.4 g) were then added at ambient temperature, and the reaction solution was cooled to 0° C. Morpholine (20.4 ml) was gradually added to the reaction solution, which was then stirred at 0° C. for 45 minutes. Water (180 ml) was added at 0° C. to the reaction solution, which was then stirred at ambient temperature for one hour. Water (180 ml) was further added and the reaction solution was stirred at ambient temperature for 1.75 hours. The generated solid was collected by filtration using a Kiriyama funnel, and the resulting solid was washed twice with water (450 ml). The solid after washing with water was dried under reduced pressure to afford 86.8 g (85% yield) of the target product as a colorless solid.

Example 117

Synthesis of Fmoc-MeAsp(OAllyl)-NMe2

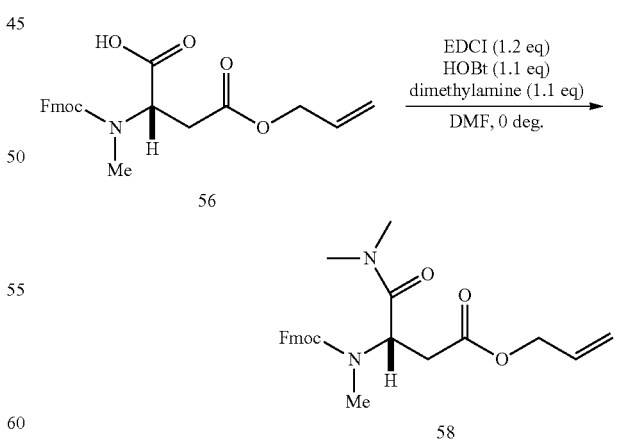

Under a nitrogen stream, EDCI hydrochloride (27.4 g) and DMF (217 ml) were added to a reaction vessel, and HOBt (17.7 g) and a solution of Fmoc-MeAsp(OAllyl)-OH (56, 48.8 g) in dichloromethane-DMF (90 ml-90 ml) were then added at 0° C. After stirring the reaction solution at 0°

C. for 30 minutes, a dimethylamine-THF solution (2 N, 65.6 ml) was added dropwise over two minutes to the reaction solution, which was then stirred at 0° C. for 30 minutes. The reaction solution was diluted with ethyl acetate (488 ml), and the organic layer was washed with 1 N hydrochloric acid (twice with 391 ml), water (488 ml), a 5% aqueous sodium bicarbonate solution (twice with 488 ml), and a 18% aqueous sodium chloride solution (488 ml) and then dried over sodium sulfate. The drying agent was removed by filtration and then the filtrate was concentrated under reduced pressure to give 51.2 g (98% yield) of the target product as a colorless oil.

Example 118

Synthesis of Fmoc-MeAsp(OH)-Mor

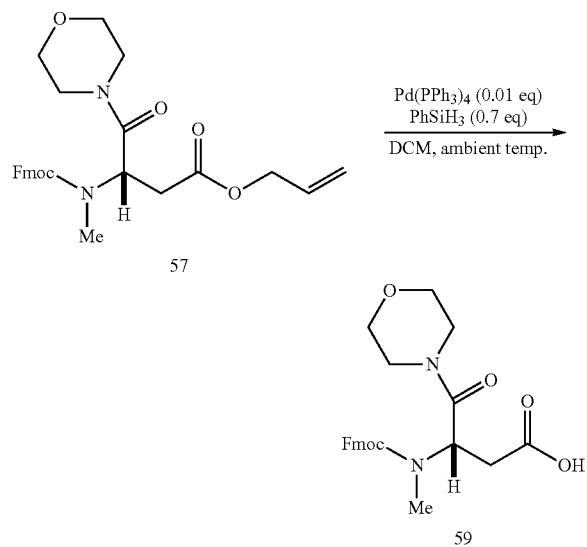

Under a nitrogen stream, Fmoc-MeAsp(OAllyl)-mor (57, 22.8 g) and dichloromethane (50 ml) were added to a reaction vessel, and tetrakistriphenylphosphine palladium (0.55 g) was then added at ambient temperature. Phenylsilane (3.61 g) was added dropwise and the reaction solution was then stirred at ambient temperature for 30 minutes. The reaction solution was diluted with MTBE (228 ml) and then extracted with a 5% aqueous sodium bicarbonate solution (228 ml). The aqueous layer was acidified to about pH 3 with a 85% aqueous phosphoric acid solution (12 ml) and extracted with MTBE (228 ml). The organic layer was washed with a 18% aqueous sodium chloride solution (twice with 228 ml) and then dried over sodium sulfate. The drying agent was removed by filtration and then the filtrate was concentrated under reduced pressure to give 20.3 g (97% yield) of the target product as colorless amorphous crystals.

Example 119

Synthesis of Fmoc-MeAsp(OH)—NMe2

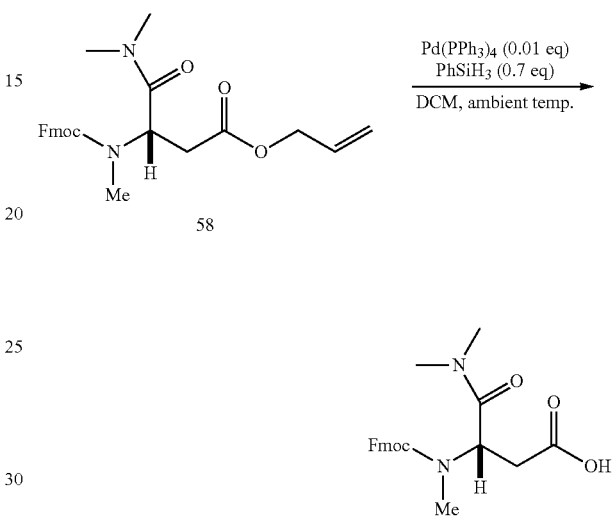

Under a nitrogen stream, Fmoc-MeAsp(OAllyl)-NMe2 (58, 32.0 g) and tetrakistriphenylphosphine palladium (0.847 g) were added to a reaction vessel, and dichloromethane (73.3 ml) was then added. Phenylsilane (5.55 g) was added dropwise to the reaction solution, which was then stirred at ambient temperature for 30 minutes. The reaction solution was diluted with MTBE (320 ml) and then extracted with a 5% aqueous sodium bicarbonate solution (308 ml). The aqueous layer was acidified to about pH 2 with a 85% aqueous phosphoric acid solution (30.1 ml) and extracted with MTBE (320 ml). The organic layer was washed with a 18% aqueous sodium chloride solution (twice with 320 ml) and then dried over sodium sulfate. The drying agent was removed by filtration and then the filtrate was concentrated under reduced pressure to give 25.1 g (86% yield) of the target product as pale brown amorphous crystals.

TABLE 157

| | | Analysis | | | |
|---|---|---|---|---|---|
| | | | | Compound data | |
| Example No. | Compound | HPLC Method | MW | m/z | Retention time (min) |
| 116 | 57 | HPLC method D | 478.21 | 479 ([M + H]+) | 2.570 |
| 117 | 58 | HPLC method E | 436.20 | 437 ([M + H]+) | 1.262 |
| 118 | 59 | HPLC method F | 438.18 | 439 ([M + H]+) | 0.670 |
| 119 | 60 | HPLC method G | 396.17 | 397 ([M + H]+) | 0.680 |

Example 120

Synthesis of Fmoc-MeAsp(OtBu)-Mor (61)

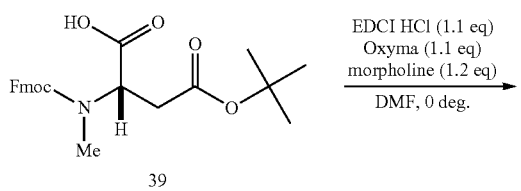

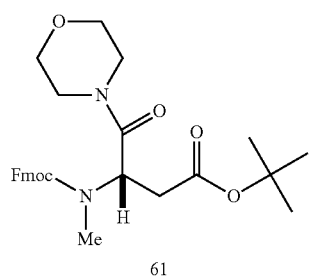

Under a nitrogen stream, Fmoc-MeAsp(OtBu)-OH (39, 3.0 g) and Oxyma (1.1 g) were added to a reaction vessel, and dimethylformamide (15 mL) was then added. 1-(3-Dimethylaminopropyl)-3-ethylcarbodiimide hydrochloride (1.5 g) and morpholine (0.74 mL) were added to the reaction solution while maintaining the temperature of the reaction solution at 10° C. or lower, and it was stirred for three hours. AcOEt (15 mL) and 0.5 N hydrochloric acid (15 mL) were added to the reaction solution. The organic layer was washed with water (15 mL) and further washed with a 5% aqueous sodium carbonate solution (15 mL). The organic layer was washed with a 5% aqueous sodium chloride solution (15 mL) and then concentrated under reduced pressure to afford 3.50 g (100%) of the target product as yellow amorphous crystals. The obtained compound was used for the next reaction without purification.

Example 121

Synthesis of Fmoc-MeAsp(OtBu)-NMe2 (62)

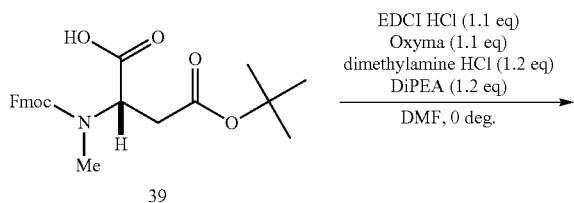

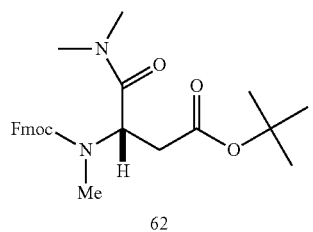

Under a nitrogen stream, Fmoc-MeAsp(OtBu)-OH (39, 3.0 g) and Oxyma (1.1 g) were added to a reaction vessel, and dimethylformamide (15 mL) was then added. 1-(3-Dimethylaminopropyl)-3-ethylcarbodiimide hydrochloride (1.5 g), dimethylamine hydrochloride (0.69 g), and N,N-diisopropylethylamine (1.5 ml) were added to the reaction solution while maintaining the temperature of the reaction solution at 10° C. or lower, and it was stirred for three hours. To the reaction solution was added ethyl acetate (15 mL), followed by 0.5 N hydrochloric acid (15 mL). The organic layer was washed with water (15 mL) and further washed with a 5% aqueous sodium carbonate solution (15 mL). The organic layer was washed with a 5% aqueous sodium chloride solution (15 mL) and then concentrated under reduced pressure to afford 3.17 g (95%) of the target product as a colorless oily substance. The obtained compound was used for the next reaction without purification.

Example 122

Synthesis of Fmoc-MeAsp(OH)-Mor (59)

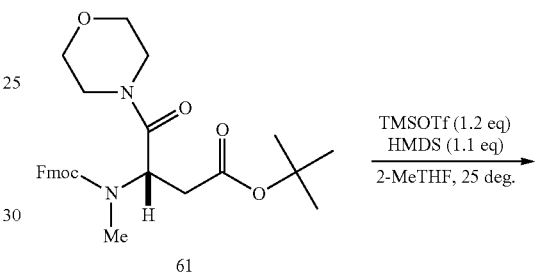

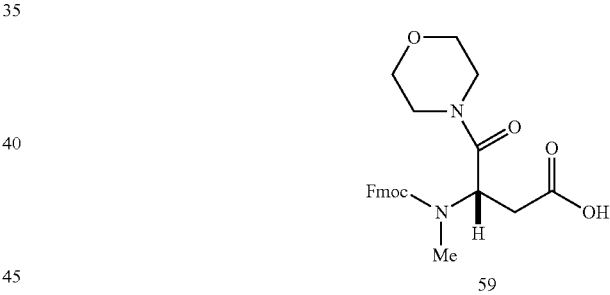

Under a nitrogen stream, Fmoc-MeAsp(OtBu)-mor (61, 1.8 g) and 2-methyltetrahydrofuran (9.2 mL) were added to a reaction vessel, and HMDS (0.86 mL) was then added. The reaction vessel was cooled to 0° C., TMSOTf (0.81 mL) was added, and the reaction solution was stirred at 25° C. for one hour. The reaction vessel was cooled to 0° C., a 5% aqueous potassium dihydrogenphosphate solution (9.2 mL) was added to the reaction solution, and the organic layer was separated. A 5% aqueous sodium carbonate solution (9.2 mL) was added, and the aqueous layer was separated. MTBE (9.2 mL) and 2 N hydrochloric acid (5.0 mL) were added to the aqueous layer, and the organic layer was separated. The organic layer was washed with a 5% aqueous potassium dihydrogenphosphate solution (9.2 mL) and then with a 10% aqueous sodium chloride solution (9.2 mL). The organic layer was concentrated under reduced pressure to afford 1.31 g (97%) of the target product as yellow amorphous crystals.

Example 123

Synthesis of Fmoc-MeAsp(OH)—NMe2 (60)

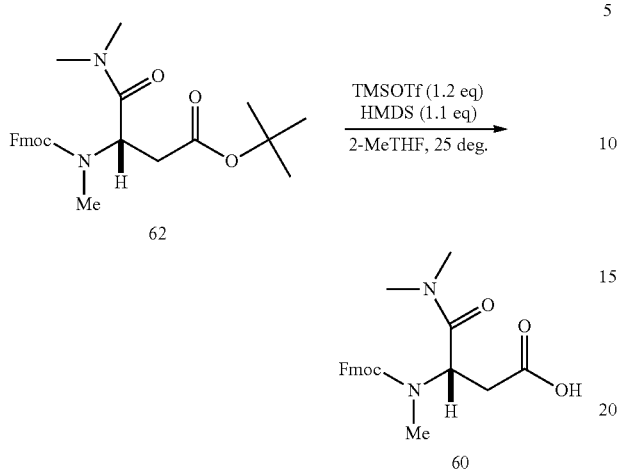

Under a nitrogen stream, Fmoc-MeAsp(OtBu)-NMe2 (62, 1.6 g) and 2-methyltetrahydrofuran (7.9 mL) were added to a reaction vessel, and HMDS (0.80 mL) was then added. The reaction vessel was cooled to 0° C., TMSOTf (0.75 mL) was added, and the reaction solution was stirred at 25° C. for one hour. A 5% aqueous potassium dihydrogenphosphate solution (7.9 mL) was added to the reaction solution, and the organic layer was separated. A 5% aqueous sodium carbonate solution (7.9 mL) was added, and the aqueous layer was separated. MTBE (7.9 mL) and 2 N hydrochloric acid (5.0 mL) were added to the aqueous layer, and the organic layer was separated. The organic layer was washed with a 5% aqueous potassium dihydrogenphosphate solution (7.9 mL) and then with a 10% aqueous sodium chloride solution (7.9 mL). The organic layer was concentrated under reduced pressure to afford 1.31 g (95%) of the target product as a colorless oily substance.

TABLE 158

Analysis

| | | | Compound data | | |
|---|---|---|---|---|---|
| Example No. | Compound | HPLC Method | MW | m/z | Retention time (min) |
| 120 | 61 | HPLC method H | 494.24 | 495.6 ([M + H]+) | 2.75 |
| 121 | 62 | HPLC method H | 452.23 | 453.6 ([M + H]+) | 2.77 |
| 122 | 59 | HPLC method H | 438.18 | 439.5 ([M + H]+) | 1.84 |
| 123 | 60 | HPLC method H | 396.17 | 397.5 ([M + H]+) | 1.89 |

INDUSTRIAL APPLICABILITY

The present invention provides methods of producing peptide compounds by novel deprotection and/or resin removal methods using silylating agents. The present invention can provide industrially applicable and efficient techniques of peptide synthesis.

The invention claimed is:

1. A method of producing a peptide compound in which a protecting group removable by a silylating agent is removed, the method comprising the step of contacting a starting peptide compound comprising natural amino acid residues and/or amino acid analog residues with the silylating agent in a solvent and thereby removing the protecting group from the starting peptide compound,
wherein the silylating agent is prepared by:
(i) mixing a silyl compound with an electrophilic species scavenger, or
(ii) mixing an acid with a silyl-containing electrophilic species scavenger,
wherein the starting peptide compound comprises at least one protecting group removable by the silylating agent, and
wherein the starting peptide compound comprises at least one N-alkylated amino acid residue;
wherein the electrophilic species scavenger in (i) has a formula of formula (11) as defined below; and
wherein the silyl-containing electrophilic species scavenger in (ii) is a compound having a formula of formula (11) as defined below, provided that the compound has a silyl group:

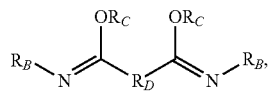

(11)

wherein in formula 11,
$R_B$ is a substituted silyl group and $R_C$ is a substituted silyl group, or
$R_B$ and $R_C$, together with the nitrogen atom and oxygen atom to which they are attached, form a 5- to 7-membered ring; and
$R_D$ is optionally substituted methylene.

2. A method of producing a peptide compound in which a resin for solid-phase synthesis that is removable by a silylating agent is removed, the method comprising the step of contacting a starting peptide compound comprising natural amino acid residues and/or amino acid analog residues with the silylating agent in a solvent and thereby removing the resin for solid-phase synthesis from the starting peptide compound,
wherein the silylating agent is prepared by:
(i) mixing a silyl compound with an electrophilic species scavenger, or
(ii) mixing an acid with a silyl-containing electrophilic species scavenger,
wherein the starting peptide compound is linked to the removable resin for solid-phase synthesis, and
wherein the starting peptide compound comprises at least one N-substituted amino acid residue;
wherein the electrophilic species scavenger in (i) has a formula of formula (11) as defined below; and wherein the silyl-containing electrophilic species scavenger in (ii) is a compound having a formula of formula (11) as defined below, provided that the compound has a silyl group:

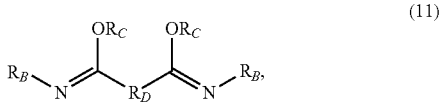

wherein in formula 11,
$R_B$ is a substituted silyl group and $R_C$ is a substituted silyl group, or
$R_B$ and $R_C$, together with the nitrogen atom and oxygen atom to which they are attached, form a 5- to 7-membered ring; and
$R_D$ is optionally substituted methylene.

3. The method of claim 1, wherein the starting peptide compound comprises at least one structure in which at least two amino acid residues are linked to each other, wherein the structure is represented by general formula (I) below:

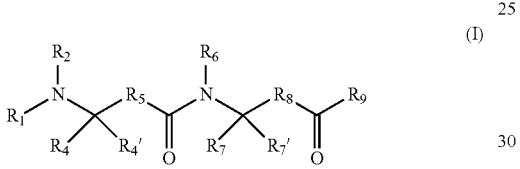

wherein
$R_1$ is hydrogen, $PG_1$, a natural amino acid residue, or an amino acid analog residue;
$R_2$ is selected from the group consisting of hydrogen and $C_1$-$C_6$ alkyl, or $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy, wherein $R_{4'}$ is hydrogen when $R_2$ and $R_4$ together form the heterocyclic ring, and $R_4$ is hydrogen when $R_2$ and $R_{4'}$ together form the heterocyclic ring;
except when $R_2$ and $R_4$, or $R_2$ and $R_{4'}$ together form the heterocyclic ring,
(a) $R_{4'}$ is hydrogen, and $R_4$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_2$, N-$PG_3$-indol-3-ylmethyl, 4-($PG_2$O)benzyl, $PG_2$-O-methyl, 1-($PG_2$O)ethyl, 2-($PG_2$O)ethyl, $PG_2$-OCO($CH_2$)—, $PG_2$—OCO($CH_2$)$_2$—, $PG_3$N-n-butyl, —CON($R_{14A}$)($R_{14B}$), —$CH_2$—CON($R_{14A}$)($R_{14B}$), and —($CH_2$)$_2$CON($R_{14A}$)($R_{14B}$),
(b) $R_4$ and $R_{4'}$ are independently optionally substituted $C_1$-$C_6$ alkyl, or
(c) $R_4$ and $R_{4'}$, together with the carbon atom to which they are attached, form a 3- to 7-membered alicyclic ring;
$R_5$ is a single bond or —$C(R_{5A})(R_{5B})$—;
$R_{5A}$ and $R_{5B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;

$R_6$ is selected from the group consisting of hydrogen and $C_1$-$C_6$ alkyl, or $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy, wherein $R_{7'}$ is hydrogen when $R_6$ and $R_7$ together form the heterocyclic ring, and $R_7$ is hydrogen when $R_6$ and $R_{7'}$ together form the heterocyclic ring;
except when $R_6$ and $R_7$ or $R_6$ and $R_{7'}$ together form the heterocyclic ring,
(a) $R_{7'}$ is hydrogen, and $R_7$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_4$, N-$PG_5$-indol-3-ylmethyl, 4-($PG_4$O)benzyl, $PG_4$-O-methyl, 1-($PG_4$O)ethyl, 2-($PG_4$O)ethyl, $PG_4$-OCO($CH_2$)—, $PG_4$-OCO($CH_2$)$_2$—, $PG_5$N-n-butyl, —CON($R_{15A}$)($R_{15B}$), —$CH_2$—CON($R_{15A}$)($R_{15B}$), and —($CH_2$)$_2$CON($R_{15A}$)($R_{15B}$), or
(b) $R_7$ and $R_{7'}$ are independently optionally substituted $C_1$-$C_6$ alkyl, or
(c) $R_7$ and $R_{7'}$, together with the carbon atom to which they are attached, form a 3- to 7-membered alicyclic ring;
$R_8$ is a single bond or —$C(R_{5A})(R_{5B})$—;
$R_{8A}$ and $R_{8B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
$R_9$ is hydroxy, —O—$PG_6$, a natural amino acid residue, an amino acid analog residue, —O—RES, or —NH—RES;
RES is a resin for solid-phase synthesis;
$R_{14A}$ and $R_{14B}$ are independently hydrogen or $C_1$-$C_4$ alkyl, or $R_{14A}$ and $R_{14B}$, together with the nitrogen atom to which they are attached, form a 4- to 8-membered ring optionally comprising one or more additional heteroatoms;
$R_{15A}$ and $R_{15B}$ are independently hydrogen or $C_1$-$C_4$ alkyl, or $R_{15A}$ and $R_{15B}$, together with the nitrogen atom to which they are attached, form a 4- to 8-membered ring optionally comprising one or more additional heteroatoms;
$PG_1$ is selected from the group consisting of Fmoc, Boc, Alloc, Cbz, Teoc, and trifluoroacetyl;
$PG_2$ and $PG_4$ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;
$PG_3$ and $PG_8$ are independently selected from the group consisting of hydrogen, Fmoc, Boc, Alloc, Cbz, Teoc, methoxycarbonyl, t-Bu, trityl, cumyl, and benzyl; and
$PG_6$ is selected from the group consisting of t-Bu, trityl, cumyl, benzyl, methyl, ethyl, allyl, and 2-(trimethylsilyl)ethyl.

4. The method of claim 1, wherein the starting peptide compound comprises at the C-terminus a structure in which at least two amino acid residues are linked to each other, wherein the structure is represented by general formula (II) below:

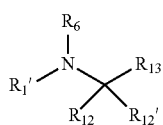

(II)

wherein
$R_{1'}$ is a group represented by the formula (III):

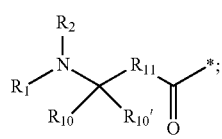

(III)

* represents the point of attachment;
$R_1$ is hydrogen, $PG_1$, a natural amino acid residue, or an amino acid analog residue;
$R_2$ is selected from the group consisting of hydrogen and $C_1$-$C_6$ alkyl, or $R_2$ and $R_{10}$, or $R_2$ and $R_{10'}$, together with the nitrogen atom and carbon atom to which they are attached, form a 3- to 7-membered heterocyclic ring optionally substituted with hydroxy or $C_1$-$C_4$ alkoxy, wherein $R_{10'}$ is hydrogen when $R_2$ and $R_{10}$ together form the heterocyclic ring, and $R_{10}$ is hydrogen when $R_2$ and $R_{10'}$ together form the heterocyclic ring;
except when $R_2$ and $R_{10}$ or $R_2$ and $R_{10'}$ together form the heterocyclic ring,
(a) $R_{10'}$ is hydrogen, and $R_{10}$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —$CH_2SPG_8$, N-$PG_9$-indol-3-ylmethyl, 4-($PG_8$O)benzyl, $PG_8$-O-methyl, 1-($PG_8$O)ethyl, 2-($PG_8$O)ethyl, $PG_8$-OCO($CH_2$)—, $PG_8$-OCO($CH_2$)$_2$—, $PG_9$N-n-butyl, —$CON(R_{16A})(R_{16B})$, —$CH_2$—$CON(R_{16A})(R_{16B})$, and —$(CH_2)_2CON(R_{16A})(R_{16B})$, or
(b) $R_{10}$ and $R_{10'}$ are independently optionally substituted $C_1$-$C_6$ alkyl, $C_3$-$C_6$ cycloalkyl, or $C_3$-$C_6$ cycloalkyl-$C_1$-$C_4$ alkyl, or
(c) $R_{10}$ and $R_{10'}$, together with the carbon atom to which they are attached, form a 3- to 7-membered alicyclic ring;
$R_{11}$ is a single bond or —$C(R_{11A})(R_{11B})$—;
$R_{11A}$ and $R_{11B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
$R_{12}$ and $R_{12'}$ are independently selected from the group consisting of hydrogen, $PG_{10}$-O-methyl, —$(CH_2)_n$COO—$PG_{10}$, —$(CH_2)_n$COO—RES, and —$(CH_2)_n$CONH—RES;
RES is a resin for solid-phase synthesis;
n is 0, 1, or 2;
$R_6$ is selected from the group consisting of hydrogen and $C_1$-$C_6$ alkyl;
$R_{13}$ is $C_1$-$C_4$ alkyl or —$(CH_2)_m CON(R_{17A})(R_{17B})$;
m is 0, 1, or 2;
$R_{16A}$ and $R_{16B}$ are independently hydrogen or $C_1$-$C_4$ alkyl, or $R_{16A}$ and $R_{16B}$, together with the nitrogen atom to which they are attached, form a 4- to 8-membered ring optionally comprising one or more additional heteroatoms;
$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;
$PG_1$ is independently selected from the group consisting of Fmoc, Boc, Alloc, Cbz, Teoc, and trifluoroacetyl;
$PG_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;
$PG_9$ is selected from the group consisting of hydrogen, Fmoc, Boc, Alloc, Cbz, Teoc, methoxycarbonyl, t-Bu, trityl, cumyl, and benzyl; and
$PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl.

5. A method of producing an amide compound in which a protecting group removable by a silylating agent is removed, the method comprising the step of contacting a starting amide compound with the silylating agent in a solvent and thereby removing the protecting group from the starting amide compound,
wherein the silylating agent is prepared by:
(i) mixing a silyl compound with an electrophilic species scavenger, or
(ii) mixing an acid with a silyl-containing electrophilic species scavenger,
wherein the starting amide compound is represented by general formula (II) below:

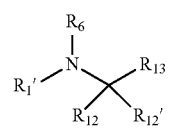

(II)

wherein
$R_{1'}$ is a hydrogen atom or $PG_7$;
$R_{12}$ and $R_{12'}$ are independently selected from the group consisting of hydrogen, $PG_{10}$-O-methyl, —$(CH_2)_n$COO-$PG_{10}$, —$(CH_2)_n$COO—RES, and —$(CH_2)_n$CONH—RES;
RES is a resin for solid-phase synthesis;
n is 0, 1, or 2;
$R_6$ is selected from the group consisting of hydrogen and $C_1$-$C_6$ alkyl;
$R_{13}$ is $C_1$-$C_4$ alkyl or —$(CH_2)_m CON(R_{17A})(R_{17B})$;
m is 0, 1, or 2;
$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;
$PG_7$ is selected from the group consisting of Fmoc, Boc, Alloc, Cbz, Teoc, and trifluoroacetyl; and
$PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl, and wherein the starting amide compound comprises at least one protecting group removable by the silylating agent;

wherein the electrophilic species scavenger in (i) has a formula of formula (11) as defined below; and wherein the silyl-containing electrophilic species scavenger in (ii) is a compound having a formula of formula (11) as defined below, provided that the compound has a silyl group:

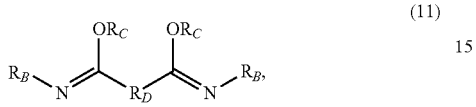

(11)

wherein in formula 11, $R_B$ is a substituted silyl group and $R_C$ is a substituted silyl group, or $R_B$ and $R_C$, together with the nitrogen atom and oxygen atom to which they are attached, form a 5- to 7-membered ring; and $R_D$ is optionally substituted methylene.

6. A method of producing an amide compound in which a resin for solid-phase synthesis is removed, the method comprising the step of contacting a starting amide compound with a silylating agent in a solvent and thereby removing the starting amide compound from the resin for solid-phase synthesis, wherein the silylating agent is prepared by:
 (i) mixing a silyl compound with an electrophilic species scavenger, or
 (ii) mixing an acid with a silyl-containing electrophilic species scavenger, and wherein the starting amide compound is represented by general formula (II) below:

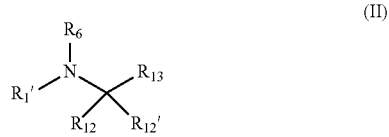

(II)

wherein $R_{1'}$ is a hydrogen atom or $PG_7$;

$R_{12}$ and $R_{12'}$ are independently selected from the group consisting of hydrogen, $PG_{10}$-O-methyl, —$(CH_2)_n$COO—$PG_{10}$, —$(CH_2)_n$COO—RES, and —$(CH_2)_n$CONH—RES;

RES is a resin for solid-phase synthesis, wherein at least one of $R_{12}$ and $R_{12'}$ is —$(CH_2)_n$COO—RES or —$(CH_2)_n$CONH—RES;

RES is a resin for solid-phase synthesis;

n is 0, 1, or 2;

$R_6$ is selected from the group consisting of hydrogen and $C_1$-$C_6$ alkyl;

$R_{13}$ is $C_1$-$C_4$ alkyl or —$(CH_2)_m$CON($R_{17A}$)($R_{17B}$);

m is 0, 1, or 2;

$R_{17A}$ and $R_{17B}$ are independently hydrogen or $C_1$-$C_4$ alkyl, or $R_{17A}$ and $R_{17B}$, together with the nitrogen atom to which they are attached, form a 4- to 8-membered ring optionally comprising one or more additional heteroatoms;

$PG_7$ is selected from the group consisting of Fmoc, Boc, Alloc, Cbz, Teoc, and trifluoroacetyl; and $PG_{10}$ is selected from the group consisting of t-Bu, trityl, cumyl, benzyl, methyl, ethyl, allyl, optionally substituted aryl, optionally substituted aryl-$C_1$-$C_4$ alkyl, optionally substituted heteroaryl-$C_1$-$C_4$ alkyl, and 2-(trimethylsilyl)ethyl;

wherein the electrophilic species scavenger in (i) has a formula of formula (11) as defined below; and wherein the silyl-containing electrophilic species scavenger in (ii) is a compound having a formula of formula (11) as defined below, provided that the compound has a silyl group:

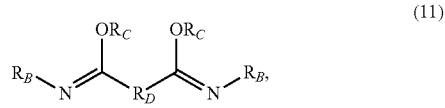

(11)

wherein in formula 11, $R_B$ is a substituted silyl group and $R_C$ is a substituted silyl group, or $R_B$ and $R_C$, together with the nitrogen atom and oxygen atom to which they are attached, form a 5- to 7-membered ring; and $R_D$ is optionally substituted methylene.

7. The method of claim 1, wherein the removable protecting group is selected from the group consisting of t-Bu, triphenylmethyl, 2-(trimethylsilyl)-ethyl, Boc, Teoc, Cbz, methoxycarbonyl, tetrahydropyranyl, 1-ethoxyethyl, methoxytrityl, and cumyl.

8. The method of claim 1, wherein the silyl compound is represented by formula 1 below:

(1)

wherein $R_{AX}$, $R_{AY}$, and $R_{AZ}$ are independently $C_1$-$C_4$ alkyl or phenyl, and X is selected from the group consisting of —OTf, —$OClO_3$, Cl, Br, and I.

9. The method of claim 8, wherein the silyl compound is selected from the group consisting of TMSOTf, TESOTf, TBSOTf, TIPSOTf, TBDPSOTf, TTMSOTf, TMSCl, TMSBr, $TMSOClO_3$, and TMSI.

10. The method of claim 1, wherein the acid is represented by HX, wherein X is selected from the group consisting of —OTf, —$OClO_3$, Cl, Br, and I.

11. The method of claim 1, wherein the silylating agent is prepared by mixing the silyl compound with the electrophilic species scavenger.

12. The method of claim 11, wherein the electrophilic species scavenger is 2,2'-isopropylidenebis[(4S)-4-tert-butyl-2-oxazoline] represented by formula 2-2-1-1

(2-2-1-1)

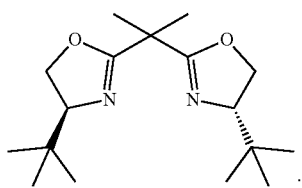

13. The method of claim 1, wherein per one equivalent of the protecting group to be removed, 1 to 5 equivalents of the silyl compound and 1 to 10 equivalents of the electrophilic species scavenger are mixed.

14. The method of claim 1, wherein per one equivalent of the protecting group to be removed,
   a) 0.1 to 0.5 equivalent of the silyl compound is mixed with the electrophilic species scavenger,
      wherein the silyl compound is selected from the group consisting of TMSOTf, TESOTf, TBSOTf, TIPSOTf, TBDPSOTf, TTMSOTf, TMSCl, TMSBr, and TMSOClO$_3$, or
   b) 0.1 to 0.5 equivalent of the acid is mixed with the silyl-containing electrophilic species scavenger,
      wherein the acid is represented by HX, wherein X is selected from the group consisting of —OTf, —OClO$_3$, Cl, Br, and I.

15. The method of claim 1, wherein the starting peptide compound comprises 1 to 30 amino acid residues and is linear or cyclic.

16. The method of claim 2, wherein the resin for solid-phase synthesis is CTC resin, Wang resin, or SASRIN resin.

17. The method of claim 1, wherein the method comprises mixing the starting peptide compound with the solvent, then
   (1) with the electrophilic species scavenger, and subsequently with the silyl compound, or
   (2) with the silyl-containing electrophilic species scavenger, and subsequently with the acid.

18. The method of claim 2, wherein the starting peptide compound comprises at least one structure in which at least two amino acid residues are linked to each other, wherein the structure is represented by general formula (I) below:

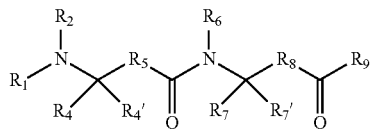
(I)

wherein
   $R_1$ is hydrogen, $PG_1$, a natural amino acid residue, or an amino acid analog residue;
   $R_2$ is selected from the group consisting of hydrogen and $C_1$-$C_6$ alkyl, or $R_2$ and $R_4$ or $R_2$ and $R_{4'}$, together with the nitrogen atom and carbon atom to which they are attached, form a 3- to 7-membered heterocyclic ring optionally substituted with hydroxy or $C_1$-$C_4$ alkoxy, wherein $R_{4'}$ is hydrogen when $R_2$ and $R_4$ together form the heterocyclic ring, and $R_4$ is hydrogen when $R_2$ and $R_{4'}$ together form the heterocyclic ring;
   except when $R_2$ and $R_4$, or $R_2$ and $R_{4'}$ together form the heterocyclic ring,
   (a) $R_{4'}$ is hydrogen, and $R_4$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —CH$_2$SPG$_2$, N-PG$_3$-indol-3-ylm-ethyl, 4-(PG$_2$O)benzyl, PG$_2$-O-methyl, 1-(PG$_2$O)ethyl, 2-(PG$_2$O)ethyl, PG$_2$-OCO(CH$_2$)—, PG$_2$-OCO(CH$_2$)$_2$—, PG$_3$N-n-butyl, —CON($R_{14A}$)($R_{14B}$), —CH$_2$—CON($R_{14A}$)($R_{14B}$), and —(CH$_2$)$_2$CON($R_{14A}$)($R_{14B}$),
   (b) $R_4$ and $R_{4'}$ are independently optionally substituted $C_1$-$C_6$ alkyl, or
   (c) $R_4$ and $R_{4'}$, together with the carbon atom to which they are attached, form a 3- to 7-membered alicyclic ring;
   $R_5$ is a single bond or —C($R_{5A}$)($R_{5B}$)—;
   $R_{5A}$ and $R_{5B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
   $R_6$ is selected from the group consisting of hydrogen and $C_1$-$C_6$ alkyl, or $R_6$ and $R_7$ or $R_6$ and $R_{7'}$, together with the nitrogen atom and carbon atom to which they are attached, form a 3- to 7-membered heterocyclic ring optionally substituted with hydroxy or $C_1$-$C_4$ alkoxy, wherein $R_{7'}$ is hydrogen when $R_6$ and $R_7$ together form the heterocyclic ring, and $R_7$ is hydrogen when $R_6$ and $R_{7'}$ together form the heterocyclic ring;
   except when $R_6$ and $R_7$ or $R_6$ and $R_{7'}$ together form the heterocyclic ring,
   (a) $R_{7'}$ is hydrogen, and $R_7$ is selected from the group consisting of hydrogen, optionally substituted $C_1$-$C_6$ alkyl, $C_3$-$C_6$ cycloalkyl, $C_3$-$C_6$ cycloalkyl-$C_1$-$C_4$ alkyl, optionally substituted phenyl, optionally substituted phenylmethyl, optionally substituted phenylethyl, 2-(methylthio)ethyl, —CH$_2$SPG$_4$, N-PG$_5$-indol-3-ylm-ethyl, 4-(PG$_4$O)benzyl, PG$_4$-O-methyl, 1-(PG$_4$O)ethyl, 2-(PG$_4$O)ethyl, PG$_4$-OCO(CH$_2$)—, PG$_4$-OCO(CH$_2$)$_2$—, PG$_5$N-n-butyl, —CON($R_{15A}$)($R_{15B}$), —CH$_2$—CON($R_{15A}$)($R_{15B}$), and —(CH$_2$)$_2$CON($R_{15A}$)($R_{15B}$), or
   (b) $R_7$ and $R_{7'}$ are independently optionally substituted $C_1$-$C_6$ alkyl, or
   (c) $R_7$ and $R_{7'}$, together with the carbon atom to which they are attached, form a 3- to 7-membered alicyclic ring;
   $R_8$ is a single bond or —C($R_{8A}$)($R_{8B}$)—;
   $R_{8A}$ and $R_{8B}$ are independently selected from the group consisting of hydrogen, $C_1$-$C_6$ alkyl, optionally substituted aryl, optionally substituted heteroaryl, optionally substituted aryl-$C_1$-$C_4$ alkyl, and optionally substituted heteroaryl-$C_1$-$C_4$ alkyl;
   $R_9$ is hydroxy, —O-PG$_6$, a natural amino acid residue, an amino acid analog residue, —O—RES, or —NH—RES;
   RES is a resin for solid-phase synthesis;
   $R_{14A}$ and $R_{14B}$ are independently hydrogen or $C_1$-$C_4$ alkyl, or $R_{14A}$ and $R_{14B}$, together with the nitrogen atom to which they are attached, form a 4- to 8-membered ring optionally comprising one or more additional heteroatoms;
   $R_{15A}$ and $R_{15B}$ are independently hydrogen or $C_1$-$C_4$ alkyl, or $R_{15A}$ and $R_{15B}$, together with the nitrogen atom to which they are attached, form a 4- to 8-membered ring optionally comprising one or more additional heteroatoms;
   $PG_1$ is selected from the group consisting of Fmoc, Boc, Alloc, Cbz, Teoc, and trifluoroacetyl;

PG$_2$ and PG$_4$ are independently selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-C$_1$-C$_4$ alkyl, optionally substituted heteroaryl-C$_1$-C$_4$ alkyl, and 2-(trimethylsilyl)ethyl;

PG$_3$ and PG$_5$ are independently selected from the group consisting of hydrogen, Fmoc, Boc, Alloc, Cbz, Teoc, methoxycarbonyl, t-Bu, trityl, cumyl, and benzyl; and PG$_6$ is selected from the group consisting of t-Bu, trityl, cumyl, benzyl, methyl, ethyl, allyl, and 2-(trimethylsilyl)ethyl.

19. The method of claim 2, wherein the starting peptide compound comprises at the C-terminus a structure in which at least two amino acid residues are linked to each other, wherein the structure is represented by general formula (II) below:

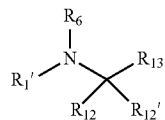

(II)

wherein

R$_1$' is a group represented by the formula (III):

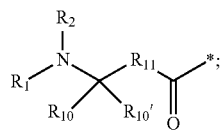

(III)

* represents the point of attachment;

R$_1$ is hydrogen, PG$_1$, a natural amino acid residue, or an amino acid analog residue;

R$_2$ is selected from the group consisting of hydrogen and C$_1$-C$_6$ alkyl, or R$_2$ and R$_{10}$, or R$_2$ and R$_{10}$', together with the nitrogen atom and carbon atom to which they are attached, form a 3- to 7-membered heterocyclic ring optionally substituted with hydroxy or C$_1$-C$_4$ alkoxy, wherein R$_{10}$' is hydrogen when R$_2$ and R$_{10}$ together form the heterocyclic ring, and R$_{10}$ is hydrogen when R$_2$ and R$_{10}$' together form the heterocyclic ring;

except when R$_2$ and R$_{10}$ or R$_2$ and R$_{10}$' together form the heterocyclic ring, (a) R$_{10}$' is hydrogen, and R$_{10}$ is selected from the group consisting of hydrogen, optionally substituted C$_1$-C$_6$ alkyl, C$_3$-C$_6$ cycloalkyl, C$_3$-C$_6$ cycloalkyl-C$_1$-C$_4$ alkyl, optionally substituted phenyl, optionally substituted phenylmethyl, optionally substituted phenylethyl, 2-(methylthio)ethyl, —CH$_2$SPG$_8$, N-PG$_9$-indol-3-ylmethyl, 4-(PG$_8$O)benzyl, PG$_8$-O-methyl, 1-(PG$_8$O)ethyl, 2-(PG$_8$O)ethyl, PG$_8$-OCO(CH$_2$)—, PG$_8$-OCO(CH$_2$)$_2$—, PG$_9$N-n-butyl, —CON(R$_{16A}$)(R$_{16B}$), —CH$_2$—CON(R$_{16A}$)(R$_{16B}$), and —(CH$_2$)$_2$CON(R$_{16A}$)(R$_{16B}$), or (b) R$_{10}$ and R$_{10}$' are independently optionally substituted C$_1$-C$_6$ alkyl, C$_3$-C$_6$ cycloalkyl, or C$_3$-C$_6$ cycloalkyl-C$_1$-C$_4$ alkyl, or (c) R$_{10}$ and R$_{10}$', together with the carbon atom to which they are attached, form a 3- to 7-membered alicyclic ring;

R$_{11}$ is a single bond or —C(R$_{11A}$)(R$_{11B}$)—;

R$_{11A}$ and R$_{11B}$ are independently selected from the group consisting of hydrogen, C$_1$-C$_6$ alkyl, optionally substituted aryl, optionally substituted heteroaryl, optionally substituted aryl-C$_1$-C$_4$ alkyl, and optionally substituted heteroaryl-C$_1$-C$_4$ alkyl;

R$_{12}$ and R$_{12}$' are independently selected from the group consisting of hydrogen, PG$_{10}$-O-methyl, —(CH$_2$)$_n$COO-PG$_{10}$, —(CH$_2$)$_n$COO—RES, and —(CH$_2$)$_n$CONH—RES;

RES is a resin for solid-phase synthesis;

n is 0, 1, or 2;

R$_6$ is selected from the group consisting of hydrogen and C$_1$-C$_6$ alkyl;

R$_{13}$ is C$_1$-C$_4$ alkyl or —(CH$_2$)$_m$CON(R$_{17A}$)(R$_{17B}$);

m is 0, 1, or 2;

R$_{16A}$ and R$_{16B}$ are independently hydrogen or C$_1$-C$_4$ alkyl, or R$_{16A}$ and R$_{16B}$, together with the nitrogen atom to which they are attached, form a 4- to 8-membered ring optionally comprising one or more additional heteroatoms;

R$_{17A}$ and R$_{17B}$ are independently hydrogen or C$_1$-C$_4$ alkyl, or R$_{17A}$ and R$_{17B}$, together with the nitrogen atom to which they are attached, form a 4- to 8-membered ring optionally comprising one or more additional heteroatoms;

PG$_1$ is independently selected from the group consisting of Fmoc, Boc, Alloc, Cbz, Teoc, and trifluoroacetyl;

PG$_8$ is selected from the group consisting of hydrogen, t-Bu, trityl, methoxytrityl, cumyl, benzyl, THP, 1-ethoxyethyl, methyl, ethyl, allyl, optionally substituted aryl, optionally substituted aryl-C$_1$-C$_4$ alkyl, optionally substituted heteroaryl-C$_1$-C$_4$ alkyl, and 2-(trimethylsilyl)ethyl;

PG$_9$ is selected from the group consisting of hydrogen, Fmoc, Boc, Alloc, Cbz, Teoc, methoxycarbonyl, t-Bu, trityl, cumyl, and benzyl; and PG$_{10}$ is selected from the group consisting of t-Bu, trityl, cumyl, benzyl, methyl, ethyl, allyl, optionally substituted aryl, optionally substituted aryl-C$_1$-C$_4$ alkyl, optionally substituted heteroaryl-C$_1$-C$_4$ alkyl, and 2-(trimethylsilyl)ethyl.

20. The method of claim 2, wherein the silyl compound is represented by formula 1 below:

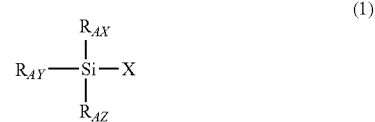

(1)

wherein R$_{AX}$, R$_{AY}$, and R$_{AZ}$ are independently C$_1$-C$_4$ alkyl or phenyl, and X is selected from the group consisting of —OTf, —OClO$_3$, Cl, Br, and I.

21. The method of claim 20, wherein the silyl compound is selected from the group consisting of TMSOTf, TESOTf, TBSOTf, TIPSOTf, TBDPSOTf, TTMSOTf, TMSCl, TMSBr, TMSOClO$_3$, and TMSI.

22. The method of claim 2, wherein the acid is represented by HX, wherein X is selected from the group consisting of —OTf, —OClO$_3$, Cl, Br, and I.

23. The method of claim 2, wherein the silylating agent is prepared by mixing the silyl compound with the electrophilic species scavenger.

24. The method of claim 23, wherein the electrophilic species scavenger is 2,2'-isopropylidenebis[(4S)-4-tert-butyl-2-oxazoline] represented by formula 2-2-1-1

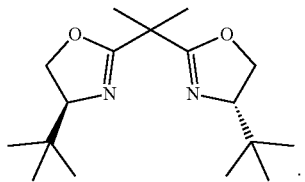

(2-2-1-1)

25. The method of claim 2, wherein per one equivalent of the resin to be removed, 1 to 5 equivalents of the silyl compound and 1 to 10 equivalents of the electrophilic species scavenger are mixed.

26. The method of claim 2, wherein per one equivalent of the resin to be removed,
  a) 0.1 to 0.5 equivalent of the silyl compound is mixed with the electrophilic species scavenger,
    wherein the silyl compound is selected from the group consisting of TMSOTf, TESOTf, TBSOTf, TIPSOTf, TBDPSOTf, TTMSOTf, TMSCl, TMSBr, and TMSOClO$_3$, or
  b) 0.1 to 0.5 equivalent of the acid is mixed with the silyl-containing electrophilic species scavenger,
    wherein the acid is represented by HX, wherein X is selected from the group consisting of —OTf, —OClO$_3$, Cl, Br, and I.

27. The method of claim 2, wherein the starting peptide compound comprises 1 to 30 amino acid residues and is linear or cyclic.

28. The method of claim 2, wherein the method comprises mixing the starting peptide compound with the solvent, then
  (1) with the electrophilic species scavenger, and subsequently with the silyl compound, or
  (2) with the silyl-containing electrophilic species scavenger, and subsequently with the acid.

29. The method of claim 1, wherein the silylating agent is prepared by mixing the acid with the silyl-containing electrophilic species scavenger.

30. The method of claim 2, wherein the silylating agent is prepared by mixing the acid with the silyl-containing electrophilic species scavenger.

31. The method of claim 5, wherein the silylating agent is prepared by mixing the silyl compound with the electrophilic species scavenger.

32. The method of claim 31, wherein the electrophilic scavenger is 2,2'-isopropylidenebis[(4S)-4-tert-butyl-2-oxazoline] represented by formula 2-2-1-1

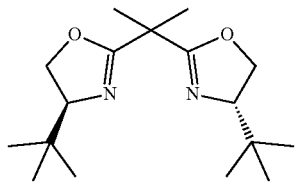

(2-2-1-1)

33. The method of claim 5, wherein the silylating agent is prepared by mixing the acid with the silyl-containing electrophilic species scavenger.

34. The method of claim 6, wherein the silylating agent is prepared by mixing the silyl compound with the electrophilic species scavenger.

35. The method of claim 34, wherein the electrophilic species scavenger is 2,2'-isopropylidenebis[(4S)-4-tert-butyl-2-oxazoline] represented by formula 2-2-1-1

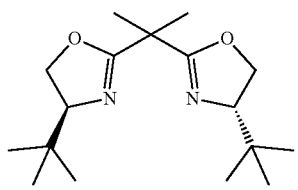

(2-2-1-1)

36. The method of claim 6, wherein the silylating agent is prepared by mixing the acid with the silyl-containing electrophilic species scavenger.

* * * * *

UNITED STATES PATENT AND TRADEMARK OFFICE
CERTIFICATE OF CORRECTION

PATENT NO. : 12,331,072 B2
APPLICATION NO. : 18/203371
DATED : June 17, 2025
INVENTOR(S) : Iwasaki et al.

It is certified that error appears in the above-identified patent and that said Letters Patent is hereby corrected as shown below:

In the Claims

In Claim 3, Column 188, at Line 28, please replace "$R_8$ is a single bond or -C($R_{5A}$)($R_{5B}$)-;" with -- $R_8$ is a single bond or -C($R_{8A}$)($R_{8B}$)-; --.

In Claim 3, Column 188, at Line 56, please replace "$PG_3$ and $PG_8$ are independently selected from the group" with -- $PG_3$ and $PG_5$ are independently selected from the group --.

Signed and Sealed this
Second Day of September, 2025

Coke Morgan Stewart
*Acting Director of the United States Patent and Trademark Office*